(12) United States Patent
Teshima et al.

(10) Patent No.: US 10,605,792 B2
(45) Date of Patent: Mar. 31, 2020

(54) METHOD OF AND APPARATUS FOR FORMULATING MULTICOMPONENT DRUG

(71) Applicant: TSUMURA & CO., Minato-ku, Tokyo (JP)

(72) Inventors: Shoichi Teshima, Kitahiroshima (JP); Yoshikazu Mori, Ibaraki (JP); Keiichi Noda, Ibaraki (JP)

(73) Assignee: Tsumura & Co., Tokyo (JP)

( * ) Notice: Subject to any disclaimer, the term of this patent is extended or adjusted under 35 U.S.C. 154(b) by 213 days.

(21) Appl. No.: 15/261,462

(22) Filed: Sep. 9, 2016

(65) Prior Publication Data

US 2017/0007502 A1 Jan. 12, 2017

Related U.S. Application Data

(63) Continuation-in-part of application No. 13/806,725, filed as application No. PCT/JP2012/003618 on May 31, 2012, now abandoned.

(30) Foreign Application Priority Data

Jun. 1, 2011 (JP) ................................ 2011-123849

(51) Int. Cl.
*G01N 30/74* (2006.01)
*G01N 30/86* (2006.01)
(Continued)

(52) U.S. Cl.
CPC ......... *G01N 30/74* (2013.01); *G01N 30/8631* (2013.01); *G01N 30/8686* (2013.01);
(Continued)

(58) Field of Classification Search
CPC ....... A61J 3/02; G01N 30/8631; G01N 30/74; G01N 2030/027; G06F 19/708; A61K 45/06
See application file for complete search history.

(56) References Cited

U.S. PATENT DOCUMENTS 3,023,664 A 3/1962 Coleman et al.
7,178,386 B1 * 2/2007 Gamble ............... G01N 30/466
210/198.2

(Continued)

FOREIGN PATENT DOCUMENTS

EP 1 626 274 2/2006
JP 2002-214215 7/2002
(Continued)

OTHER PUBLICATIONS

Pharmaceuticals Monthly, vol. 28, No. 3, pp. 67-71, (1986) (Cited in parent U.S. Appl. No. 13/806,725).

(Continued)

*Primary Examiner* — Lisa E Peters
(74) *Attorney, Agent, or Firm* — Norris McLaughlin, P.A.

(57) ABSTRACT

Provided are a method of and an apparatus for formulating a multicomponent drug capable of surely making a multicomponent drug meeting criteria for productization with high accuracy into a product. The method and apparatus obtain a chromatogram from an extract or a base of a multicomponent drug, evaluate whether the base meets the criteria for productization based on the obtained chromatogram with high accuracy, and subject the base determined in the high-accuracy evaluating as an accepted one meeting the criteria to dosage form processing, to produce a formulated drug having a given dosage-form. The high quality evaluation is realized by using fingerprint area segmentation feature values obtained from a fingerprint formed from a chromatogram and segmented into a plurality of areas.

12 Claims, 97 Drawing Sheets

(51) Int. Cl.
*G16C 20/20* (2019.01)
*G05B 15/00* (2006.01)
*G01N 30/88* (2006.01)
*G01N 30/02* (2006.01)

(52) U.S. Cl.
CPC ............ *G01N 30/88* (2013.01); *G05B 15/00* (2013.01); *G16C 20/20* (2019.02); *G01N 2030/027* (2013.01); *G01N 2030/8886* (2013.01)

(56) References Cited

U.S. PATENT DOCUMENTS

| | | |
|---|---|---|
| 2003/0124610 A1 | 7/2003 | Kvalheim et al. |
| 2006/0194326 A1 | 8/2006 | Usui et al. |
| 2006/0194329 A1 | 8/2006 | Ogiwara et al. |
| 2008/0140375 A1 | 6/2008 | Yano |
| 2009/0175766 A1 | 7/2009 | deCorral |
| 2010/0104153 A1 | 4/2010 | Hunt et al. |
| 2011/0312010 A1 | 12/2011 | Manuilov |
| 2012/0197541 A1* | 8/2012 | Lewis .................. A61K 31/00 702/22 |

FOREIGN PATENT DOCUMENTS

| | | |
|---|---|---|
| JP | 2004-264051 | 9/2004 |
| JP | 2006-170647 | 6/2006 |
| JP | 2007-085868 | 4/2007 |
| JP | 2007-315941 | 12/2007 |
| JP | 2008-541095 | 11/2008 |
| JP | 2010-118053 | 5/2010 |

OTHER PUBLICATIONS

Jianqiu Zhang, et al.; "Review of Peak Detection Algorithms in Liquid-Chromatography-Mass Spectometry", Current Genomics, 2009, 10, pp. 388-401.

Varhegyi G. et al.: "Use of Histograms in Computer-Aided Comparison of Chromatograms", Journal of Chromatography A, Elsevier, Amsterdam, NL, vol. 318, Jan. 1, 1985 (Jan. 1, 1985), pp. 247-253, XP026526634.

* cited by examiner

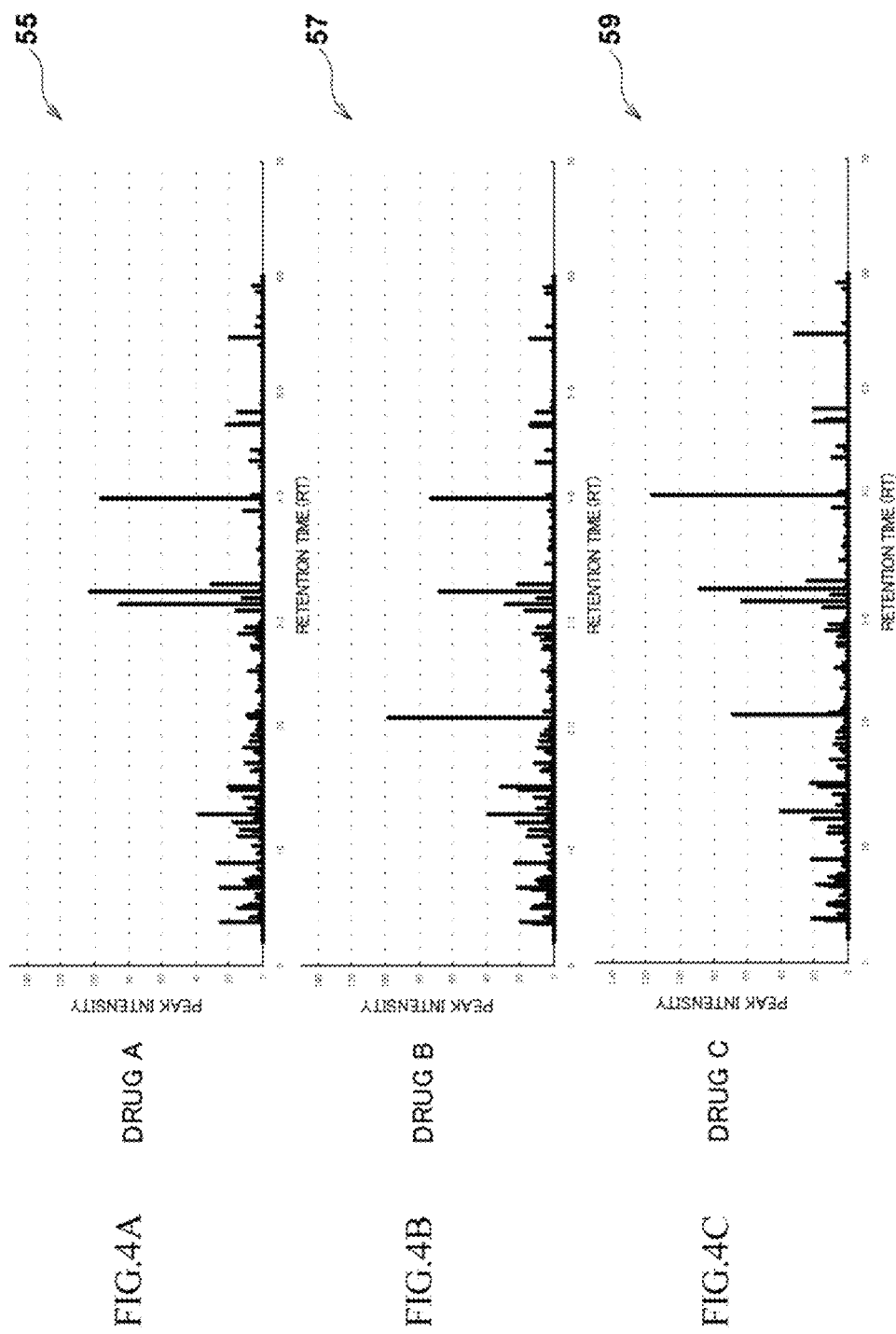

FIG.8

NUMBER OF MATCHES IN RETENTION TIME POINT APPEARANCE DISTANCE 111

| | | REFERENCE FP RETENTION TIME APPEARANCE PATTERN | | | | | | | | | |
|---|---|---|---|---|---|---|---|---|---|---|---|
| | | 1ROW | 2ROW | 3ROW | 4ROW | 5ROW | 6ROW | 7ROW | 8ROW | 9ROW | 10ROW |
| TARGET FP RETENTION TIME APPEARANCE PATTERN | 1ROW | 7 | 7 | 7 | 6 | 6 | 5 | 4 | 4 | 3 | 2 |
| | 2ROW | 6 | 6 | 6 | 6 | 5 | 2 | 3 | 3 | 2 | 2 |
| | 3ROW | 3 | 6 | 5 | 4 | 5 | 5 | 4 | 2 | 2 | 2 |
| | 4ROW | 6 | 2 | 7 | 6 | 5 | 4 | 4 | 3 | 2 | 1 |
| | 5ROW | 3 | 4 | 5 | 6 | 5 | 4 | 3 | 3 | 2 | 1 |
| | 6ROW | 4 | 3 | 4 | 4 | 5 | 3 | 3 | 2 | 2 | 1 |
| | 7ROW | 2 | 4 | 2 | 2 | 1 | 4 | 3 | 2 | 2 | 2 |
| | 8ROW | 3 | 1 | 3 | 2 | 3 | 3 | 3 | 3 | 3 | 1 |
| | 9ROW | 2 | 2 | 2 | 1 | 1 | 2 | 2 | 2 | 2 | 2 |

FIG.9

DEGREE OF MATCHING IN RETENTION TIME APPEARANCE PATTERN 113

| | | REFERENCE FP RETENTION TIME APPEARANCE PATTERN | | | | | | | | | |
|---|---|---|---|---|---|---|---|---|---|---|---|
| | | 1ROW | 2ROW | 3ROW | 4ROW | 5ROW | 6ROW | 7ROW | 8ROW | 9ROW | 10ROW |
| TARGET FP RETENTION TIME APPEARANCE PATTERN | 1ROW | 2.00 | 2.00 | 2.00 | 3.00 | 3.00 | 4.13 | 5.35 | 5.35 | 6.67 | 8.05 |
| | 2ROW | 9.50 | 3.00 | 3.00 | 3.00 | 4.13 | 8.05 | 6.67 | 6.67 | 8.05 | 8.05 |
| | 3ROW | 6.67 | 1.15 | 4.13 | 5.35 | 4.13 | 4.13 | 5.35 | 8.05 | 8.05 | 8.05 |
| | 4ROW | 3.00 | 8.05 | 2.00 | 3.00 | 4.13 | 5.35 | 5.35 | 6.67 | 8.05 | 9.50 |
| | 5ROW | 6.67 | 5.35 | 4.13 | 3.00 | 4.13 | 5.35 | 6.67 | 6.67 | 8.05 | 9.50 |
| | 6ROW | 5.35 | 6.67 | 5.35 | 5.35 | 4.13 | 6.67 | 6.67 | 8.05 | 8.05 | 9.50 |
| | 7ROW | 8.05 | 5.35 | 8.05 | 8.05 | 9.50 | 5.35 | 6.67 | 8.05 | 8.05 | 8.05 |
| | 8ROW | 6.67 | 9.50 | 6.67 | 8.05 | 6.67 | 6.67 | 6.67 | 6.67 | 6.67 | 9.50 |
| | 9ROW | 8.05 | 8.05 | 8.05 | 9.50 | 9.50 | 8.05 | 8.05 | 8.05 | 8.05 | 8.05 |

DEGREE OF MATCHING BETWEEN RETENTION TIME APPEARANCE PATTERNS =
(1 − (NUMBER OF MATCHES IN APPEARANCE DISTANCE/(NUMBER OF PEAKS OF TARGET FP + NUMBER OF PEAKS OF REFERENCE FP − NUMBER OF MATCHES IN APPEARANCE DISTANCE)) × (NUMBER OF PEAKS OF TARGET FP − NUMBER OF MATCHES IN APPEARANCE DISTANCE + 1)

UV_Sim(73-95) = RMSD (135 vs 139)

| d202 | |
|---|---|
| RT | Height |
| 3.925331 | 1.965691 |
| 6.300108 | 3.775012 |
| 10.723539 | 0.203477 |
| 15.979399 | 1.596914 |
| 21.158157 | 1.393369 |
| 26.761017 | 0.444316 |
| 36.193111 | 2.420560 |
| 36.457962 | 1.296542 |
| 56.460197 | 2.449590 |

| d207 | |
|---|---|
| RT | Height |
| 3.922288 | 2.646249 |
| 7.984150 | 0.444279 |
| 12.103620 | 1.399326 |
| 17.886545 | 0.718228 |
| 23.298538 | 0.524566 |
| 29.953604 | 0.922448 |
| 37.014805 | 2.744914 |
| 37.954102 | 2.222302 |
| 53.491627 | 1.013341 |
| 53.927883 | 2.109898 |

| d208 | |
|---|---|
| RT | Height |
| 3.922784 | 1.708236 |
| 6.326376 | 3.713409 |
| 11.007607 | 1.778159 |
| 16.626104 | 0.891248 |
| 22.643625 | 1.847071 |
| 28.160902 | 1.040604 |
| 35.362377 | 0.893375 |
| 35.862019 | 0.556278 |
| 40.229908 | 1.148475 |
| 41.681339 | 0.453854 |
| 53.924591 | 2.270233 |

| d202 | |
|---|---|
| RT | Height |
| 3.925331 | 1.965691 |
| 6.300108 | 3.775012 |
| 10.723539 | 0.203477 |
| 15.979399 | 1.596914 |
| 21.158157 | 1.393369 |
| 26.761017 | 0.444316 |
| 36.193111 | 2.420560 |
| 36.457962 | 1.296542 |
| 56.460197 | 2.449590 |

SUM OF ALL PEAK HEIGHTS

⇩

15.545472

| FILE NAME | HORIZONTAL 1ST | VERTICAL 1ST | AREA 1 | AREA 2 | · | · | · | AREA 30 |
|---|---|---|---|---|---|---|---|---|
| d202 | 1 | 1 | 0.128655 | 0.064327 | · | · | · | 0 |

ACTUAL DATA IN THICK-BORDERED BOX

| FILE NAME | HORIZONTAL 1ST | VERTICAL 1ST | AREA 1 | AREA 2 | · | · | · | AREA 30 |
|---|---|---|---|---|---|---|---|---|
| d202 | 0.5 | 0 | 0.128655 | 0.064327 | · | · | · | 0 |
| | 0.5 | 0.2 | 0.128655 | 0.064129 | · | · | · | 0 |
| | 0.5 | 0.4 | 0.128655 | 0.057696 | · | · | · | 0 |
| | 0.5 | · | · | · | · | · | · | · |
| | 0.5 | · | · | · | · | · | · | · |
| | 0.5 | · | · | · | · | · | · | · |

ACTUAL DATA IN THICK-BORDERED BOX

FIG.85

| FILE NAME | HORIZONTAL 1ST | VERTICAL 1ST | AREA 1 | AREA 2 | · | · | · | AREA 30 |
|---|---|---|---|---|---|---|---|---|
| d202 | 0.5 | 0 | 0.128655 | 0.064327 | · | · | · | 0 |
| | 0.5 | 0.2 | 0.128655 | 0.064129 | · | · | · | 0 |
| | 0.5 | 0.4 | 0.128655 | 0.057696 | · | · | · | 0 |
| | 0.5 | · | · | · | · | · | · | · |
| | 0.5 | · | · | · | · | · | · | · |
| | 0.5 | · | · | · | · | · | · | · |
| | 0.6 | 0 | 0.128655 | 0.064327 | | | | 0 |
| | 0.6 | 0.2 | 0.128655 | 0.064129 | | | | 0 |
| | · | · | · | · | · | · | · | · |
| | · | · | · | · | · | · | · | · |

ACTUAL DATA IN THICK-BORDERED BOX

FIG.86

| FILE NAME | HORIZONTAL 1ST | VERTICAL 1ST | AREA 1 | AREA 2 | · | · | · | AREA 30 |
|---|---|---|---|---|---|---|---|---|
| d210 | 1 | 1 | 0.128655 | 0.064327 | · | · | · | 0 |

ACTUAL DATA IN THICK-BORDERED BOX

FIG.100 TARGET FP ASSIGNING PROCESS 3 (POST-PROCESS: SPECIFYING CORRESPONDING PEAKS FROM PLURAL CANDIDATE PEAKS)

FEATURE VALUE QUANTIFICATION OF TARGET FP THROUGH AREA SEGMENTATION

PEAK DATA FEATURE VALUE PROCESS (PREPARATION OF REFERENCE GROUP FP)

FEATURE VALU QUANTIFICATION PROCESS OF REFERENCE FP THROUGH AREA SEGMENTATION

FIG.117

| DAD-Data | 203 | 204 | 205 | 206 | 207 | ... | 296 | 297 | 298 | 299 | 300 ← DETECTION WAVELENGTH (nm) |
|---|---|---|---|---|---|---|---|---|---|---|---|
| 2.02167 | 0.236511 | 0.184536 | 0.198364 | 0.132561 | 0.192642 | ... | 0.031471 | 0.034332 | -0.00715 | 0.031471 | 0.000954 |
| 2.03833 | 0.24128 | 0.193119 | 0.205994 | 0.142574 | 0.206847 | ... | 0.026703 | 0.034332 | -0.00572 | 0.039577 | -0.00095 |
| 2.0155 | 0.247955 | 0.199795 | 0.216007 | 0.157356 | 0.22316 | ... | 0.01812 | 0.030994 | 0.001431 | 0.048637 | -0.00238 |
| 2.02167 | 0.258923 | 0.208378 | 0.226498 | 0.173569 | 0.239372 | ... | 0.011444 | 0.027657 | 0.009537 | 0.052929 | -0.00238 |
| 2.03833 | 0.270367 | 0.222208 | 0.237842 | 0.188304 | 0.252724 | ... | 0.008583 | 0.023842 | 0.016689 | 0.053406 | 0.000954 |
| 2.0355 | 0.283241 | 0.240328 | 0.249386 | 0.208855 | 0.263214 | ... | 0.010967 | 0.017643 | 0.024319 | 0.060545 | 0.007153 |
| 2.04167 | 0.300084 | 0.257989 | 0.259876 | 0.230789 | 0.271797 | ... | 0.015259 | 0.013828 | 0.032902 | 0.044823 | 0.014782 |
| 2.04833 | 0.323772 | 0.273705 | 0.271797 | 0.252247 | 0.28181 | ... | 0.021935 | 0.015736 | 0.03767 | 0.039577 | 0.021835 |
| 2.0555 | 0.352383 | 0.289917 | 0.283241 | 0.272274 | 0.293732 | ... | 0.027657 | 0.024319 | 0.035286 | 0.039577 | 0.026226 |
| 2.06167 | 0.382423 | 0.306129 | 0.298977 | 0.293255 | 0.306129 | ... | 0.030994 | 0.033855 | 0.030518 | 0.037193 | 0.025749 |
| 2.06833 | 0.418663 | 0.323772 | 0.325203 | 0.321388 | 0.319958 | ... | 0.030041 | 0.044823 | 0.027657 | 0.0453 | 0.025272 |
| 2.0755 | 0.460625 | 0.34606 | 0.36335 | 0.352383 | 0.339985 | ... | 0.023365 | 0.059128 | 0.025749 | 0.052929 | 0.025272 |
| 2.08167 | 0.511189 | 0.383377 | 0.412464 | 0.387669 | 0.366688 | ... | 0.015736 | 0.069141 | 0.021458 | 0.060081 | 0.02861 |
| 2.08833 | 0.570297 | 0.435352 | 0.485867 | 0.431538 | 0.402451 | ... | 0.01049 | 0.071526 | 0.016212 | 0.066757 | 0.030994 |
| ... | ... | ... | ... | ... | ... | ... | ... | ... | ... | ... | ... |
| 59.94833 | 266.1746 | 208.0026 | 160.8496 | 125.2108 | 98.0444 | ... | 0.685215 | 0.713346 | 0.657558 | 0.6814 | 0.639915 |
| 59.9555 | 266.3458 | 208.1509 | 160.9607 | 125.2985 | 98.11354 | ... | 0.684738 | 0.716209 | 0.657062 | 0.680447 | 0.638485 |
| 59.96217 | 266.5189 | 208.2896 | 161.0661 | 125.3839 | 98.176 | ... | 0.683308 | 0.712395 | 0.656605 | 0.679016 | 0.638962 |
| 59.96883 | 268.693 | 208.4146 | 161.1671 | 125.4654 | 98.23656 | ... | 0.681877 | 0.702381 | 0.658939 | 0.676632 | 0.634485 |
| 59.9755 | 268.858 | 208.528 | 161.2618 | 125.5417 | 98.29617 | ... | 0.6814 | 0.690837 | 0.665665 | 0.674725 | 0.634439 |
| 59.98217 | 269.0167 | 208.6339 | 161.3479 | 125.6094 | 98.35434 | ... | 0.679997 | 0.681877 | 0.671397 | 0.877586 | 0.841823 |
| 59.98883 | 269.1703 | 208.7336 | 161.428 | 125.67 | 98.40822 | ... | 0.877586 | 0.874725 | 0.672817 | 0.881877 | 0.844804 |
| 59.9955 | 269.3124 | 208.8246 | 161.5 | 125.7191 | 98.45866 | ... | 0.874725 | 0.67091 | 0.671864 | 0.884738 | 0.846114 |
| ↑ RETENTION TIME (MINUTE) | | | | | | | | | | | |

183

SIGNAL INTENSITY (columns 203–300)

FIG. 118

| HeaderName | HeaderValue | Flags | PeakType | RetTime | Area | Height | Width | ... | AreaPercent |
|---|---|---|---|---|---|---|---|---|---|
| NumberOfRows | 118 | 2 | 8 | 3.737342119 | 149.1629486 | 24.95452835 | 0.089736186 | ... | 1.65592471 |
| NumberOfCol | 21 | 32 | 8 | 3.925331116 | 9.433002472 | 1.965691447 | 0.075986251 | ... | 0.104719988 |
| NumberOfHead | 9 | 0 | 8 | 4.191194803 | 76.68452454 | 7.853988171 | 0.139910638 | ... | 0.851309257 |
| Modified | | 0 | 8 | 4.611811161 | 13.87264156 | 1.980707884 | 0.111711942 | ... | 0.154086408 |
| DateTime | | 2 | 8 | 4.961237089 | 140.9757385 | 14.70096874 | 0.137878135 | ... | 1.565034823 |
| IntegStart | 0 | 34 | 8 | 5.159340382 | 99.85542297 | 11.33216706 | 0.128793851 | ... | 1.10853978 |
| IntegEnd | 0 | 32 | 8 | 5.294465542 | 53.13053131 | 8.221708298 | 0.099339263 | ... | 0.569825828 |
| Errors | 0 | 0 | 8 | 5.789111137 | 30.95186141 | 3.765951157 | 0.129886086 | ... | 0.3406107 |
| IntegMode | 2 | 2 | 8 | 6.094525814 | 31.32414055 | 3.210045815 | 0.147845194 | ... | 0.347743316 |
| | | 34 | 8 | 6.300107956 | 31.41418457 | 3.775012255 | 0.121085465 | ... | 0.348742935 |
| | | 34 | 8 | 6.729168415 | 337.5208696 | 25.2769146 | 0.161787893 | ... | 3.747059177 |
| | | 32 | 8 | 7.14134407 | 128.023819 | 8.847929955 | 0.196809128 | ... | 1.421249762 |
| | | ... | ... | ... | ... | ... | ... | ... | ... |
| | | 0 | 8 | 53.9373436 | 15.90642643 | 1.939949751 | 0.127659678 | ... | 0.176584365 |
| | | 0 | 8 | 54.85077972 | 184.8139801 | 19.59946349 | 0.144011214 | ... | 2.051702278 |
| | | 0 | 8 | 55.67518234 | 27.47281837 | 3.244963169 | 0.132773459 | ... | 0.304968063 |
| | | 0 | 8 | 56.46019745 | 28.83960353 | 2.449530445 | 0.169354796 | ... | 0.320162246 |
| | | 0 | 8 | 58.57313156 | 27.80234528 | 3.295254707 | 0.132432669 | ... | 0.308646289 |
| | | 0 | 8 | 59.13926315 | 56.54888153 | 5.344749451 | 0.157430646 | ... | 0.627774465 |

RETENTION TIME (MINUTE)    PEAK AREA    PEAK HEIGHT

| RETENTION TIME (MINUTES) | PEAK HEIGHT | 220 | 221 | 222 | 223 | 224 | ... | 297 | 298 | 299 | 300 |
|---|---|---|---|---|---|---|---|---|---|---|---|
| 3.737342119 | 24.95453835 | 1 | 0.846988 | 0.893759 | 0.840576 | 0.786823 | ... | 0.102588 | 0.100418 | 0.098715 | 0.098144 |
| 3.925331116 | 1.965691447 | 1 | 0.86883 | 0.933862 | 0.899785 | 0.870409 | ... | 0.148963 | 0.145538 | 0.142684 | 0.138863 |
| 4.191946030 | 7.853988171 | 1 | 0.851353 | 0.905206 | 0.861315 | 0.822883 | ... | 0.858285 | 0.854974 | 0.853741 | 0.842492 |
| 4.611811161 | 1.980707884 | 1 | 0.866231 | 0.934717 | 0.902057 | 0.875049 | ... | 0.536382 | 0.505956 | 0.476373 | 0.444965 |
| 4.961337090 | 14.70086874 | 1 | 0.855319 | 0.911156 | 0.86973 | 0.833565 | ... | 0.207648 | 0.205572 | 0.206256 | 0.203732 |
| 5.159340362 | 11.33216708 | 1 | 0.853257 | 0.872526 | 0.822505 | 0.784413 | ... | 0.307071 | 0.303897 | 0.303275 | 0.302085 |
| 5.294465542 | 8.221708298 | 1 | 0.864049 | 0.924894 | 0.884593 | 0.847809 | ... | 0.425285 | 0.425389 | 0.427005 | 0.425129 |
| 5.789111137 | 3.765851157 | 1 | 0.852409 | 0.907016 | 0.880134 | 0.816736 | ... | 0.210023 | 0.211059 | 0.209317 | 0.207167 |
| 6.094525814 | 3.210045815 | 1 | 0.962636 | 0.923002 | 0.885678 | 0.852812 | ... | 0.154766 | 0.149538 | 0.148322 | 0.146499 |
| 6.300107956 | 3.775012255 | 1 | 0.861981 | 0.924493 | 0.885414 | 0.885061 | ... | 0.161201 | 0.157036 | 0.157225 | 0.154385 |
| 6.729188415 | 25.27691460 | 1 | 0.863209 | 0.929871 | 0.988246 | 0.870401 | ... | 0.151135 | 0.147084 | 0.146431 | 0.146295 |
| 7.141134407 | 8.847829955 | 1 | 0.882428 | 0.927794 | 0.892649 | 0.86298 | ... | 0.232462 | 0.226918 | 0.228348 | 0.227739 |
| ... | ... | ... | ... | ... | ... | ... | ... | ... | ... | ... | ... |
| 47.04151535 | 21.10215187 | 1 | 0.946357 | 0.898223 | 0.85577 | 0.821346 | ... | 0.010338 | 0.003716 | 0.002477 | -0.00068 |
| 47.262146 | 12.78088965 | 1 | 0.849657 | 0.903068 | 0.858554 | 0.822637 | ... | -0.00652 | -0.01092 | -0.00954 | -0.01201 |
| 48.20507431 | 14.44223309 | 1 | 0.866953 | 0.938847 | 0.912835 | 0.889156 | ... | 0.018335 | 0.011833 | 0.010432 | 0.008717 |
| 48.8165741 | 0.589508497 | 1 | 0.91256 | 0.839808 | 0.770762 | 0.707069 | ... | -0.00419 | -0.00796 | -0.00323 | -0.00631 |
| 53.93734360 | 1.939849751 | 1 | 0.913891 | 0.839232 | 0.771945 | 0.711194 | ... | 0.028755 | 0.023475 | 0.02933 | 0.024207 |
| 54.65077972 | 19.59848249 | 1 | 0.868395 | 0.940957 | 0.913986 | 0.892413 | ... | 0.031448 | 0.027065 | 0.026584 | 0.023791 |
| 55.67518234 | 3.244863169 | 1 | 0.918351 | 0.839363 | 0.77256 | 0.718174 | ... | 0.035946 | 0.032618 | 0.033752 | 0.029644 |
| 56.46019745 | 2.449590445 | 1 | 0.923738 | 0.850274 | 0.788056 | 0.736899 | ... | 0.035911 | 0.087788 | 0.065269 | 0.077858 |
| 58.57313158 | 3.295234707 | 1 | 0.921651 | 0.849726 | 0.781768 | 0.714406 | ... | 0.04279 | 0.042018 | 0.043071 | 0.041386 |
| 59.13926315 | 5.344749451 | 1 | 0.918037 | 0.841855 | 0.773269 | 0.718908 | ... | 0.051443 | 0.050853 | 0.050617 | 0.048258 |

UV SPECTRUM (DATA NORMALIZED WITH USE OF MAXIMUM VALUE OF "1" IN UV SPECTRUM OF DETECTION WAVELENGTHS OF 220 TO 300 nm)

FIG.120

DETERMINATION RESULT FILE

| TARGET FP | | | REFERENCE FP | | | | | | |
|---|---|---|---|---|---|---|---|---|---|
| PEAK NUMBER | RETENTION | PEAK HEIGHT | 6 | 5 | 4 | 3 | 2 | 1 | |
| 7 | 5.79 | 6.02 | 5.30 | 5.14 | 4.96 | 4.19 | 3.92 | 3.73 | ←PEAK NUMBER ←RETENTION ←PEAK HEIGHT |
| 6 | 5.18 | 17.28 | 6.32 | 11.70 | 11.70 | 5.85 | 2.06 | 24.11 | |
| 5 | 4.91 | 12.07 | 114.46 | 888888 | 888888 | 888888 | 888888 | 888888 | |
| 4 | 4.58 | 3.12 | 27.09 | 4.05 | 36.11 | 888888 | 888888 | 888888 | |
| 3 | 4.17 | 5.26 | 148.07 | 27.67 | 3.27 | 888888 | 888888 | 888888 | |
| 2 | 3.87 | 2.63 | 888888 | 888888 | 399.00 | 96.93 | 194.22 | 800.99 | |
| 2 | 3.87 | 2.63 | 888888 | 888888 | 888888 | 4.59 | 1.07 | 83.51 | |
| 1 | 2.70 | 26.53 | 888888 | 888888 | 888888 | 178.46 | 103.15 | 0.59 | |
| | | | 888888 | 888888 | 888888 | 706.02 | | | |

PEAK NUMBER  RETENTION  PEAK HEIGHT

189

FIG.122
COLLATION RESULT FILE

| REFERENCE FP PEAK NUMBER | REFERENCE FP RETENTION TIME | REFERENCE FP PEAK DATA | TARGET FP PEAK DATA 195 |
|---|---|---|---|
| 6 | 5.77 | 0.00 | 6.02 |
| 5 | 5.30 | 6.32 | 0.00 |
| 4 | 5.14 | 11.78 | 17.28 |
|  | 4.96 | 11.70 | 12.07 |
| 3 | 4.62 | 0.00 | 3.12 |
|  | 4.19 | 5.85 | 5.26 |
| 2 | 3.92 | 2.06 | 2.63 |
| 1 | 3.73 | 24.11 | 26.53 |

FIG.123

| | P1 | P2 | P3 | P4 | P5 | P6 | ... | P59 | P60 | P61 | P62 |
|---|---|---|---|---|---|---|---|---|---|---|---|
| | 3.74 | 4.19 | 4.97 | 5.18 | 5.3 | 5.79 | ... | 54.63 | 55.65 | 58.56 | 59.13 |
| REFERENCE FP01 | 24.85454 | 7.853888 | 14.70097 | 11.33317 | 8.221708 | 3.785951 | ... | 19.59948 | 3.244963 | 3.295255 | 5.344749 |
| REFERENCE FP02 | 24.64909 | 5.854984 | 11.60893 | 13.22757 | 8.280517 | 4.831429 | ... | 29.02091 | 4.153991 | 5.682264 | 6.408809 |
| REFERENCE FP03 | 23.41309 | 6.5214 | 12.75418 | 10.8282 | 6.856493 | 6.392059 | ... | 30.30344 | 3.538835 | 4.372816 | 6.136991 |
| REFERENCE FP04 | 24.16606 | 7.157524 | 12.22046 | 11.29149 | 6.495305 | 5.647078 | ... | 26.63015 | 4.352538 | 3.193285 | 5.196698 |
| REFERENCE FP05 | 24.39492 | 5.397262 | 11.57015 | 12.50578 | 7.025057 | 3.989343 | ... | 24.84871 | 3.971656 | 4.57817 | 6.042276 |
| REFERENCE FP06 | 23.79346 | 6.513098 | 12.60338 | 11.08297 | 6.917242 | 5.876327 | ... | 31.78834 | 3.842261 | 3.717728 | 6.79227 |
| ... | . | . | . | . | . | . | ... | . | . | . | . |
| REFERENCE FP74 | 24.54318 | 7.229315 | 12.54595 | 11.2069 | 6.476972 | 5.933669 | ... | 28.67843 | 3.249248 | 3.390216 | 4.883753 |
| REFERENCE FP75 | 24.29694 | 4.890836 | 9.386555 | 12.18806 | 5.953234 | 5.645267 | ... | 31.22406 | 3.530962 | 3.596655 | 6.64429 |
| REFERENCE FP76 | 23.70935 | 6.477378 | 12.64439 | 10.87211 | 6.866796 | 5.588339 | ... | 31.43591 | 4.058423 | 4.047005 | 6.010718 |
| REFERENCE FP77 | 24.36124 | 6.815094 | 12.57119 | 10.80901 | 6.628489 | 5.446465 | ... | 27.19873 | 3.325639 | 2.963221 | 5.730851 |
| REFERENCE FP78 | 25.64983 | 5.101483 | 9.69347 | 12.87496 | 6.267442 | 7.07402 | ... | 32.01024 | 3.422246 | 4.078995 | 6.913398 |
| REFERENCE FP79 | 24.30647 | 6.390844 | 11.81865 | 11.80368 | 6.251297 | 4.853024 | ... | 30.00299 | 3.375931 | 3.21543 | 5.605225 |
| REFERENCE FP80 | 25.70864 | 6.55578 | 11.58949 | 11.24369 | 7.099552 | 5.819771 | ... | 28.78977 | 3.235093 | 4.217419 | 5.674382 |
| REFERENCE FP81 | 24.95631 | 6.882163 | 12.10839 | 11.19636 | 7.243779 | 5.99508 | ... | 27.85074 | 3.186492 | 2.711059 | 5.909272 |
| REFERENCE FP82 | 25.13536 | 6.896024 | 12.17865 | 11.21373 | 7.208914 | 5.946516 | ... | 28.11332 | 3.297449 | 3.585845 | 5.951847 |

REFERENCE FP NAME

REFERENCE GROUP FP PEAK NUMBER
REFERENCE GROUP FP RETENTION TIME (MINUTE)
PEAK HEIGHT

|  | P1 | P2 | P3 | P4 | P5 | P6 | ... | P59 | P60 | P61 | P62 | ← REFERENCE GROUP FP PEAK NUMBER |
|---|---|---|---|---|---|---|---|---|---|---|---|---|
|  | 3.74 | 4.19 | 4.97 | 5.25 | 5.3 | 5.79 | ... | 54.61 | 55.66 | 58.39 | 59.13 | ← REFERENCE GROUP FP RETENTION TIME (MINUTE) |
| TARGET FP NAME | M105-364 | 25.17530 | 7.446256 | 13.59407 | 10.48504 | 7.926013 | 13.50302 | ... | 1.962201 | 3.445913 | 3.4460 | 5.51216 | ← PEAK DATA FEATURE VALUE OF TARGET FP |

| RETENTION TIME (MINUTES) | PEAK HEIGHT | ← HEADER |
|---|---|---|
| 3.925331118 | 1.965691447 | |
| 4.611811161 | 1.980707884 | |
| 6.094525814 | 3.210045815 | PEAKS THAT ARE NOT INCLUDED IN PEAK DATA FEATURE VALUES |
| 6.300107956 | 3.775012255 | |
| ⋮ | ⋮ | |
| 48.8165741 | 0.599506497 | |
| 53.9373436 | 1.939949751 | |
| 56.46019745 | 2.449590445 | |

|  | E1 | E2 | E3 | E4 | E5 | E6 | ... | E27 | E28 | E29 | E30 | ← AREA NUMBER |
|---|---|---|---|---|---|---|---|---|---|---|---|---|
|  | - | - | - | - | - | - | ... | - | - | - | - | ← ADJUSTMENT ROW OF HEADER |
| TARGET FP | 0.961 | 0.117 | 0.127 | 0.079 | 0.031 | 0.022 | ... | 0.000 | 0.000 | 0.000 | 0.000 | ← AREA SEGMENTATION FEATURE VALUE OF TARGET FP |

TARGET FP NAME

|  | P1 | P2 | P3 | ... | P61 | P62 | E1 | E2 | E3 | ... | E29 | E30 | |
|---|---|---|---|---|---|---|---|---|---|---|---|---|---|
|  | 3.74 | 4.19 | 4.97 | ... | 58.36 | 59.13 | - | - | - | ... | - | - | ← HEADER ROW |
| TARGET FP NAME | 25.175 | 7.446 | 13.594 | ... | 3.446 | 5.512 | 0.961 | 0.117 | 0.127 | ... | 0.000 | 0.000 | ← INTEGRATED FEATURE VALUE |

TARGET FP NAME | PEAK DATA FEATURE VALUE | AREA SEGMENTATION FEATURE VALUE

| | AREA NUMBER ADJUSTMENT ROW OF HEADER | AREA SEGMENTATION FEATURE VALUE | | | | | | | | | | |
|---|---|---|---|---|---|---|---|---|---|---|---|---|
| | | E1 | E2 | E3 | E4 | E5 | E6 | ... | E27 | E28 | E29 | E30 |
| REFERENCE FP 1 | | 0.075 | 0.114 | 0.121 | 0.075 | 0.030 | 0.023 | ... | 0.000 | 0.000 | 0.000 | 0.000 |
| REFERENCE FP 1 | | 0.074 | 0.106 | 0.118 | 0.067 | 0.028 | 0.023 | ... | 0.000 | 0.000 | 0.000 | 0.000 |
| REFERENCE FP 1 | | 0.073 | 0.098 | 0.114 | 0.059 | 0.027 | 0.023 | ... | 0.000 | 0.000 | 0.000 | 0.000 |
| REFERENCE FP 1 | | 0.072 | 0.091 | 0.111 | 0.051 | 0.026 | 0.023 | ... | 0.000 | 0.000 | 0.000 | 0.000 |
| ... | | ... | ... | ... | ... | ... | ... | ... | ... | ... | ... | ... |
| REFERENCE FP 2 | | 0.054 | 0.116 | 0.124 | 0.105 | 0.027 | 0.017 | ... | 0.000 | 0.000 | 0.000 | 0.000 |
| REFERENCE FP 2 | | 0.053 | 0.107 | 0.117 | 0.099 | 0.025 | 0.016 | ... | 0.000 | 0.000 | 0.000 | 0.000 |
| REFERENCE FP 2 | | 0.051 | 0.097 | 0.111 | 0.094 | 0.023 | 0.015 | ... | 0.000 | 0.000 | 0.000 | 0.000 |
| REFERENCE FP 2 | | 0.050 | 0.089 | 0.105 | 0.087 | 0.021 | 0.014 | ... | 0.000 | 0.000 | 0.000 | 0.000 |
| ... | | ... | ... | ... | ... | ... | ... | ... | ... | ... | ... | ... |
| REFERENCE FP 3 | | 0.072 | 0.102 | 0.133 | 0.103 | 0.020 | 0.011 | ... | 0.000 | 0.000 | 0.000 | 0.000 |
| REFERENCE FP 3 | | 0.068 | 0.095 | 0.127 | 0.097 | 0.017 | 0.011 | ... | 0.000 | 0.000 | 0.000 | 0.000 |
| REFERENCE FP 3 | | 0.065 | 0.088 | 0.120 | 0.091 | 0.016 | 0.011 | ... | 0.000 | 0.000 | 0.000 | 0.000 |
| REFERENCE FP 3 | | 0.060 | 0.082 | 0.112 | 0.084 | 0.014 | 0.011 | ... | 0.000 | 0.000 | 0.000 | 0.000 |
| ... | | ... | ... | ... | ... | ... | ... | ... | ... | ... | ... | ... |
| REFERENCE FP 4 | | 0.061 | 0.117 | 0.127 | 0.079 | 0.031 | 0.022 | ... | 0.000 | 0.000 | 0.000 | 0.000 |
| REFERENCE FP 4 | | 0.059 | 0.111 | 0.120 | 0.071 | 0.028 | 0.022 | ... | 0.000 | 0.000 | 0.000 | 0.000 |
| REFERENCE FP 4 | | 0.058 | 0.105 | 0.115 | 0.063 | 0.025 | 0.022 | ... | 0.000 | 0.000 | 0.000 | 0.000 |
| REFERENCE FP 4 | | 0.057 | 0.098 | 0.110 | 0.056 | 0.022 | 0.022 | ... | 0.000 | 0.000 | 0.000 | 0.000 |
| TARGET PF NAME | | | | | | | | | | | | |

| | | HEADER ROW | | | | | | | | | | | | |
|---|---|---|---|---|---|---|---|---|---|---|---|---|---|---|
| | | P1 | P2 | P3 | ... | P61 | P62 | 209 | E1 | E2 | E3 | ... | E29 | E30 |
| | | 3.74 | 4.19 | 4.97 | ... | 58.56 | 59.13 | | | | | | | |
| REFERENCE FP 01 | | 24.955 | 7.854 | 14.701 | ... | 3.295 | 5.345 | | 0.075 | 0.114 | 0.121 | ... | 0.000 | 0.000 |
| REFERENCE FP 01 | | 24.955 | 7.854 | 14.701 | ... | 3.295 | 5.345 | | 0.074 | 0.106 | 0.118 | ... | 0.000 | 0.000 |
| REFERENCE FP 01 | | 24.955 | 7.854 | 14.701 | ... | 3.295 | 5.345 | | 0.073 | 0.098 | 0.114 | ... | 0.000 | 0.000 |
| REFERENCE FP 01 | | 24.955 | 7.854 | 14.701 | ... | 3.295 | 5.345 | | 0.072 | 0.091 | 0.111 | ... | 0.000 | 0.000 |
| ... | | ... | ... | ... | ... | ... | ... | | ... | ... | ... | ... | ... | ... |
| REFERENCE FP 02 | | 24.641 | 5.855 | 11.607 | ... | 5.682 | 6.407 | | 0.054 | 0.116 | 0.124 | ... | 0.000 | 0.000 |
| REFERENCE FP 02 | | 24.641 | 5.855 | 11.607 | ... | 5.682 | 6.407 | | 0.053 | 0.107 | 0.117 | ... | 0.000 | 0.000 |
| REFERENCE FP 02 | | 24.641 | 5.855 | 11.607 | ... | 5.682 | 6.407 | | 0.051 | 0.097 | 0.111 | ... | 0.000 | 0.000 |
| REFERENCE FP 02 | | 24.641 | 5.855 | 11.607 | ... | 5.682 | 6.407 | | 0.050 | 0.089 | 0.105 | ... | 0.000 | 0.000 |
| ... | | ... | ... | ... | ... | ... | ... | | ... | ... | ... | ... | ... | ... |
| REFERENCE FP 03 | | 23.413 | 6.521 | 12.754 | ... | 4.373 | 6.137 | | 0.072 | 0.102 | 0.133 | ... | 0.000 | 0.000 |
| REFERENCE FP 03 | | 23.413 | 6.521 | 12.754 | ... | 4.373 | 6.137 | | 0.068 | 0.095 | 0.127 | ... | 0.000 | 0.000 |
| REFERENCE FP 03 | | 23.413 | 6.521 | 12.754 | ... | 4.373 | 6.137 | | 0.065 | 0.088 | 0.120 | ... | 0.000 | 0.000 |
| REFERENCE FP 03 | | 23.413 | 6.521 | 12.754 | ... | 4.373 | 6.137 | | 0.060 | 0.082 | 0.112 | ... | 0.000 | 0.000 |
| ... | | ... | ... | ... | ... | ... | ... | | ... | ... | ... | ... | ... | ... |
| REFERENCE FP 04 | | 24.161 | 7.158 | 12.220 | ... | 3.193 | 5.197 | | 0.061 | 0.117 | 0.127 | ... | 0.000 | 0.000 |
| REFERENCE FP 04 | | 24.161 | 7.158 | 12.220 | ... | 3.193 | 5.197 | | 0.059 | 0.111 | 0.120 | ... | 0.000 | 0.000 |
| REFERENCE FP 04 | | 24.161 | 7.158 | 12.220 | ... | 3.193 | 5.197 | | 0.058 | 0.105 | 0.115 | ... | 0.000 | 0.000 |
| REFERENCE FP 04 | | 24.161 | 7.158 | 12.220 | ... | 3.193 | 5.197 | | 0.057 | 0.098 | 0.110 | ... | 0.000 | 0.000 |
| ... | | ... | ... | ... | ... | ... | ... | | ... | ... | ... | ... | ... | ... |

REFERENCE FP NAME | PEAK DATA FEATURE VALUE | AREA SEGMENTATION FEATURE VALUE

INTEGRATED FEATURE VALUE

FIG.131

| UV DATA | a1 | a2 | a3 | a4 | a5 | a6 | a7 |
|---|---|---|---|---|---|---|---|
| MOVING AVERAGE (CASE OF INTERVAL 1 (w1 = 3)) | | | m1=(a1+a2+a3)/3 | m2=(a2+a3+a4)/3 | m3=(a3+a4+a5)/3 | m4=(a4+a5+a6)/3 | m5=(a5+a6+a7)/3 |
| MOVING INCLINATION (CASE OF INTERVAL 2 (w2 = 3)) | | | | | s1=(m3−m1)/3 | s1=(m4−m2)/3 | s1=(m5−m3)/3 |

METHOD OF AND APPARATUS FOR FORMULATING MULTICOMPONENT DRUG

REFERENCE TO RELATED APPLICATIONS

The present application is a continuation-in-part application of U.S. patent application Ser. No. 13/806,722, filed Feb. 6, 2013, currently pending, which in turn is the U.S. national stage of PCT/JP2012/003618, filed May 31, 2012. The contents of these applications are incorporated herein by reference in their entirety.

BACKGROUND OF THE INVENTION

1. Field of the Invention

The present invention relates to a method of and an apparatus for formulating a multicomponent drug such as kampo medicine.

2. Description of the Prior Art

As multicomponent materials, for example, there are natural product-originated drugs such as kampo medicines that are drugs (hereinafter, referred to as multicomponent drugs) that are composed of multiple components. The quantitative and qualitative profiles of such drugs change due to a geological factor, an ecological factor, collecting season, a collecting area, a collecting aetas, weather during the growing period, and the like of raw material crude drugs.

Thus, for such multicomponent drugs and the like, predetermined criteria are regulated as qualities for securing the safety and the effectiveness thereof, and national supervising agencies, chemical organizations, manufacturing companies, and the like perform quality evaluations based on the criteria.

Then, a multicomponent drug meeting the criteria for productization is subjected to dosage form processing to produce granules, tablets or the like and thereafter is made into a product through packing.

In general, however, the determination criteria on the quality and the like of a multicomponent drug are set based on the content and the like of one or several distinctive components selected from components in the multicomponent drug.

For example, in 1986. Pharm Tech Japan vol. 28, No. 3, pp 67 to 71, in a case where effective components of a multicomponent drug are not identified, it selects a plurality of components that have physical properties such as a quantitatively analyzability, high water-solubility, a undegradability in hot water, and non-chemical reactability with other components and uses the contents of the components acquired through chemical analysis as evaluation criteria.

In addition, it is well known to apply chromatography to a multicomponent drug, obtain an ultraviolet-visible absorption spectrum for each retention time, and set evaluation criteria based on some pieces of component information included therein.

For example, according to JP 2002-214215 A, some peaks included in HPLC chromatogram data are selected and encoded as barcodes, thereby evaluating a multicomponent drug.

However, in such methods, evaluation targets are limited to a "contents of a specific component" or a "chromatogram peaks of specific components", and thus only some components contained in a multicomponent drug are set as the evaluation targets. Accordingly, since a multicomponent drug includes many components other than components that are evaluation targets, such methods are insufficient as a method of evaluating a multicomponent drug in terms of accuracy.

In order to accurately evaluate the quality of a multicomponent drug, it is necessary for evaluation to cover information of all peaks or almost all peaks without small peaks corresponding to several %. Accordingly, it is necessary to associate all the peaks or almost all peaks with each other between multicomponent drugs.

However, it is difficult to efficiently associate a plurality of peaks with high accuracy. This interferes with an efficient evaluation of multicomponent drugs with high accuracy.

Described more, crude drugs are natural products, and therefore, multicomponent drugs even which have the same product name may have slightly different components. Hence, even if drugs have the same quality, content ratios of components thereof may be different from each other or a component present in one drug may not be present in the other drug (hereinafter, referred to as an inter-drug error). In addition, there is also a factor that peak intensity or peak elution time in a chromatogram has no precise repeatability (hereinafter, referred to as an analysis error). Accordingly, all peaks or almost all peaks may not be associated with peaks that are originated from the same components between the multicomponent drugs (hereinafter, referred to as peak assignment), thereby interfering with an efficient evaluation with high accuracy.

If quality evaluation of a multicomponent drug can be conducted with high accuracy, it reduces the variation in multicomponent drugs to be subjected to the dosage form processing and the packing. As a result, high-quality multicomponent drugs can be made into products.

SUMMARY OF THE INVENTION

A problem to be solved is that there is a limit on an efficient evaluation of the quality and the like of a multicomponent drug with high accuracy with use of an existing evaluation method and it is difficult to make multicomponent drugs into products with little variation.

A first aspect of the present invention provides a method of formulating a multicomponent drug capable of surely making a multicomponent drug meeting criteria for productization with high accuracy into a product. The method obtains a chromatogram from a base of a multicomponent drug, evaluates whether the base meets criteria for productization based on the obtained chromatogram, and subjects the base determined in the evaluating of the base as an accepted one meeting the criteria for productization to dosage form processing, to produce a formulated drug having a given dosage-form.

Evaluating whether the base meets the criteria segments a fingerprint gathering peaks in which each one peak has a height that is a maximum value or an area value in signal strength and retention time points of the peaks detected from the chromatogram of the multicomponent drug into a plurality of areas so that the peaks of the fingerprint are subdivided into pieces and obtaining fingerprint area segmentation feature values of the respective segmented areas based on an existence rate or existence amount of the subdivided peaks existing in each area, the existence rate obtained by dividing a sum of heights of the peaks within said each area by a sum of heights of all the peaks of the fingerprint and the existence amount being the sum of the heights of the peaks within said each area, and determines the base of the multicomponent drug having the fingerprint area segmentation feature values within a permissible range as the accepted one meeting the criteria for productization.

A second aspect of the present invention provides an apparatus for formulating a multicomponent drug. The apparatus includes a chromatographic device obtaining a chromatogram from a base of a multicomponent drug, an evaluating device evaluating whether the base meets criteria for productization based on the obtained chromatogram, and a dosage form processing device subjecting the base determined in the evaluating of the base as an accepted one meeting the criteria for productization to dosage form processing, to produce a formulated drug having a given dosage-form.

The evaluating device includes a fingerprint area segmentation feature value preparing part segmenting a fingerprint gathering peaks in which each one peak has a height that is a maximum value or an area value in signal strength and retention time points of the peaks detected from the chromatogram of the multicomponent drug into a plurality of areas so that the peaks of the fingerprint are subdivided into pieces and obtaining fingerprint area segmentation feature values of the respective segmented areas based on an existence rate or existence amount of the subdivided peaks existing in each area, the existence rate obtained by dividing a sum of heights of the peaks within said each area by a sum of heights of all the peaks of the fingerprint and the existence amount being the sum of the heights of the peaks within said each are, and an evaluating part determining the base of the multicomponent drug having the fingerprint area segmentation feature values within a permissible range as the accepted one meeting the criteria for productization.

The first aspect of the present invention can simply acquire the feature values of the fingerprint through the area segmentation. Accordingly, feature values can be prepared while capturing, for example, fine peaks. This improves accuracy of the evaluation of whether the base of the multicomponent drug meets the criteria for productization.

As a result, the first aspect of the present invention subjects the base of the multicomponent drug determined as an accepted one meeting the criteria for productization with high accuracy to the dosage form processing to make the base into a product. This reduces variation in multicomponent drugs to be subjected to the dosage form processing and realizes high quality of products.

The second aspect of the present invention operates each part of the evaluating device to simply acquire the feature values of the fingerprint and prepare feature values while capturing, for example, fine peaks, thereby to improve accuracy of the evaluation of whether the base of the multicomponent drug meets the criteria for productization.

As a result, the second aspect of the present invention also subjects the base of the multicomponent drug determined as an accepted one meeting the criteria for productization with high accuracy to the dosage form processing to make the base into a product. This reduces variation in multicomponent drugs to be subjected to the dosage form processing and realizes high quality of products.

BRIEF DESCRIPTION OF THE DRAWINGS

FIG. 4 is a graph illustrating FPs of respective drugs in which FIG. 4 A is a drug A, FIG. 4 B is a drug B, and FIG. 4 C is a drug C according the first embodiment;

FIG. 8 is a table illustrating the numbers of matches in a retention time appearance distance between the target FP and the reference FP according the first embodiment;

FIG. 9 is a table illustrating the degrees of matching between the retention time appearance patterns of the target FP and the reference FP according the first embodiment;

FIG. 85 is a table illustrating a feature value of each area that is formed by sequentially changing a position of the horizontal 1st according the first embodiment;

FIG. 86 is a table illustrating feature values in one way in which the positions of the vertical and horizontal segmenting lines are not changed according the first embodiment;

FIG. 117 is table illustrating a data example of a 3D chromatogram according the first embodiment;

FIG. 118 is a table illustrating a data example of peak information according the first embodiment;

FIG. 119 is a table illustrating a data example of a FP according the first embodiment;

FIG. 120 is a table illustrating an assignment score calculation result example (determination result file) of a target FP to a reference FP according the first embodiment;

FIG. 121 is a table illustrating a process of collating corresponding peaks between a target FP and a reference FP according the first embodiment;

FIG. 122 is a table illustrating a result example (collation result file) specifying corresponding peaks between a target FP and a reference FP according the first embodiment;

FIG. 123 is a table illustrating a data example of a reference group FP according the first embodiment;

FIG. 124 is a table illustrating a reference FP peak feature value file example according the first embodiment;

FIG. 125 is a table illustrating a data example of a target and reference FP type-2 according the first embodiment;

FIG. 126 is a table illustrating a target FP area segmentation feature value file example according the first embodiment;

FIG. 127 is a table illustrating a target FP integrated feature value file an example according the first embodiment;

FIG. 128 is a table illustrating a reference type-2 group FP example according the first embodiment;

Figure 104:
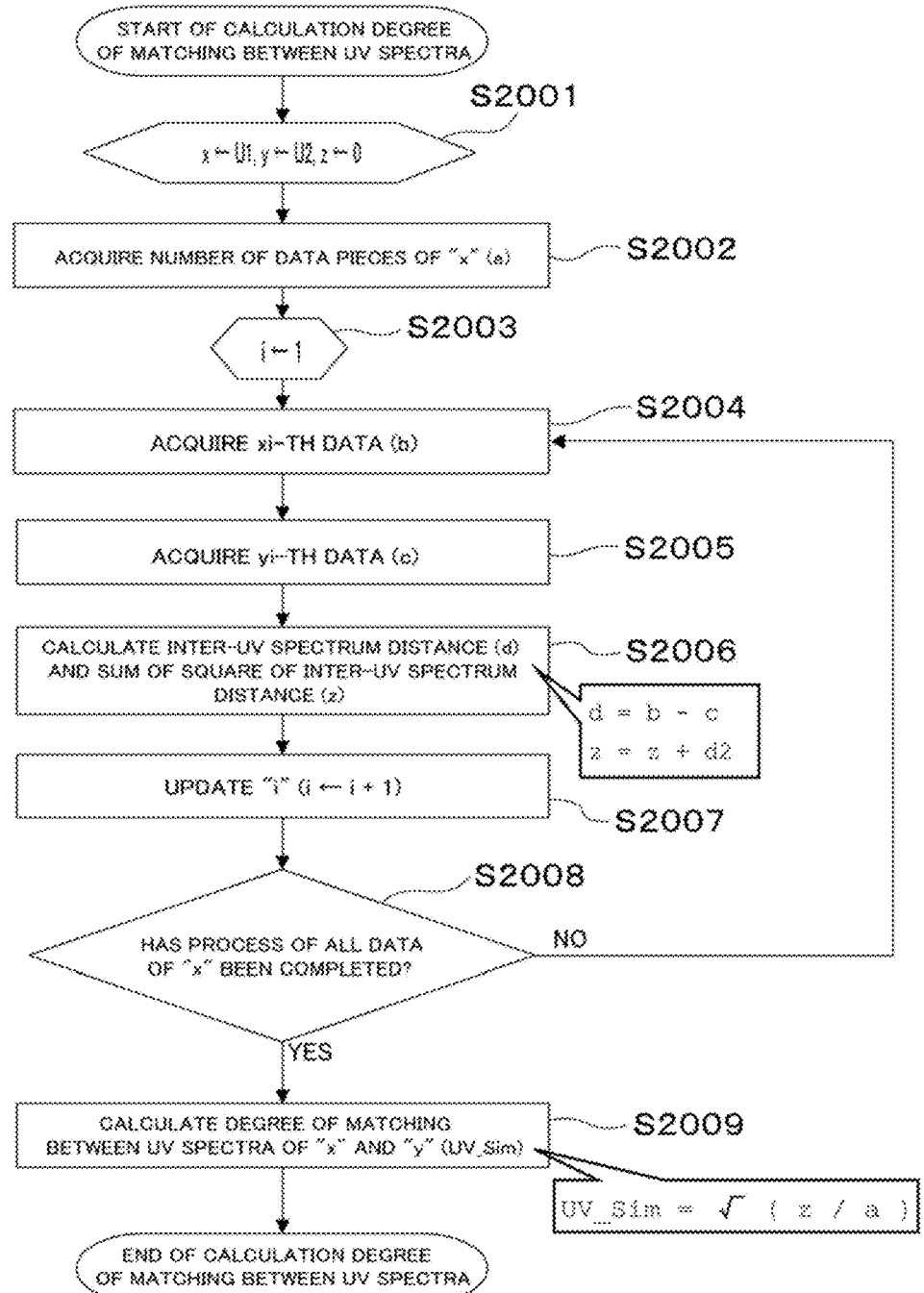
FIG. 104 is a flowchart of a process of calculating the degree of matching between UV spectra in the peak assigning process 2 (calculation of an assignment score) according the first embodiment.
Figure 130:
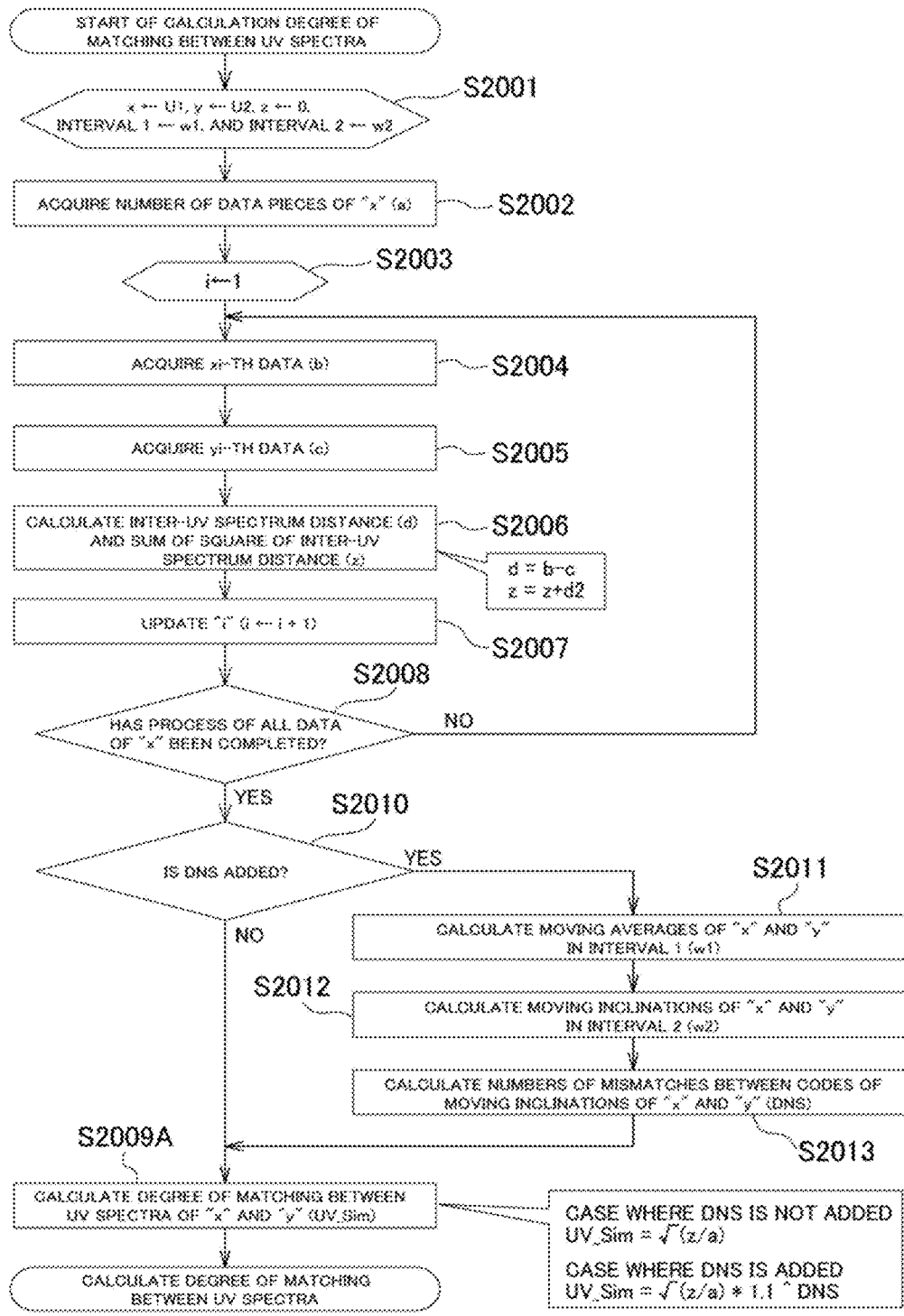
Figure 132:
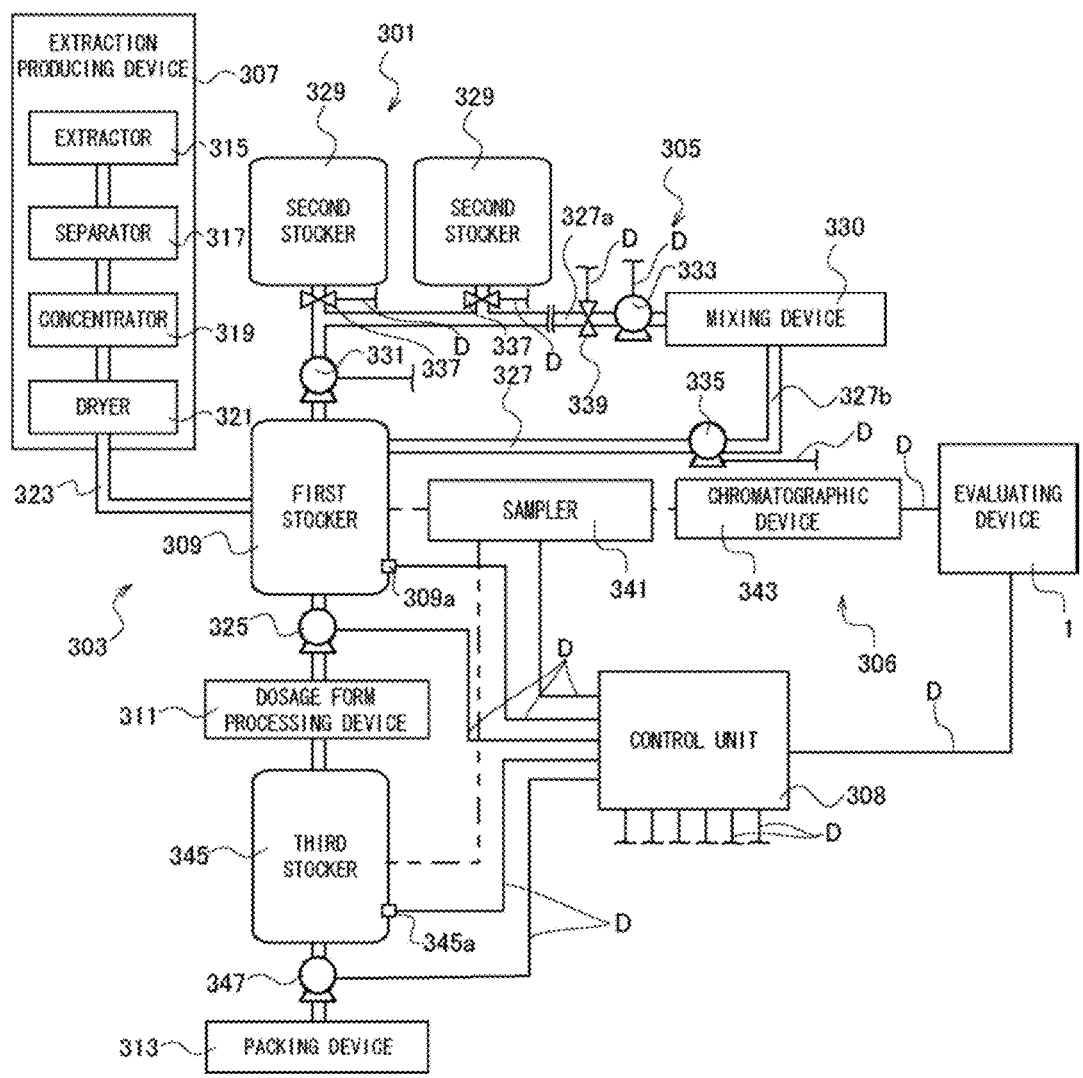
Figure 133:
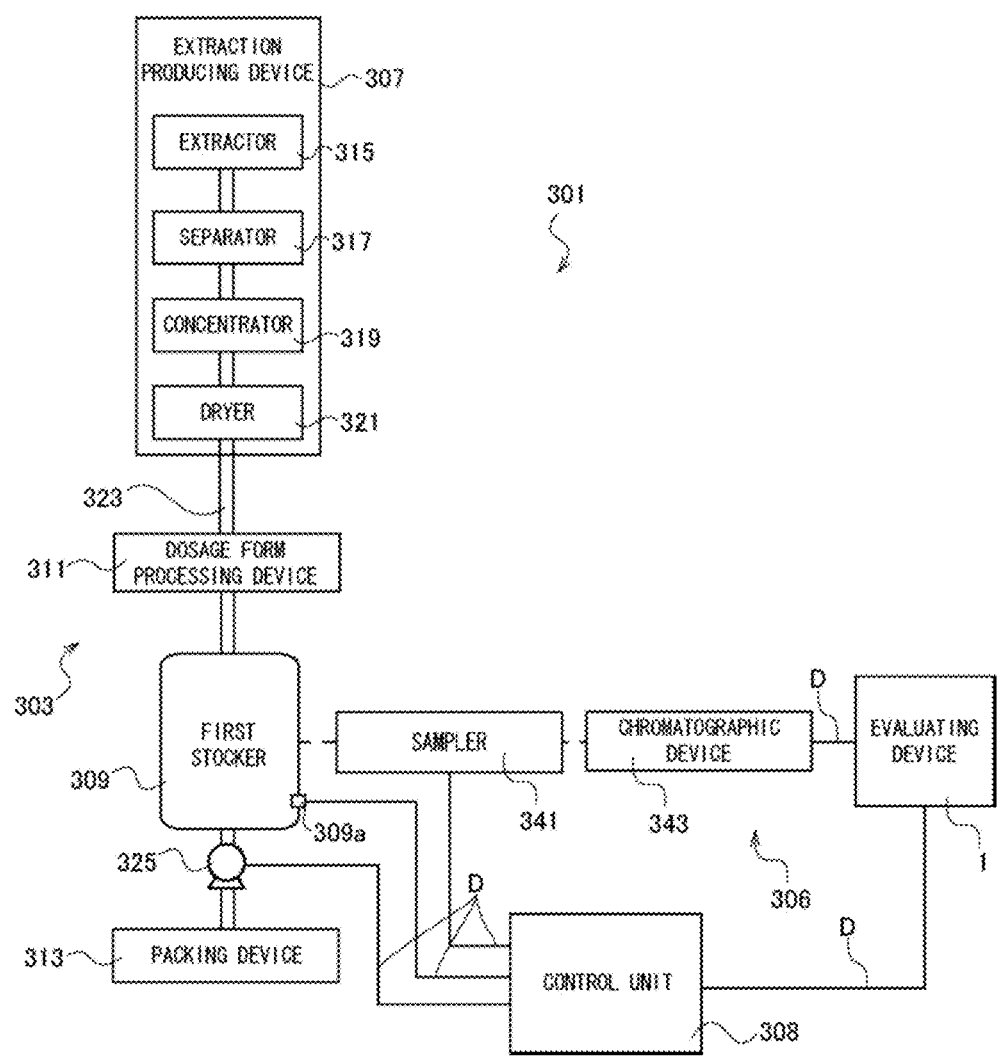

FIG. 129 is a table illustrating a reference group integrated data example according the first embodiment;

FIG. 130 is a flowchart illustrating a modified example of Subroutine 2 that is applied instead of FIG. 104 according the first embodiment;

FIG. 131 is a table illustrating a calculation example of moving averages and moving inclinations;

FIG. 132 is a schematic block diagram illustrating a formulating apparatus according to a second embodiment of the present invention; and FIG. 133 is a schematic block diagram illustrating a formulating apparatus according to a third embodiment of the present invention.

DETAILED DESCRIPTION OF EMBODIMENTS

Embodiments of the present invention accomplish the object of surely making a multicomponent drug highly meeting criteria for productization into a product. For this, the embodiments evaluate a multicomponent drug with high accuracy and subject the multicomponent drug to dosage form processing according to the evaluating result.

Evaluating the multicomponent drug segments a FP composed of peaks and retention time points thereof detected from a chromatogram of a base of a multicomponent drug into a plurality of areas and preparing FP area segmentation feature values based on an existence rate or existence amount of peaks existing in each area and evaluates the FP area segmentation feature values.

In the first embodiment of the present invention, there are provided a formulating method and an formulating apparatus serving as a method of and an apparatus for formulating a multicomponent drug, the formulating method and the formulating apparatus subjecting the base of the multicomponent to dosage form processing to produce a formulated drug having a given dosage form.

A multicomponent drug is defined as a drug that contains a plurality of effective chemical components. Examples of the multicomponent drug include a crude drug, a combination of crude drugs, an extract thereof, and a kampo medicine, but are not limited thereto. In addition, the dosage form is not particularly limited, and, examples include a liquid medicine, an extract, a capsule, a granule, a pill, suspension·emulsion, a powder, a spiritus, a tablet, an infusion·decoction, a tincture, a troche, aromatic water, a fluid extract, which are specified in "general rule for preparations" of "The Japanese Pharmacopoeia", Fifteenth Edition. The embodiment exemplifies that granules of a kampo medicine as a formulated-multicomponent drug are produced from a raw material crude drug. The base of the multicomponent drug is an extract or essence extracted from the raw material crude drug in powder form, liquid form or the like. According to the embodiment, the base of the multicomponent drug is a powder extract as explained later.

Specific examples of the kampo medicine are written in Industry Standard and Voluntarily Revision of "Precautions" in 148 Prescriptions for Medical Kampo Drug Formulation and in Guide to General Kampo Prescription (1978).

Figure 1A:
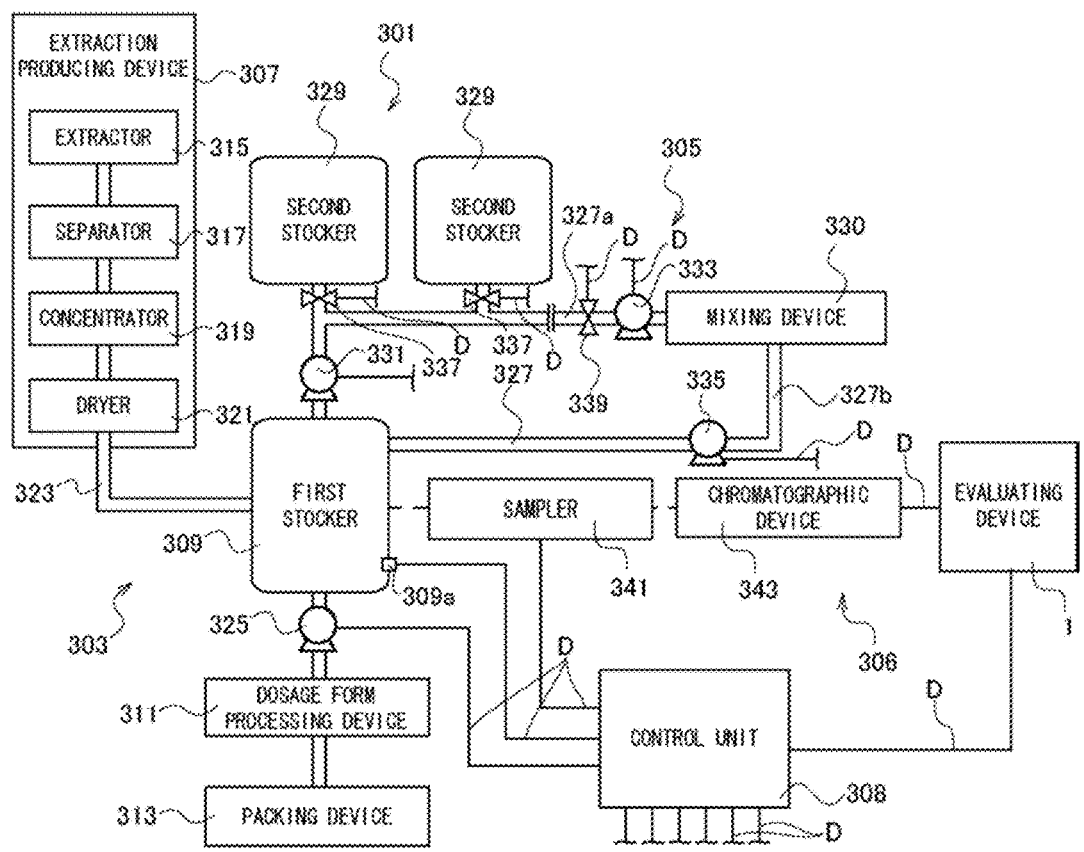
FIG. 1A is a schematic block diagram illustrating a formulating apparatus according to a first embodiment of the present invention.

FIG. 1A is a schematic block diagram illustrating the formulating apparatus 301 according to the first embodiment. The formulating apparatus 301 has a formulating line 303, a mixing line 305, and an evaluating line 306, and a control unit 308.

The formulating line 303 includes a first pipeline 323 serving as a first conveyor, an extract producing device 307 serving as a base producing device, a first stocker 309, a dosage form processing device 311, and a packing device 313. With this, the formulating line 303 is configured to extract an essence as the base of the multicomponent drug from the raw material crude drug, subject the extracted essence or extract of the multicomponent drug meeting criteria for productization to dosage form processing to produce a formulated drug and thereafter pack the formulated drug. The evaluation of whether the extract meets the criteria is conducted at the evaluating line 306 as explained later.

The first pipeline 323 is led from the extract producing device 307 to the packing device 313 through the first stocker 309 and the dosage form processing device 311, convey an extract produced by the extract producing device 307.

The extract producing device 307 is composed of an extractor 315, a separator 317, a concentrator 319 and a dryer 321 that are connected to each other through the first pipeline 323. The configuration of the extract producing device 307 is an example and therefore may exclude the dryer 321, for example. The excluded dryer may be laid downstream of the first stocker 309. The embodiment produces the extract with the extract producing device 307. The extract producing device 307 and the production of the extract, however, may be omitted.

The extractor 315 receives the raw material crude drug therein and extracts an essence as a liquid extract using a solvent. The extractor 315 is realized by, for example, a multipurpose extractor "TEX2015" manufactured by IZUMI FOOD MACHINERY Co., Ltd., a rotocel extractor manufactured by Mitsubishi Kakoki Kaisha, Ltd., a centrifugal extractor "Ultrex" manufactured by Hitachi, Ltd., or the like.

The raw material crude drug in this embodiment is cut and compounded in advance. The raw material crude drug, however, may be an uncut one. As the solvent, water, ethanol, acetic acid and the like are exemplified for hot and cold extraction. In a case of the kampo medicine according to the embodiment, it is preferred that the hot extraction is conducted at temperature of 90-100° C. using water as the solvent. The liquid extract, i.e., extraction liquid produced at the extractor 315 is conveyed to the separator 317 through the first pipeline 323.

The separator 317 removes impurities from the extraction liquid through solid-liquid separation. The separator 317 is realized by, for example, a basket type centrifugal separator "TEC-48" or decanter type centrifugal separator manufactured by TANABE WILLTEC INC., the centrifugal extractor "Ultrex" manufactured by Hitachi, Ltd., or the like. From the separator 317, the extraction liquid is conveyed to the concentrator 319 through the first pipeline 323.

The concentrator 319 concentrates or condenses the extraction liquid and is realized by, for example, flash method concentration equipment "REV-100/90" or global concentration equipment manufactured by HISAKA WORKS, LTD., a centrifugal thin film concentrator or centritherm evaporator Alfa Laval Ltd., or the like. As the concentration method for the extraction liquid, vacuum concentration is used in general. As the condition of the vacuum concentration for the kampo medicine, the degree of vacuum is set in a range of 30-760 mmHg, the evaporating temperature is set equal to or less than 100° C., preferably in a range of 30-50° C., and the like, for example. The concentrated extraction liquid, i.e., concentrated liquid is conveyed from the concentrator 319 to the dryer 321 through the first pipeline 323.

The dryer 321 dries the concentrated liquid to convert the same into powder. The dryer 321 is realized by, for example, a vacuum belt dryer (SBD) manufactured by HISAKA WORKS, LTD., a spray dryer "OC-20" manufactured by OKAWARA MFGCO., LTD., a spray dryer for producing medicines manufactured by GEA Process Engineering Inc., or the like.

The drying method employs but is not limited to a spray drying method, a vacuum drying method or a freeze drying method depending on a kind of dryer 321. For example, the spray drying method sprays with an atomizer the concentrated liquid into a thermal current within a drying chamber maintained at high temperature of 60-300° C. so that the solvent instantly evaporates to dry the concentrated liquid. The vacuum drying method dries, under the condition in which the degree of vacuum is equal to or less than the 760 mmHg and the temperature is in a range of 5-100° C., the concentrated liquid that is the extraction liquid sufficiently subjected to the vacuum concentration. The freeze drying method freezes the concentrated liquid at the temperature of −80-0° C. and then dries the same by directly sublimating the solvent in a vacuum state being equal to or less than 1 mmHg. The powder extract due to such drying is conveyed to the first stocker 309 through the first pipeline 323.

The first stocker 309 is arranged or laid downstream of the extract producing device 307 on the first pipeline 323 to accommodate the powder extract produced at the extract producing device 307. In particular, the first stocker 309 tentatively stores the powder extract during the evaluating line 306 evaluates the powder extract.

The first stocker 309 is realized by, for example, a general tank or the like. On the downstream side of the first stocker 309, the first pipeline 323 has a blower 325. With the blower 325, the powder extract is conveyed from the first stocker 309 to the dosage form processing device 311.

The dosage form processing device 311 subjects the powder extract of the multicomponent drug to the dosage form processing to make the same into a formulated drug having a given dosage form. For example, the dosage form processing device 311 produces granules or tablets according to an intended dosage form.

According to the embodiment, the dosage form processing device 311 is configured to produce the granules and realized by, for example, a horizontal extrusion granulator "Granumaster" manufactured by OKAWARA MFG CO., LTD., a multistage roll granulator manufactured by Kurimoto, Ltd., or the like. In the case of producing tablets, the dosage form processing device 311 may be realized by, for example, a tableting machine "AQUARIUS G" manufactured by KIKUSUI SEISAKUSHO LTD., "αX-MS type" medium-sized tableting machine manufactured by HATA TEKKOSHO CO., LTD., or the like.

The granules produced at the dosage form processing device 311 are conveyed to the packing device 313 through the first pipeline 323.

The packing device 313 subdivides and packs the granules or tablets to complete productization. The packing device 313 for the granules is realized by, for example, a powder and granule packing machine "MS101" manufactured by SANKO MACHINERY CO., LTD. or the like. In the case of the tablets, the packing device 313 is realized by, for example, a tablet four side sealing machine manufacture by ASAHI SHIKO Corporation or the like.

The mixing line 305 includes a second pipeline 327, a plurality of second stockers 329, and a mixing device 330. With this, the mixing line 305 is configured to obtain a powder extract that does not meet the criteria for productization from the first stocker 309 and store the same, mix two or more stored powder extracts and return the mixed powder extracts to the first stocker 309. In FIG. 1A, two second stockers 329 are indicated, however, the number of the second stockers 329 is not limited thereto.

The second pipeline 327 is led from and back to the first stocker 309 so as to make a loop. The second pipeline 327 includes a taking-out line 327a led out from the first stocker 309 and a return line 327b returning back to the first stocker 309.

The taking-out line 327a has a blower 331 for storing a powder extract and a blower 333 for mixing powder extracts. The return line 327b has a blower 335 for returning a powder extract.

Further, the second pipeline 327 has valves 337 and 339 laid upstream of the second stockers 329 and the mixing device 330 for storing a powder extract and mixing powder extracts, respectively.

The taking-out line 327a is configured to selectively convey a powder extract to one of the second stockers 329 according to control of the blower 331 and the valves 337. Further, the taking-out line 327a is configured to selectively take out stored powder extracts from the second stockers 329 and convey the same to the mixing device 330 according to control of the blower 333 and the valves 337 and 339. The return line 327b is configured to convey a mixed extract as a mixed base from the mixing device 330 to the first stocker 309 according to control of the blower 335.

In this specification, the powder extract means the individual powder extract produced by the extract producing device 307 and the mixed extract means a mixture of the individual powder extracts.

The second stockers 329 are laid on the second pipeline 327, in particular the taking-out line 327a to store a powder extract that does not meet the criteria for productization and is conveyed from the first stoker 309. The second stocker 329 is realized by, for example, a general tank or the like similar to the first stocker 309.

The mixing device 330 is arranged on the second pipeline 327 so that the taking-out line 327a is connected to an inlet of the mixing device 330 and the return line 327b is connected to an outlet thereof. The mixing device 330 mixes two or more stored powder extracts to produce a mixed extract. The produced mixed extract is conveyed to the first stocker 309 through the return line 327a.

The evaluating line 306 includes a sampler 341, a chromatographic device 343, and an evaluating device 1 and is configured to evaluate or examine whether a powder extract or a mixed extract in the first stocker 309 meets the criteria for productization.

The sampler 341 is arranged accessibly to the first stocker 309 and the chromatographic device 343. The sampler 341 obtains a sample of the powder extract or the mixed extract from the first stocker 309 and supplies the sample to the chromatographic device 343. According to the embodiment, the sampler 341 is realized by, for example, a powder sampler or the like that is driven by an actuator (not illustrated).

The chromatographic device 343 subjects the sample of the powder or mixed extract to high performance liquid chromatograph (HPLC) to prepare and obtain a three-dimensional chromatogram (3D chromatogram). The chromatographic device 343 is realized by a commercially-available device such as "Agilent 1100 system" manufactured by Agilent Technologies, or the like. Furthermore, the chromatography is not limited to the HPLC, and any other type of chromatography may be employed. The chromatographic device 343 is connected to the evaluating device 1 through a data line D and outputs the prepared 3D chromatogram to the evaluating device 1.

The evaluating device 1 has a function to evaluate or determine whether the powder or mixed extract meets the criteria for productization based on the input 3D chromatogram. The details of the evaluating device 1 will be explained later. The evaluating device 1 is connected to the control unit 308 through a data line D and outputs the determination or evaluating result to the control unit 308.

The control unit 308 is configured by a computer and controls each part of the formulating apparatus 301. According to the embodiment, the control unit 308 is a discrete unit separated from the evaluating device 1. The control unit 308 and the evaluating device 1, however, may be configured by a single unit.

The control unit 308 of this embodiment is connected to a sensor 309a of the first stocker 309, the sampler 341, the blowers 325, 331, 333 and 335, and the valves 337 and 339 through data lines D, respectively.

Then, the control unit 308 automatically causes the evaluating device 1 to evaluate whether the powder extract (or mixed extract) meets the criteria for productization, the dosage form processing device 311 to make the powder extract (or mixed extract) into the granules and the packing device 313 to pack the granules.

In particular, the control unit 308 determines a conveying state of the powder extract to the first stocker 309 based on a detecting signal sent from the sensor 309a of the first stocker 309. The sensor 309a is for example a load cell to detect the weight of the first stocker 309 and output the detecting signal to the control unit 308. The sensor 309a may be a flowmeter or the like.

The determination of the conveying state is performed by, for example, monitoring the rate of change of the weight of the first stocker 309. If the rate of change of the weight becomes zero, it can be determined that the conveying of the powder extract is completed. If the rate of change of the weight becomes reduced, it can be determined that the conveying of the powder extract approaches completion. The sensor may be provided to the extract producing device 307 to determine a producing state of the powder extract.

According to the conveying state of the powder extract, the control unit 308 controls the sampler 341 to feed the sample of the powder extract to the chromatographic device 343. The feeding of the sample can be performed whenever a conveyed amount of the powder extract in the first stocker 309 is sufficient to obtain the sample.

Further, the control unit 308 causes the first pipeline 323 to convey the powder extract from the first stocker 309 to the dosage form processing device 311 or one of the second stockers 329 based on the determination or evaluating result sent from the evaluating device 1.

In particular, if the evaluating device 1 determines that the powder extract meets the criteria for productization, the control unit 308 controls the first pipeline 323, in particular the blower 325 to convey the powder extract from the first stocker 309 to the dosage form processing device 311.

If the evaluating device 1 determines that the powder extract does not meet the criteria for productization, the control unit 308 controls the second pipeline 327, in particular the blower 331 and the valves 337 to convey the powder extract from the first stocker 309 to an empty one of the second stockers 329 and store the same. The determination whether the second stockers 329 are empty may be performed on the basis of detecting signals sent from sensors such as load cell provided to the respective second stockers 329.

Further, the control unit 308 controls the second pipeline 327, in particular the valves 337 and 339 and the blower 333 to convey two or more stored powder extracts in the second stockers 329 to the mixing device 330 and mix the same.

The mixing is initiated at any time during the first stocker is empty. It, however, is required that the extract producing device 307 does not start to produce the next powder extract. The determination of whether the first stocker 309 is empty can be conducted based on the detecting signal from the sensor 309a.

The selection of powder extracts to be mixed and the mixing rate is based on Mahalanobis distance (hereinafter, referred to as MD value). As explained later, the evaluation of the powder extract finds a MD value using Mahalanobis-Taguchi method (hereinafter, referred to as MT method) and determines that a powder extract meets the criteria for productization if the found MD value is equal to or less than a threshold value. According to the embodiment, the powder extracts to be mixed and the mixing rate are determined using the MD values and the determined powder extracts are mixed at the determined mixing rate to produce a mixed extract having a MD value being equal to or less than the threshold value. A MD value is used to determine whether target FP integrated feature values including target FP area segmentation feature values are within the permissible range as explained later. The producing of the mixed extract using the MD values, therefore, means that the mixed extract having the target FP area segmentation feature values within the permissible range is produced by mixing the powder extracts that do not meet the criteria for productization with the mixing rate determined on the basis of the target FP area segmentation feature values.

After producing the mixed extract, the control unit 308 controls the second pipeline 327, in particular the blower 335 to convey the mixed extract from the mixing device 330 to the first stocker 309 and store the same. In response to the storage of the mixed extract, the control unit 308 controls the sampler 341 to feed the sample of the mixed extract to the chromatographic device 343.

As a result, the evaluating device 1 outputs the determination or evaluating result to the control unit 308. The control unit 308 conveys the mixed extract from the first stocker 309 to the dosage form processing device 311 or one of the second stockers 329 in the same way as the aforementioned powder extract.

Figure 1B:
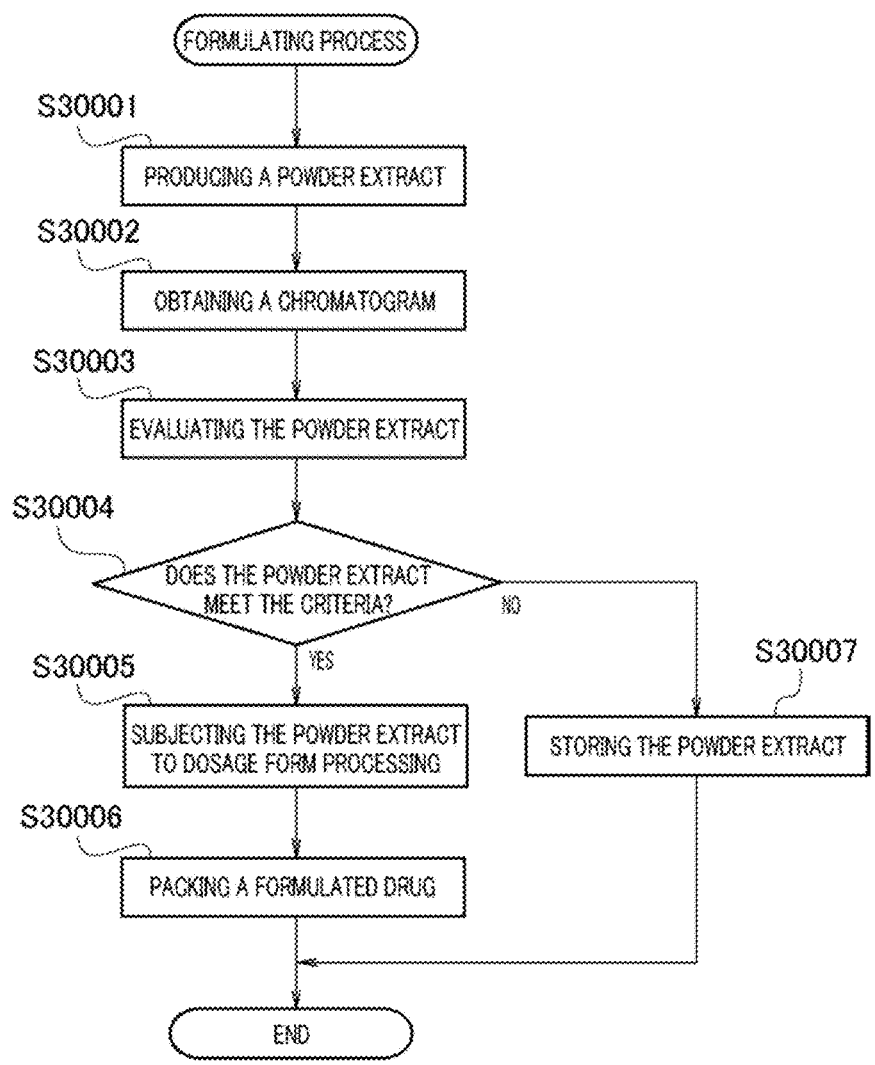
FIG. 1B is a flowchart illustrating a formulating process of a formulating method according to the first embodiment.

FIG. 1B is a flowchart illustrating a formulating process of a formulating method according to the first embodiment.

The formulating process of the formulating method of the first embodiment is started by putting the raw material crude drug into the extractor 315 of the extract producing device 307.

First, in Step S30001, a powder extract is produced. Namely, the extract producing device 307 extracts an essence as a liquid extract or an extraction liquid from the raw material crude drug at the extractor 315, subjects the extraction liquid to the solid-liquid separation at the separator 317, concentrates the extraction liquid to produce a concentrated liquid at the concentrator 319, and dries the concentrated liquid to make the same into a powder extract at the dryer 321 in sequence.

In Step S30002, a chromatogram is obtained. Namely, the powder extract produced in Step S30001 is conveyed from the extract producing device 307 to the first stocker 309 and is accommodated in the first stocker 309.

Figure 3A:
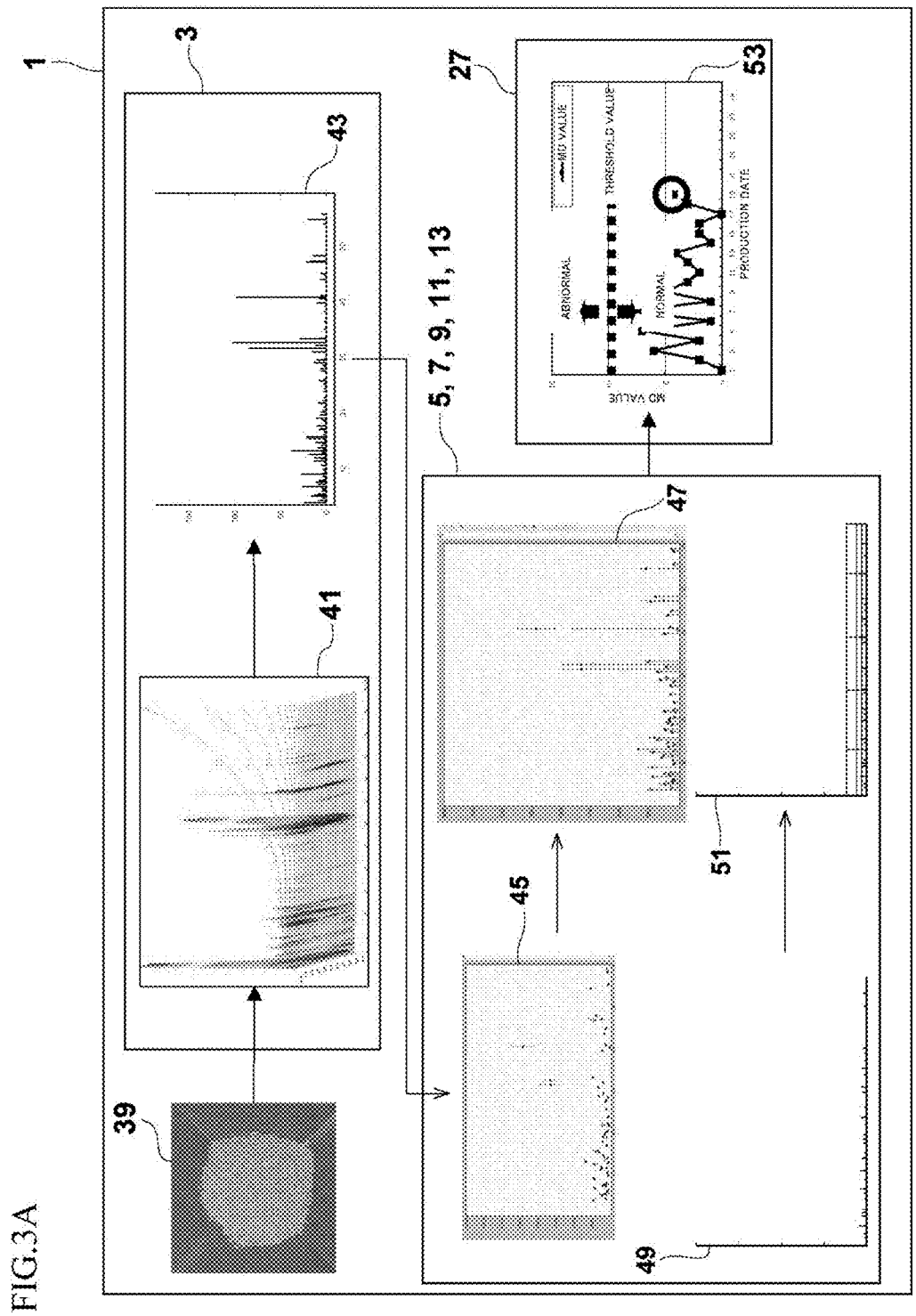
FIG. 3A is a block diagram illustrating procedures of evaluating a multicomponent drug according the first embodiment.
Figure 3B:
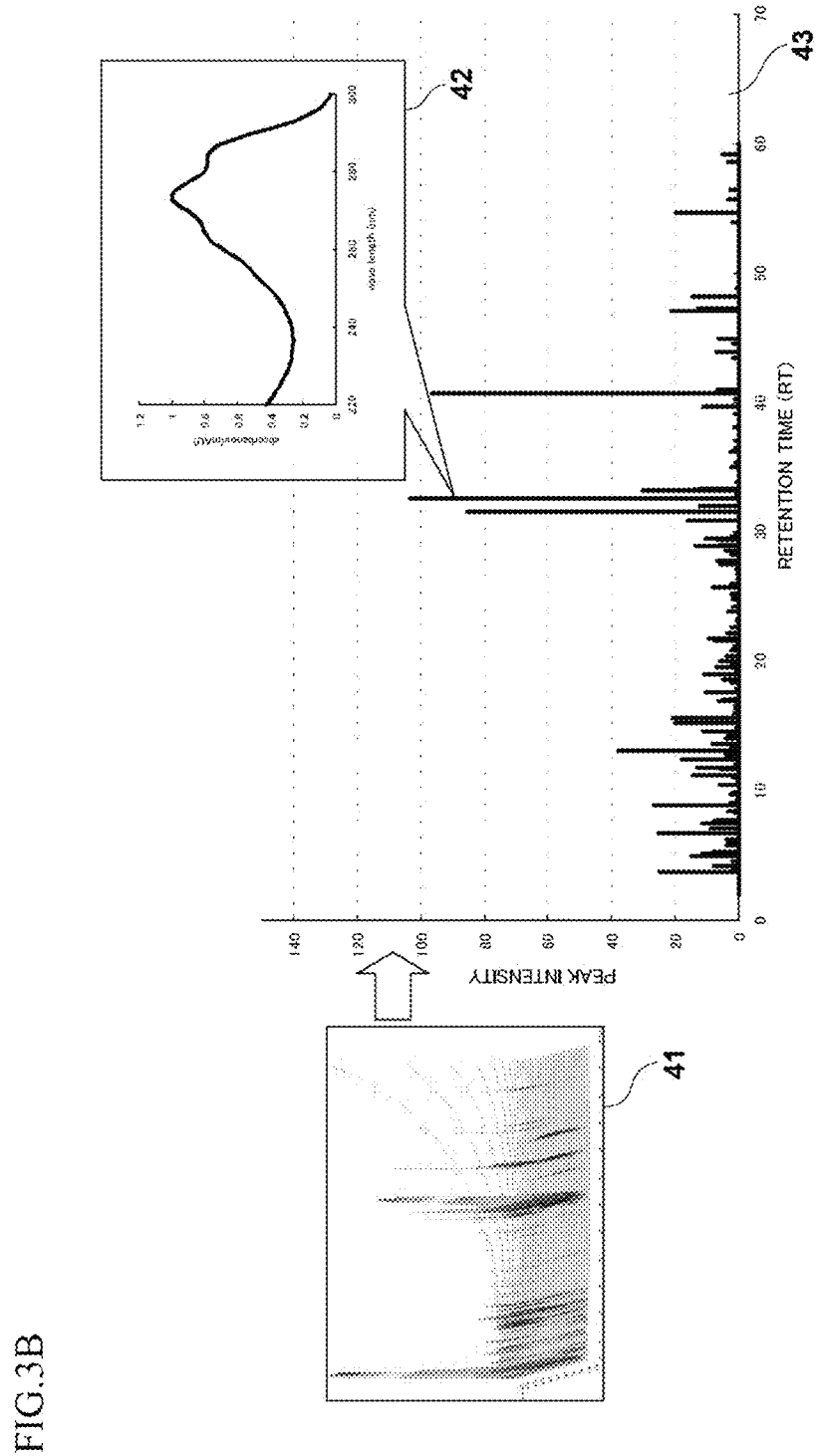
FIG. 3B is an explanatory diagram of a fingerprint (hereinafter, referred to as FP) that is prepared from three-dimensional chromatogram data (hereinafter, referred to as 3D chromatogram) according the first embodiment.

At this time, the control unit 308 causes the sampler 341 to obtain a sample of the powder extract and feed the obtained sample to the chromatographic device 343 according to the conveying state of the powder extract to the first stocker 309. The chromatographic device 343 subjects the fed sample to the HPLC to prepare a 3D chromatogram (FIGS. 3A and 3B).

In Step S30003, the powder extract is evaluated. Namely, the chromatographic device 343 outputs the 3D chromatogram obtained in Step S30002 to the evaluating device 1. As explained later, the evaluating device 1 evaluates or determines whether the powder extract meets the criteria for productization based on the input 3D chromatogram.

In Step S30004, the formulating process is branched according to the evaluation of the powder extract. Namely, the evaluating device 1 outputs the determination or evaluating result of Step S30003 to the control unit 308. If the powder extract meets the criteria for productization, the control unit 308 transfers the formulating process to Step S30005. If the powder extract does not meet the criteria, the control unit 308 transfers the formulating process to Step S30007.

In Step S30005, the powder extract is subjected to the dosage form processing. Namely, the control unit 308 controls the blower 325 to convey the powder extract determined as an accepted one meeting the criteria to the dosage form processing device 311. Accordingly, the dosage form processing device 311 subjects the powder extract to the dosage form processing to produce a formulated drug, in particular granules in this embodiment.

In Step S30006, the formulated drug is packed. Namely, the granules produced in Step S30005 are subdivided and packed at the packing device 313. In this way, the productization of the powder extract is completed and the formulating process is terminated.

On the other hand, in Step S30007, the powder extract is stored. Namely, the control unit 308 controls the blower 331 and the valve 337 to convey the powder extract determined as a rejected one that does not meet the criteria to an empty one of the second stockers 329 and store that powder extract.

With this, the formulating process is terminated without producing granules for the powder extract that does not meet the criteria. At this time, the MD value of the powder extract used in the determination or evaluation of the stored powder extract is registered in a database or the like.

Figure 1C:
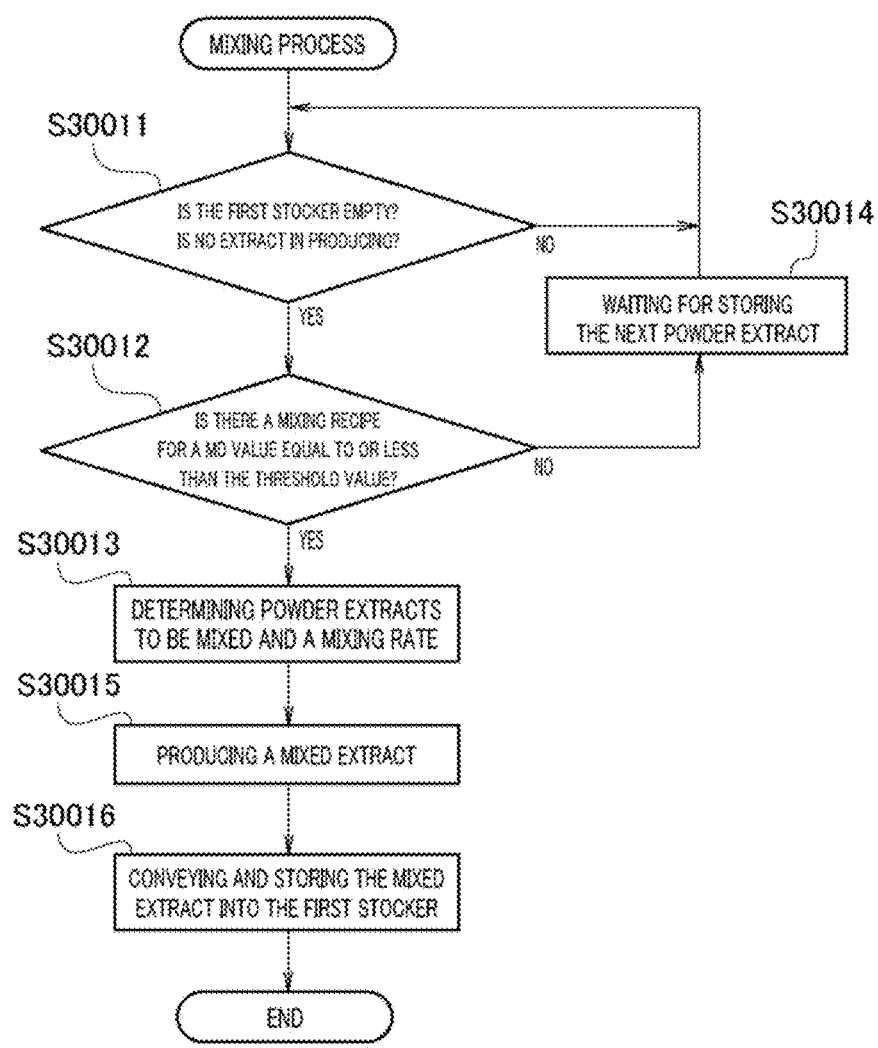
FIG. 1C is a mixing process of the formulating method according to the first embodiment.

FIG. 1C is a mixing process of the formulating method according to the first embodiment.

The mixing process of the formulating method of the first embodiment is started by storing two or more powder extracts in the second stokers 329.

In Step S30011, it is determined whether the first stocker 309 is empty and no extract is in producing. Namely, the control unit 308 determines whether the first stocker 309 is empty and no extract is producing based on the detecting signal of the sensor 309a. The presence or absence of an extract in producing may be more correctly determined in view of an operating signal of the extract producing device 307.

The control unit 309 transfers the mixing process to Step S30012 if the first stocker 309 is empty and no extract is in producing, and repeats Step S30011 otherwise.

In Step S30012, it is determined whether there is a mixing recipe for the stored powder extracts in the second stockers 329 capable of forming a mixed extract having a MD value being equal to or less than the threshold value.

Namely, the control unit 308, in the case where two or more powder extracts to be mixed are selected from among the stored powder extracts based on the MD values and the selected powder extracts are mixed, determines whether there is a combination and a mixing rate of two or more stored powder extracts to be mixed as a mixing recipe capable of forming a mixed extract having a MD value being equal to or less than the threshold value. The MD values for the determination may be obtained from the database or the like.

The control unit 308 transfers the mixing process to Step S30013 if there is such a mixing recipe, and to Step S30014 otherwise.

In Step S30013, a combination and a mixing rate of powder extracts to be mixed are determined. Namely, the control unit 308 determines the powder extracts to be mixed and the mixing rate based on the mixing recipe of Step S30012.

In Step S30014, it waits for storing the next powder extract. Namely, the control unit 308 cannot produce a mixed extract having a MD value being equal to or less than the threshold value from the presently stored powder extracts and waits until the next powder extract is stored.

In Step S30015, a mixed extract is produced using the determined combination and mixing rate of the powder extracts to be mixed. Namely, the control unit 308 controls the valves 337 corresponding to the second stockers 329 storing the powder extracts to be mixed, the valve 339 and the blower 333 for the mixing device 330 to convey the powder extracts to be mixed to the mixing device 330. As the control of the valves 337, 339 and the blower 333, the control unit 308 controls the open time of the valves 337 and the operating time of the blower 333 to adjust the amount of the powder extracts to be conveyed according to the mixing rate. As a result, the mixing device 330 produces the mixed extract using the combination and the mixing rate of the powder extract determined in Step S30013.

In Step S30016, the mixed extract is conveyed to and stored in the first stocker 309. Namely, the control unit 308 controls the blower 335 to convey the produced mixed extract to the first stocker 309 and accommodate the same in the first stocker 309.

In this way, the mixing process is terminated. Thereafter, the formulating method performs for the mixed extract Step S30002 and the following steps of the formulating process of FIG. 1B in sequence. Accordingly, if the mixed extract is determined as an accepted one meeting the criteria for productization, granules are produced from the mixed extract and packed. On the other hand, if the mixed extract is determined as a rejected one that does not meet the criteria for productization, the mixed extract is stored in an empty one of the second stockers 329 again. The mixed extract, however, is produced so as to meet the criteria and therefore the latter case is extremely rare. With this, in the formulating process for the mixed extract, the evaluation of whether the mixed extract meet the criteria may be omitted.

The formulating method and apparatus 301 surely make a powder extract of a multicomponent drug meeting the criteria for productization based on the high accuracy evaluation of whether the powder extract meets that criteria.

Hereinafter, the high accuracy evaluation of a powder extract or a multicomponent drug will be explained in detail.

In the evaluation of the multicomponent drug, it evaluates whether or not an evaluation target drug is equivalent to a plurality of drugs that are defined as normal products. For this, first, a first target FP (hereinafter, simply referred to as target FP) is prepared by extracting information unique to the drug from a three-dimensional chromatogram data (hereinafter, referred to as a 3D chromatogram) of the evaluation target drug.

Next, each peak of the target FP is assigned to peak correspondence data (hereinafter, referred to as a reference group FP) of all reference FPs, which is prepared by performing a peak assigning process to all the reference FPs, whereby peak feature values are acquired.

In addition, a second target FP or FP type-2 is prepared by remaining peaks with the exclusion of assigned peaks from the target FP, and area segmentation feature values are acquired by performing area segmentation of the FP type-2.

By integrating these two feature values, target FP integrated feature values are acquired.

Based on the target FP integrated feature values and reference FP integrated feature values acquired from all the reference FPs, the equivalency between the reference group FP and the target FP is evaluated by MT method. Finally, an acquired evaluation value (hereinafter, referred to as a MD value) and a preset determination value (an upper limit value or threshold value of the MD value) are compared with each other, thereby determining whether or not an evaluation target drug is equivalent to a normal product.

This embodiment determines whether the target FP integrated feature values including area segmentation feature values are within the permissible range by the determination or evaluation of whether the MD value is equal to or less than the threshold value. As a result, if the MD value is equal to or less than the threshold value, i.e., the target FP integrated feature values including area segmentation feature values are within the permissible range, the base of the multicomponent drug is determined as the accepted one meeting the criteria for productization.

Figure 2:
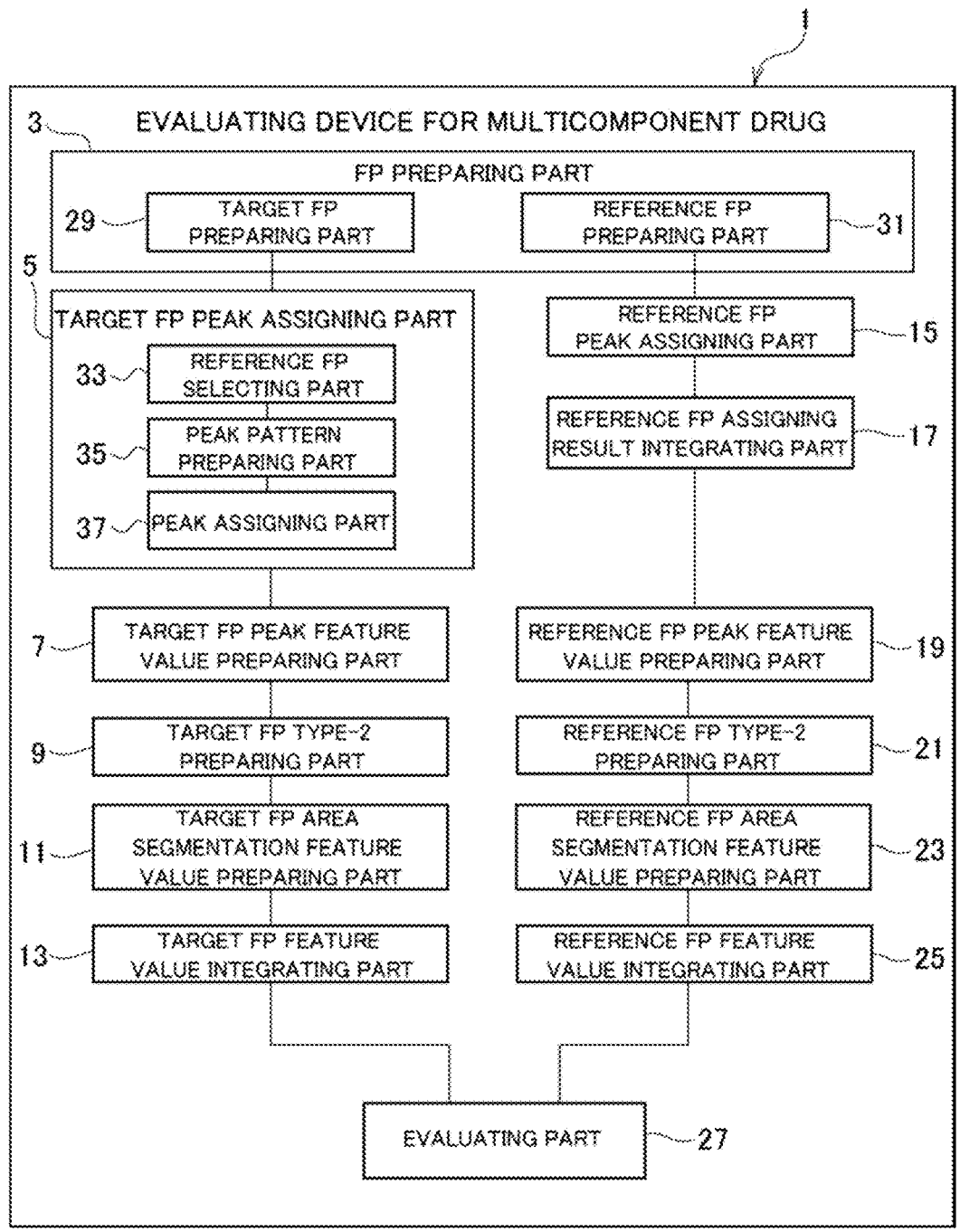
FIG. 2 is a block diagram of an evaluating apparatus for a multicomponent drug according a first embodiment.

FIG. 2 is a block diagram of an evaluating apparatus for a multicomponent drug, FIG. 3A is a block diagram illustrating a procedure of evaluating a multicomponent drug, FIG. 3B is an explanatory diagram of a FP that is prepared based on a 3D chromatogram, and FIG. 4A is a FP of a drug A, FIG. 4B is a FP of a drug B, and FIG. 4C is a FP of a drug C.

As illustrated in FIG. 2, the evaluating apparatus for a multicomponent drug 1 includes a FP preparing part 3 as a first FP preparing part, a target FP peak assigning part 5, a target FP peak feature value preparing part 7, a target FP type-2 preparing part 9 as a second target FP preparing part, a target FP area segmentation feature value preparing part 11, a target FP feature value integrating part 13, a reference FP peak assigning part 15, a reference FP assigning result integrating part 17, a reference FP peak feature value preparing part 19, a reference FP type-2 preparing part 21, a reference FP area segmentation feature value preparing part 23, a reference FP feature value integrating part 25, and an evaluating part 27. The evaluating device 1 for a multicomponent drug includes a feature value preparing device for a FP being a pattern.

The FP preparing part 3 includes a target FP preparing part 29 and a reference FP preparing part 31.

The target FP peak assigning part 5 includes a reference FP selecting part 33, a peak pattern preparing part 35, and a peak assigning part 37.

The evaluating device 1 for a multicomponent drug is configured by a computer and, although not illustrated in the drawings, includes a CPU, a ROM, a RAM, and the like. The evaluating device 1 for a multicomponent drug can acquire feature values of a FP by implementing a feature value preparing program for a FP a feature value preparing program for a pattern that is installed in the computer. However, the acquisition of the feature values of a FP may be realized by using a feature value preparing program recording medium for a FP that stores the feature value preparing program and by reading out it with the evaluating device 1 configured by the computer for a multicomponent drug.

The parts of the evaluating apparatus for a multicomponent drug 1 may be configured by discrete computers, and, for example, the target FP peak assigning part 5, the target FP peak feature value preparing part 7, the target FP type-2 preparing part 9, the target FP area segmentation feature value preparing part 11, the target FP feature value integrating part 13, and the evaluating part 27 may be configured by a single computer, and the reference FP preparing part 31, the reference FP peak assigning part 15, the reference FP assigning result integrating part 17, the reference FP peak feature value preparing part 19, the reference FP type-2 preparing part 21, the reference FP area segmentation feature value preparing part 23, and the reference FP feature value integrating part 25 are configured by another computer.

In such a case, the reference FP integrated feature values are prepared by the another computer and are input to the evaluating part 27 of the evaluating device 1.

Then, the target FP integrated feature values are prepared by the target FP preparing part 29, the target FP peak assigning part 5, the target FP peak feature value preparing part 7, the target FP type-2 preparing part 9, the target FP area segmentation feature value preparing part 11, and the target FP feature value integrating part 13. The reference FP integrated feature values are prepared by the reference FP preparing part 31, the reference FP peak assigning part 15, the reference FP assigning result integrating part 17, the reference FP peak feature value preparing part 19, the reference FP type-2 preparing part 21, the reference FP area segmentation feature value preparing part 23, and the reference FP feature value integrating part 25. These are compared and evaluated so as to evaluate the equivalency between the target FP 43 and the reference group FP 45.

The target FP preparing part 29 of the FP preparing part 3 gathers as a target FP peaks in which each one peak has a height that is a maximum value or an area value in signal strength and retention time points of the respective peaks detected from the 3D chromatogram. According to the embodiment, the peak height is the maximum value in signal strength. More specifically, the target FP preparing part 29, for example, as illustrated in FIGS. 3A and 3B, is a functional part that prepares a target FP 43 (hereinafter, it may be simply referred to as an "FP 43") as a target pattern by extracting a plurality of peaks at a specific detection wavelength, retention time points thereof, and UV spectra from a 3D chromatogram 41 that is a three-dimensional chromatogram data as a chromatogram of a kampo medicine 39.

The FP 43, similarly to the 3D chromatogram 41, is configured by three-dimensional information (peaks, retention time points, and UV spectra).

The FP 43, therefore, is data that directly succeed to information unique to the drug. In spite of that, the data volume is compressed at the ratio of about 1/70, and therefore, the amount of information to be processed is much smaller than that of the 3D chromatogram 41, thereby increasing processing speed.

The 3D chromatogram 41 is a result of applying high performance liquid chromatography (HPLC) to a powder extract of a kampo medicine 39 as the multicomponent drug in the chromatographic device 343 (FIG. 1A). In the 3D chromatogram 41, a movement speed of each component appears to represent as a movement distance during specific time, or an appearance in a time series from a column end is represented in a chart. In the HPLC, detector responses are plotted with respect to the time axis, and appearance time points of peaks are called retention time points.

Although the detector is not particularly limited, an absorbance detector employing an optical characteristic is used as the detector. A peak is three-dimensionally acquired as a signal strength according to a detection wavelength of ultraviolet (UV). As a detector employing an optical characteristic, a transmittance detector may be used.

The detection wavelengths are not particularly limited, and are a plurality of wavelengths selected preferably from a range of 150 nm to 900 nm, selected more preferably from a range of 200 nm to 400 nm corresponding to a UV-visible absorption range, and selected further more preferably from a range of 200 nm to 300 nm.

The 3D chromatogram 41 at least includes a number (lot number), retention time points, detection wavelengths, and peaks of a kampo medicine as data.

In addition, the 3D chromatogram 41 can be also acquired by using a device commercially-available devices. As such a commercially-available device, there is an "Agilent 1100 system" or the like. Furthermore, the chromatograph is not limited to the HPLC, and any other type of chromatography may be employed.

In the 3D chromatogram 41, as illustrated in FIGS. 3A and 3B, the x-axis represents the retention time point, the y-axis represents the detection wavelength, and the z-axis represents signal strength.

The FP 43 at least includes a number (lot number), retention time points, peaks at a specific wavelength, and UV spectra of a kampo medicine as data.

The FP 43 is two-dimensionally represented with the x-axis representing the retention time points and the y-axis representing the peaks for the specific detection wavelength as illustrated in FIGS. 3A and 3B. However, the FP 43 is data that includes UV spectrum information for each peak that is similar to the UV spectrum 42 represented with respect to one peak as illustrated in FIG. 3B.

Namely, the FP 43 is configured by the combination of the two-dimensional information, and therefore indicates the magnitudes (heights) and the retention time points of the peaks in two dimension and has a two-dimensional UV spectrum assigned at each one peak.

The specific detection wavelength for which the FP 43 is prepared is not particularly limited and may be selected in various manners. However, it is important for the FP 43 to include all the peaks of the 3D chromatogram in order to succeed to the information. Accordingly, in the first embodiment, the detection wavelength is set to 203 nm that includes all the peaks of the 3D chromatogram.

Meanwhile, there are cases where all the peaks are not included for a single wavelength. In such a case, a plurality of detection wavelengths are set to prepare a FP that includes all the peaks by combining the plurality of wavelengths as described later.

In the first embodiment, although the peak is set as the maximum value of the signal strength (peak height), the area value may be used as the peak. In addition, a FP may not include UV spectra, so that the FP is set as two-dimensional display information in which the x-axis represents the retention time points and the y-axis represents the peaks for a specific detection wavelength. In such a case, the FP can be prepared from a 2D chromatogram as a chromatogram that includes a number (lot number) and retention time points of a kampo medicine as data.

FIG. 4A is a FP 55 of Drug A, FIG. 4B is a FP 57 of Drug B, and FIG. 4C is a FP 59 of Drug C.

The target FP peak assigning part 5 is a functional part that compares peaks of a target FP and peaks of a reference FP that corresponds to the target FP of a multicomponent material and is an evaluation criteria to specify corresponding peaks between the target FP and the reference FP. The target FP peak assigning part 5 comprises a reference FP selecting part 33, a peak pattern preparing part 35, and a peak assigning part 37.

The reference FP selecting part 33 is a functional part that selects a FP of a multicomponent material that is appropriate to the assignment of the peaks to the target FP from among a plurality of reference FPs. In other words, in order to perform peak assignment of each peak of the target FP with high accuracy, as illustrated in FIGS. 5 to 9 (to be described later), the degree of matching in the retention time appearance pattern of peaks between the target FP and reference FPs to select a reference FP with the minimum degree of matching from among all the reference FPs.

Figure 10:
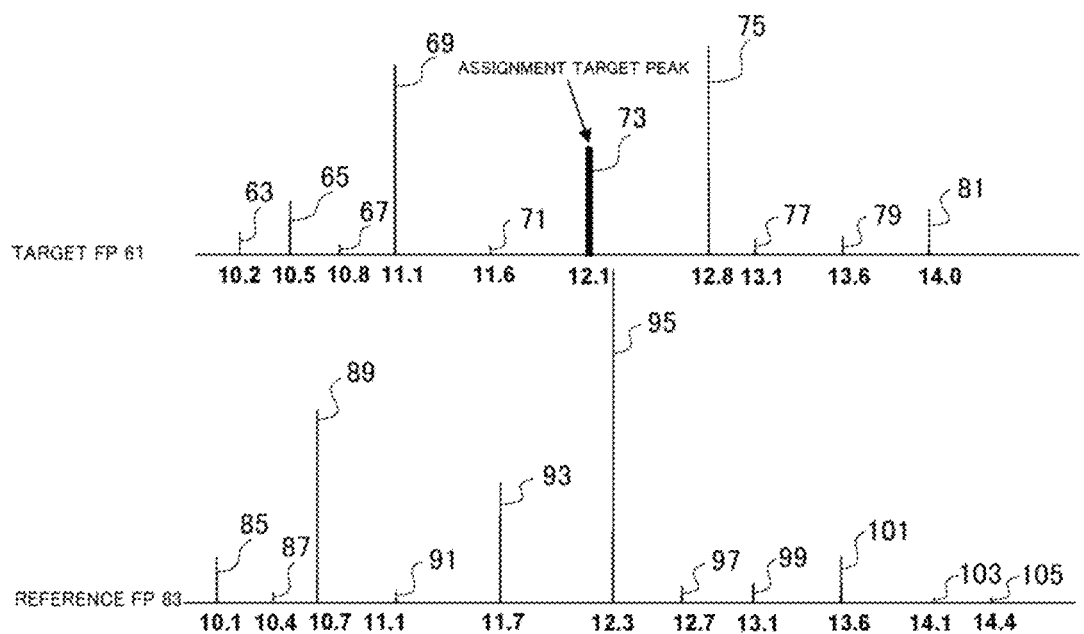
FIG. 10 is diagram illustrating an assignment target peak of the target FP according the first embodiment.
Figure 11:
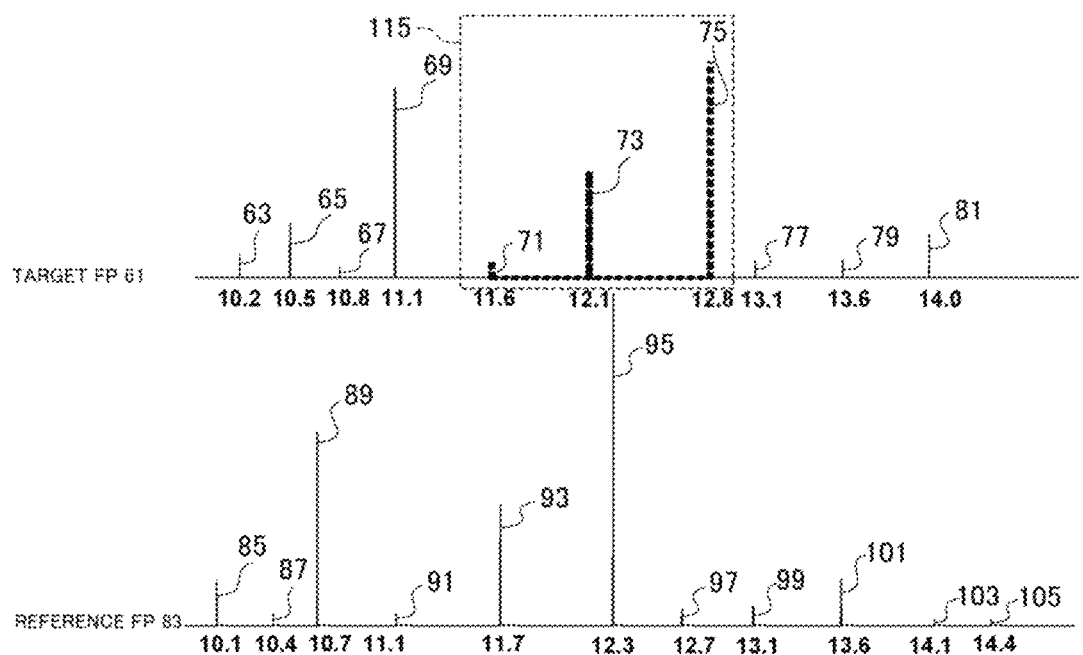
FIG. 11 is a peak pattern diagram according to three peaks including the assignment target peak according the first embodiment.
Figure 12:
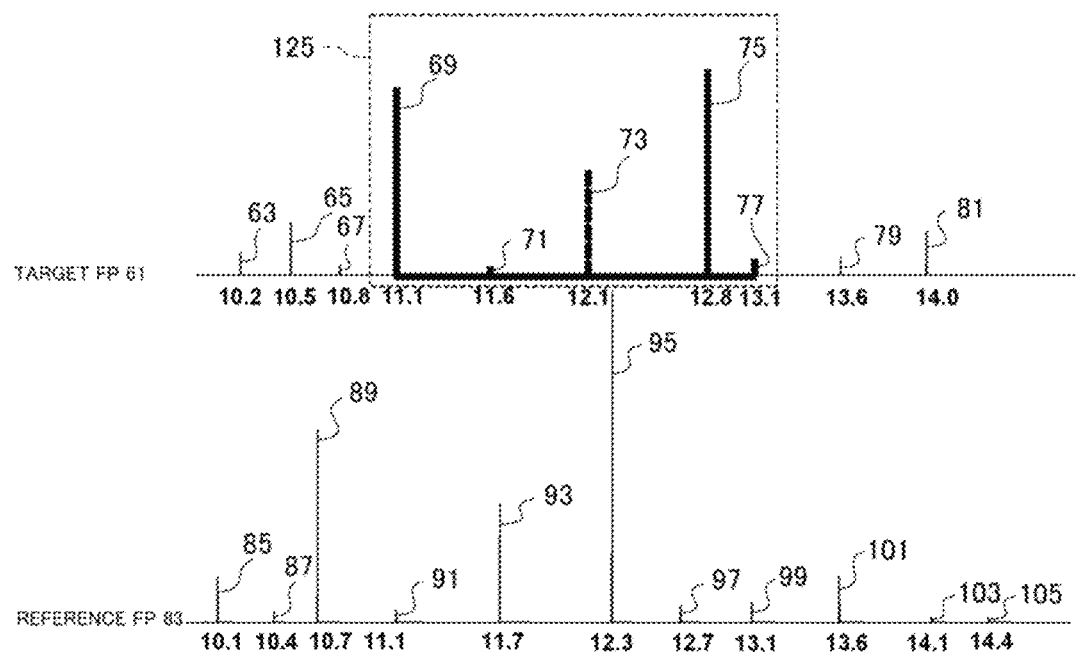
FIG. 12 is a peak pattern diagram according to five peaks including the assignment target peak according the first embodiment.

The peak pattern preparing part 35 is a functional part that, as illustrated in FIGS. 10 to 12 (to be described later), prepares a peak pattern configured by a total of n+1 peaks including n peaks that are present at least on one of sides located in front and in the rear in the direction of the time axis for a peak (hereinafter, referred to as an assignment target peak) of the target FP 61 that is a target to be assigned, as a peak pattern of an assignment target peak. Here, "n" is a natural number.

FIG. 11 (to be described later) illustrates a peak pattern configured by a total of three peaks that include two peaks being present at least on one of sides located in front and in the rear in the time axis direction, and FIG. 12 (to be described later) illustrates a peak pattern configured by a total of five peaks that include four peaks being present at least on one of sides located in front and in the rear in the time axis direction.

In addition, the peak pattern preparing part 35 is a functional part that, as illustrated in FIGS. 13 to 22 (to be described later), prepares peak patterns each configured by a total of n+1 peaks including n peaks that are present at least on one of sides located in front and in the rear in the time axis direction for all the peaks (hereinafter, referred to as assignment candidate peaks) each having a difference from the retention time point of the assignment target peak within a set range (allowable range) in the reference FP 83, as the peak patterns of the assignment candidate peaks. FIGS. 15 to 18 (to be described later) illustrate peak patterns each configured by a total of three peaks including two peaks that are located at least on one of sides located in front and in the rear in the time axis direction. FIGS. 19 to 22 (to be described later) illustrate peak patterns each configured by a total of five peaks including four peaks that are located at least on one of sides located in front and in the rear in the time axis direction.

The allowable range is not particularly limited, but is preferably in the range of 0.5 minutes to two minutes with the object of the accuracy and efficiency. In the first embodiment, the allowable range is set to one minute.

In addition, the peak pattern preparing part 35 is configured to be able to flexibly respond to even a case where there is a difference between the numbers of the peaks of the target FP 61 and the reference FP 83 (in other words, there are one or more peaks that are not present on one side). For this, as illustrated in FIGS. 23 to 61 (to be described later), peak patterns are comprehensively prepared by changing peaks configuring the peak patterns (hereinafter, referred to as peak pattern configuring peaks) for both assignment target peaks and assignment candidate peaks. FIGS. 23 to 61 illustrate cases where the peak pattern is configured by a total of three peaks including two peaks that are located at least on one of sides located in front and in the rear in the time axis direction.

The peak assigning part 37 is a functional part that compares the peak patterns of the respective target FP and reference FP to specify corresponding peaks. In the embodiment, the corresponding peaks are specified by calculating the degree of matching between the peak pattern of the assignment target peak and the peak patterns of the assignment candidate peaks and the degree of matching between the UV spectra.

In addition, the peak assigning part 37 is a functional part that calculates the degrees of matching for the assignment candidate peaks by integrating the two kinds of the degrees of matching to assign each peak of the target FP 61 to each peak of the reference FP 83 based on the calculated degrees of matching.

Figure 62:
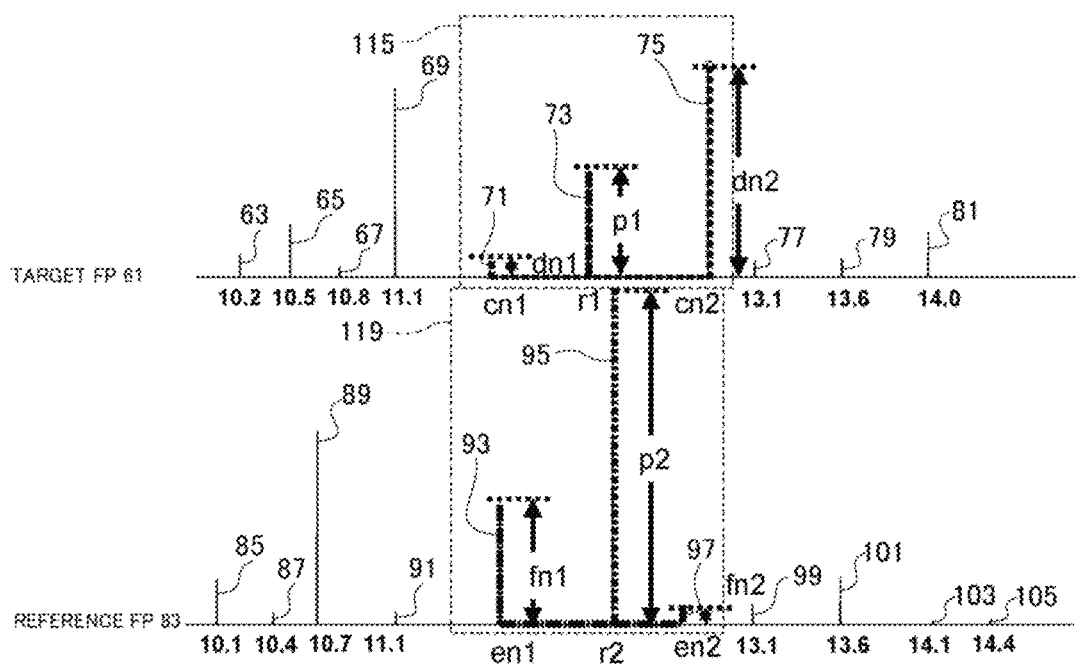
FIG. 62 is a diagram illustrating a calculating method of the degree of matching between peak patterns of the assignment target peak and an assignment candidate peak according to three peaks according the first embodiment.
Figure 63:
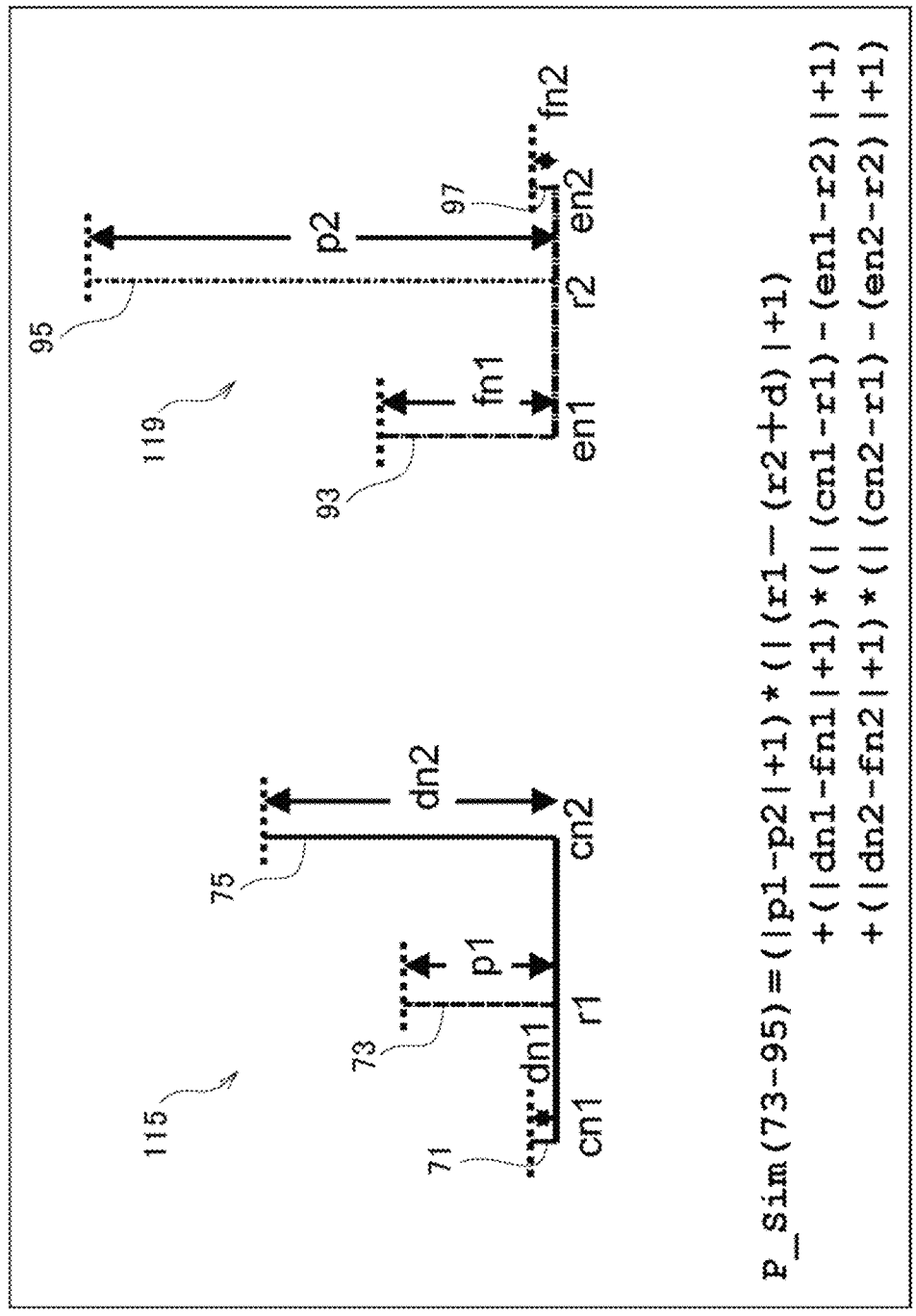
FIG. 63 is a diagram illustrating a calculating method of the degree of matching between peak patterns of the assignment target peak and the assignment candidate peak according to three peaks according the first embodiment.
Figure 64:
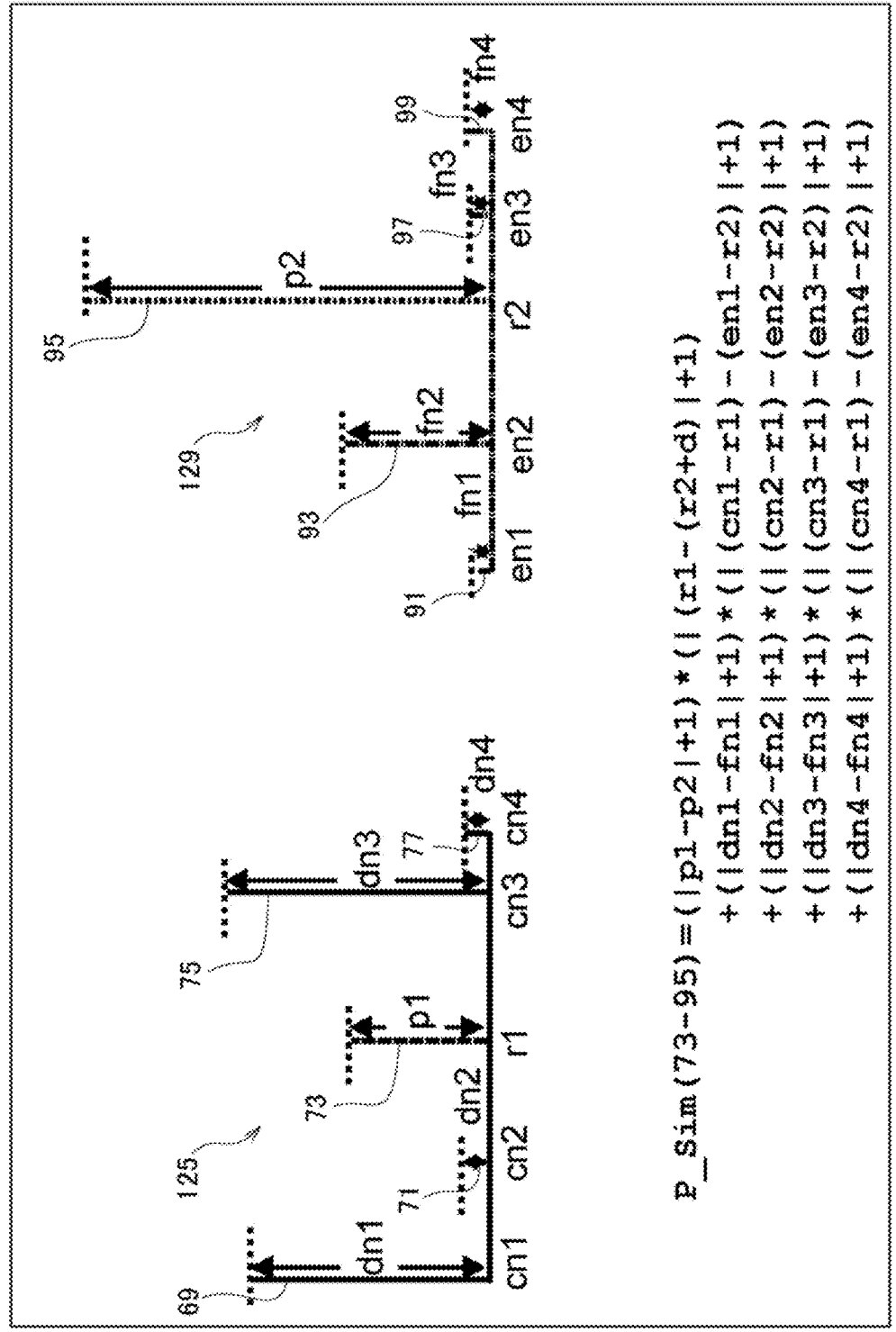
FIG. 64 is a diagram illustrating a calculating method of the degree of matching between peak patterns of the assignment target peak and the assignment candidate peak according to five peaks according the first embodiment.
Figure 65:
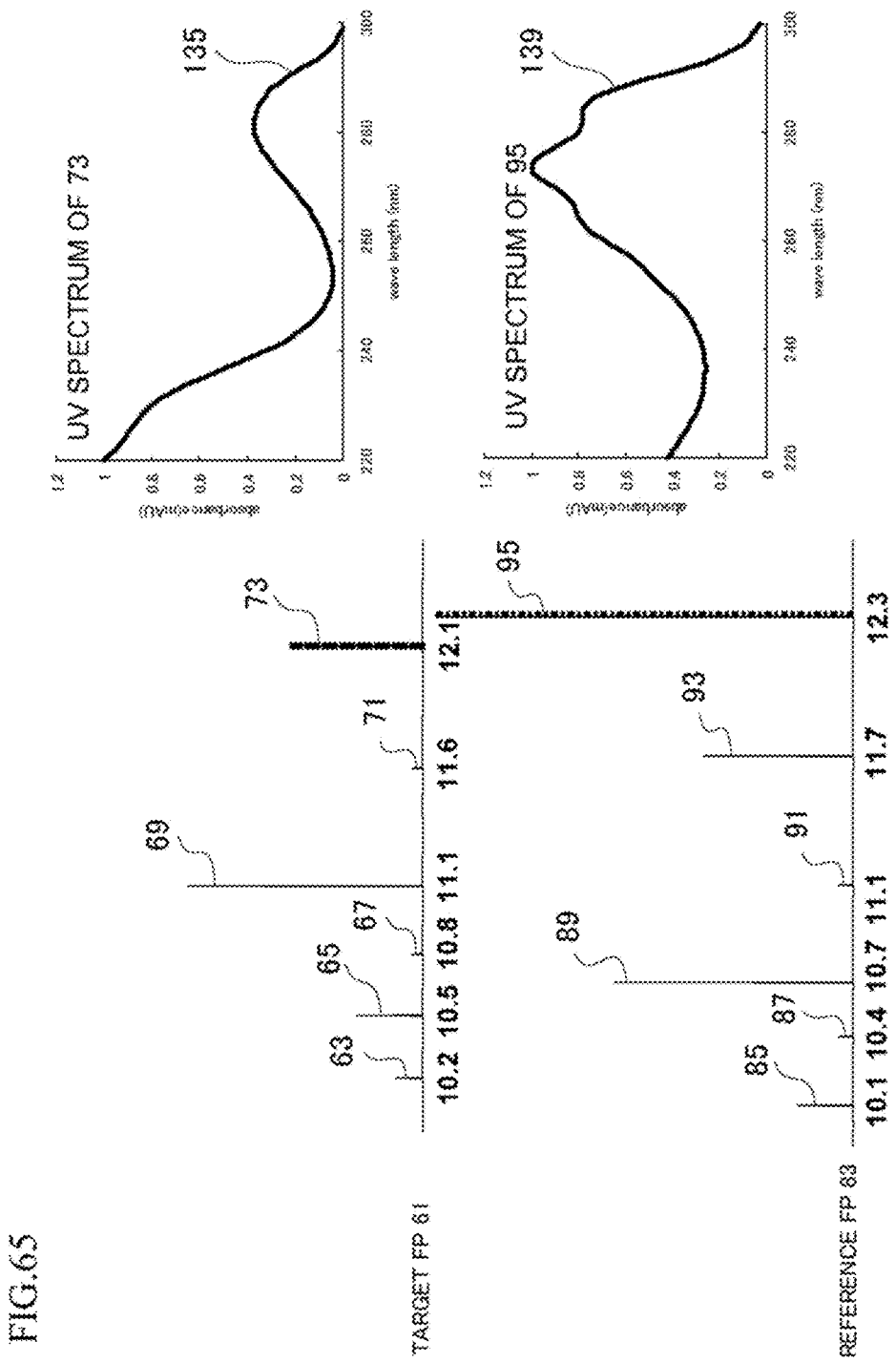
FIG. 65 is a diagram illustrating UV spectra of an assignment target peak and an assignment candidate peak according the first embodiment.
Figure 66:
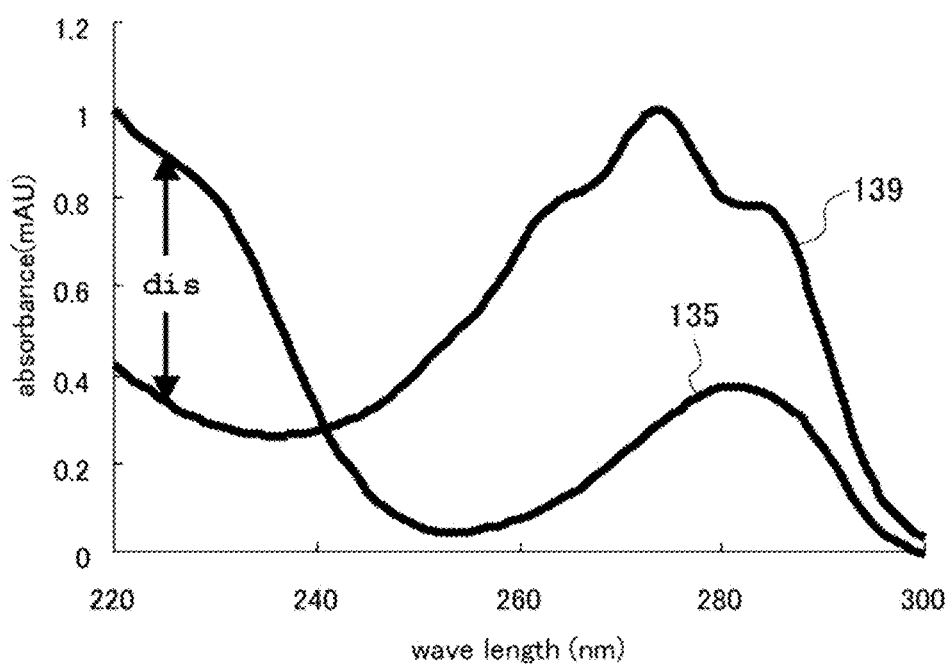
FIG. 66 is an explanatory diagram illustrating the degree of matching between the UV spectra of the assignment target peak and the assignment candidate peak according the first embodiment.
Figure 67:
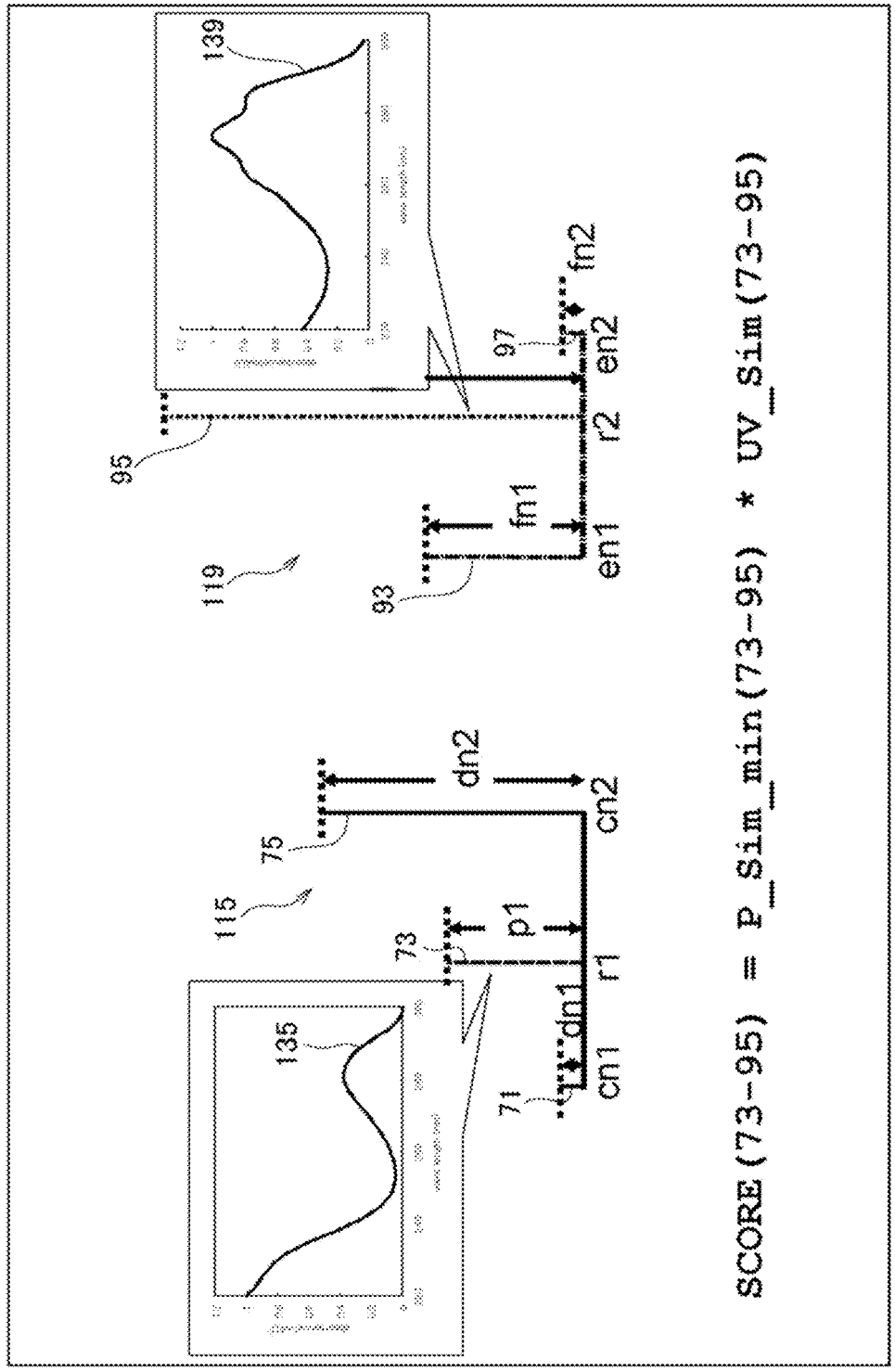
FIG. 67 is an explanatory diagram illustrating the degree of matching of the assignment candidate peak by comparison of both the peak patterns and the UV spectra together according the first embodiment.

The peak assigning part 37 calculates the degree of matching between peak patterns, as illustrated in FIGS. 62 to 64 (to be described later) based on differences in corresponding peaks and retention time points between the peak patterns of the assignment target peak and the assignment candidate peak. The degree of matching between the UV spectra is calculated based on a difference between the absorbance of the UV spectrum 135 of the assignment target peak 73 and the absorbance of the UV spectrum 139 of the assignment candidate peak 95 for each wavelength as illustrated in FIGS. 65 and 66 (to be described later). Further, as illustrated in FIG. 67 (to be described later), the degree of matching of the assignment candidate peak 95 is calculated by multiplying these two kinds of the degrees of matching together.

The target FP peak feature value preparing part 7 is a functional part that prepares target FP peak feature values that are quantified as feature values through comparisons and evaluations of peaks specified by the target FP peak assigning part 5 so as to be assigned and peaks of the reference group FP 45 that are plural reference FPs. The plurality of reference FPs are prepared in correspondence with a plurality of kampo medicines that are multicomponent materials as evaluation criteria, and the plurality of kampo medicines are reputed as normal products.

Figure 68:
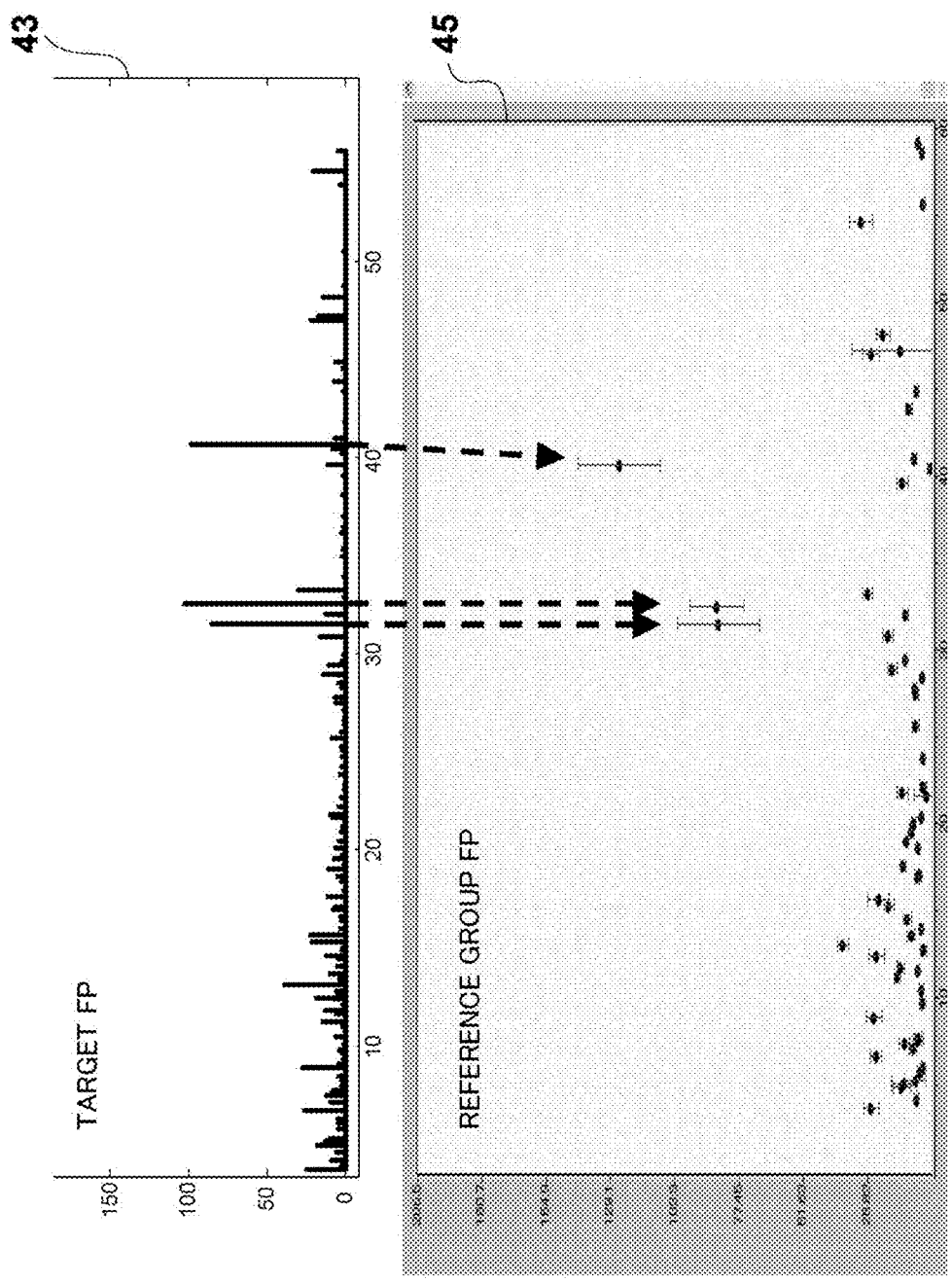
FIG. 68 is an explanatory diagram illustrating assignment of the target FP to a reference group FP according the first embodiment.
Figure 69:
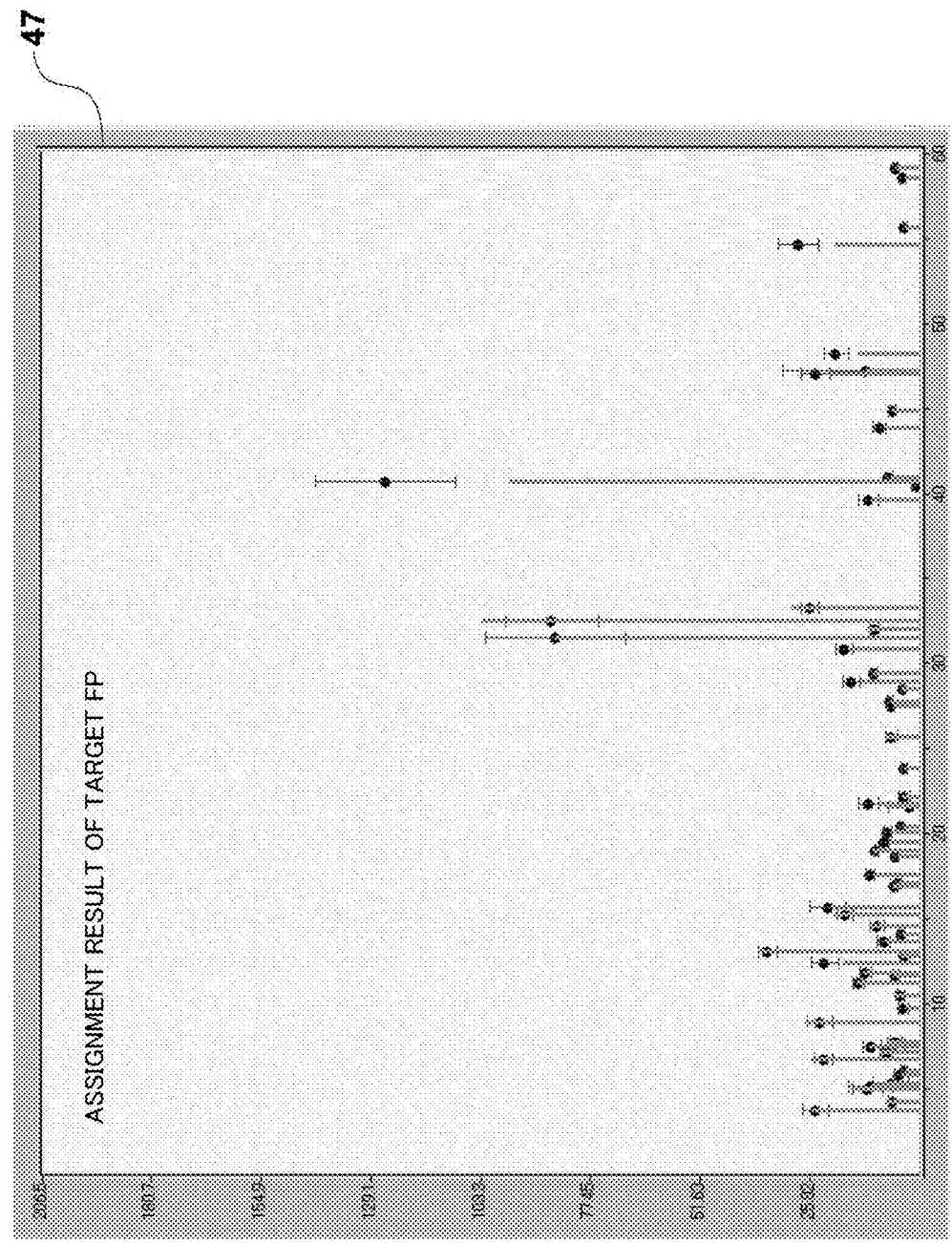
FIG. 69 is a diagram illustrating a state in which the target FP is assigned to the reference group FP according the first embodiment.

In other words, the target FP peak feature value preparing part 7 is a functional part that, based on the assigning result of the target FP 61 and the reference FP 83, finally assigns the peaks of the target FP 43 to the peaks of the reference group FP 45 to prepare target FP peak feature values 47 that are quantified as feature values as illustrated in FIGS. 2, 68, and 69 (to be described later).

The target FP type-2 preparing part 9 gathers as a second target FP or a target FP type-2 that is composed of remaining peaks in which each one peak has a height that is a maximum value or an area value in signal strength and retention time points of the respective remaining peaks with the exclusion of the assigned peaks that are quantified as feature values from the target FP. According to the embodiment, the peak height of the FP type-2 is the maximum value in signal strength similar to the target FP. For example, the target FP type-2 preparing part 9 is a functional part that prepares a FP as a target pattern type-2 that is a target FP type-2 (49) illustrated in FIG. 3A composed of remaining peaks with the exclusion of peaks 47 specified by the target FP peak feature value preparing part 7 from the original target FP 43 and of the retention time points thereof.

This target FP type 2 (49) is set as a FP by collecting peaks that are not quantified as feature values by the target FP peak feature value preparing part 7. By quantifying the target FP type-2 (49) as feature values to be added to the evaluation, it performs more accurate evaluation.

The target FP area segmentation feature value preparing part 11 is a functional part that segments the target FP type-2 (49) into a plurality of areas so that the peaks of the target FP type-2 are subdivided into pieces and obtains target FP area segmentation feature values as the target pattern area segmentation feature values based on the existence rate of subdivided peaks existing in each area.

In addition, the target FP area segmentation feature value preparing part 11 may use an existence amount instead of the existence rate. The existence rate, as will be described later, is a value acquired by dividing an existence amount of the peak heights in each area by a sum of all the peak heights (in other words, an existence amount of a total peak height). Accordingly, it may be configured to prepare area segmentation feature values with use of the existence amount of the peak heights in each area as itself. The existence amount is the sum of the peak heights within each area.

Figure 70:
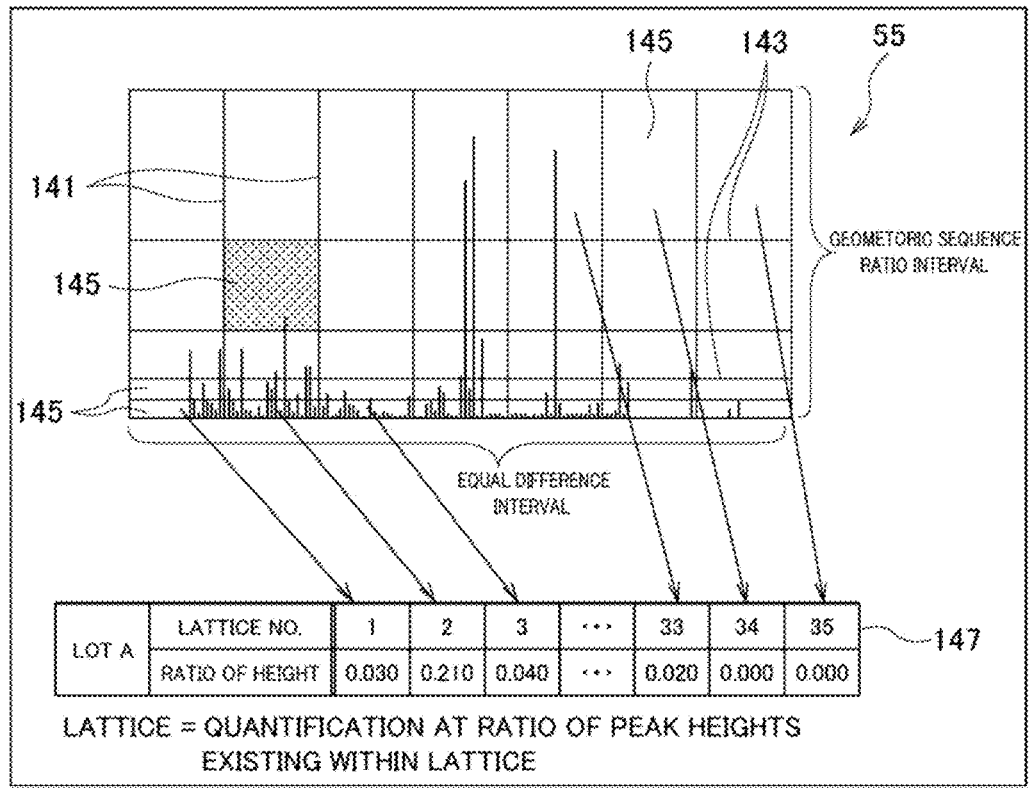
FIG. 70 is a diagram illustrating quantification according to area segmentation according the first embodiment.

This target FP area segmentation feature value preparing part 11, for example, segments the target FP type-2 (49) into lattice-shaped areas with a plurality of vertical segmenting lines parallel to a signal strength axis and a plurality of horizontal segmenting lines parallel to the time axis as illustrated in FIG. 70 (to be described later) to prepare the target FP area segmentation feature values 51 illustrated in FIG. 3A.

The target FP feature value integrating part 13 is a functional part that combines target FP integrated feature values by integrating the target FP peak feature values 47 prepared by the target FP peak feature value preparing part 7 and the target FP area segmentation feature values 51 prepared by the target FP area segmentation feature value preparing step 11.

Meanwhile, the reference FP preparing part 31 of the FP preparing part 3 is a functional part that, similarly to the target FP preparing part 29, prepares a plurality of reference FPs. For example, the reference FP preparing part 31 prepares a first reference FP (hereinafter, simply referred to as reference FP) for each reference kampo medicine by extracting a plurality of peaks at a specific detection wavelength, retention time points thereof, and UV spectra from each 3D chromatogram that is three-dimensional chromatogram data of a plurality of kampo medicines (reference kampo medicines) that are determined as normal products.

The reference FP peak assigning part 15, similarly to the target peak assigning part 5, is a functional part that specifies peaks to be assigned through pattern recognition. However, the reference FP peak assigning part 15, for all the reference FPs, specifies peaks by calculating assignment scores for a selected combination in a selected order.

The reference FP assigning result integrating part 17 is a functional part that prepares a reference peak correspondence table (to be described later) by integrating peaks that are specified and assigned by the reference peak assigning part 15.

The reference FP peak feature value preparing part 19 is a functional part that prepares reference FP peak feature values by quantifying the plurality of reference FPs as feature values based on the reference peak correspondence table prepared by the reference FP assigning result integrating part 17.

The reference FP type-2 preparing part 21 functions similar to the target FP type-2 preparing part 9 and is a functional part that gathers as a second reference FP or a reference FP type-2 that is composed of remaining peaks with the exclusion of the peaks that are quantified as feature values from the plurality of reference FPs and of retention time points thereof.

The reference FP area segmentation feature value preparing part 23 functions similar to the target FP area segmentation feature value preparing part 11 and is a functional part that segments the reference FP type-2 into a plurality of areas so that the peaks of the reference FP type-2 are subdivided into pieces and prepares reference FP area segmentation feature values based on an existence rate of the subdivided peaks existing in each area.

However, the reference FP area segmentation feature value preparing part 23 changes a position of each segmented area to prepare reference FP area segmentation feature values before and after the change. In other words, by changing and setting a position of each of the vertical and horizontal segmenting lines so as to move parallel within a set range, the position of each area is changed.

The reference FP feature value integrating part 25 functions similar to the target FP feature value integrating part 13 and is a functional part that prepares reference FP integrated feature values by integrating the reference FP peak feature values and the reference FP area segmentation feature values.

The evaluating part 27 compares and evaluates the target pattern integrated feature values and the reference pattern integrated feature values that correspond to the target pattern integrated feature values and are based on a plurality of reference patterns being evaluation criteria. In other words, the evaluating part 27 is a functional part that compares and evaluates the target FP integrated feature values as the target pattern integrated feature values and the reference FP integrated feature values as the reference pattern integrated feature values. In the embodiment, the equivalency between the target FP integrated feature values and the reference FP integrated feature values is evaluated using MT method.

MT method represents a calculation technique that is generally known in quality engineering. For example, MT method is described in pp 136 to 138 of "Mathematics for Quality Engineering" published by Japanese Standards Association (2000); pp 454 to 456 of Quality Engineering of Application Course of "Technical Developments in Chemistry, Pharmacy and Biology" published by Japanese Standards Association (1999); pp 78 to 84 of Quality Engineering 11(5) (2003); and "Introduction to MT System" (2008).

In addition, MT method program software that is commercially available in the market can be used. As such commercially-available MT method program software, there are "ATMTS" provided by Angle Try Associates, "TM- ANOVA" provided by Japanese Standards Association, an "MT method for Windows" provided by OHKEN Co., Ltd, and the like.

The evaluating part 27 assigns a variable axis according to MT method to one of the lot number and the retention time point of a kampo medicine or the UV detection wavelength of the target FP 43 and sets the peaks as feature values according to MT method.

Although the assignment of the variable axis is not particularly limited, it is preferable that the retention time point is assigned to a so-called category-axis according to MT method, the number of a multicomponent-based drug is assigned to a so-called number row axis, and the peak is assigned to a so-called feature value according to MT method.

Here, the category axis and the number row axis are defined as below. According to MT method, an average value $m_j$ and a standard deviation $\sigma_j$ are acquired for a data set $X_{ij}$, a correlation coefficient "r" between "i" and "j" is acquired from a value $x_{ij}=(X_{ij}-m_j)/\sigma_j$ that is standardized $X_{ij}$, and accordingly, a unit space or a Mahalanobis distance is acquired. At this time, the category axis and the number row axis are defined such that "the average value $m_j$ and the standard deviation $\sigma_j$ are acquired for each value of the category axis by changing the value of the number row axis."

Based on the data and the feature value to which axes are assigned, a reference point and an unit quantity (hereinafter, it may be abbreviated as an "unit space") are acquired using MT method. Here, the reference point, the unit quantity, and the unit space are defined in accordance with the description of MT method presented in the above-described literatures.

According to MT method, a MD value is acquired as a value that represents the degree of a difference between a drug to be evaluated and the unit space. Here, the MD value is defined in the same way as the description of MT method presented in the literatures, and the MD value is acquired with the method described in the literatures.

By using the MD value acquired in this manner, the drug to be evaluated can be evaluated by determining the degree of a difference from a plurality of drugs defined as normal products.

For example, by performing an assignment process for each target FP illustrated in FIGS. 87 to 91 as above, a MD value (MD values: 0.26, 2.20, and the like) can be acquired in accordance with MT method.

When this MD value is evaluated with respect to a MD value of a normal product, MD values are similarly acquired for a plurality of drugs defined as normal products. A threshold value is set from the MD values of these normal products, the MD value of the evaluation target drug is plotted as an evaluation result 53 of the evaluating part 27 illustrated in FIG. 3A to determine a normal product or an abnormal product. In the evaluation result 53 of the evaluating part 27 illustrated in FIG. 3A, for example, a MD value of 10 or less is determined as a normal product.

In addition, it is sufficient for the evaluating part 27 to be able to compare and evaluate the equivalency between the target FP integrated feature values and the reference FP integrated feature values, and therefore, a pattern recognition technique other than MT method or the like can be used.

Figure 5:
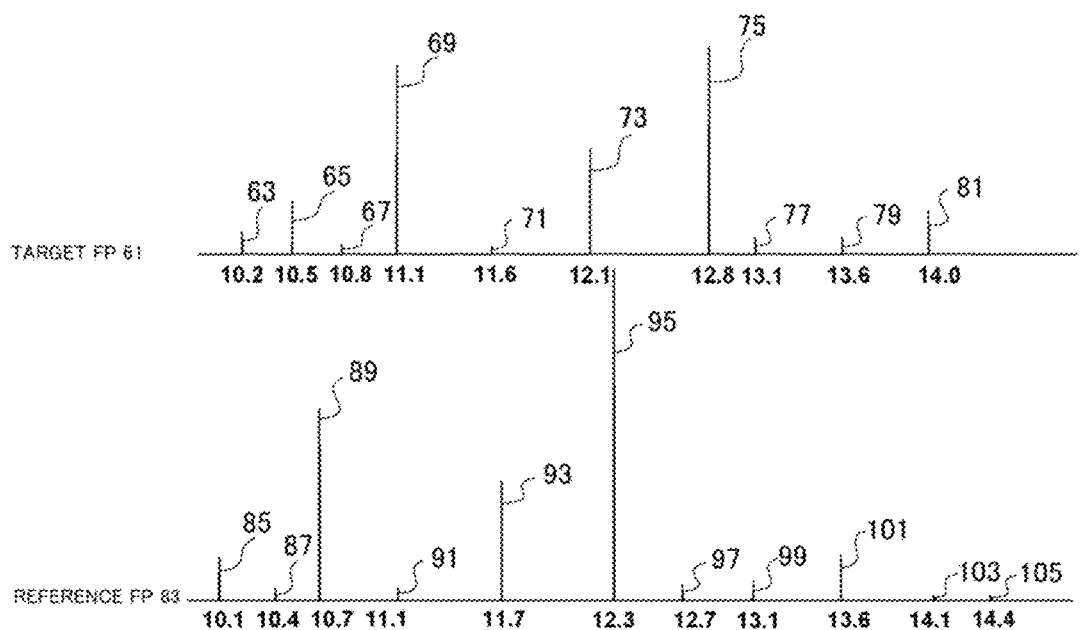
FIG. 5 is a diagram illustrating retention time points of a target FP and a reference FP according the first embodiment.

FIGS. 5 to 69 illustrate an operating principle of the reference FP selecting part 33, the peak pattern preparing part 35, the peak assigning part 37, and the target FP peak feature value preparing part 7.

Figure 6:
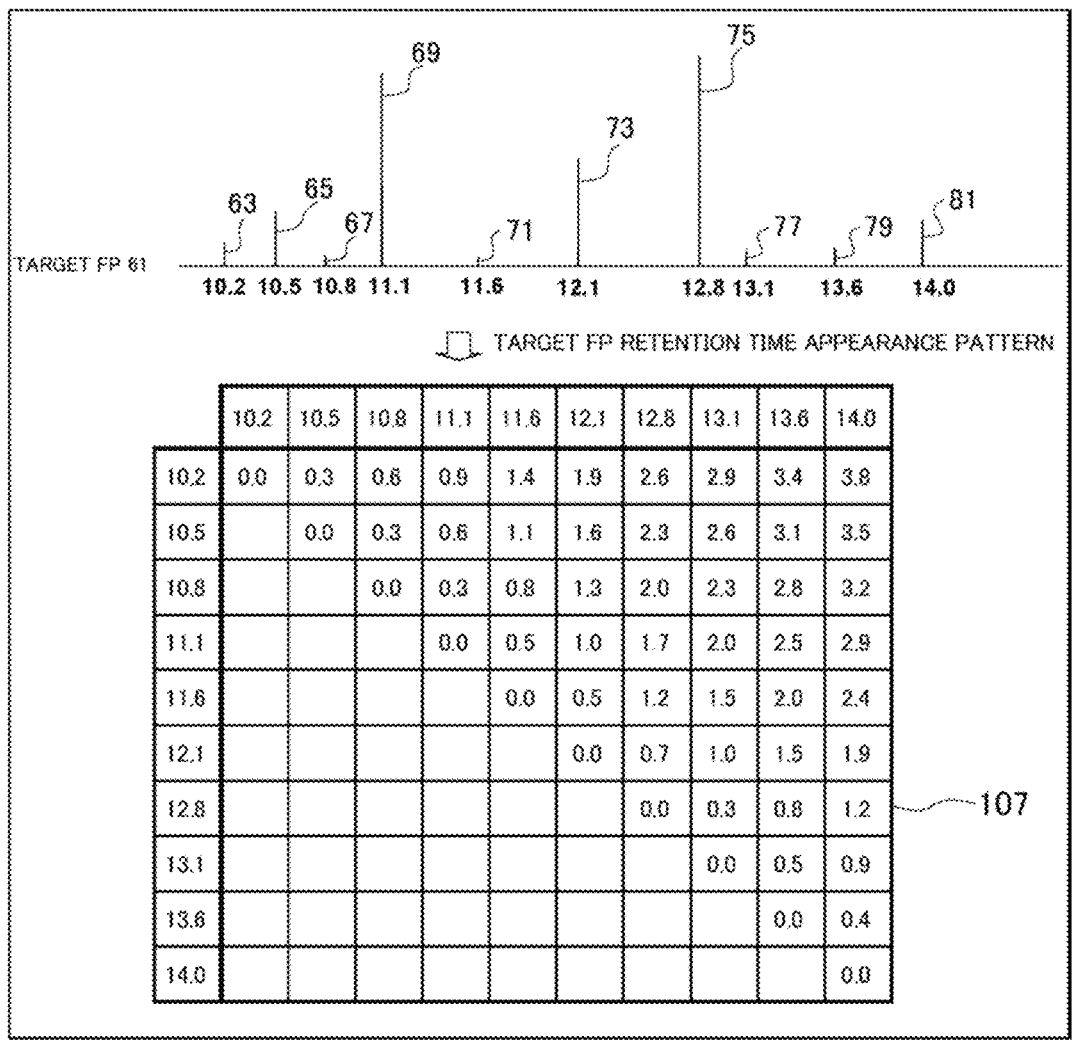
FIG. 6 is a diagram illustrating a retention time appearance pattern of the target FP according the first embodiment.
Figure 7:
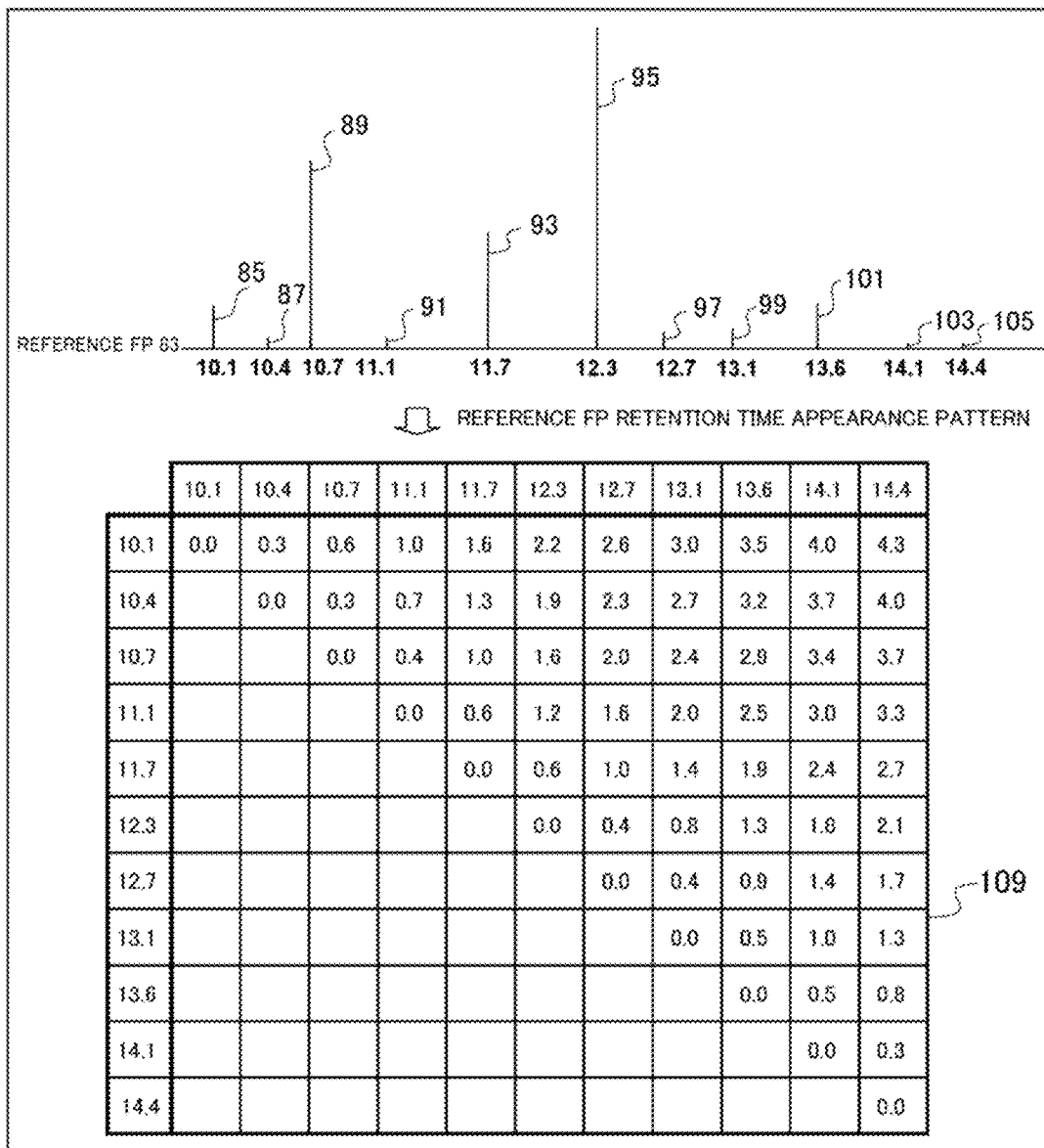
FIG. 7 is a diagram illustrating a retention time appearance pattern of the reference FP according the first embodiment.

FIGS. 5 to 9 are diagrams each illustrating the degree of matching between the retention time appearance patterns of the target FP and the reference FP according to the reference FP selecting part 33. FIG. 5 is a diagram illustrating retention time points of the target FP and the reference FP, FIG. 6 is a diagram illustrating the retention time appearance patterns of the target FP, and FIG. 7 is a diagram illustrating the retention time appearance patterns of the reference FP. FIG. 8 is a diagram illustrating the numbers of matches in the retention time appearance distance between the target FP and the reference FP, and FIG. 9 is a diagram illustrating the degrees of matching in the retention time appearance pattern between the target FP and the reference FP.

FIG. 5 shows the retention time points of the target FP 61 and the reference FP 83. FIGS. 6 and 7 show the retention time appearance patterns in which all of inter-retention time point distances calculated based on the retention time points of the target FP 61 and the reference FP 83 are arranged in a table form. FIG. 8 shows the numbers of matches between the retention time appearance distances calculated based on the appearance patterns and arranged in a table form. FIG. 9 shows the degrees of matching between the retention time appearance patterns calculated based on the number of matches and arranged in a table form.

FIGS. 10 to 12 are diagrams explaining a peak pattern that is prepared with use of an assignment target peak and peripheral peaks thereof by the peak pattern preparing part 35. FIG. 10 is a diagram illustrating an assignment target peak of the target FP, FIG. 11 is diagram illustrating a peak pattern prepared with use of three peaks including two peripheral peaks, and FIG. 12 is a diagram illustrating a peak pattern prepared with use of five peaks including four peripheral peaks.

Figure 13:
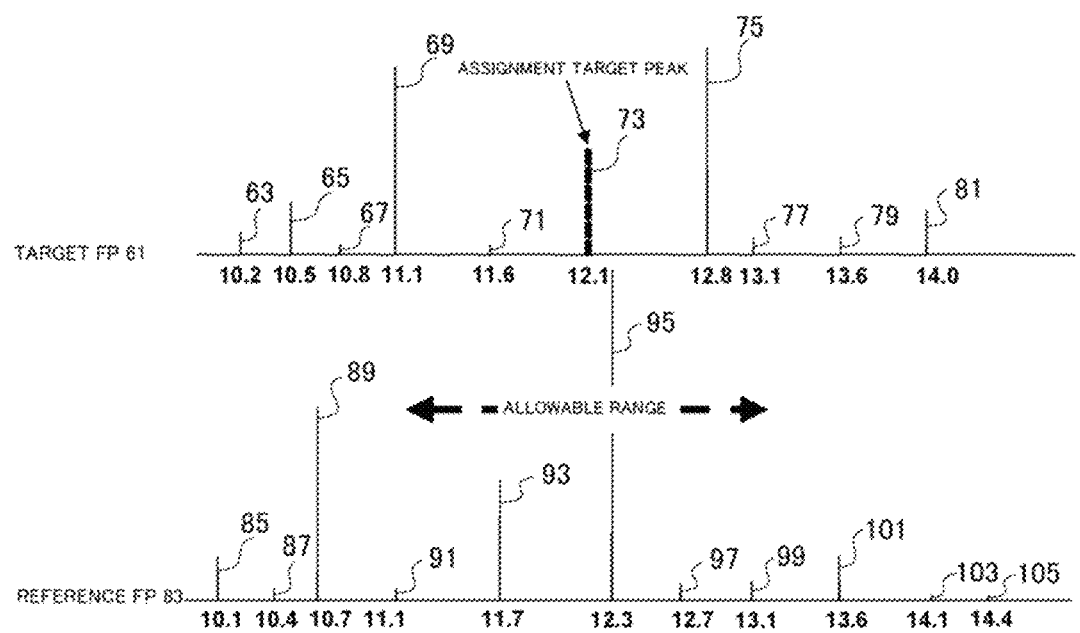
FIG. 13 is a diagram illustrating an allowable range for the assignment target peak according the first embodiment.
Figure 14:
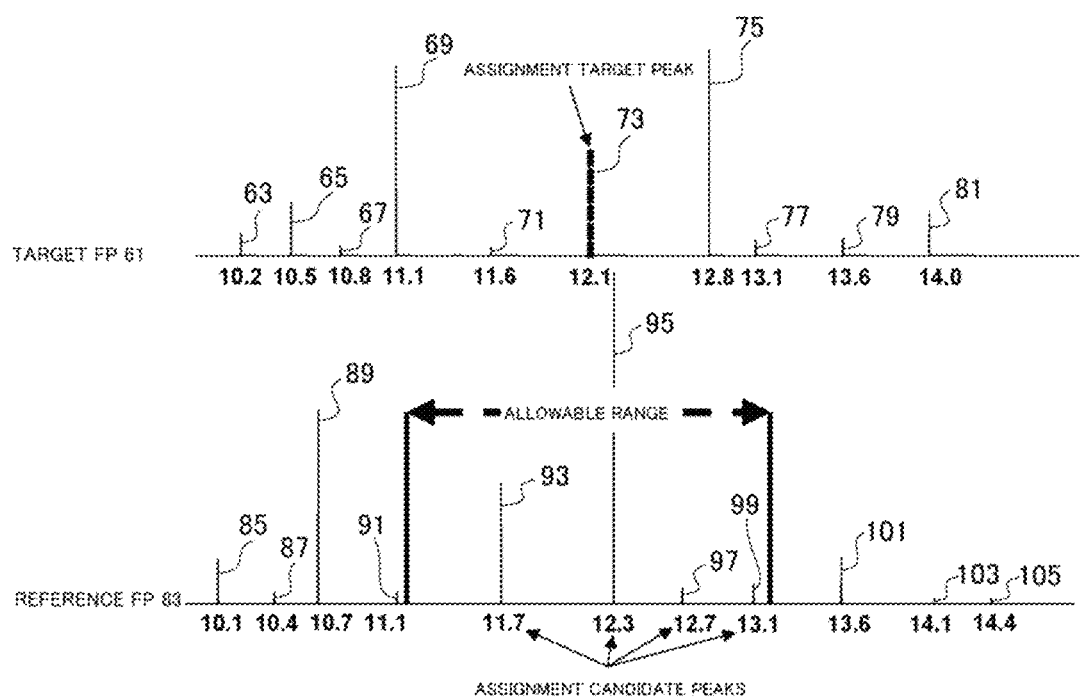
FIG. 14 is a diagram illustrating assignment candidate peaks of the reference FP for the assignment target peak according the first embodiment.

FIGS. 13 and 14 explain a relation between the assignment target peak and assignment candidate peaks according to the peak pattern preparing part 35, FIG. 13 is a diagram illustrating an allowable range of the assignment target peak, and FIG. 14 is a diagram illustrating assignment candidate peaks of the reference FP for the assignment target peak.

Figure 15:
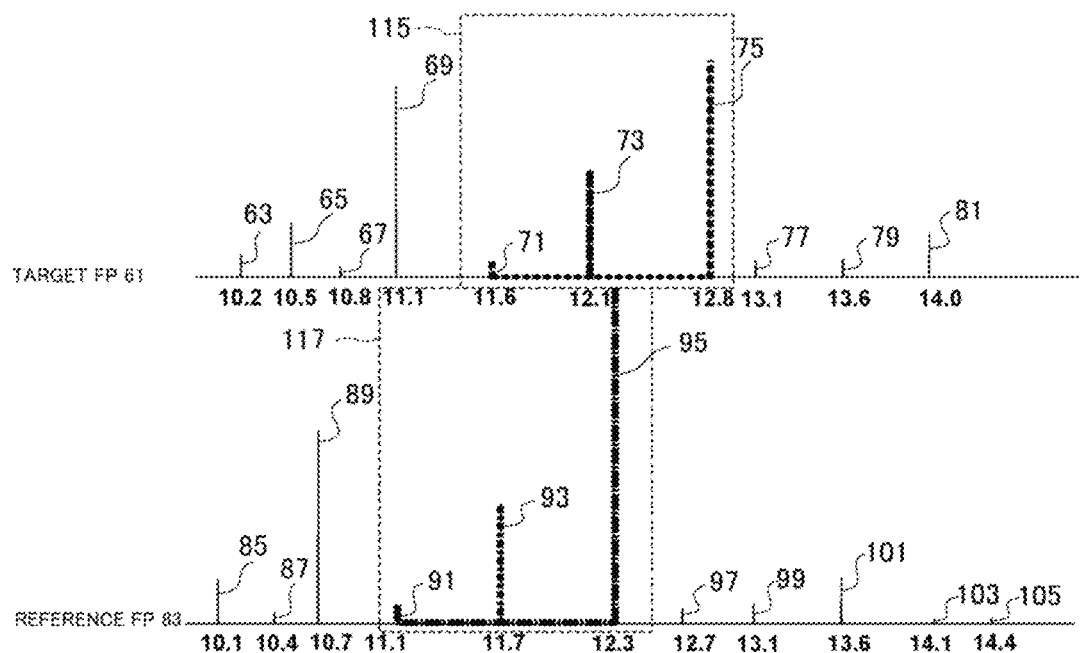
FIG. 15 is a peak pattern diagram according to three peaks of assignment candidate peaks for the assignment target peak according the first embodiment.
Figure 16:
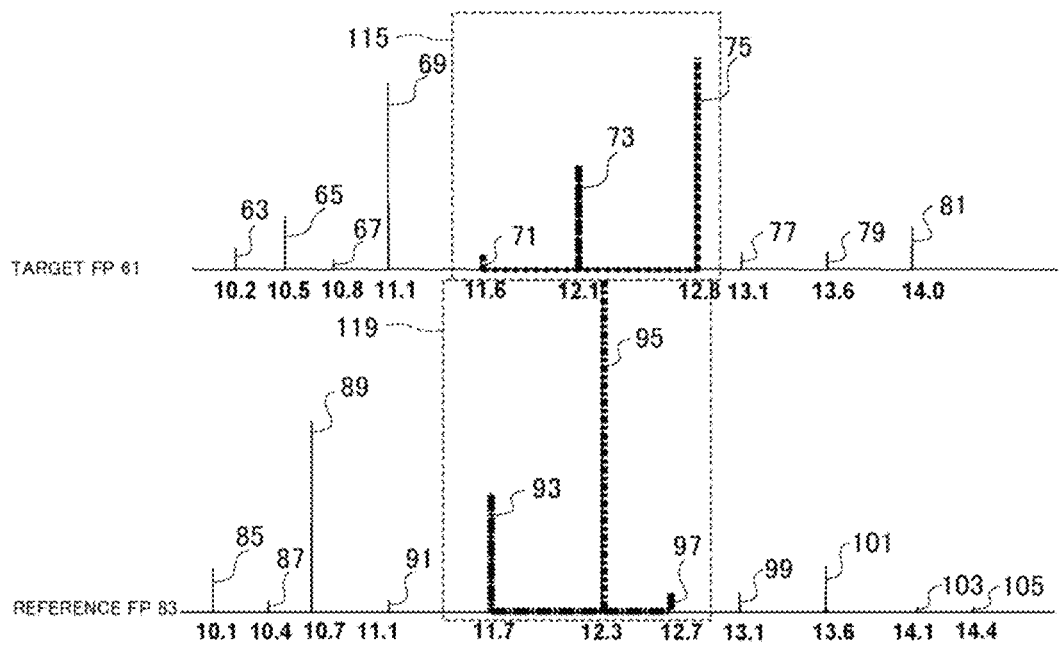
FIG. 16 is a peak pattern diagram according to three peaks of another assignment candidate peaks for the assignment target peak according the first embodiment.
Figure 17:
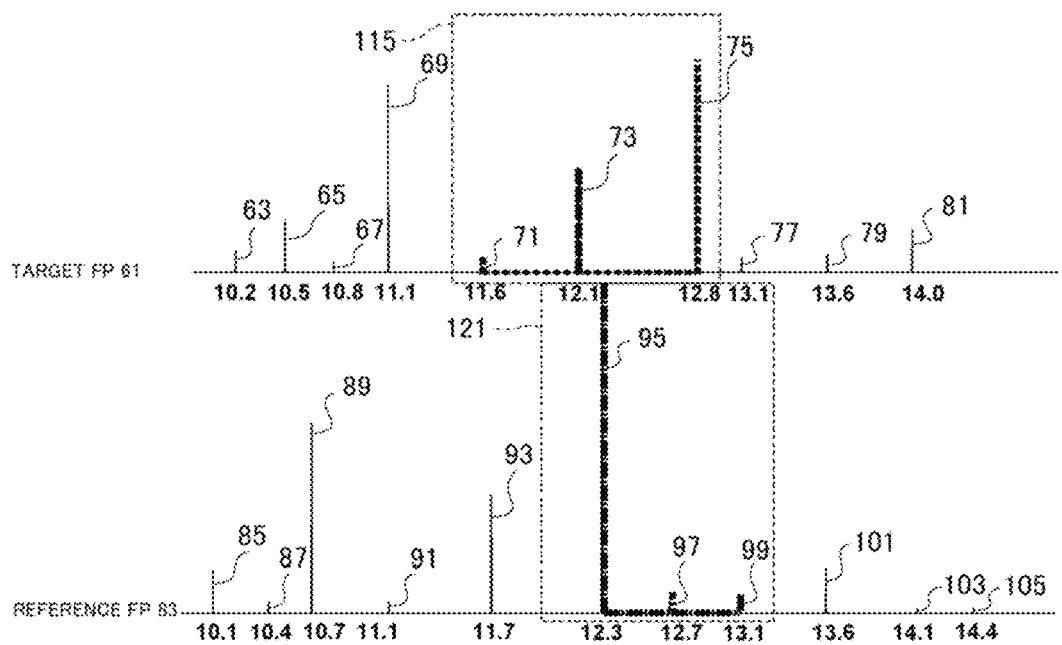
FIG. 17 is a peak pattern diagram according to three peaks of another assignment candidate peaks for the assignment target peak according the first embodiment.
Figure 18:
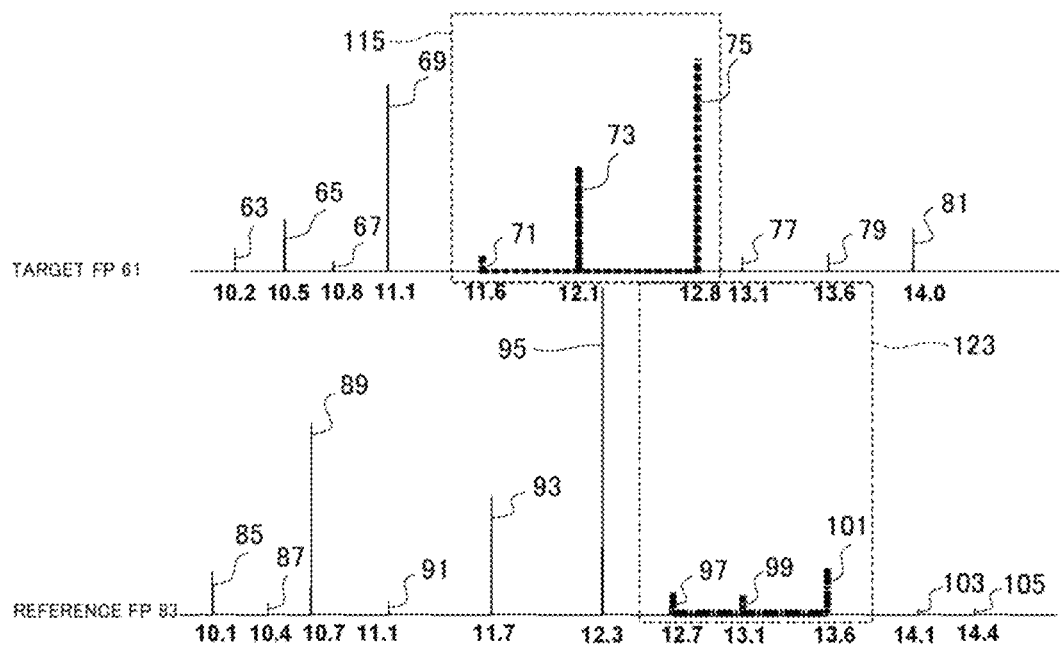
FIG. 18 is a peak pattern diagram according to three peaks of another assignment candidate peaks for the assignment target peak according the first embodiment.

FIGS. 15 to 18 are peak pattern examples of the assignment target peak and assignment candidate peaks that are prepared by three peaks according to the peak pattern preparing part 35. FIG. 15 is a peak pattern diagram according to three peaks of the assignment target peak and assignment candidate peaks, FIG. 16 is a peak pattern diagram according to three peaks of another assignment candidate peaks for the assignment target peak, FIG. 17 is a peak pattern diagram according to three peaks of another assignment candidate peaks for the assignment target peak, and FIG. 18 is a peak pattern diagram according to three peaks of another assignment candidate peaks for the assignment target peak.

FIGS. 19 to 22 are peak pattern diagrams of an assignment target peak and assignment candidate peaks that are prepared with use of five peaks according to the peak pattern preparing part 35.

FIGS. 23 to 61 are diagrams explaining the principle of comprehensive comparison in which peak patterns of the assignment target peak and assignment candidate peak according to the peak pattern preparing part 35 are comprehensively prepared and compared with each other.

FIGS. 62 and 63 are diagrams explaining a calculating method of the degree of matching between peak patterns prepared with use of three peaks according to the peak assigning part 37.

FIG. 64 is a diagram explaining a calculating method of the degree of matching between peak patterns prepared with use of five peaks according to the peak assigning part 37.

FIG. 65 is a diagram illustrating UV spectra 135 and 139 of an assignment target peak 73 and an assignment candidate peak 95 according to the peak assigning part 37.

FIG. 66 is a diagram explaining the degree of matching between the UV spectrum 135 of the assignment target peak 73 and the UV spectrum 139 of the assignment candidate peak 95 according to the peak assigning part 37.

FIG. 67 is a diagram explaining the degree of matching between assignment candidate peaks that is calculated based on the degree of matching between peak patterns of the assignment target peak 73 and the assignment candidate peak 95 and the degree of matching between UV spectra according to the peak assigning part 37.

FIG. 68 is a diagram explaining the assignment of each peak of the target FP 43 to the reference group FP 45 according to the peak assigning part 37.

FIG. 69 is a diagram explaining a target FP peak feature value 47 that represents a state in which each peak of the target FP 43 is assigned to the reference group FP 45 according to the peak assigning part 37.

The function of the above-described reference FP selecting part 33 will be further described with reference to FIGS. 5 to 9.

FIG. 5 is the diagram illustrating retention time points of the target FP and the reference FP, FIG. 6 is the diagram illustrating the retention time appearance patterns of the target FP, and FIG. 7 is the diagram illustrating the retention time appearance patterns of the reference FP. FIG. 8 is the diagram illustrating the numbers of matches in the retention time appearance distance between the target FP and the reference FP, and FIG. 9 is the diagram illustrating the degrees of matching in the retention time appearance pattern between the target FP and the reference FP.

FIG. 5 shows the retention time points of the target FP 61 and the reference FP 83. FIGS. 6 and 7 show the retention time appearance patterns in which all of inter-retention time point distances calculated based on the respective retention time points of the target FP 61 and the reference FP 83 are arranged in a table form. FIG. 8 shows the numbers of matches between the retention time appearance distances calculated based on the appearance patterns and arranged in a table form. FIG. 9 shows the degrees of matching between the retention time appearance patterns calculated based on the number of matches and arranged in a table form.

In the peak assigning process for the target FP 61, the peaks of the target FP 61 are assigned to a reference FP whose FP pattern is closest to the target FP 61 as much as possible. Selecting this reference FP that is closest to the target FP 61 from among a plurality of reference FPs is an important point for performing assignment with high accuracy.

Thus, as a method of evaluating similarity to the FP pattern of the target FP 61 in an objective and simplified manner, the similarity of the FP pattern is evaluated based on the degree of matching in the retention time appearance pattern.

For example, in a case where the retention time points of the target FP 61 and the reference FP 83 are as illustrated in FIG. 5, retention time appearance patterns of the target FP 61 and the reference FP 83 are as illustrated in FIGS. 6 and 7. In FIGS. 6 and 7, for the target FP 61 and the reference FP 83 illustrated on the upper side, as tables illustrated on the lower side, patterns are prepared in the form of tables in which the value of each cell is configured by an inter-retention time point distance.

In FIG. 6, the retention time points of peaks (63, 65, 67, 69, 71, 73, 75, 77, 79, and 81) of the target FP 61 are (10.2), (10.5), (10.8), (11.1), (11.6), (12.1), (12.8), (13.1), (13.6), and (14.0).

Accordingly, an inter-retention time point distance between the peaks 63 and 65 is (10.5)−(10.2)=(0.3). Similarly, an inter-retention time point distance between the peaks 63 and 67 is (0.6), an inter-retention time point distance between the peaks 65 and 67 is (0.3), etc. The followings are similarly acquired and a target FP appearance pattern is formed into a table on the lower side of FIG. 6.

As illustrated in FIG. 7, the retention time points of the peaks (85, 87, 89, 91, 93, 95, 97, 99, 101, 103, and 105) of the reference FP 83 are (10.1), (10.4), (10.7), (11.1), (11.7), (12.3), (12.7), (13.1), (13.6), (14.1), and (14.4).

Accordingly, in the same way, inter-retention time point distances form a reference FP appearance pattern into a table on the lower side of FIG. 7.

The individual peaks patterned as illustrated in FIGS. 6 and 7 are compared in a round-robin so as to acquire the number of matches. For example, the value of each cell of the target FP appearance pattern represented in the table illustrated on the lower side of FIG. 6 is compared with the value of each cell of the reference FP appearance pattern represented in the table on the lower side of FIG. 7, thereby acquiring the number of matches as illustrated in FIG. 8.

Namely, all the inter-retention time point distances of the retention time appearance patterns of the target FP 61 and the reference FP 83 are sequentially compared with each other in units of rows in a round-robin, thereby calculating the number of the distances that match within a set range.

For example, comparing the first rows of the target and reference FP retention time appearance patterns illustrated in FIGS. 6 and 7, the number of matches is seven. This number of matches of seven is written into the first row of the target and reference FP retention time appearance pattern illustrated in FIG. 8. For the other rows in FIGS. 6 and 7, similarly, the first to ninth rows of the target FP retention time appearance pattern are compared with the first to tenth rows of the reference FP retention time appearance pattern in a round-robin, thereby acquiring the numbers of matches, respectively.

The results are represented in FIG. 8. In FIG. 8, a leftmost circled number of 7 is a result of the comparison between the first rows of the target and reference FP retention time appearance patterns, and a number of 7 represented next thereto is a result of the comparison between the first row of the target FP retention time appearance pattern and the second row of the reference FP retention time appearance pattern. The set range is not particularly limited, but is preferably in the rage of 0.05 minutes to 0.2 minutes. In the first embodiment, the set range is 0.1 minutes.

When the degree of matching between the retention time appearance patterns is RP, a degree ($RP_{fg}$) of matching between a retention time appearance pattern of the f-th row of the target FP 61 and the retention time appearance pattern of the g-th row of the reference FP 83 is calculated using Tanimoto coefficient as:

$$RP_{fg} = \{1-(m/(a+b-m))\} \times (a-m+1) \text{ using a Tanimoto coefficient.}$$

In the equation, "a" is the number of peaks of the target FP 61 (the number of target FP peaks), "b" is the number of peaks of the reference FP 83 (the number of reference FP peaks), and "m" is the number of matches in the retention time appearance patterns (the number of matches in an appearance distance) (see FIG. 8). The degree (RP) of matching between retention time appearance patterns is calculated using the above-described equation based on the number of matches in FIG. 8 (see FIG. 9).

RP_min that is the minimum value of these RPs is set as the degree of matching between the retention time appearance patterns of the target FP 61 and the reference FP 83. In the case illustrated in FIG. 9, (0.50) is the degree of matching of the target FP 61 with respect to the reference FP.

The degrees of matching are calculated for all the reference FPs, and a reference FP having the smallest degree of matching is selected, and the peaks of the target FP are assigned to the reference FP.

The reference FP selecting part 5 may pattern the target FP 61 and the reference FP 83 at peak height ratios.

The peaks patterned with use of the peak height ratios are compared in a round-robin, to calculate the number of matches in the height ratio within a set range. By performing such a calculation, similarly to the case of FIG. 8, the number of matches can be acquired.

In addition, if the peaks are patterned at the peak height ratios, there is a case where a plurality of similar values are present in one row, and thus these values are required not to be counted a plurality of times.

The degree of matching can be acquired by setting the Tanimoto coefficient as "the number of matches in the height ratio/(the number of target FP peaks+the number of reference FP peaks−the number of matches in the height ratio)" and approaching (1−Tanimoto coefficient) to zero.

In addition, (1−Tanimoto coefficient) is weighted by (the number of target FP peaks−the number of matches in the appearance patterns or height ratio+1) to be "(1−Tanimoto coefficient)×(the number of target FP peaks−the number of matches in the appearance pattern or the height ratio+1", whereby a reference FP that matches more peaks (63, 65, . . . ) of the target FP 61 in accordance with the weighting can be selected.

The functions of the peak pattern preparing part 35 will be described further with reference to FIGS. 10 to 67.

When the assignment target peak 73 is assigned to one of peaks of the reference FP 83 as illustrated in FIG. 10, it works out to that the peak should be assigned to which one of the peaks. If this peak assignment is carried out based on only information of the peak retention time or UV spectra, sufficient accuracy cannot be acquired by the peak assignment based on the single kind of information. This is because all the three kinds of information include errors due to the inter-drug error and the analysis error.

In addition, as illustrated in FIGS. 13 and 14, in a case of setting an allowable range of a deviation in the retention time point of each peak of the assignment target peak 73 and the reference FP 83 (hereinafter, referred to as an assignment candidate peak) and performing peak assignment based on two kinds of information including presence of peaks of the reference FP 83 within the allowable range and the UV spectrum information, an assignment destination is determined by synthesizing all the information to improve the accuracy compared to the peak assignment according to the single kind of information.

However, even in a case where the peak assignment is performed based on the three kinds of information, UV spectra with similar components are the almost same as the characteristics. Accordingly, if a plurality similar components are included in the assignment candidate peaks, the assignment is consequently performed based on only the peak information, whereby sufficient accuracy cannot be acquired. Hence, in order to perform peak assignment with high accuracy, more information is necessary in addition to be added to the three kinds of information.

Then, peak patterns including information of peripheral peaks as illustrated in FIGS. 11 and 12 are prepared, and the peak assignment is performed based on the comparison of the peak patterns.

If the peak pattern includes the peripheral peaks, the peripheral information is added to the prior three kinds of information. Accordingly, the peak assignment can be performed based on four kinds of information, whereby higher assignment accuracy can be secured.

As a result, massive peaks can be efficiently assigned all together through one assignment process with high accuracy.

In addition, by configuring data used for the peak assignment as four kinds of information including the peripheral information, there is no need of restriction conditions (definition of a peak and the like) to be set in a conventional peak assignment process.

In the case illustrated in FIG. 11, a peak pattern 115 that includes peaks 71 and 75 being present on both sides in the time axis direction is prepared for the assignment target peak 73.

In the case illustrated in FIG. 12, a peak pattern 125 including peaks 69, 71, 75, and 77 that are present on both sides in the time axis direction is prepared for the assignment target peak 73.

In the cases of FIGS. 13 and 14, an allowable range of the deviation between the retention time points of the respective peaks of the assignment target peak 73 and the reference FP 83 is set, and peaks of the reference FP 83 that are present within the allowable range are set as candidate peaks (hereinafter, referred to as assignment candidate peaks) that correspond to the assignment target peak 73.

In the case of FIG. 15, as a peak pattern to be compared with the peak pattern 115 of the assignment target peak 73, a peak pattern 117 that includes peaks 91 and 95 being present on both sides located in front and in the rear in the time axis direction is prepared for an assignment candidate peak 93.

In the cases of FIGS. 16 to 18, as a peak pattern to be compared with the peak pattern 115 of the assignment target peak 73, peak patterns 119, 121, and 123 that include peaks being present on both sides located in front and in the rear in the time axis direction are prepared for another assignment candidate peaks 95, 97, and 99, respectively.

In order to compare the peak patterns with higher accuracy, it is important to prepare a peak pattern in which the numbers of peripheral peaks are increased for both the target FP and the reference FP as illustrated in FIGS. 19 to 22.

For example, by comparing the peak patterns having a total of five peaks that includes four peripheral peaks, higher assignment accuracy is acquired.

Figure 19:
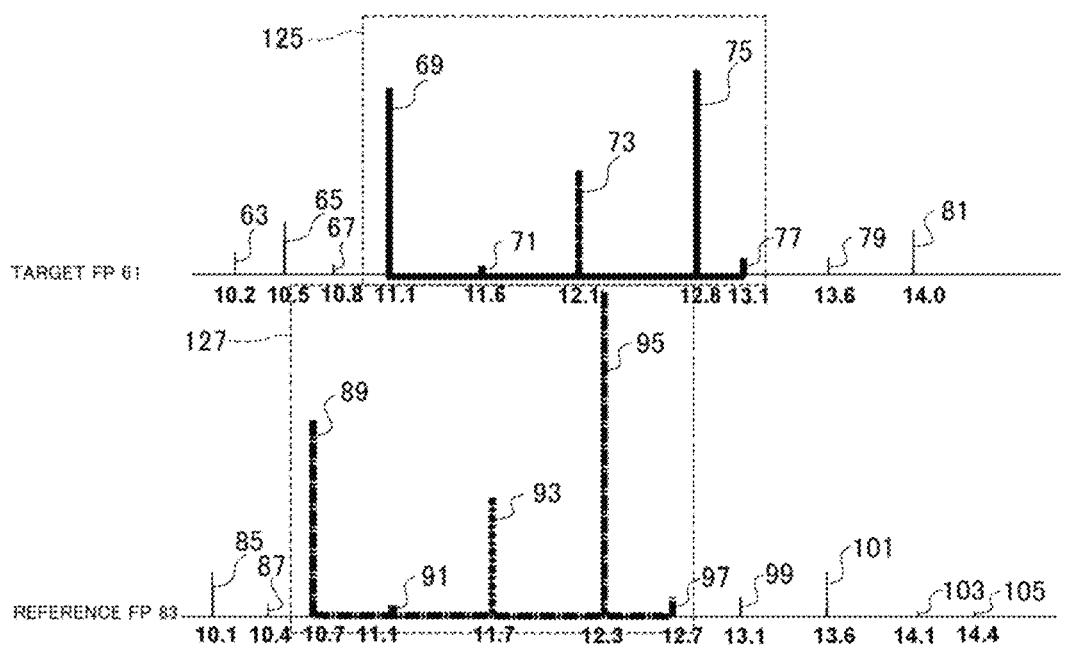
FIG. 19 is a peak pattern diagram according to five peaks of assignment candidate peaks for the assignment target peak according the first embodiment.

In the case of FIG. 19, as a peak pattern to be compared with the peak pattern 125 for the assignment target peak 73, a peak pattern 127 that includes peaks 89, 91, 95, and 97 being present on both sides in the time axis direction is prepared for the assignment candidate peak 93.

Figure 20:
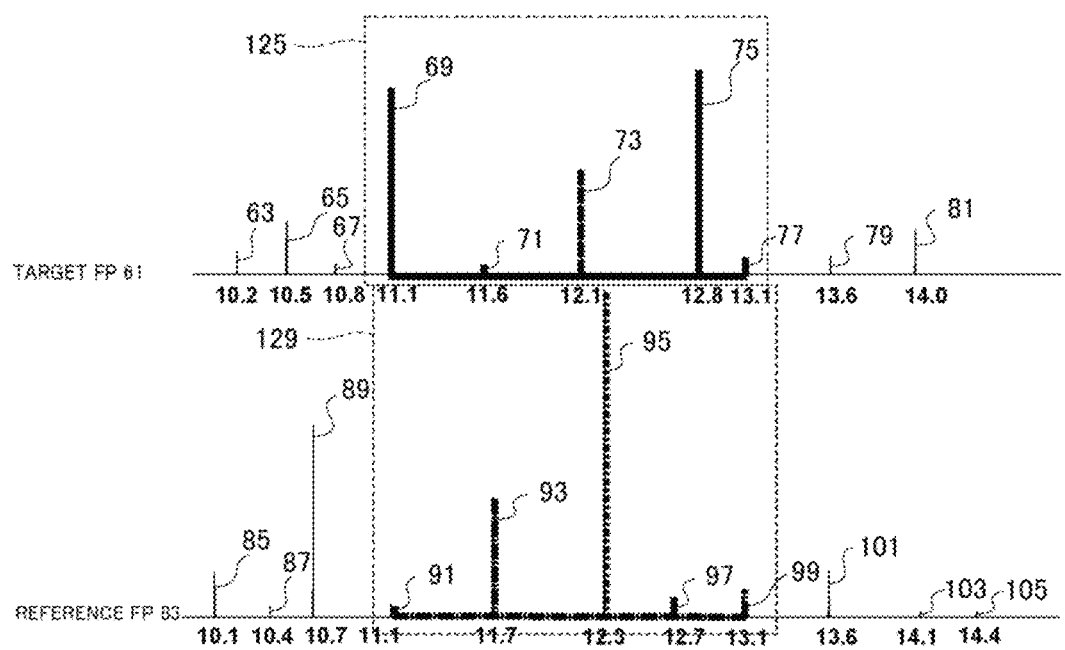
FIG. 20 is a peak pattern diagram according to five peaks of another assignment candidate peaks for the assignment target peak according the first embodiment.
Figure 21:
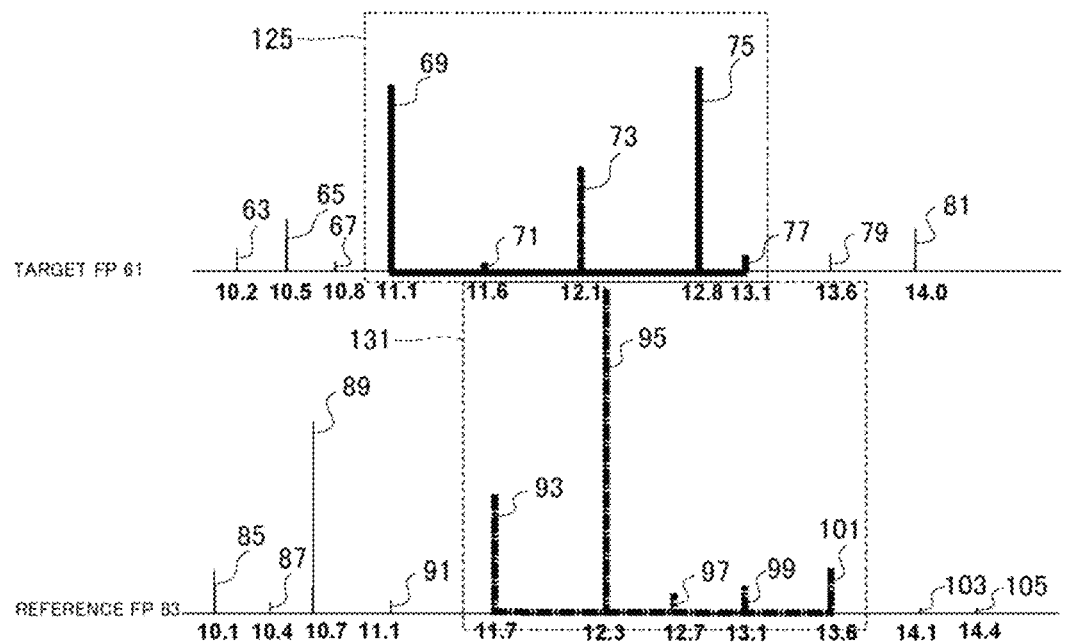
FIG. 21 is a peak pattern diagram according to five peaks of another assignment candidate peaks for the assignment target peak according the first embodiment.
Figure 22:
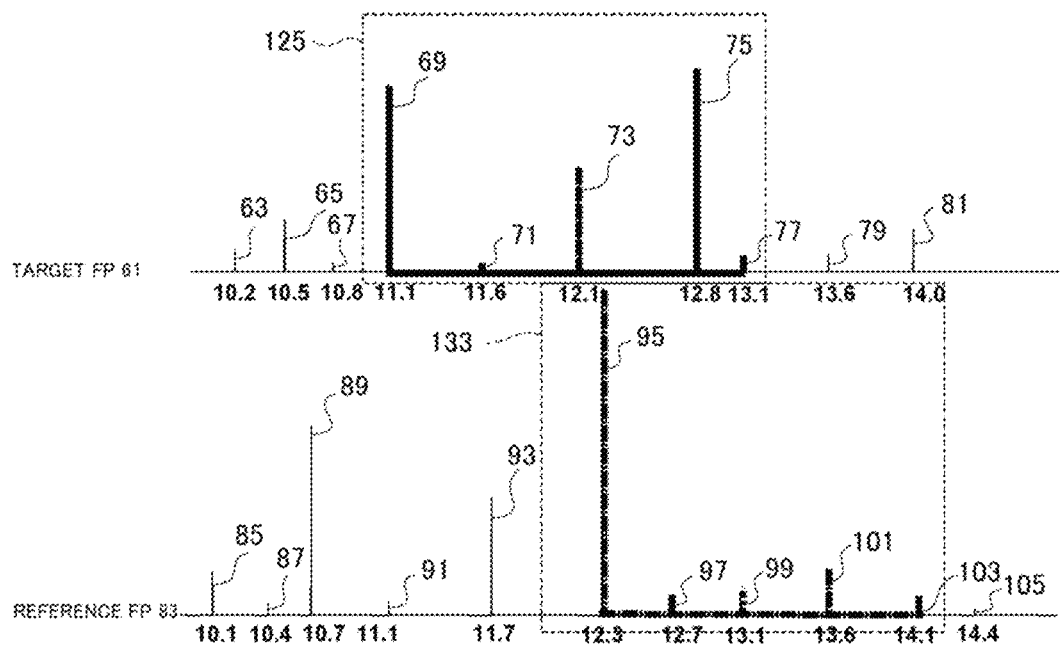
FIG. 22 is a peak pattern diagram according to five peaks of another assignment candidate peaks for the assignment target peak according the first embodiment.

In the cases of FIGS. 20 to 22, as peak patterns to be compared with a peak pattern 125 of the assignment target peak 73, peak patterns 129, 131, and 133 that include peaks being present on both sides located in front and in the rear in the time axis direction are prepared as peak patterns for another assignment candidate peaks 95, 97, and 99, respectively.

Figure 24:
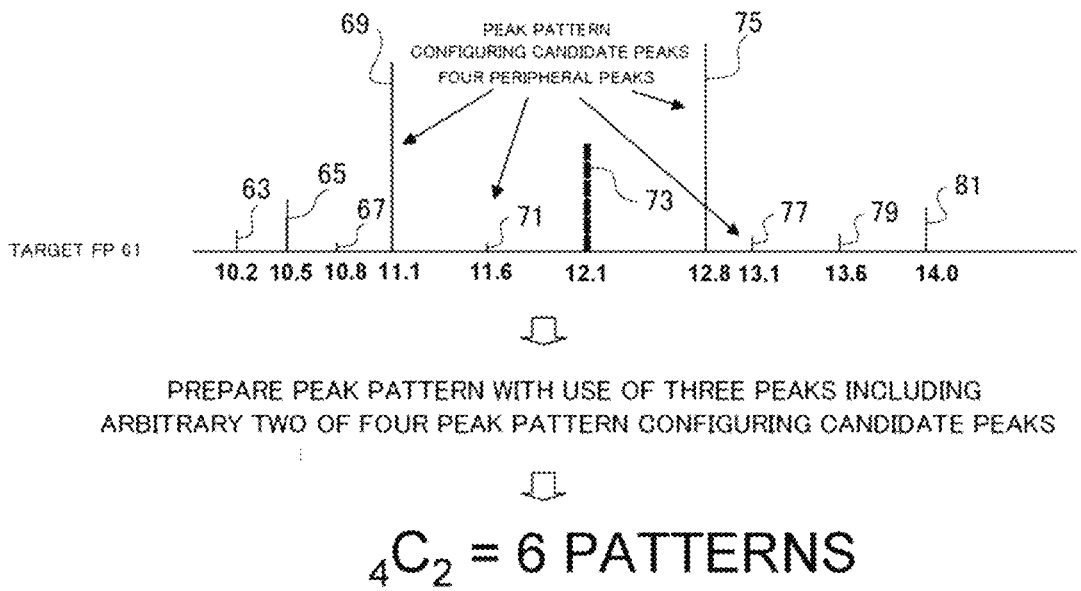
FIG. 24 is a diagram illustrating the number of all the peak patterns for the assignment target peak in a case that four peak pattern configuring candidate peaks are set according the first embodiment.
Figure 25:
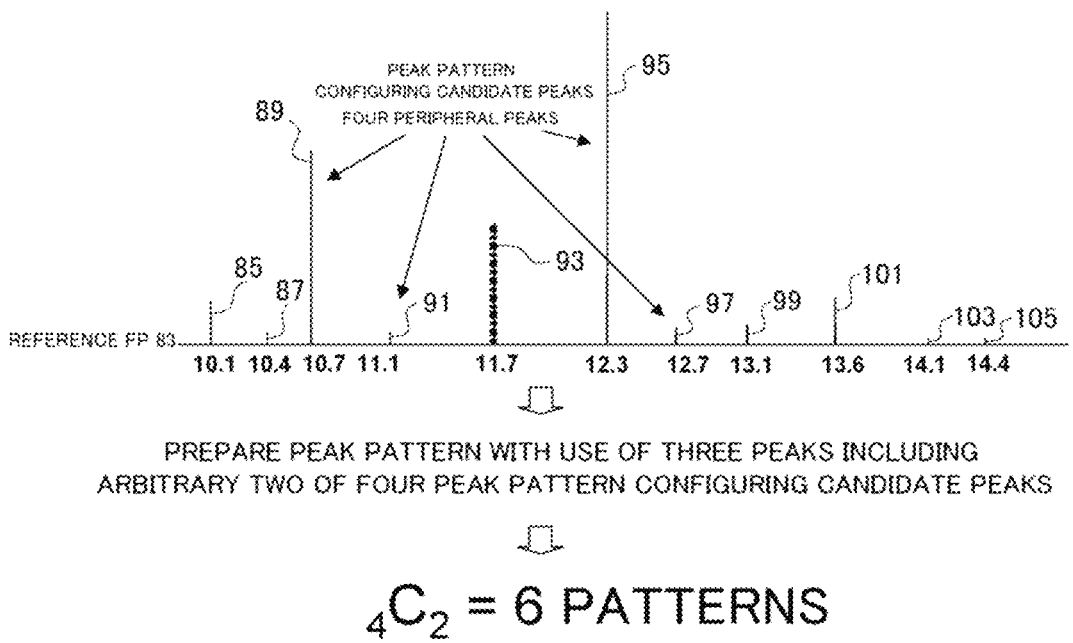
FIG. 25 is a diagram illustrating the number of all the peak patterns for an assignment candidate peak in a case that four peak pattern configuring candidate peaks are set according the first embodiment.
Figure 26:
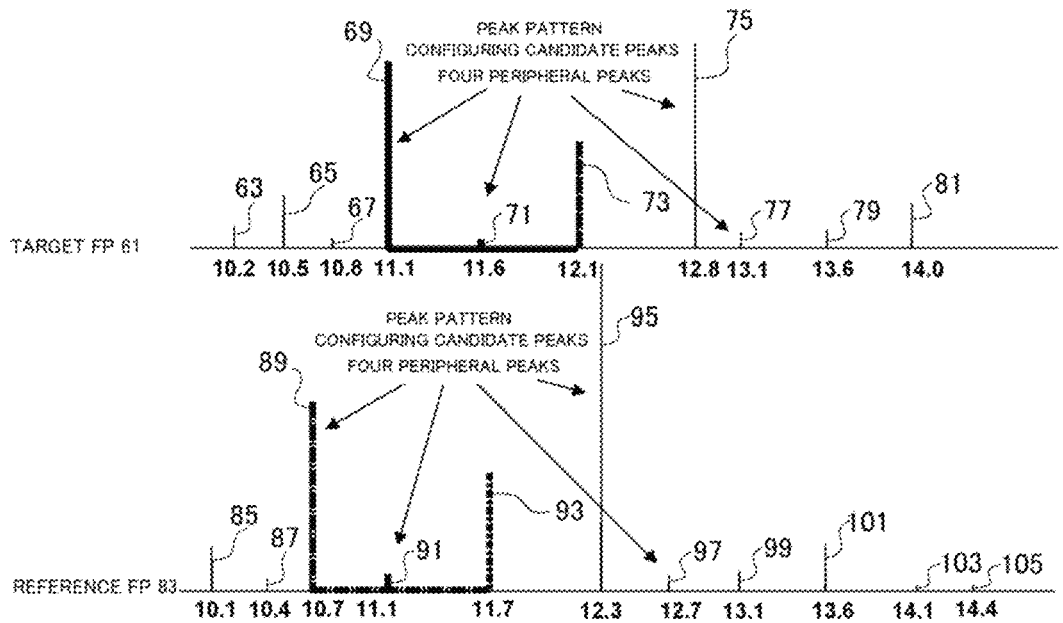
FIG. 26 is an explanatory diagram illustrating comprehensive comparison of peak patterns for the assignment target peak with respect to peak patterns for an assignment candidate peak according the first embodiment.
Figure 27:
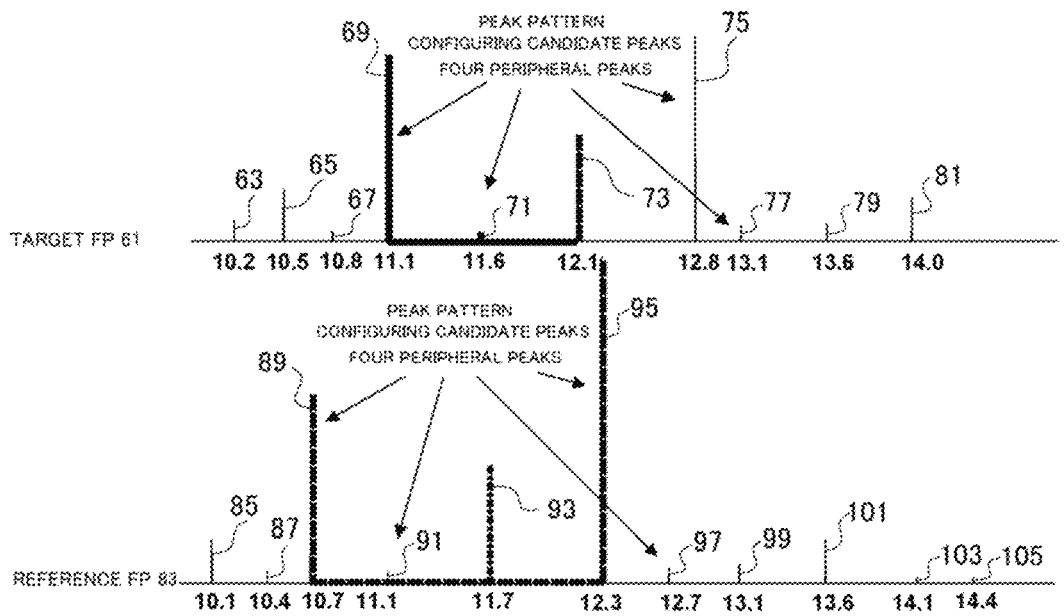
FIG. 27 is an explanatory diagram illustrating comprehensive comparison of peak patterns for the assignment target peak with respect to peak patterns for the assignment candidate peak according the first embodiment.
Figure 28:
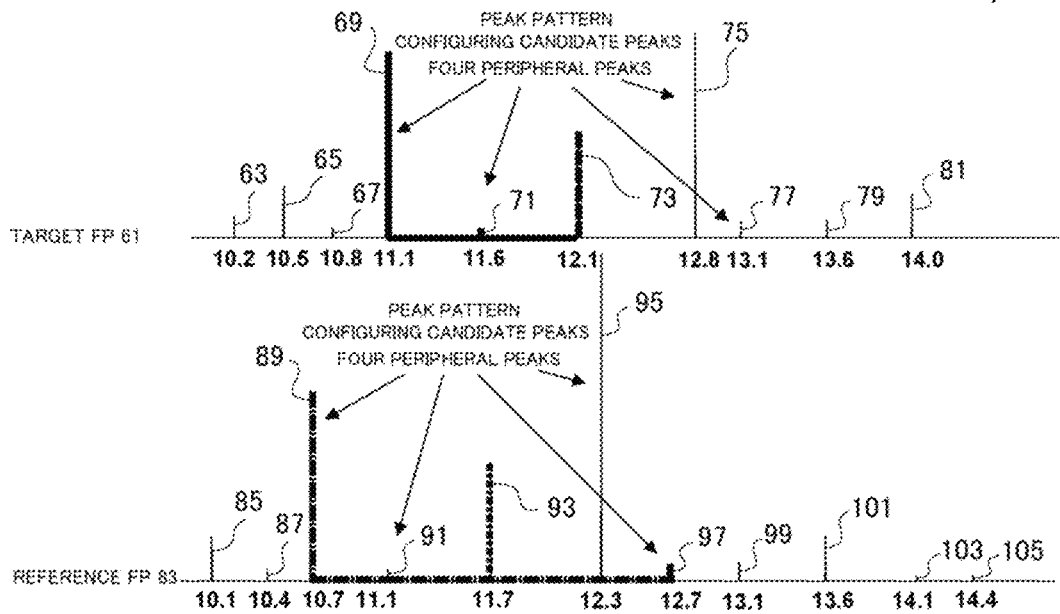
FIG. 28 is an explanatory diagram illustrating comprehensive comparison of peak patterns for the assignment target peak with respect to peak patterns for the assignment candidate peak according the first embodiment.
Figure 29:
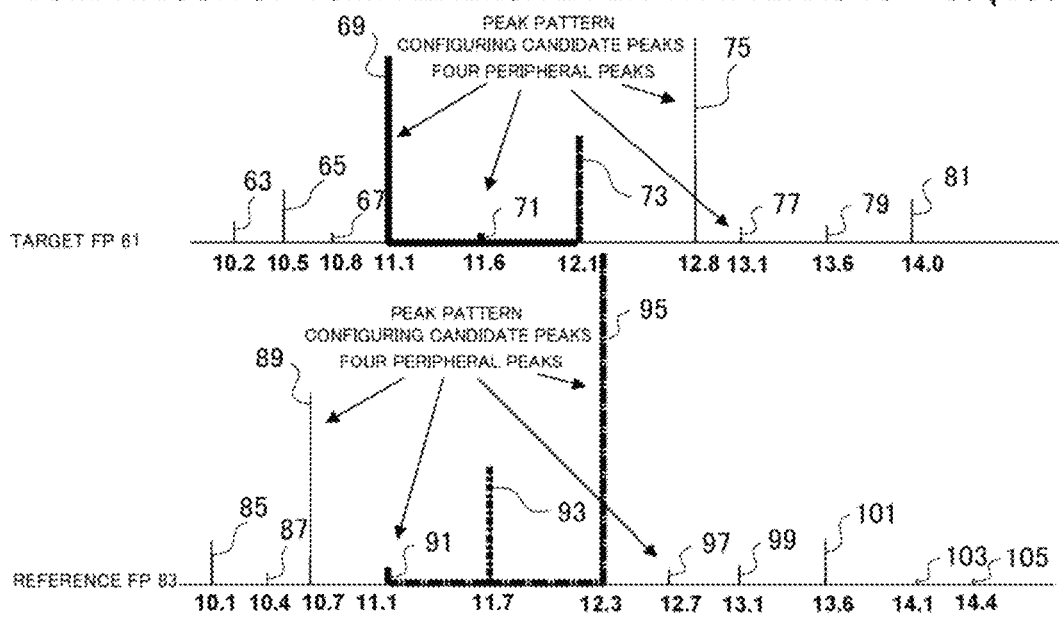
FIG. 29 is an explanatory diagram illustrating comprehensive comparison of peak patterns for the assignment target peak with respect to peak patterns for the assignment candidate peak according the first embodiment.
Figure 30:
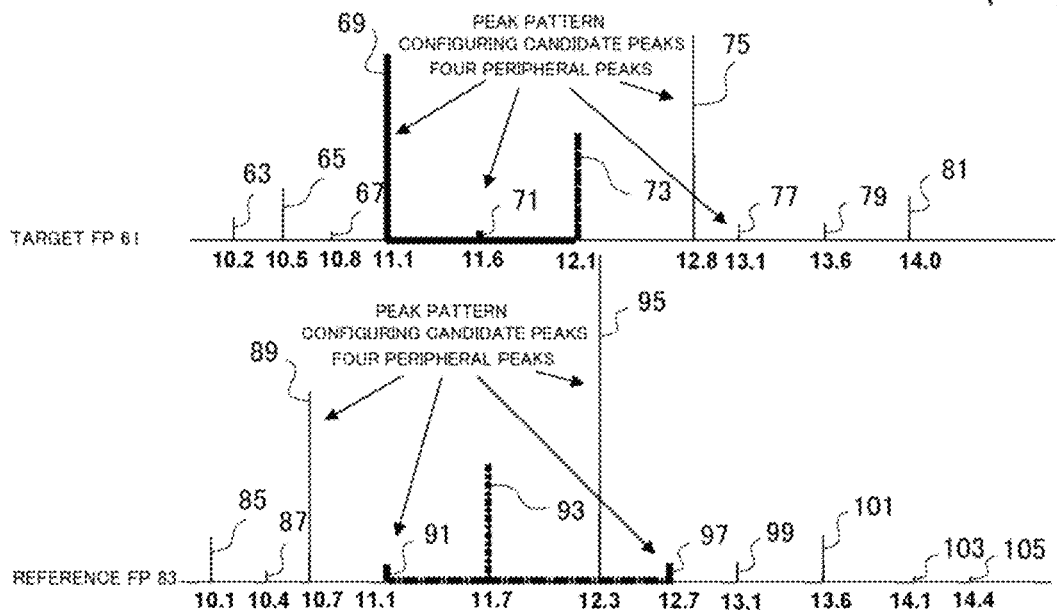
FIG. 30 is an explanatory diagram illustrating comprehensive comparison of peak patterns for the assignment target peak with respect to peak patterns for the assignment candidate peak according the first embodiment.
Figure 31:
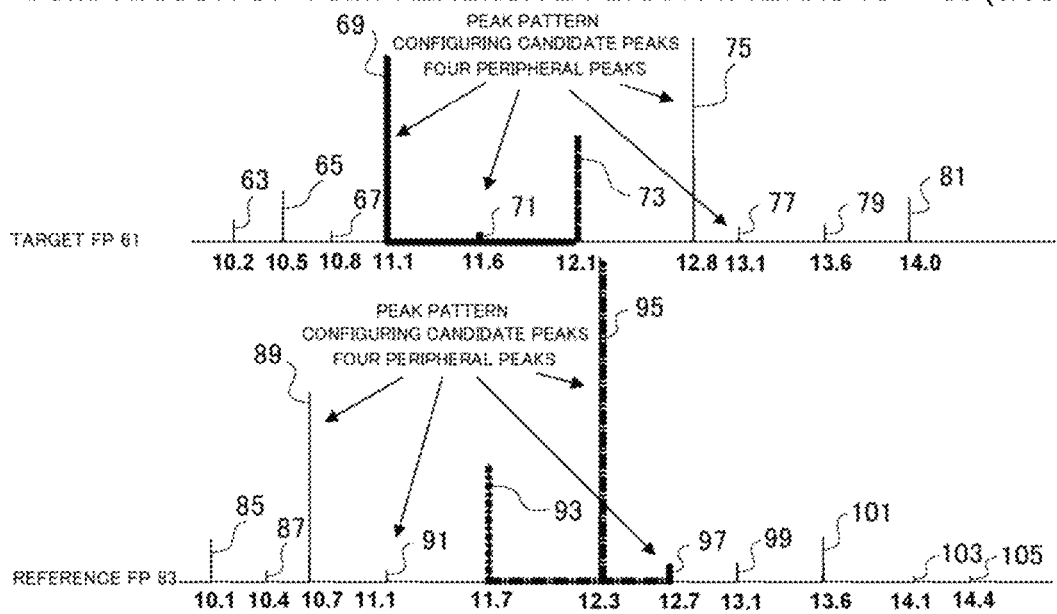
FIG. 31 is an explanatory diagram illustrating comprehensive comparison of peak patterns for the assignment target peak with respect to peak patterns for the assignment candidate peak according the first embodiment.
Figure 32:
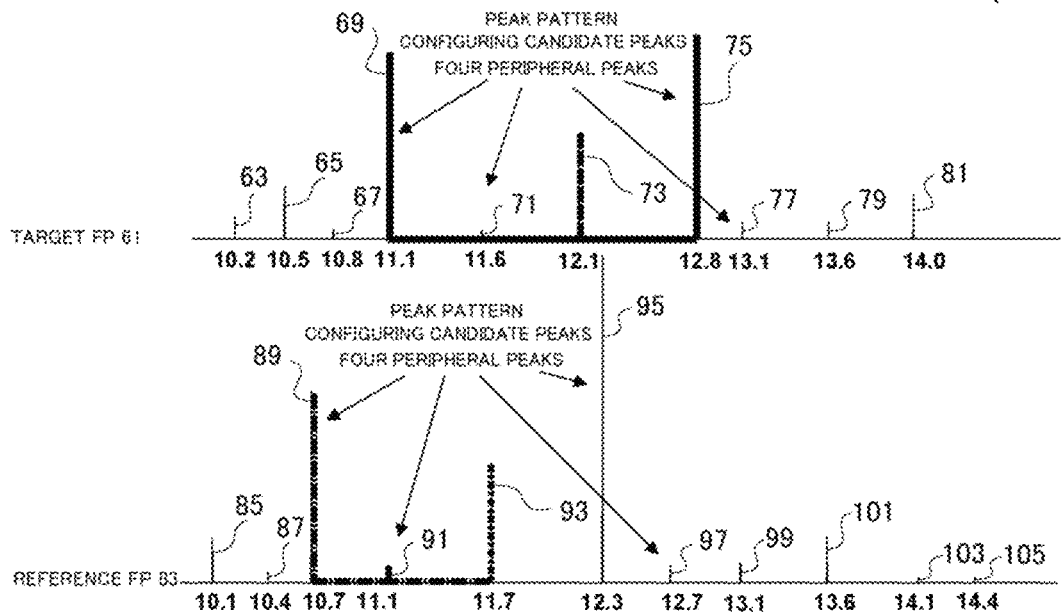
FIG. 32 is an explanatory diagram illustrating comprehensive comparison of peak patterns for the assignment target peak with respect to peak patterns for the assignment candidate peak according the first embodiment.
Figure 33:
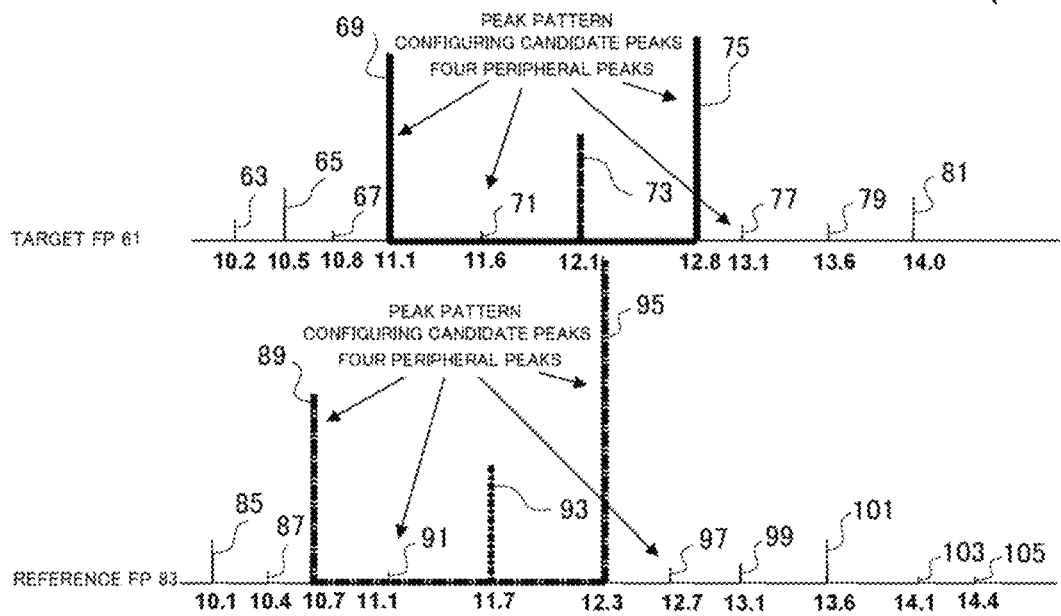
FIG. 33 is an explanatory diagram illustrating comprehensive comparison of peak patterns for the assignment target peak with respect to peak patterns for the assignment candidate peak according the first embodiment.
Figure 34:
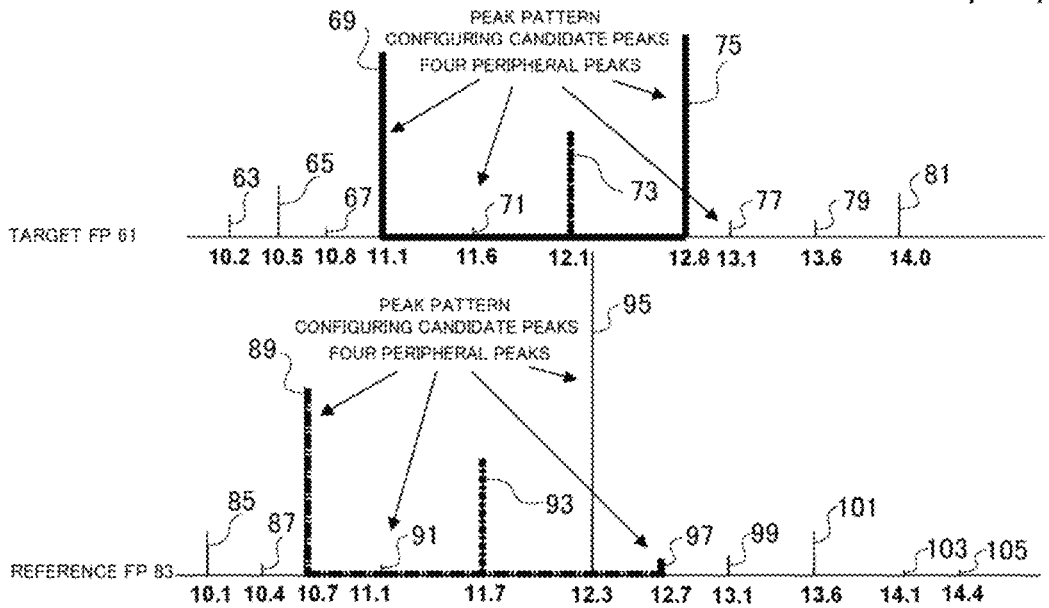
FIG. 34 is an explanatory diagram illustrating comprehensive comparison of peak patterns for the assignment target peak with respect to peak patterns for the assignment candidate peak according the first embodiment.
Figure 35:
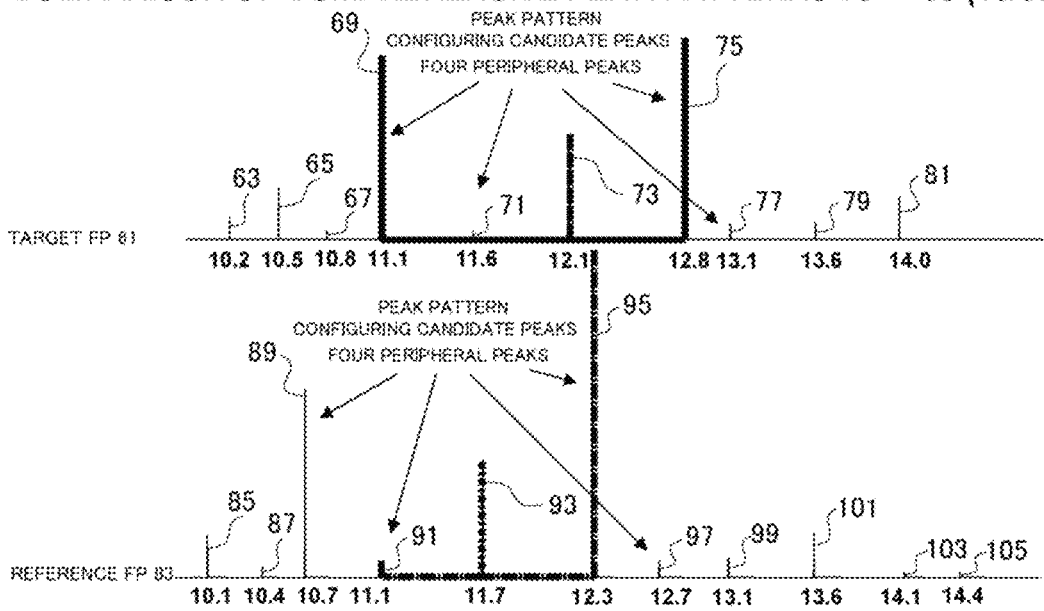
FIG. 35 is an explanatory diagram illustrating comprehensive comparison of peak patterns for the assignment target peak with respect to peak patterns for the assignment candidate peak according the first embodiment.
Figure 36:
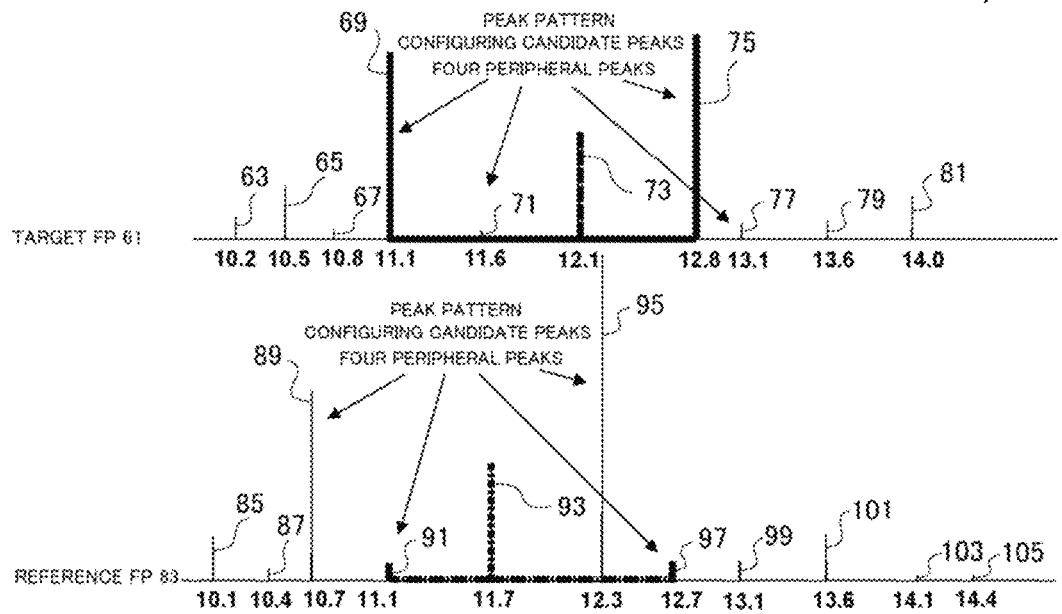
FIG. 36 is an explanatory diagram illustrating comprehensive comparison of peak patterns for the assignment target peak with respect to peak patterns for the assignment candidate peak according the first embodiment.
Figure 37:
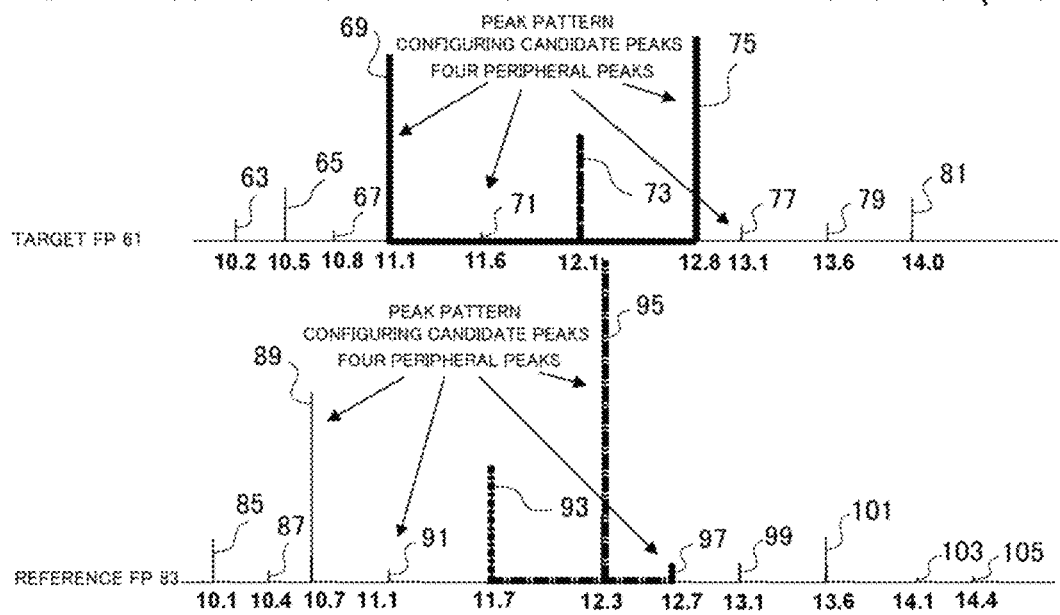
FIG. 37 is an explanatory diagram illustrating comprehensive comparison of peak patterns for the assignment target peak with respect to peak patterns for the assignment candidate peak according the first embodiment.
Figure 38:
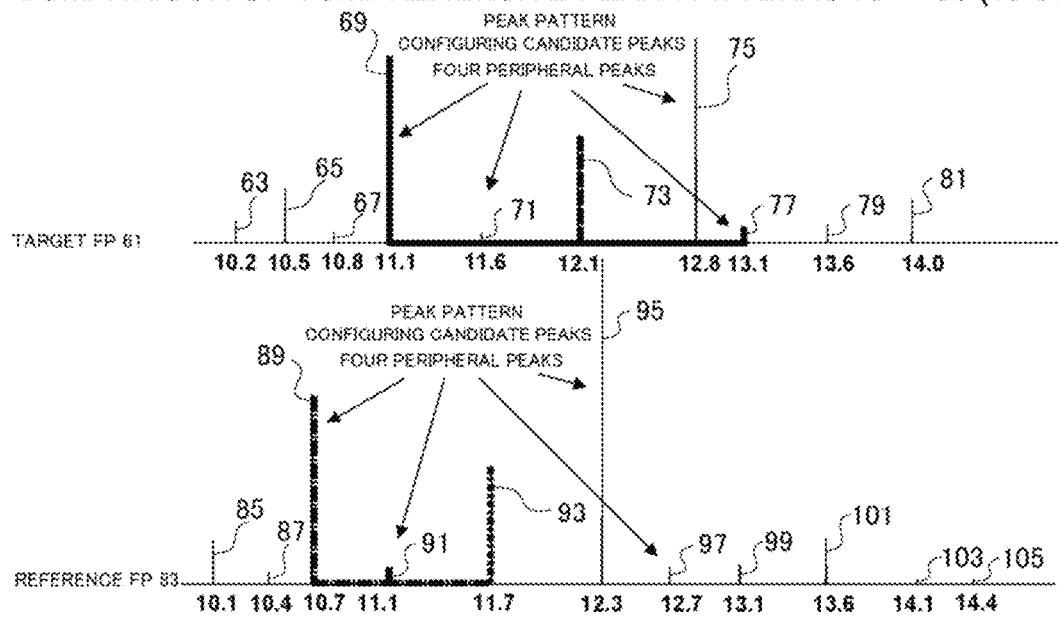
FIG. 38 is an explanatory diagram illustrating comprehensive comparison of peak patterns for the assignment target peak with respect to peak patterns for the assignment candidate peak according the first embodiment.
Figure 39:
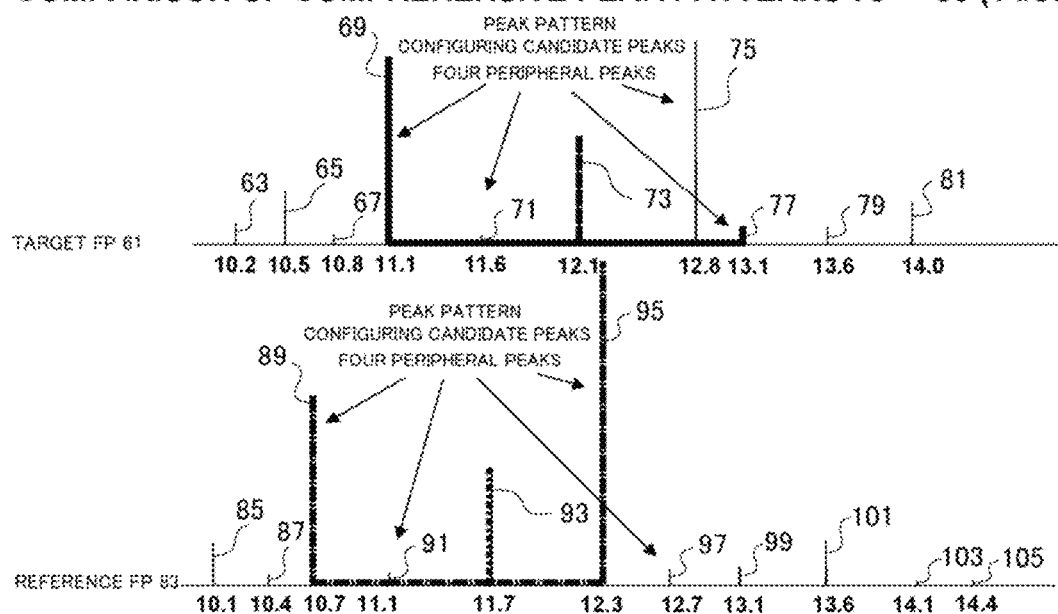
FIG. 39 is an explanatory diagram illustrating comprehensive comparison of peak patterns for the assignment target peak with respect to peak patterns for the assignment candidate peak according the first embodiment.
Figure 40:
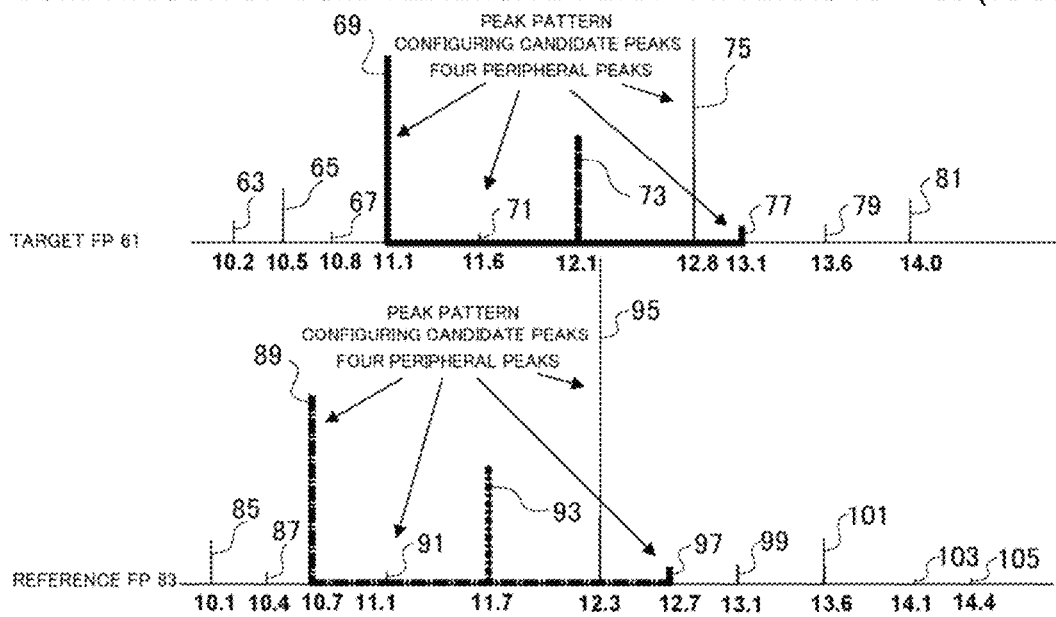
FIG. 40 is an explanatory diagram illustrating comprehensive comparison of peak patterns for the assignment target peak with respect to peak patterns for the assignment candidate peak according the first embodiment.
Figure 41:
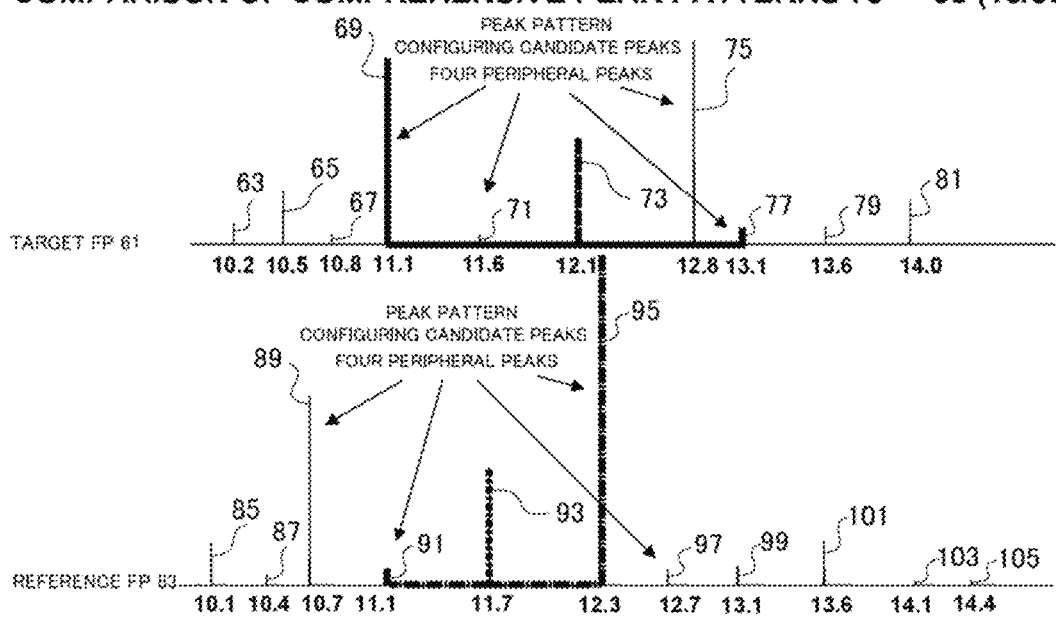
FIG. 41 is an explanatory diagram illustrating comprehensive comparison of peak patterns for the assignment target peak with respect to peak patterns for the assignment candidate peak according the first embodiment.
Figure 42:
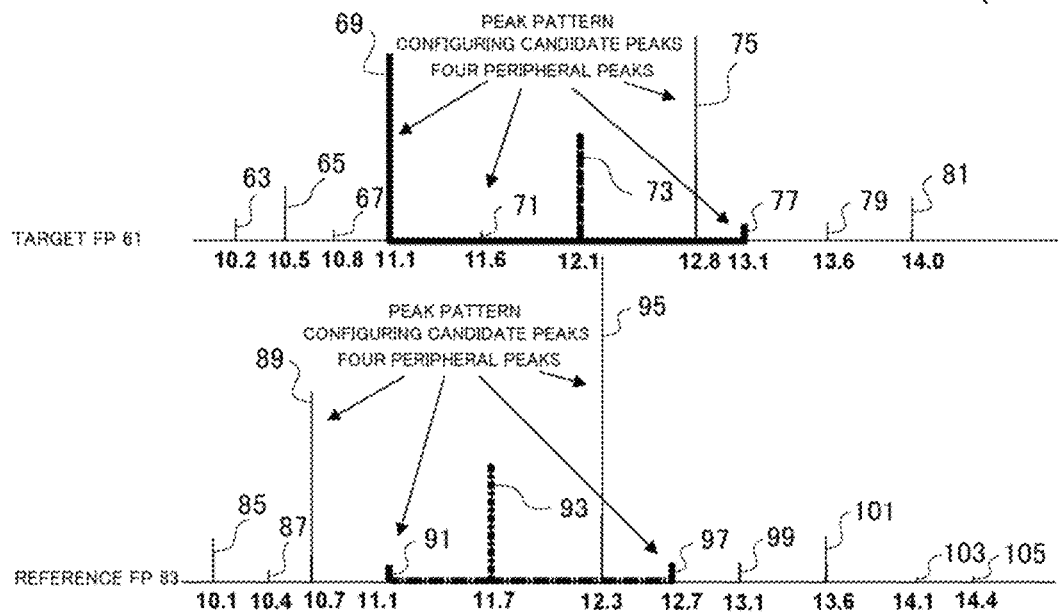
FIG. 42 is an explanatory diagram illustrating comprehensive comparison of peak patterns for the assignment target peak with respect to peak patterns for the assignment candidate peak according the first embodiment.
Figure 43:
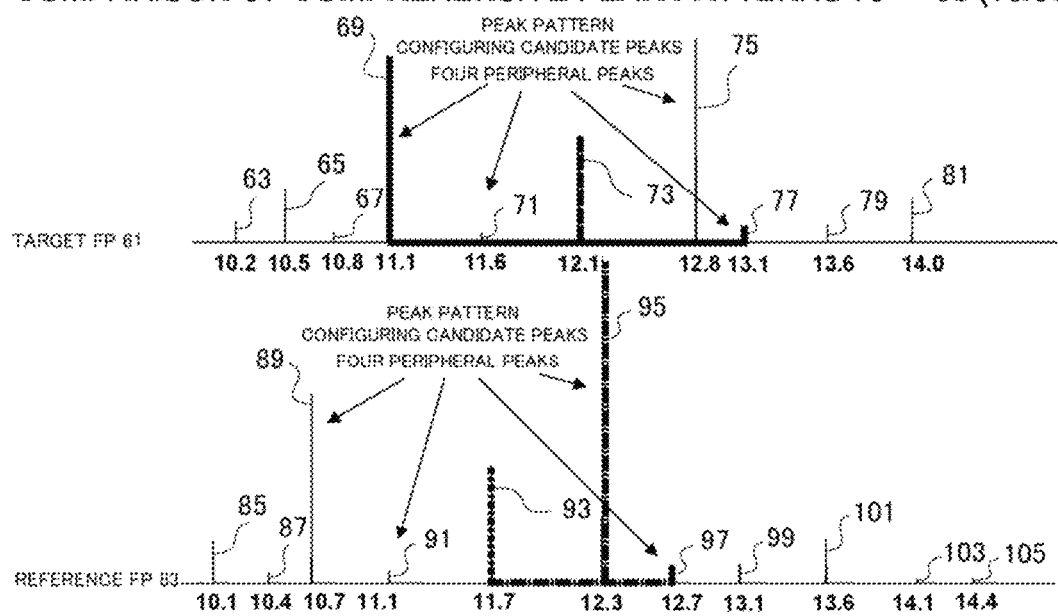
FIG. 43 is an explanatory diagram illustrating comprehensive comparison of peak patterns for the assignment target peak with respect to peak patterns for the assignment candidate peak according the first embodiment.
Figure 44:
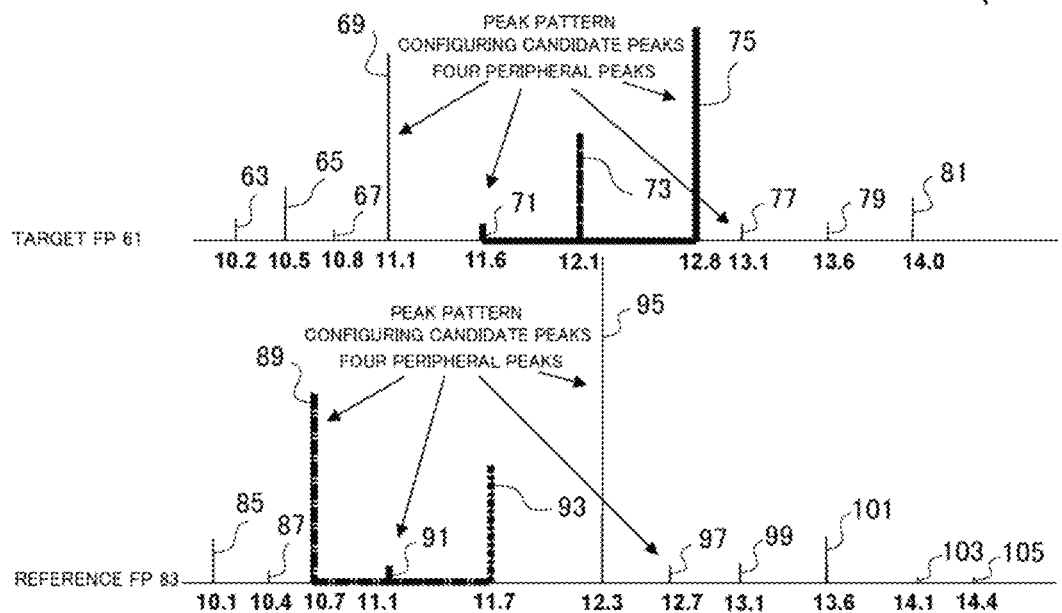
FIG. 44 is an explanatory diagram illustrating comprehensive comparison of peak patterns for the assignment target peak with respect to peak patterns for the assignment candidate peak according the first embodiment.
Figure 45:
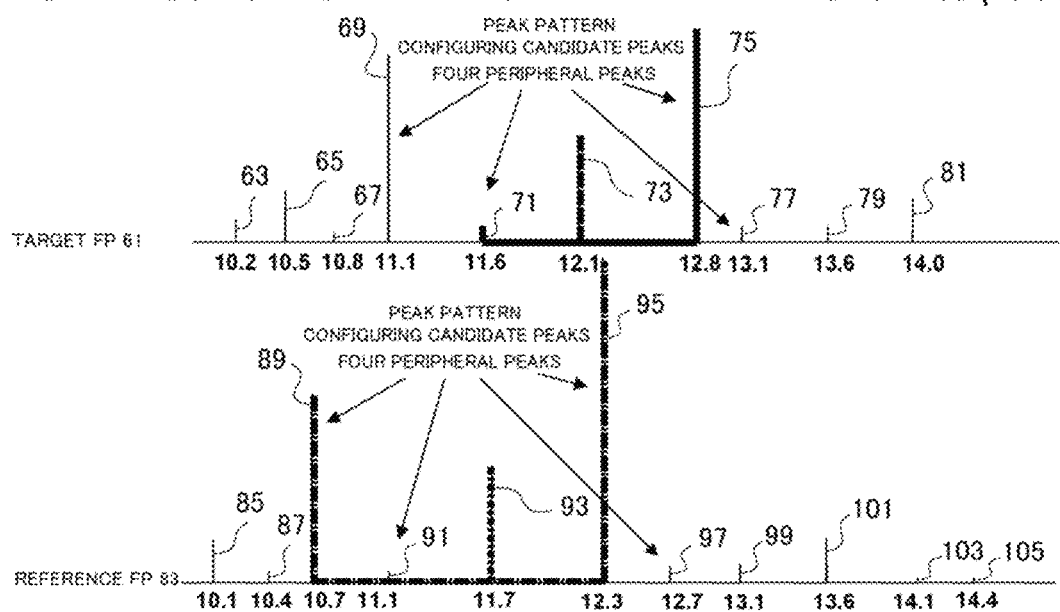
FIG. 45 is an explanatory diagram illustrating comprehensive comparison of peak patterns for the assignment target peak with respect to peak patterns for the assignment candidate peak according the first embodiment.
Figure 46:
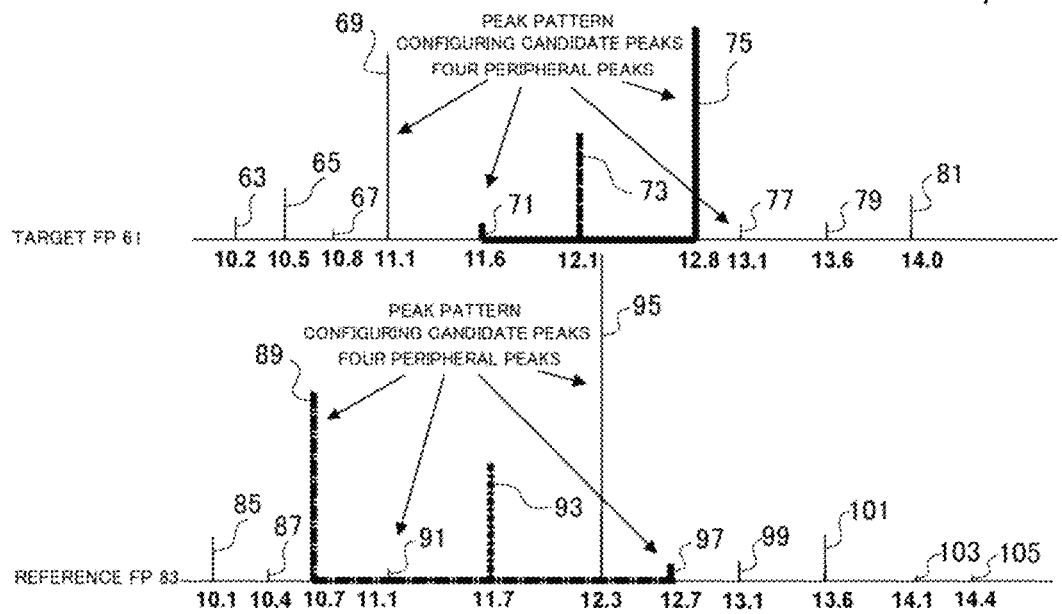
FIG. 46 is an explanatory diagram illustrating comprehensive comparison of peak patterns for the assignment target peak with respect to peak patterns for the assignment candidate peak according the first embodiment.
Figure 47:
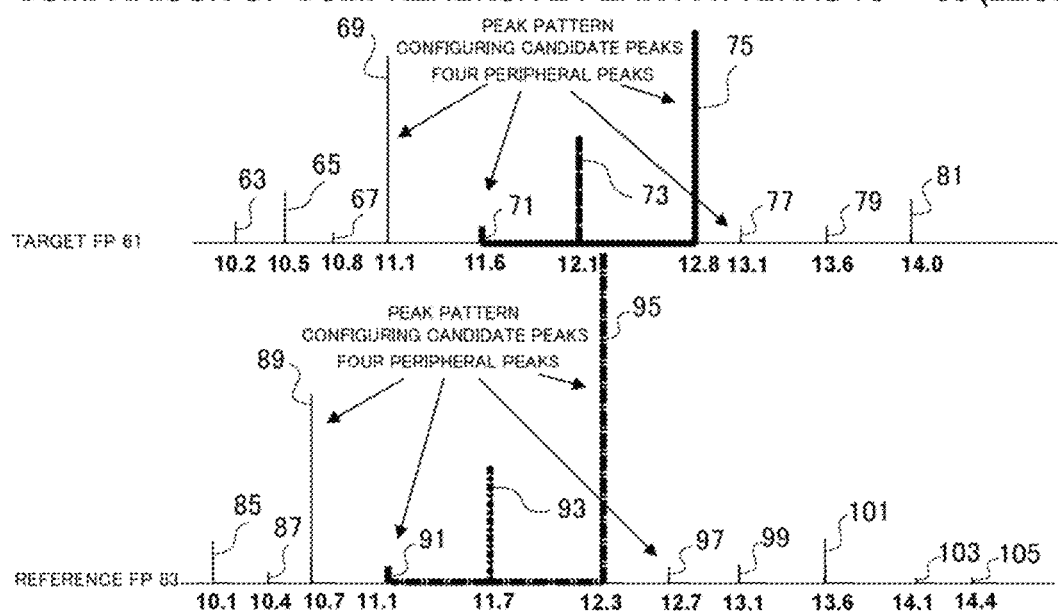
FIG. 47 is an explanatory diagram illustrating comprehensive comparison of peak patterns for the assignment target peak with respect to peak patterns for the assignment candidate peak according the first embodiment.
Figure 48:
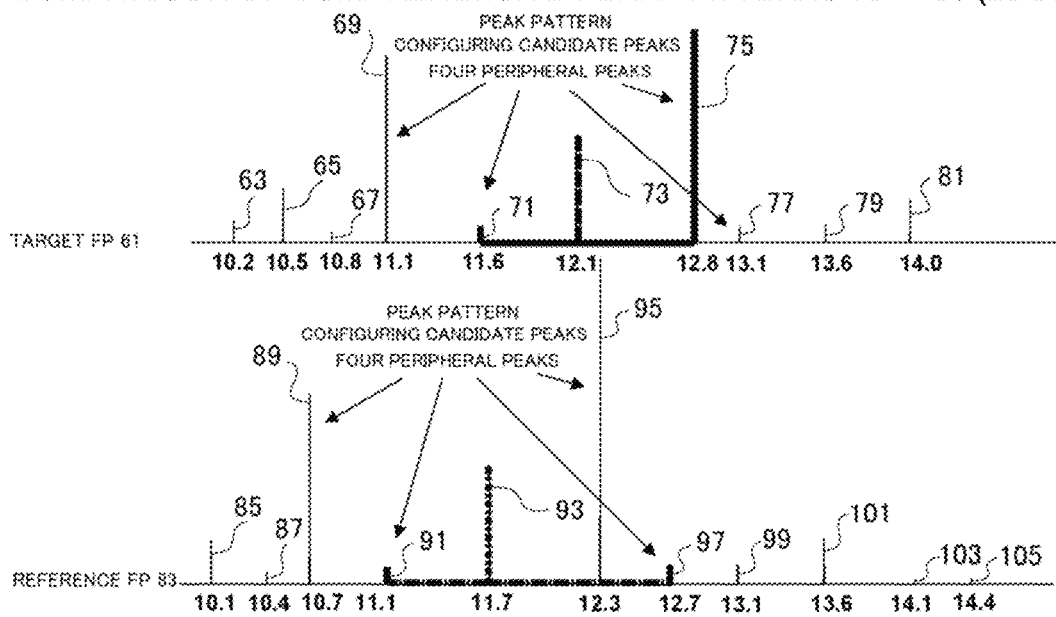
FIG. 48 is an explanatory diagram illustrating comprehensive comparison of peak patterns for the assignment target peak with respect to peak patterns for the assignment candidate peak according the first embodiment.
Figure 49:
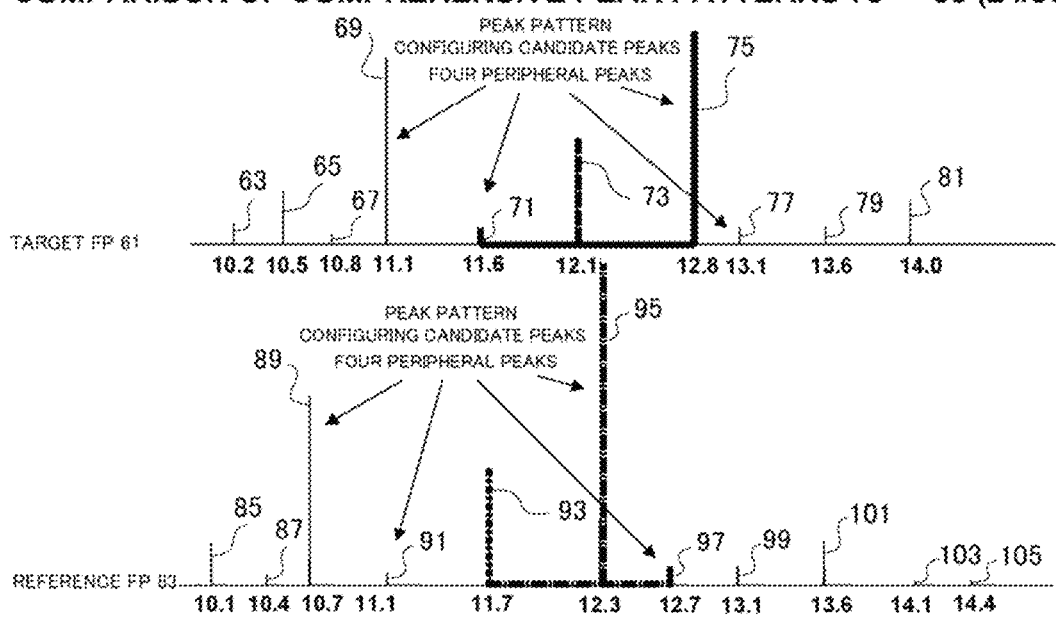
FIG. 49 is an explanatory diagram illustrating comprehensive comparison of peak patterns for the assignment target peak with respect to peak patterns for the assignment candidate peak according the first embodiment.
Figure 50:
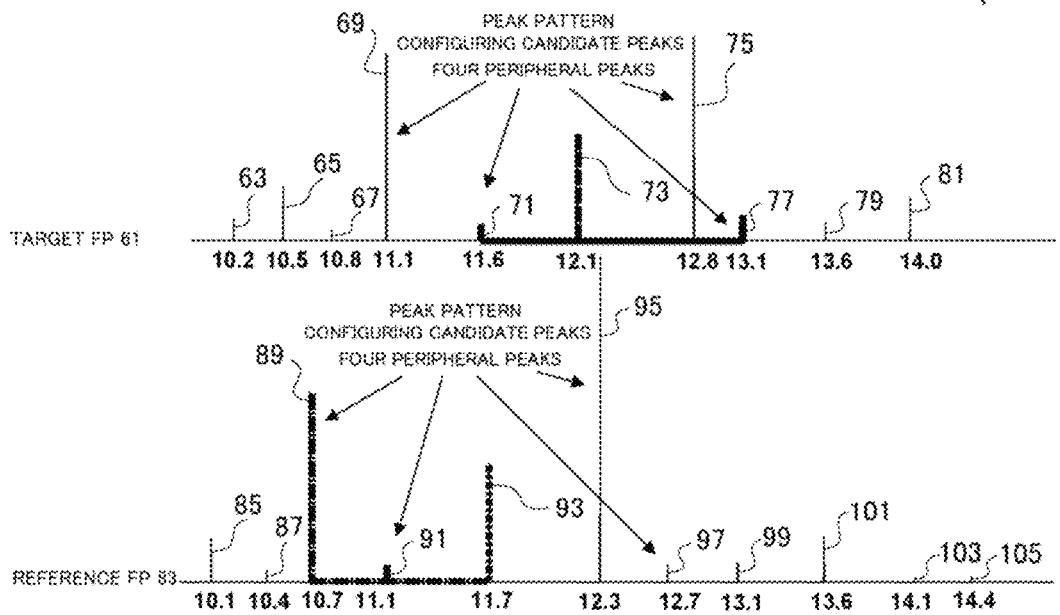
FIG. 50 is an explanatory diagram illustrating comprehensive comparison of peak patterns for the assignment target peak with respect to peak patterns for the assignment candidate peak according the first embodiment.
Figure 51:
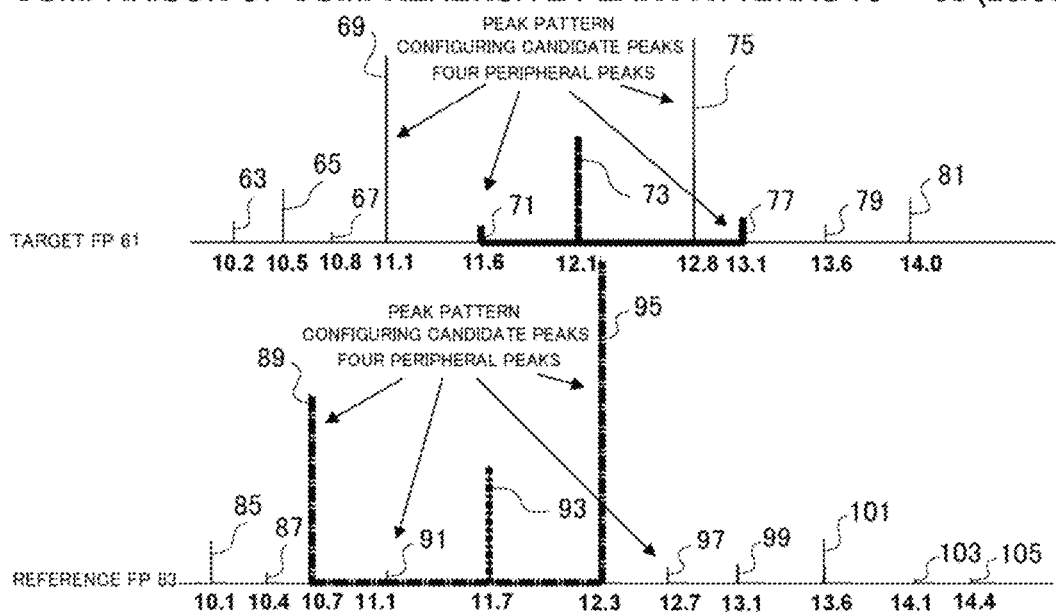
FIG. 51 is an explanatory diagram illustrating comprehensive comparison of peak patterns for the assignment target peak with respect to peak patterns for the assignment candidate peak according the first embodiment.
Figure 52:
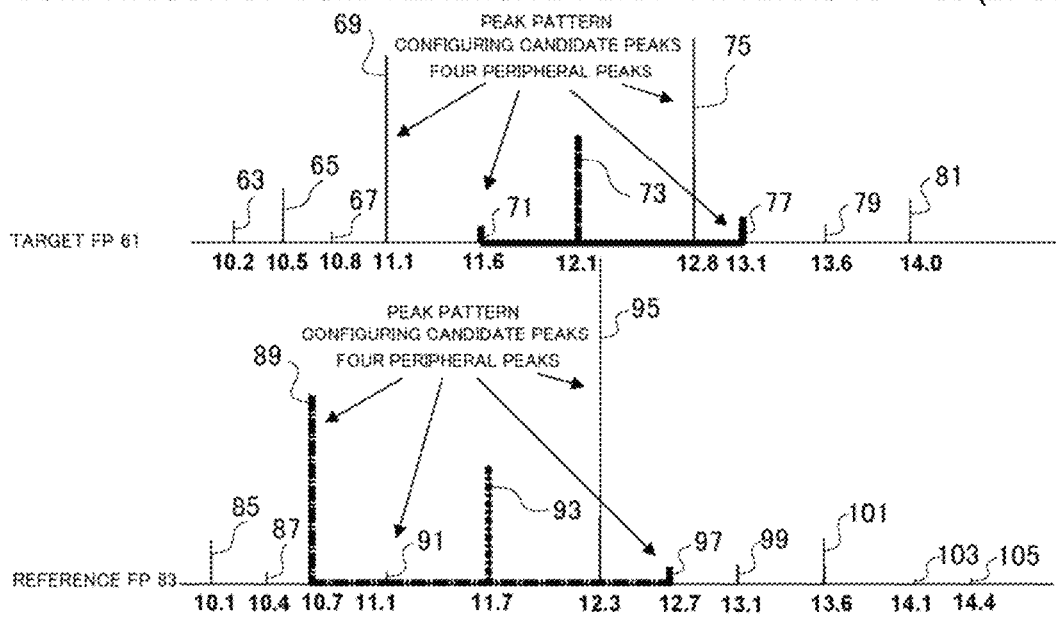
FIG. 52 is an explanatory diagram illustrating comprehensive comparison of peak patterns for the assignment target peak with respect to peak patterns for the assignment candidate peak according the first embodiment.
Figure 53:
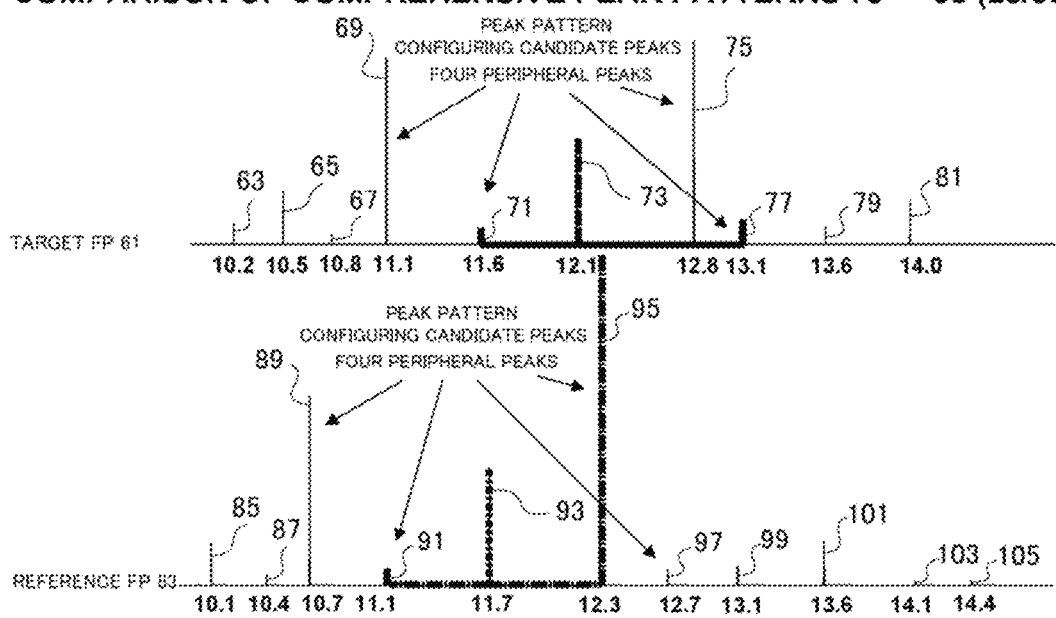
FIG. 53 is an explanatory diagram illustrating comprehensive comparison of peak patterns for the assignment target peak with respect to peak patterns for the assignment candidate peak according the first embodiment.
Figure 54:
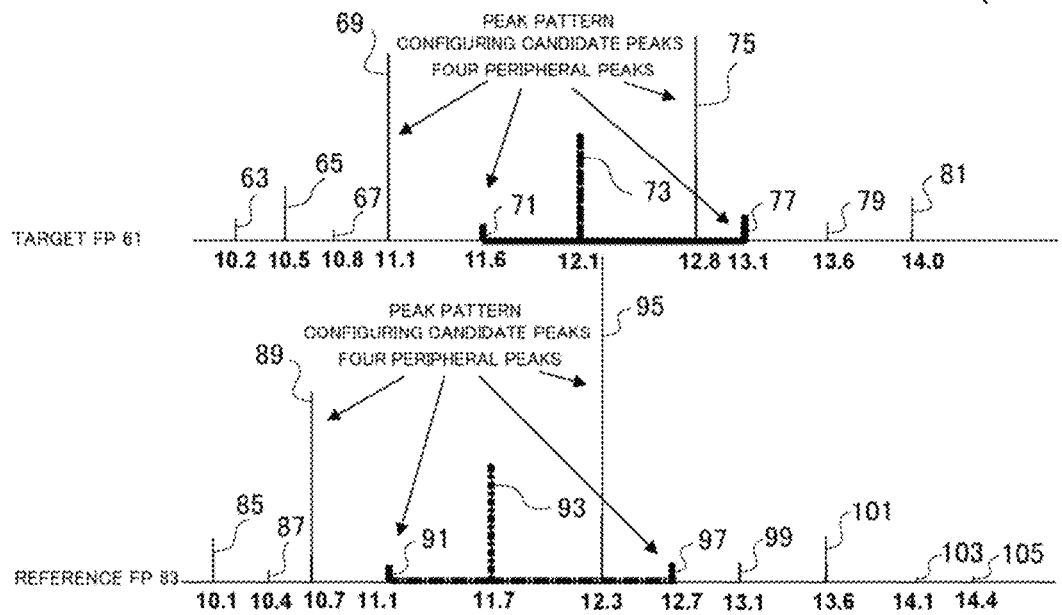
FIG. 54 is an explanatory diagram illustrating comprehensive comparison of peak patterns for the assignment target peak with respect to peak patterns for the assignment candidate peak according the first embodiment.
Figure 55:
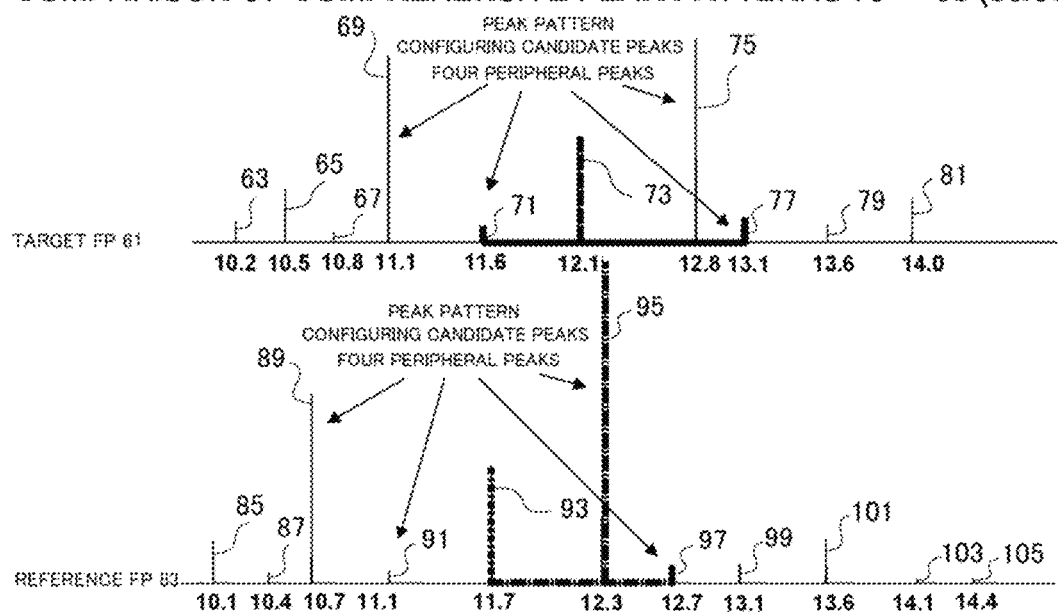
FIG. 55 is an explanatory diagram illustrating comprehensive comparison of peak patterns for the assignment target peak with respect to peak patterns for the assignment candidate peak according the first embodiment.
Figure 56:
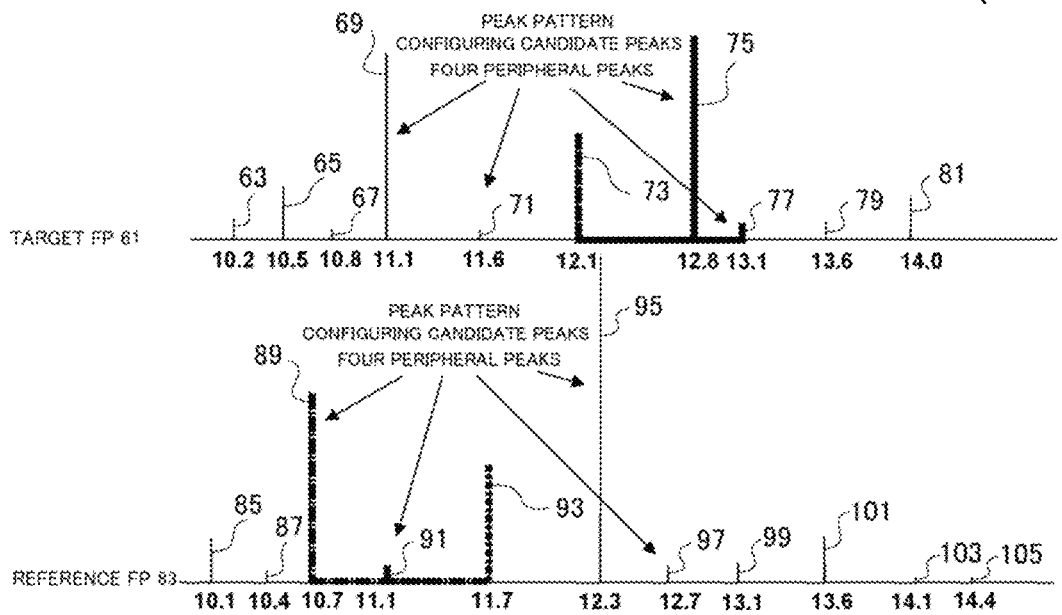
FIG. 56 is an explanatory diagram illustrating comprehensive comparison of peak patterns for the assignment target peak with respect to peak patterns for the assignment candidate peak according the first embodiment.
Figure 57:
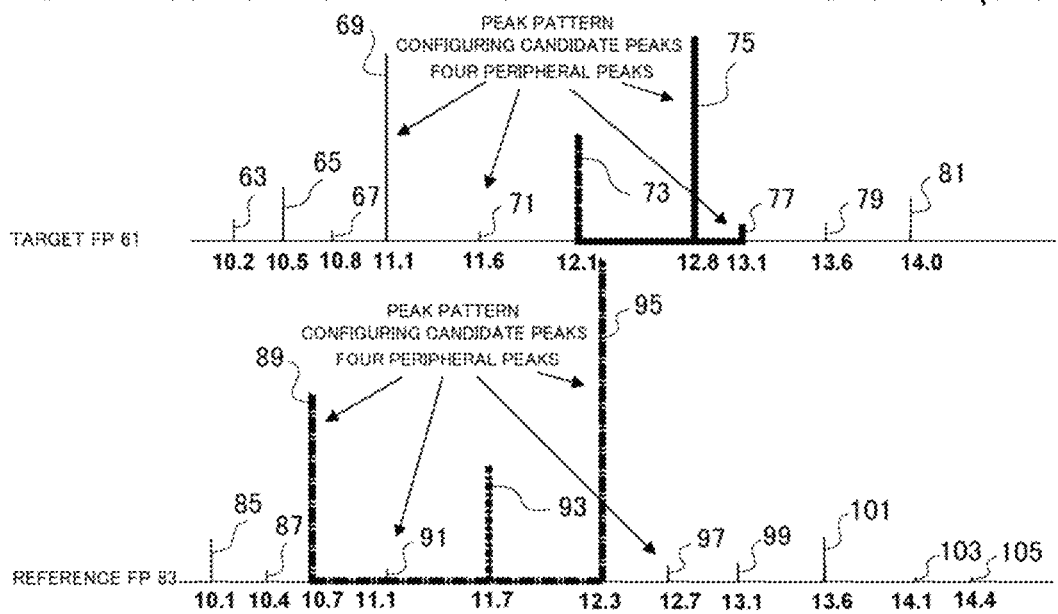
FIG. 57 is an explanatory diagram illustrating comprehensive comparison of peak patterns for the assignment target peak with respect to peak patterns for the assignment candidate peak according the first embodiment.
Figure 58:
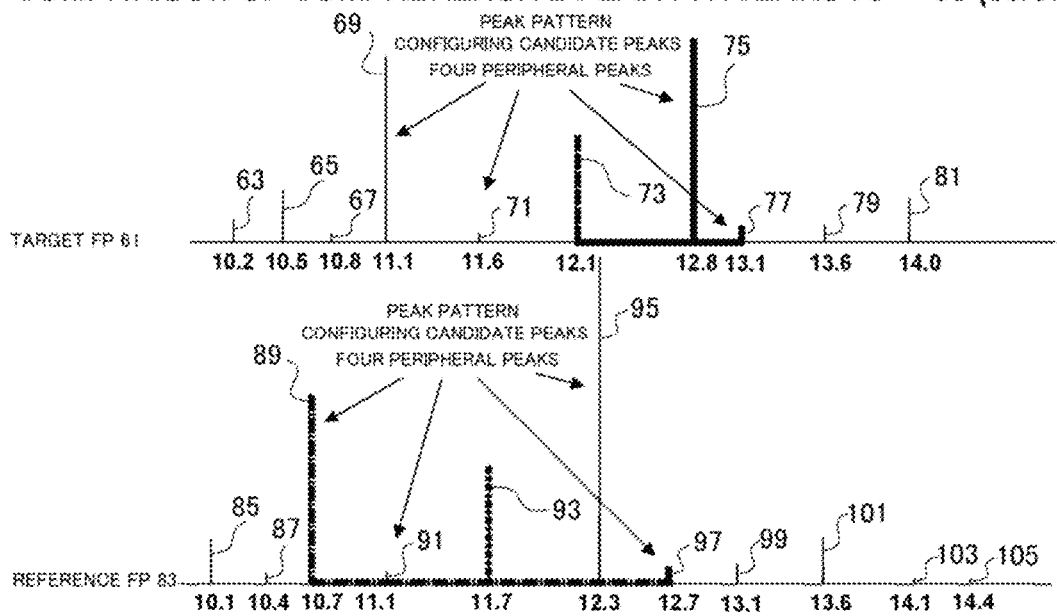
FIG. 58 is an explanatory diagram illustrating comprehensive comparison of peak patterns for the assignment target peak with respect to peak patterns for the assignment candidate peak according the first embodiment.
Figure 59:
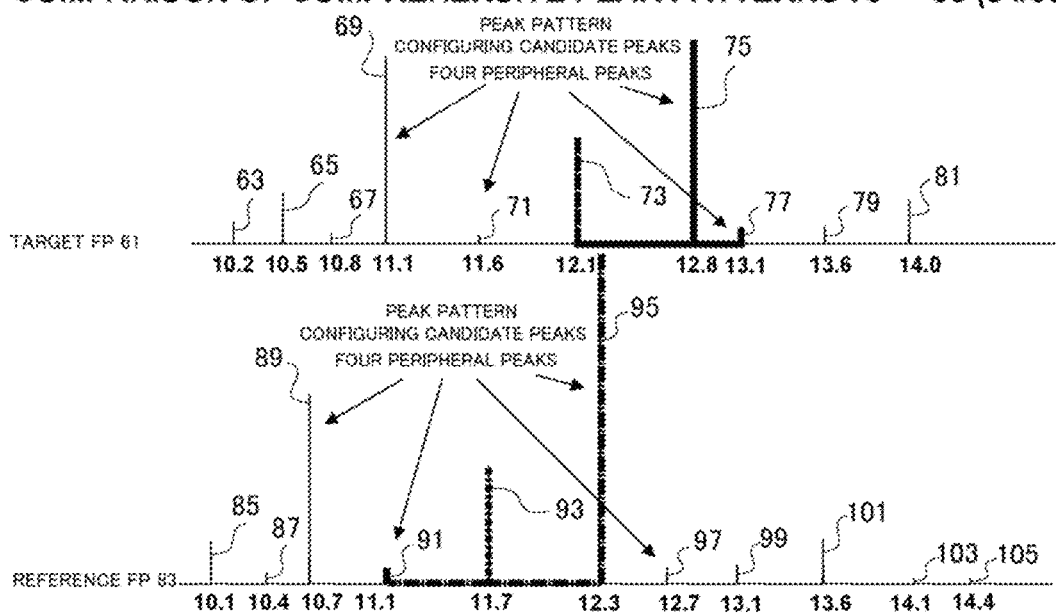
FIG. 59 is an explanatory diagram illustrating comprehensive comparison of peak patterns for the assignment target peak with respect to peak patterns for the assignment candidate peak according the first embodiment.
Figure 60:
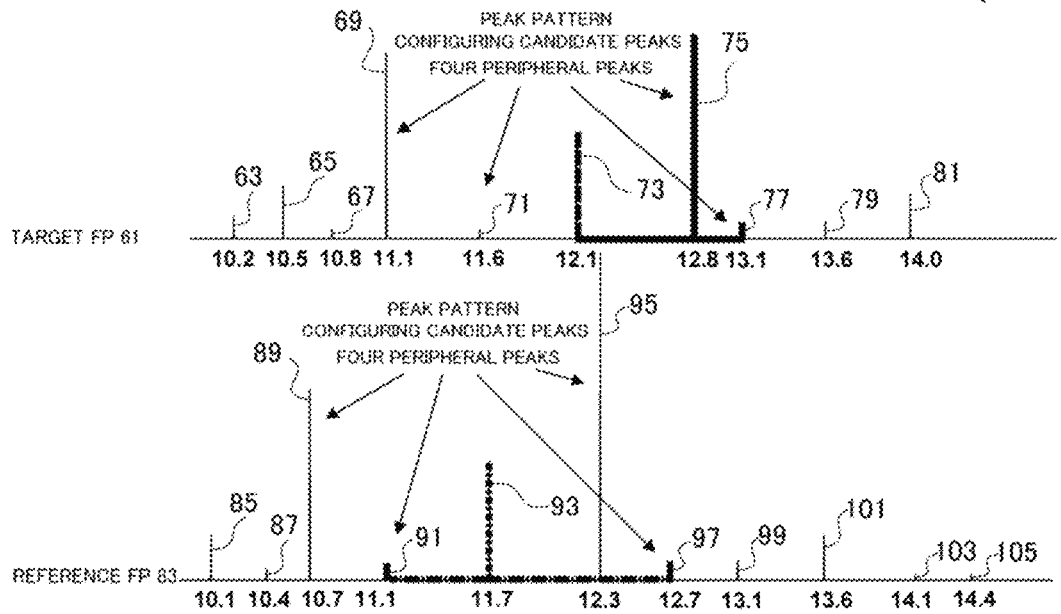
FIG. 60 is an explanatory diagram illustrating comprehensive comparison of peak patterns for the assignment target peak with respect to peak patterns for the assignment candidate peak according the first embodiment.
Figure 61:
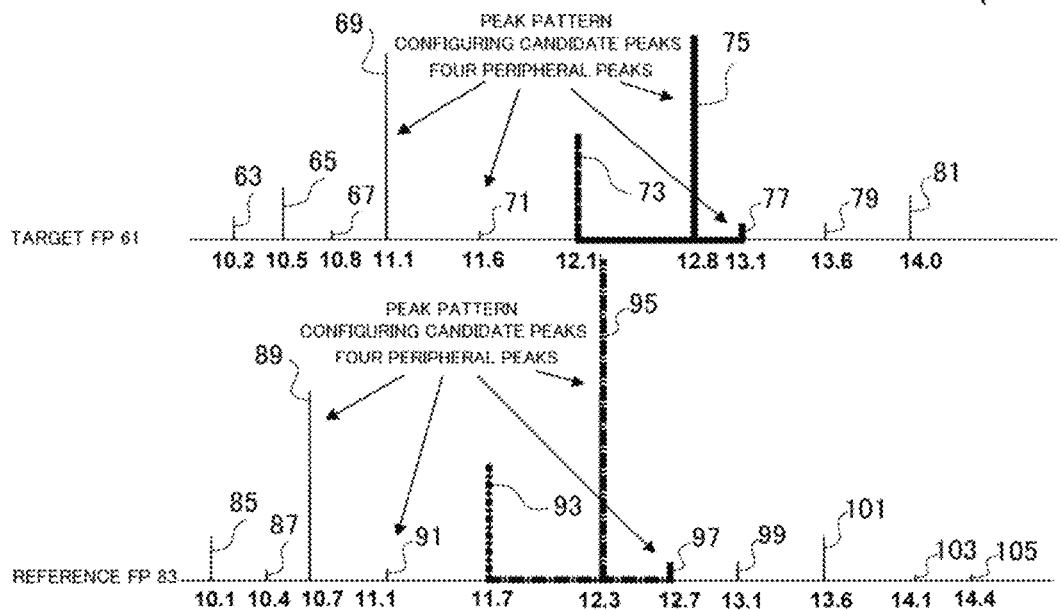
FIG. 61 is an explanatory diagram illustrating comprehensive comparison of peak patterns for the assignment target peak with respect to peak patterns for the assignment candidate peak according the first embodiment.

In addition, in order to perform the assignment according to the peak patterns with higher accuracy, it is necessary to respond to a case in which there is a difference between the number of peaks of the target FP and the number of peaks of the reference FP (in other words, there is a peak that is not present on one side). For this, it is important to prepare peak patterns in which peak pattern configuring peaks are comprehensively changed for both the assignment target peak and the assignment candidate peak, as illustrated in FIGS. 23 to 25.

More specifically, peaks being candidates for the peak pattern configuring peak (hereinafter, peak pattern configuring candidate peaks) are set from among peripheral peaks of the assignment target peak of the target FP in advance. Peak patterns are prepared by setting the peak pattern configuring candidate peaks as the peak pattern configuring peak in turns. Also for the assignment candidate peaks of the reference FP, similarly, peak pattern configuring candidate peaks are set to prepare peak patterns are by setting the peak pattern configuring candidate peaks as the peak pattern configuring peak in turn.

Figure 23:
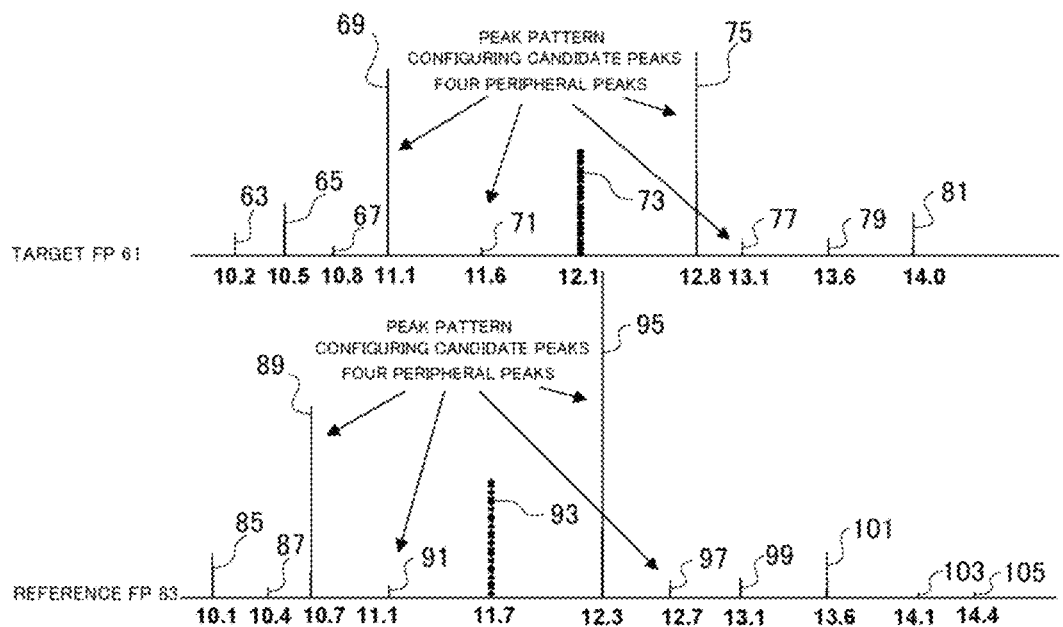
FIG. 23 is a diagram illustrating peak pattern configuring candidate peaks for the assignment target peak and an assignment candidate peak according the first embodiment.

For example, as illustrated in FIG. 23, four peaks (69, 71, 75, and 77) located on the periphery in the time axis direction are set as the peak pattern configuring candidate peaks for the assignment target peak 73, and four peaks (89, 91, 95, and 97) located on the periphery in the time axis direction are set as the peak pattern configuring candidate peaks for the assignment candidate peak 93, and the peak pattern configuring peaks are set to arbitrary two peaks. In such case, peak patterns of 4C2 (=6) patterns are prepared for each of the assignment target peak 73 and the assignment candidate peak 93 as illustrated in FIGS. 24 and 25.

In addition, in a case where ten peak pattern configuring candidate peaks are set, arbitrary two peak pattern configuring peaks are set, and peak patterns of 10C2 (=45) patterns are prepared for each of the assignment target peak and the assignment candidate peak. In a case where arbitrary four peaks are set as the peak pattern configuring peaks, peak patterns of 10C4 (=210) patterns are prepared for each of the assignment target peak and the assignment candidate peak.

The function of the peak assigning part 37 will be described further with reference to FIGS. 26 to 69.

The peak assigning part 37 calculates the degree of matching between peak patterns (hereinafter, referred to as P_Sim) based on differences in corresponding peaks and retention time points over all the peak patterns for the assignment target peak and the assignment candidate peaks prepared by the peak pattern preparing part 35. The peak assigning part 37 sets the minimum value of the P_Sim (hereinafter, referred to as P_Sim_min) as the degree of matching between peak patterns of the assignment target peak and the assignment candidate peak.

For example, as illustrated in FIGS. 26 to 61, for each one of the assignment target peak 73 and the assignment candidate peak 93, four peripheral peaks located in front and in the rear in the time axis direction are set as the peak pattern configuring candidate peaks, and two arbitrary peaks are set as the peak pattern configuring peaks. According to this setting, peak patterns of 4C2 (=6) patterns are prepared for each one of the assignment target peak and the assignment candidate peak. Accordingly, the P_Sims of the assignment target peak 73 and the assignment candidate peak 93 are calculated as 6 patterns×6 patterns (=36), and the P_Sim_min that is the minimum value of the P_Sims is set as the degree of matching between the assignment target peak 73 and the assignment candidate peak 93.

Incidentally, in a case where ten peak pattern configuring candidate peaks located in front and in the rear in the time axis direction are set and the peak pattern configuring peaks are set as two arbitrary peaks for each one of the assignment target peak 73 and the assignment candidate peak 93, peak patterns of 10C2 (=45) patterns are prepared for each one of the assignment target peak and the assignment candidate peak. Accordingly, the P_Sims of the assignment target peak 73 and the assignment candidate peak 93 are calculated as 45 patterns×45 patterns (=2025), and the P_Sim_min that is the minimum value of the P_Sims is set as the degree of matching between the assignment target peak 73 and the assignment candidate peak 93. In addition, in a case where the peak pattern configuring peaks are set as four arbitrary peaks, peak patterns of 10C4 (=210) patterns are prepared for each one of the assignment target peak and the assignment candidate peak. Accordingly, the P_Sims of the assignment target peak 73 and the assignment candidate peak 93 are calculated as 210 patterns×210 patterns (=44100), and the P_Sim_min that is the minimum value of the P_Sims is set as the degree of matching between the assignment target peak 73 and the assignment candidate peak 93.

The P_Sim is similarly calculated for all the assignment candidate peaks of the assignment target peak 73.

A calculating method of the degree of matching between peak patterns for comparing peak patterns each configured by three peaks will be described with reference to FIGS. 62 and 63. In this case, the peak pattern 115 of the assignment target peak 73 and the peak pattern 119 of the assignment candidate pattern 95 will be described as an example.

In the peak pattern 115 of the assignment target peak 73, a peak and a retention time point of the assignment target peak 73 are assumed to be p1 and r1, a peak and a retention time point of a peak pattern configuring peak 71 are assumed to be dn1 and cn1, and a peak and a retention time point of the peak pattern configuring peak 75 are assumed to be dn2 and cn2.

In the peak pattern 119 of the assignment candidate peak 95, a peak and a retention time point of the assignment candidate peak 95 are assumed to be p2 and r2, a peak and a retention time point of the peak pattern configuring peak 93 are assumed to be fn1 and en1, and a peak and a retention time point of a peak pattern configuring peak 97 are assumed to be fn2 and en2.

When the degree of matching between peak patterns is P_Sim, the degree of matching between peak patterns (P_Sim (73–95)), each configured by three peaks, of the assignment target peak 73 and the assignment candidate peak 95 is calculated as:

$$P\_Sim(73-95) = (|p1-p2|+1) \times (|(r1-(r2+d)|+1) + \\ (|dn1-fn1|+1) \times (|(cn1-r1)-(en1-r2)|+1) + \\ (|dn2-fn2|+1) \times (|(cn2-r1)-(en2-r2)|+1).$$

Here, "d" represented in the equation is a value used for correcting the deviation of the retention time point.

The calculating method of the degree of matching between peak patterns used for comparing the peak patterns each configured by five peaks will be described with reference to FIG. 64. In this case, the peak pattern 125 of the assignment target peak 73 and the peak pattern 129 of the assignment candidate peak 95 will be described as an example.

In the peak pattern 125 of the assignment target peak 73, a peak and a retention time point of the assignment target peak 73 are assumed to be p1 and r1, and peaks and retention time points of peak pattern configuring peaks 69, 71, 75, and 77 are assumed to be dn1 and cn1, dn2 and cn2, dn3 and cn3, and dn4 and cn4.

In the peak pattern 129 of the assignment candidate peak 95, a peak and a retention time point of the assignment candidate peak 95 are assumed to be p2 and r2, and peaks and retention time points of peak pattern configuring peaks 91, 93, 97, and 99 are assumed to be fn1 and en1, fn2 and en2, fn3 and en3, and fn4 and en4.

The degree of matching between peak patterns (P_Sim (73–95)), each composed of five peaks, of the assignment target peak 73 and the assignment candidate peak 95 is calculated as:

$$P\_Sim(73-95) = (|p1-p2|+1) \times (|(r1-(r2+d)|+1) + \\ (|dn1-fn1|+1) \times (|(cn1-r1)-(en1-r2)|+1) + \\ (|dn2-fn2|+1) \times (|(cn2-r1)-(en2-r2)|+1) + \\ (|dn3-fn3|+1) \times (|(cn3-r1)-(en3-r2)|+1) + \\ (|dn4-fn4|+1) \times (|(cn4-r1)-(en4-r2)|+1).$$

Here, "d" represented in the equation is a value used for correcting the deviation of the retention time point.

The peak assigning part 37 calculates the degree of matching between the UV spectra of the assignment target peak and the assignment candidate peak as illustrated in FIGS. 67 and 68.

FIG. 65 is the diagram illustrating UV spectra (135 and 139) of the assignment target peak 73 and the assignment candidate peak 95, and, as illustrated in FIG. 66, the degree of matching between these two UV spectra (UV_Sim(73–95)) is calculated as:

$$UV\_Sim(73-95) = RMSD(135 \text{ vs } 139).$$

The RMSD is defined as a mean square deviation and is defined as the square root of arithmetic average of a value that is a square of a distance between two corresponding points (dis). In other words, RMSD is calculated as $\sqrt{\{\Sigma dis^2/n\}}$.

Here, "n" is the number of dis.

Here, the waveform of the UV spectrum has a maximum wavelength and a minimum wavelength, and the degree of matching also can be calculated by comparing either the maximum wavelengths or the minimum wavelengths. However, compounds having no absorbance property, compounds having similar absorbance properties or the like, they may quite differs from each other in the waveforms as a whole while having the same maximum and minimum wavelengths. Accordingly, there is a risk that the degree of matching in the waveform may not be calculated by comparing either the maximum wavelengths or the minimum wavelengths.

In contrast to this, in a case where the RMSD is used in accordance with the waveforms of the UV spectra, the whole waveforms are compared with each other. Therefore, the degree of matching between the waveforms of the UV spectra can be calculated with accuracy, whereby even compounds having no absorbance property or compounds having similar absorbance properties can be identified with accuracy.

The degree of matching between the UV spectra is calculated similarly for all the assignment candidate peaks of the assignment target peak 73.

Further, the peak assigning part 37 calculates the degree of matching of an assignment candidate peak that is acquired by integrating the above-described two degrees of matching as illustrated in FIG. 67.

As illustrated in FIG. 67, the degree (SCORE(73–95)) of matching of the assignment candidate peaks is calculated by multiplying the degree of matching between the peak patterns by the degree of matching between the UV spectra. It is assumed that a score representing the degree of matching between peak patterns 73 and 95 is P_Sim_min(73–95), and a score representing the degree of matching between the corresponding UV waveform data 135 and 139 is UV_Sim (73–95). At this time, the degree SCORE(73–95) of matching of the assignment candidate peaks is calculated as:

$$SCORE(73-95) = P\_Sim\_min(73-95) \times UV\_Sim(73-95).$$

The degree of matching of the assignment candidate peak is similarly calculated for all the assignment candidate peaks of the assignment target peak 73.

Then, SCOREs of all the assignment candidate peaks are compared to determine an assignment candidate peak having a lowest SCORE as an assignment peak of the assignment target peak 73.

Since the peak assigning part 37 determines the peaks to which the assignment target peaks should be assigned by integrating two viewpoints, it can realize peak assignment with accuracy.

Further, the target FP peak feature value preparing part 7 assigns each peak of the target FP 43 to the reference group FP 45 based on the result of the assignment of the target FP to the reference FP as illustrated in FIG. 68.

Each peak of the target FP 43 is assigned to the reference FP that configures the reference group FP 45 through the above-described assignment process. Based on the result of the assignment, finally, the peaks are assigned to the reference group FP 45.

In addition, the reference group FP 45 is prepared by performing an assignment process like the above for the plurality of reference FPs determined as normal products, and each peak is represented by an average value (black point) of assigned peaks±standard deviation (vertical segmenting line).

FIG. 69 shows the result of assigning the target FP 43 to the reference group FP 45, and this result represents the target FP peak feature values 47 of the target FP 43.

Figure 71:
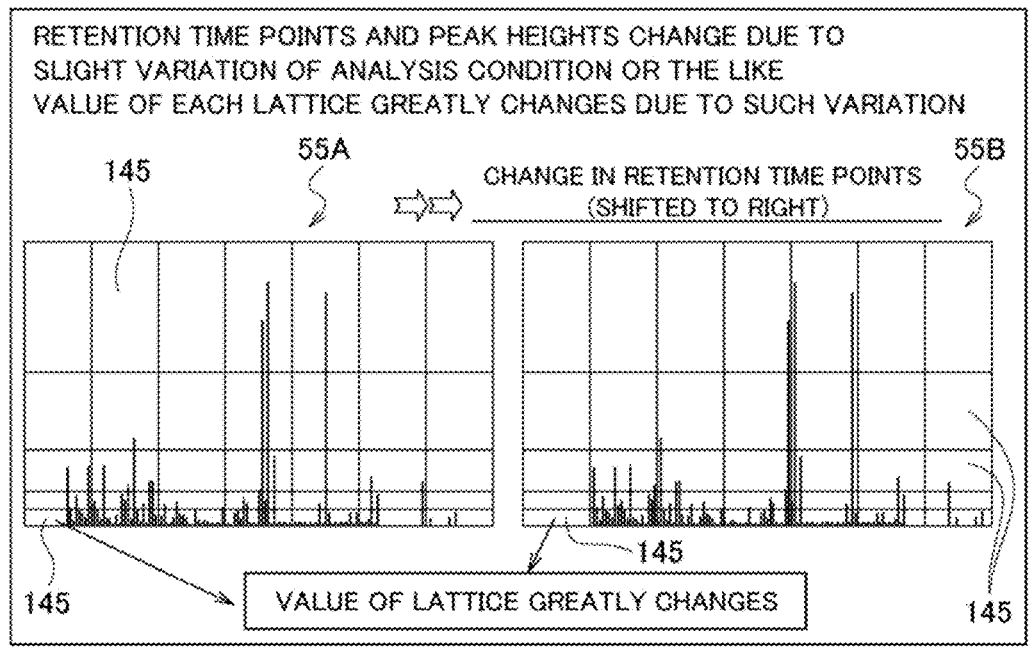
FIG. 71 is a diagram illustrating a relation with variations in retention time points and the like according the first embodiment.
Figures 72, 73:
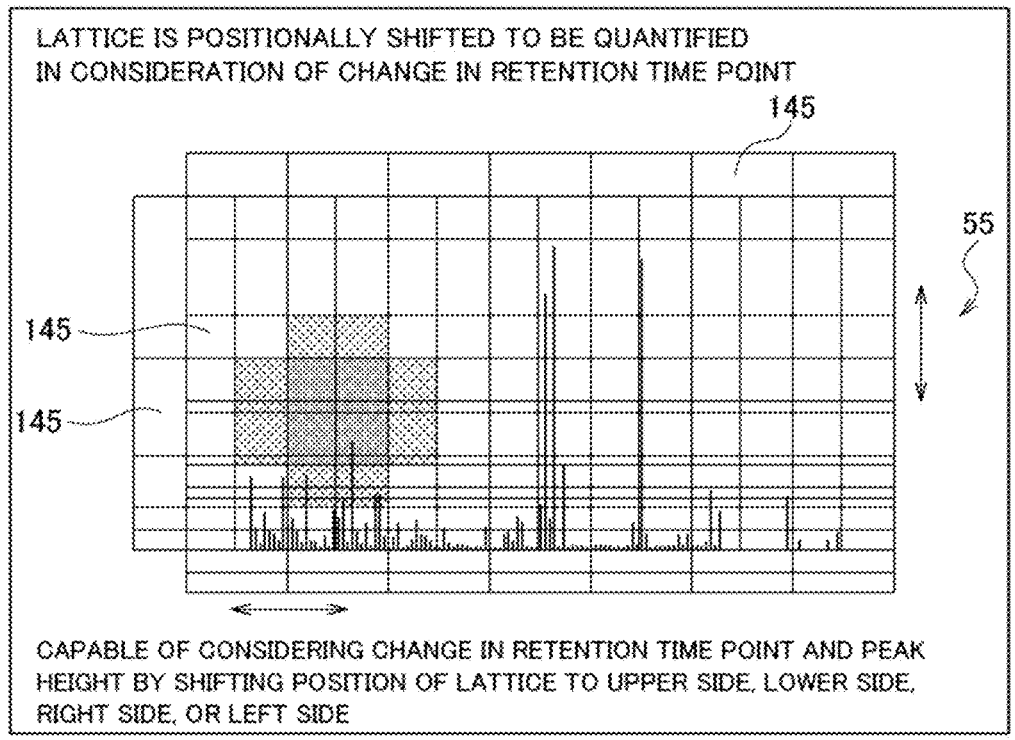
FIG. 72 is an explanatory diagram illustrating a case where quantification is carried out with changing positions of areas according the first embodiment.
FIG. 73 is a table illustrating data of FP type-2 according the first embodiment.
Figure 74:
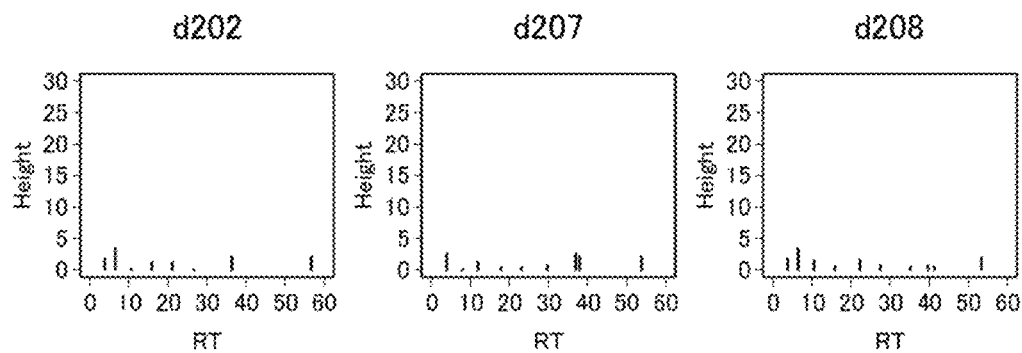
FIG. 74 is an explanatory diagram illustrating patterns of the FP type-2 according the first embodiment.
Figure 75:
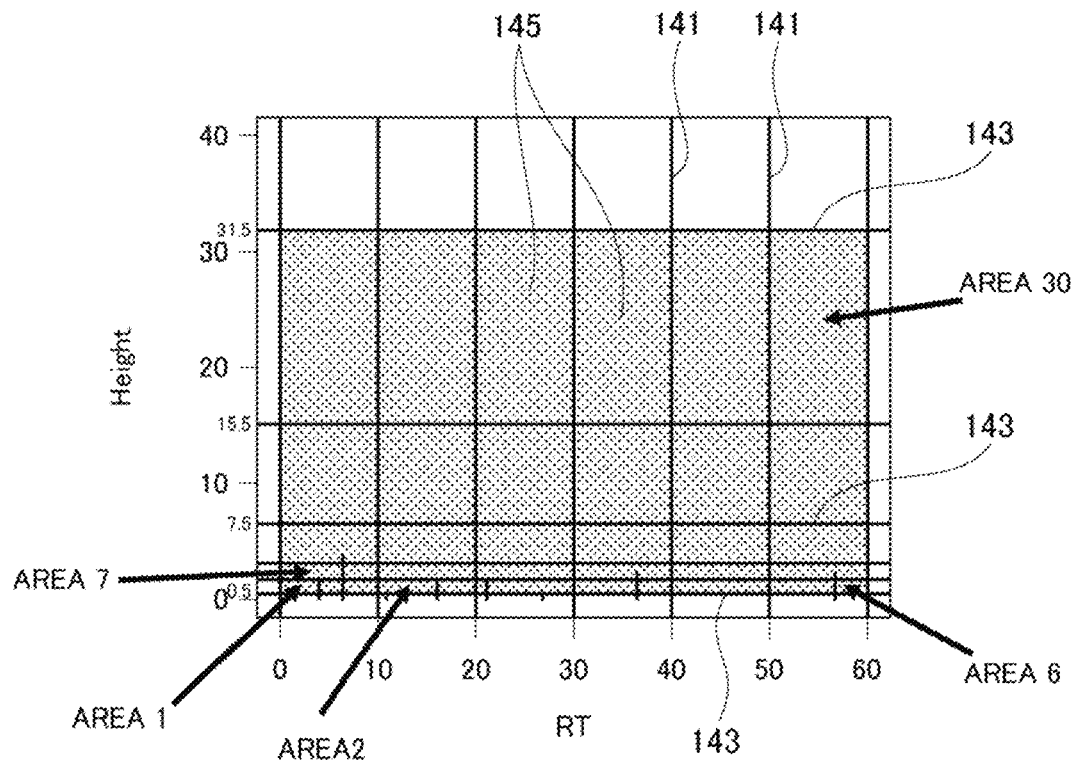
FIG. 75 is an explanatory diagram illustrating quantification of feature values for each area through area segmentation with use of vertical and horizontal segmenting lines according the first embodiment.
Figure 76:
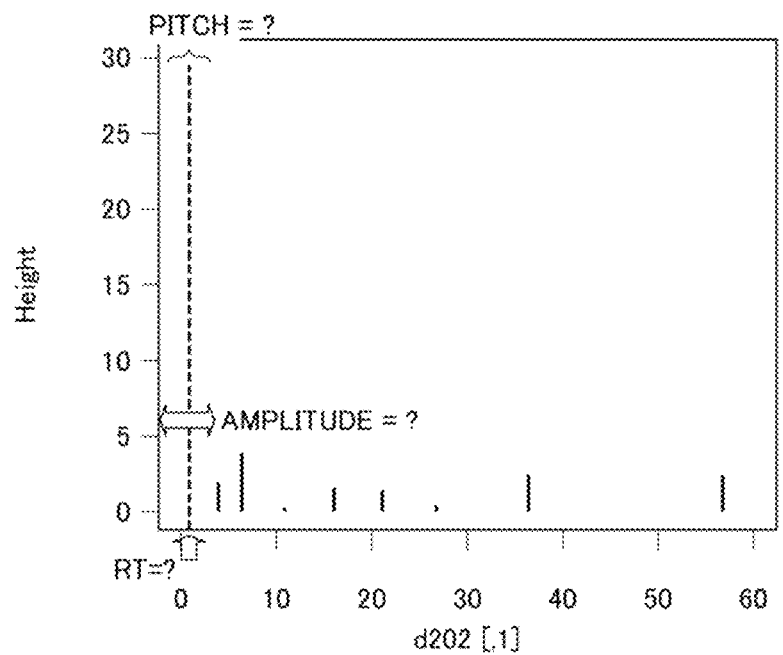
FIG. 76 is an explanatory diagram illustrating the setting of a vertical segmenting line (1st) according the first embodiment.
Figure 77:
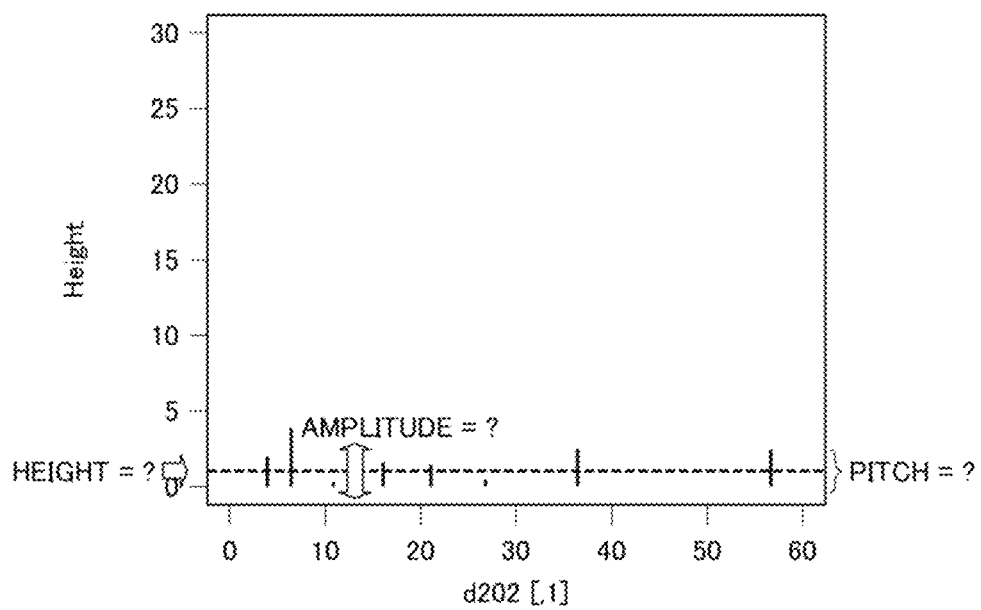
FIG. 77 is an explanatory diagram illustrating the setting of a horizontal segmenting line (1st) according the first embodiment.
Figure 78:
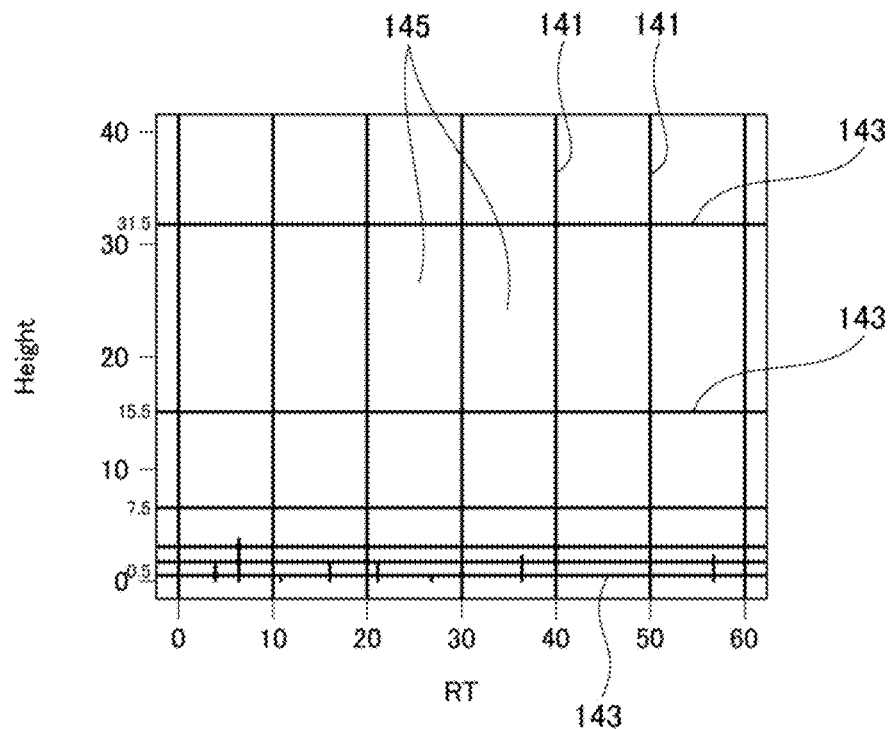
FIG. 78 is an explanatory diagram illustrating the area segmentation with use of the vertical and horizontal lines according the first embodiment.
Figure 79:
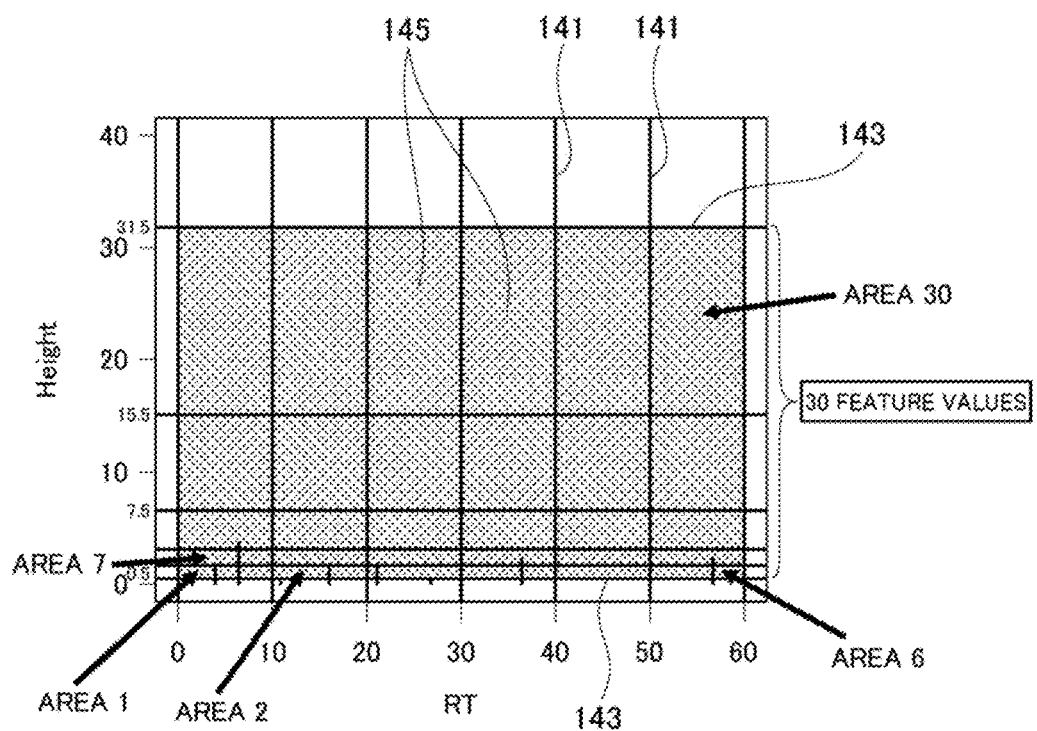
FIG. 79 is an explanatory diagram illustrating the number of the areas that are quantified as feature values according the first embodiment.
Figures 80, 81:
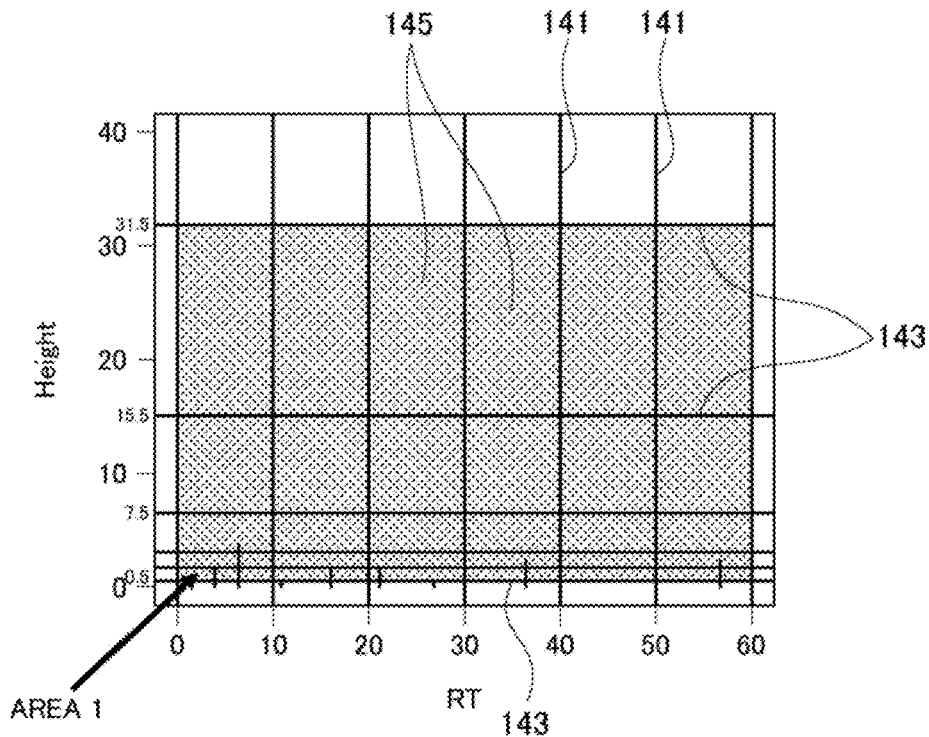
FIG. 80 is an explanatory diagram illustrating specifying areal according the first embodiment.
FIG. 81 is a table illustrating heights of all the peaks and a sum thereof according the first embodiment.
Figures 82, 83, 84:
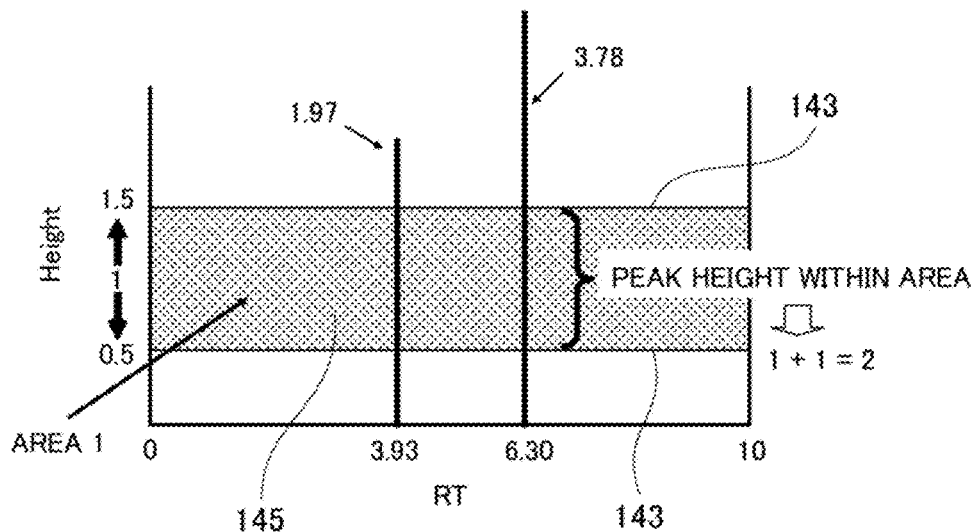
FIG. 82 is an explanatory diagram illustrating a sum of peak heights in the areal according the first embodiment.
FIG. 83 is a table illustrating feature values of all the areas according the first embodiment.
FIG. 84 is a table illustrating a feature value of each area that is formed by sequentially changing a position of the vertical 1st according the first embodiment.
Figure 87:
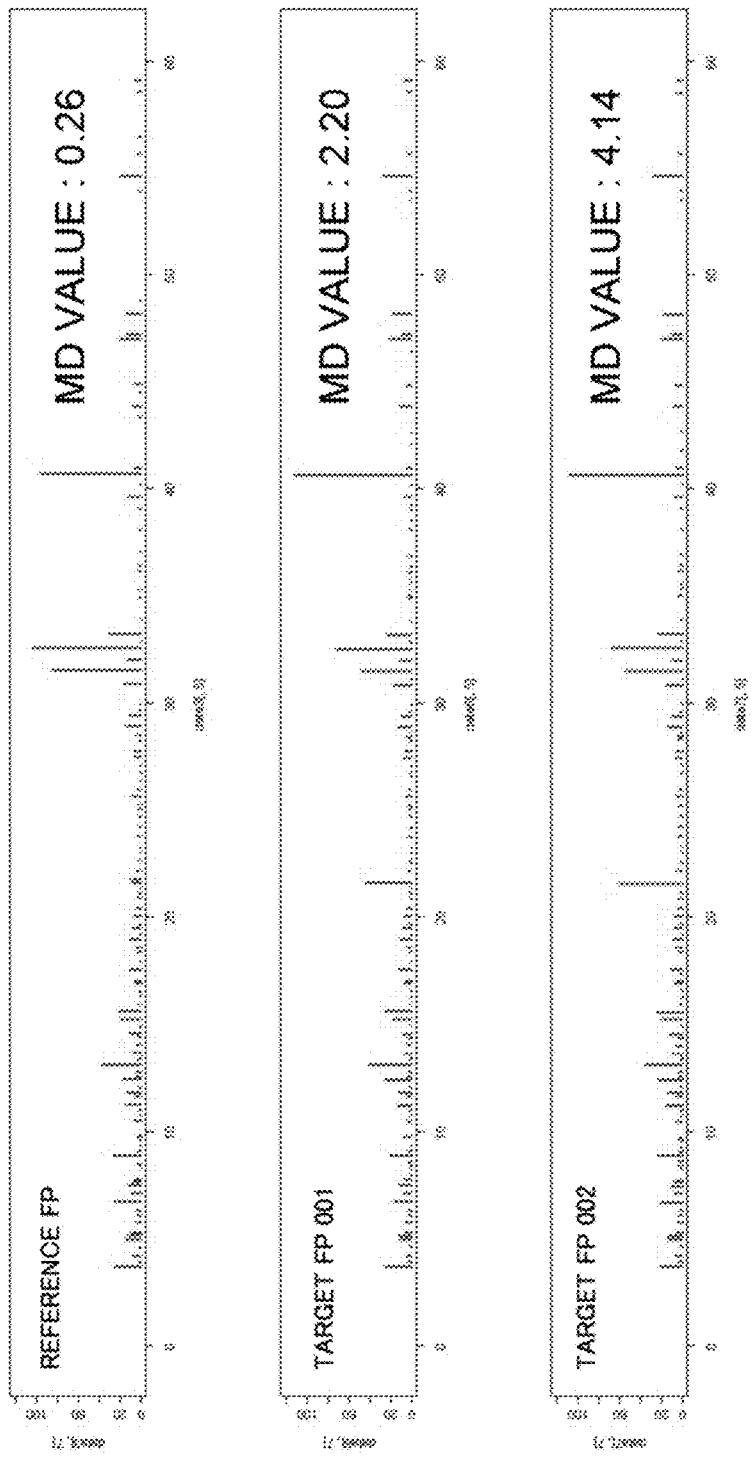
FIG. 87 is a diagram illustrating various target FPs and evaluation values (MD values) thereof according the first embodiment.
Figure 88:
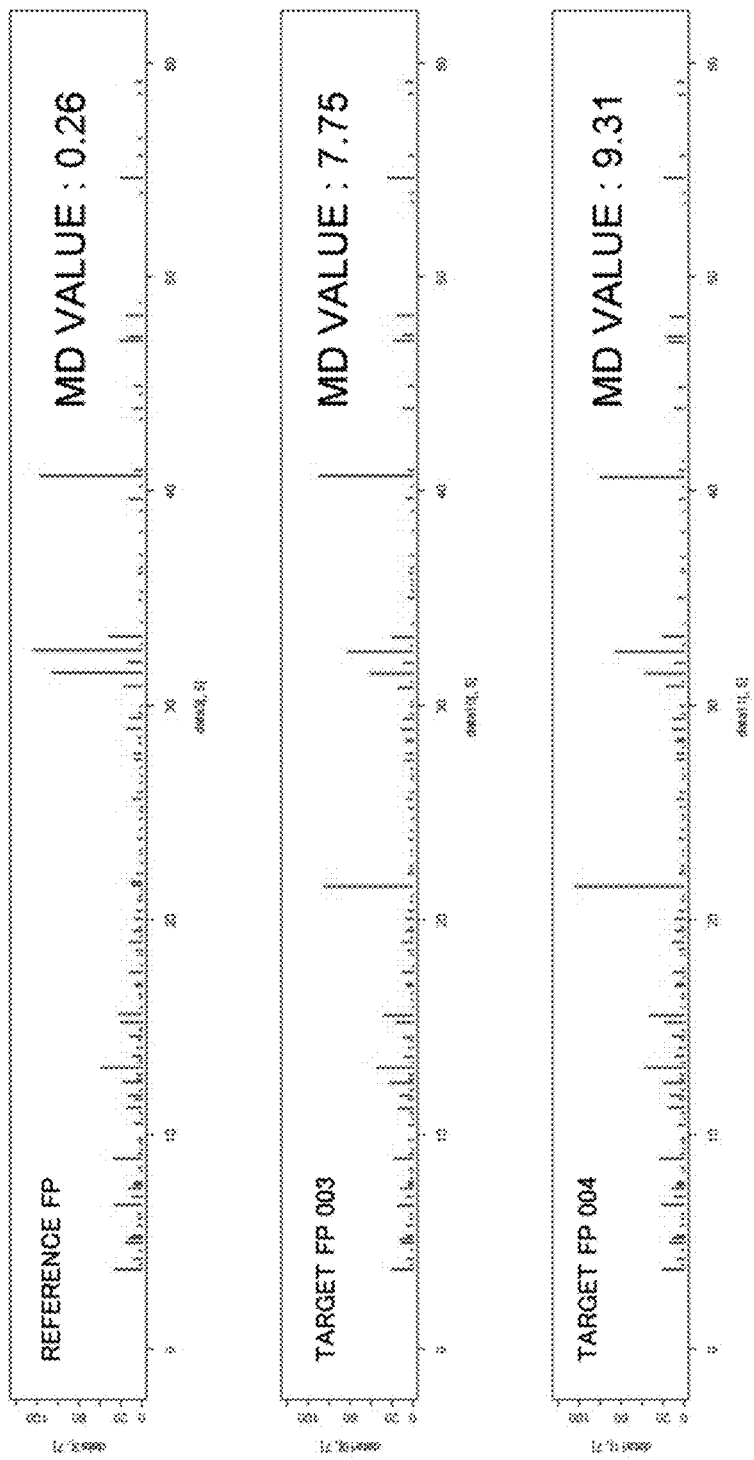
FIG. 88 is a diagram illustrating various target FPs and evaluation values (MD values) thereof according the first embodiment.
Figure 89:
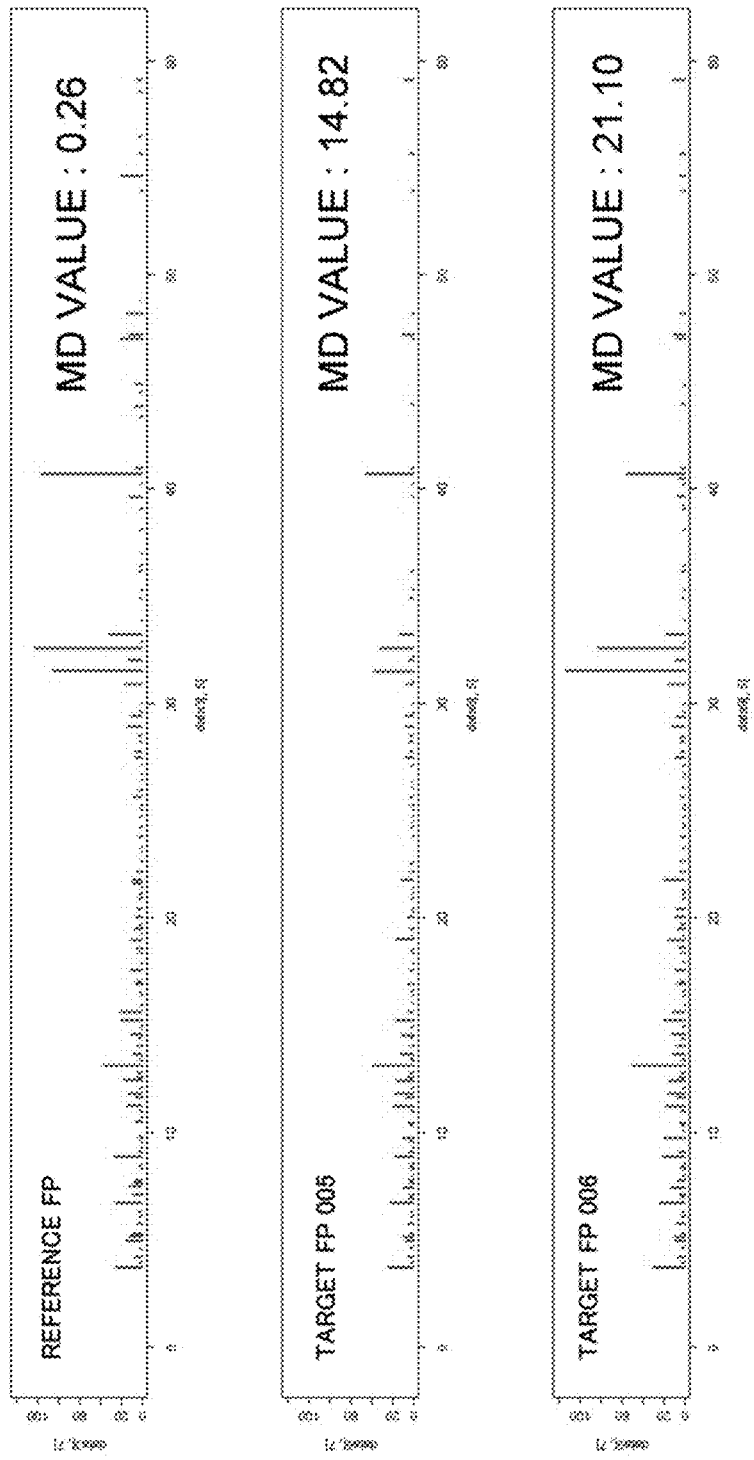
FIG. 89 is a diagram illustrating various target FPs and evaluation values (MD values) thereof according the first embodiment.
Figure 90:
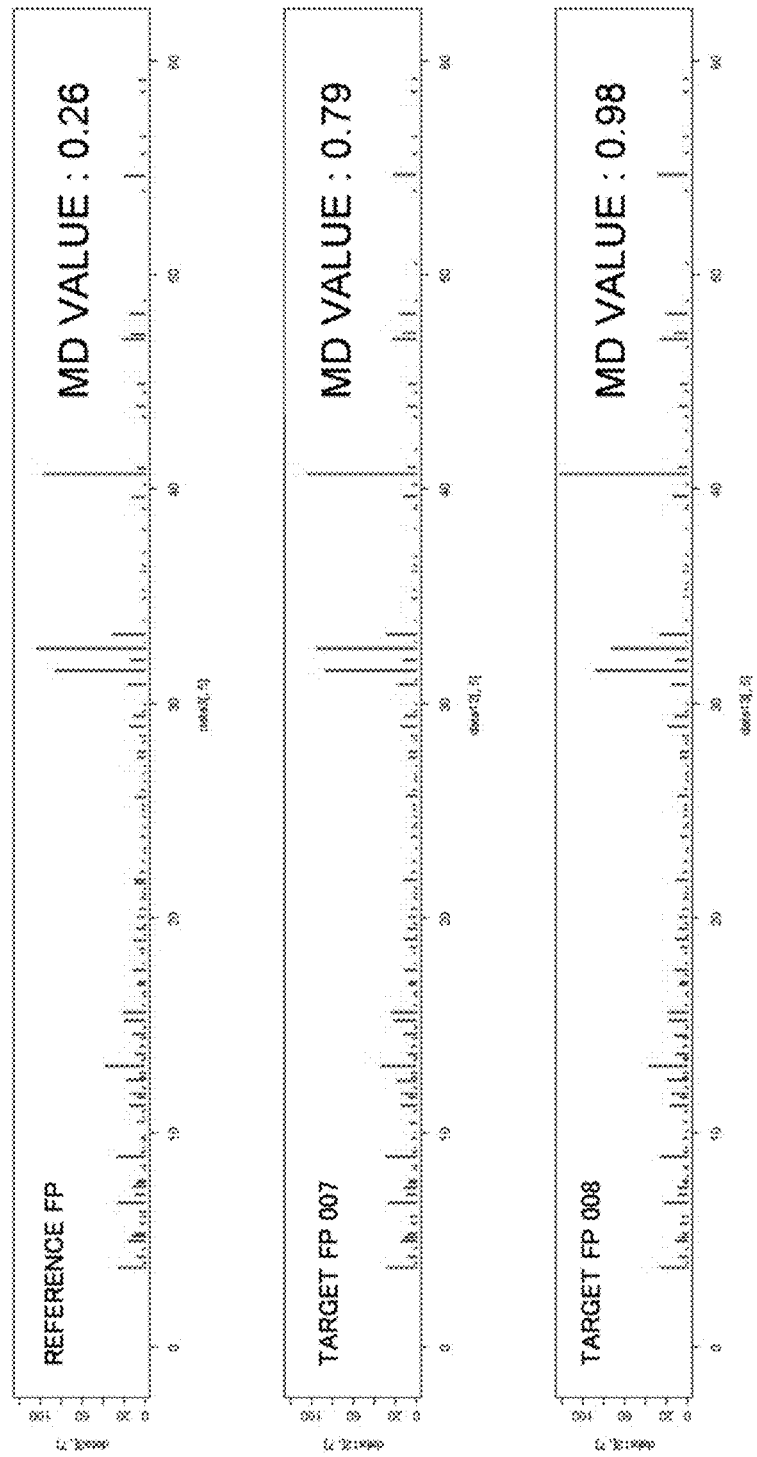
FIG. 90 is a diagram illustrating various target FPs and evaluation values (MD values) thereof according the first embodiment.
Figure 91:
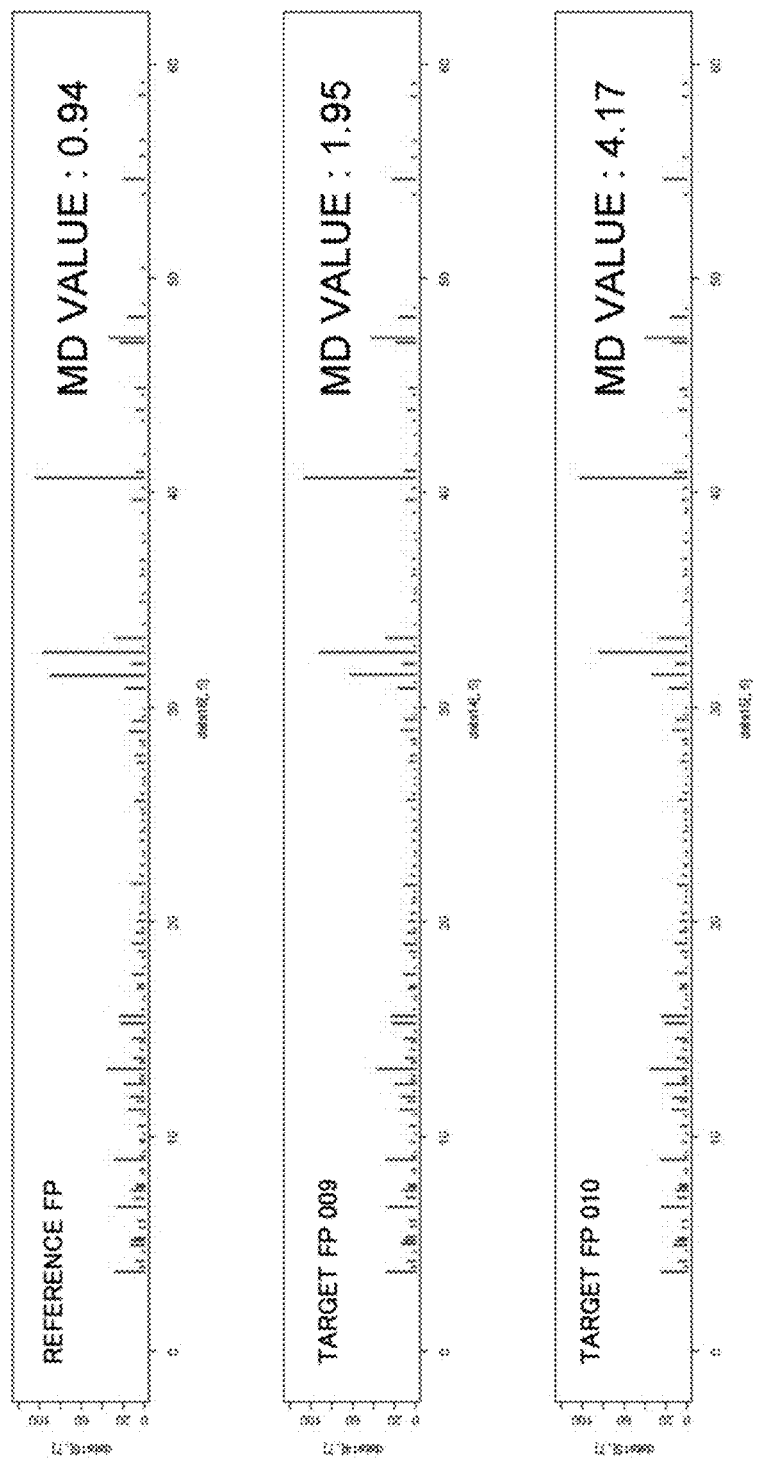
FIG. 91 is a diagram illustrating various target FPs and evaluation values (MD values) thereof according the first embodiment.

FIGS. 70 to 86 illustrate an operating principle of preparing FP area segmentation feature values. FIG. 70 is a diagram illustrating quantification according to area segmentation, FIG. 71 is a diagram illustrating the relation with variations in retention time points and the like, FIG. 72 is an explanatory diagram illustrating a case where the quantification is carried out with changing positions of the areas, FIG. 73 is a table illustrating data of FP type-2, FIG. 74 is an explanatory diagram illustrating the patterns of FP type-2, FIG. 75 is an explanatory diagram illustrating the quantification of feature values for each area through the area segmentation with use of vertical and horizontal segmenting lines, FIG. 76 is an explanatory diagram illustrating the setting of a vertical segmenting line (1st), FIG. 77 is an explanatory diagram illustrating the setting of a horizontal segmenting line (1st), FIG. 78 is an explanatory diagram illustrating the area segmentation with use of the vertical and horizontal segmenting lines, FIG. 79 is an explanatory diagram illustrating the number of areas that are quantified as feature values, FIG. 80 is an explanatory diagram illustrating specifying area1, FIG. 81 is a table illustrating heights of all the peaks and a sum thereof, FIG. 82 is an explanatory diagram illustrating a sum of peak heights in area1, FIG. 83 is a table illustrating feature values of all the areas according to the first one pattern, FIG. 84 is a table illustrating a feature value of each area that is formed by sequentially changing a position of the vertical 1st, FIG. 85 is a table illustrating a feature value of each area that is formed by sequentially changing a position of the horizontal 1st, and FIG. 86 is a table illustrating feature values in one way in which the positions of the vertical and horizontal segmenting lines are not changed.

The target FP area segmentation feature value preparing part 11 or the reference FP area segmentation feature value preparing part 23 prepares target FP area segmentation feature values or reference FP area segmentation feature values based on an existence rate of peaks existing in each area acquired by segmenting the target FP type-2 or the reference FP type-2 as described above.

The area segmentation, for example, is performed as illustrated in FIG. 70. In the case illustrated in FIG. 70, for example, the FP 55 of Drug A is segmented. A plurality of lattices 145 that are a plurality of areas are prepared by segmenting the FP with use of a plurality of vertical segmenting lines 141 that are parallel to the signal strength axis and a plurality of horizontal lines 143 that are parallel to the time axis.

In this embodiment, the plurality of horizontal segmenting lines 143 are set at geometric sequence ratio intervals in a direction in which the signal strength increases. Due to this setting, the area segmentation for a portion in which peaks are densely aggregated is finely performed, thereby more accurately grasping the existence rate of the peaks. However, the plurality of horizontal segmenting lines 143 may be set at equal difference intervals while increasing the number of the plurality of horizontal segmenting lines 143 or the like.

In each lattice 145, it is quantified at the ratio of peak heights that exist so as to be set as the feature value.

Meanwhile, as illustrated in FIG. 71, the retention time points or the peak heights change like FPs 55A and 55B due to a slight variation of the analysis condition or the like. There is a risk that the value of each lattice 145 may markedly change due to such a variation.

Thus, in the case of the reference FP type-2, as illustrated in FIG. 72, the position of each lattice 145 is changed (shifted) and quantification is performed before and after the change. Due to this operation, it is possible to accurately prepare the reference FP area segmentation feature values. The position of each lattice 145 is changed by setting so as to move each of the vertical and horizontal segmenting lines 141 and 143 parallel in a set range.

Here, the quantification for each lattice 145 with the changed position will be described further.

FIG. 73 illustrates data d202, d207, and d208 of the reference FP type-2 as an example. These data are configured only by information of retention time points (RT) and peak heights (Height). These data correspond to the reference FP type-2 that is composed by remaining peaks with the exclusion of the peaks quantified as feature values in the reference FP type-2 preparing part 21 from the plurality of reference FPs and of retention time points thereof. The UV spectra of all the peaks are excluded.

The patterns of data d202, data d207, and data d208 of the reference FP type-2 are as illustrated in FIG. 74.

These FP patterns are segmented by the vertical and horizontal segmenting lines 141 and 143, to quantify each area as a feature value.

In order to set the position of the vertical segmenting line (1st), as illustrated in FIG. 76, a retention time point (RT), an amplitude, and a pitch of the 1st are designated.

Based on these three parameters, a plurality of positions of the vertical 1st are set under the following conditions.

Vertical segmenting lines(1st)=$RT$−amplitude+(amplitude×2/pitch)×$i$(here, $i$=0,1,2, ... ,pitch−1)

For example, in a case where the RT=1, the amplitude=1, and the number of pitches=10 are designated, the vertical segmenting lines (1st)=0.0, 0.2, 0.4, 0.6, 0.8, 1.0, 1.2, 1.4, 1.6, and 1.8 are set.

In order to set the position of the horizontal line (1st), as illustrated in FIG. 77, a height, an amplitude, and a pitch of the 1st are designated.

Based on these three parameters, a plurality of positions of the horizontal 1st are set under the following conditions.

For example, in a case where the height=1, the amplitude=0.5, and the number of pitches=10 are designated:

Horizontal segmenting lines(1st)=height−amplitude+(amplitude×2/pitch)×$i$(here, $i$=0,1,2, ... , pitch−1);

For example, the height=1, the amplitude=0.5, and the number of pitches=10 are designated, so that the horizontal segmenting lines (1st)=0.5, 0.6, 0.7, 0.8, 0.9, 1.0, 1.1, 1.2, 1.3, and 1.4 are set.

In accordance with all the combinations of the set vertical and horizontal segmenting lines (1st), the 2nd and subsequent sample lines are sequentially set to perform the area segmentation.

In the above-described example, the following is performed.

Vertical segmenting lines (1st)×horizontal segmenting lines (1st)=(0.0,0.2,0.4,0.6,0.8,1.0,1.2,1.4,1.6,1.8)×(0.5,0.6,0.7,0.8,0.9,1.0,1.1,1.2,1.3,1.4)= 100 ways The 2nd and subsequent segmenting lines are sequentially set based on combinations of 100 ways, to segment the areas.

The 2nd and subsequent vertical lines are set at designated intervals (equal differences) until vertical segmenting lines of a designated number are acquired.

$i$-th vertical segmenting line=($i$−1)-th vertical segmenting line+interval (here, $i$=2, ... , the designated number)

The 2nd and subsequent horizontal segmenting lines are set at a designated intervals (equal ratio) until horizontal segmenting lines of a designated number are acquired.

$i$-th horizontal segmenting line=($i$−1)-th horizontal segmenting line+interval×2/($i$−2)(here, $i$=2, ... , the designated number)

For example, in a case of the position of the vertical 1st=0.0, the vertical interval=10, the number of vertical segmenting lines=7, the position of the first horizontal segmenting line=0.5, the horizontal interval=1, and the number of horizontal segmenting lines=6:

Vertical segmenting lines=0, 10, 20, 30, 40, 50, and 60; and

Horizontal segmenting lines=0.5, 1.5, 3.5, 7.5, 15.5, and 31.5 are set.

Representing the set vertical and horizontal segmenting lines on the original FP based on the above example, it becomes as illustrated in FIG. 78.

For each area surrounded by the vertical and horizontal lines, the FP is quantified as a feature value.

Since a total number of the areas is 30, as illustrated in FIG. 79, 30 feature values are acquired.

Each area is quantified as a feature value with use of the following equation.

Feature value=sum of peak heights within area/sum of all peak heights

Hereinafter, the feature value of area1 of d202 illustrated in FIG. 80 is acquired using the above equation.

First, calculating the sum of the heights of all the peaks, it is 15.545472 as represented in FIG. 81.

Next, the sum of peak heights in area1 is calculated as illustrated in FIG. 82.

Accordingly, the feature value of area1 is calculated as:

Feature value=2/15.545472=0.128655.

With the above-described feature value quantifying method, the feature values of all the areas according to a first pattern are calculated. The calculation result is represented in FIG. 83.

Each area set by sequentially changing the position of the 1st vertical segmenting line is quantified as a feature value by the above-described method. The result is represented in FIG. 84.

Each area is formed by changing the vertical 1st in one way whenever the position of the 1st horizontal segmenting line is quantified as feature vale. The result is represented in FIG. 85.

Due to this process, in a case where there are ten of each of the 1st vertical and horizontal segmenting lines, data is formed into;

100 rows(100 ways)×31 columns(a file name+30 feature values).

The past process is performed for all the reference data. For example, in a case where there are three reference data of d202, d207 and d208, it is formed into:

300 rows(100 ways×3 data)×31 columns(a file name+30 feature values).

In the target FP type-2, a combination of vertical and horizontal segmenting lines (1st) is one way (vertical (RT)=1, and horizontal (height)=1), and a feature value in this one way is calculated.

FIGS. 87 to 91 are the diagrams representing various target FPs and evaluation values (MD values) thereof according to the evaluating part 27 as described above. By performing the assignment process for each target FP as described above, the evaluating part 27 can acquire MD values (MD values: 0.26, 2.20, and the like) by the above-described MT method.

Figure 92:
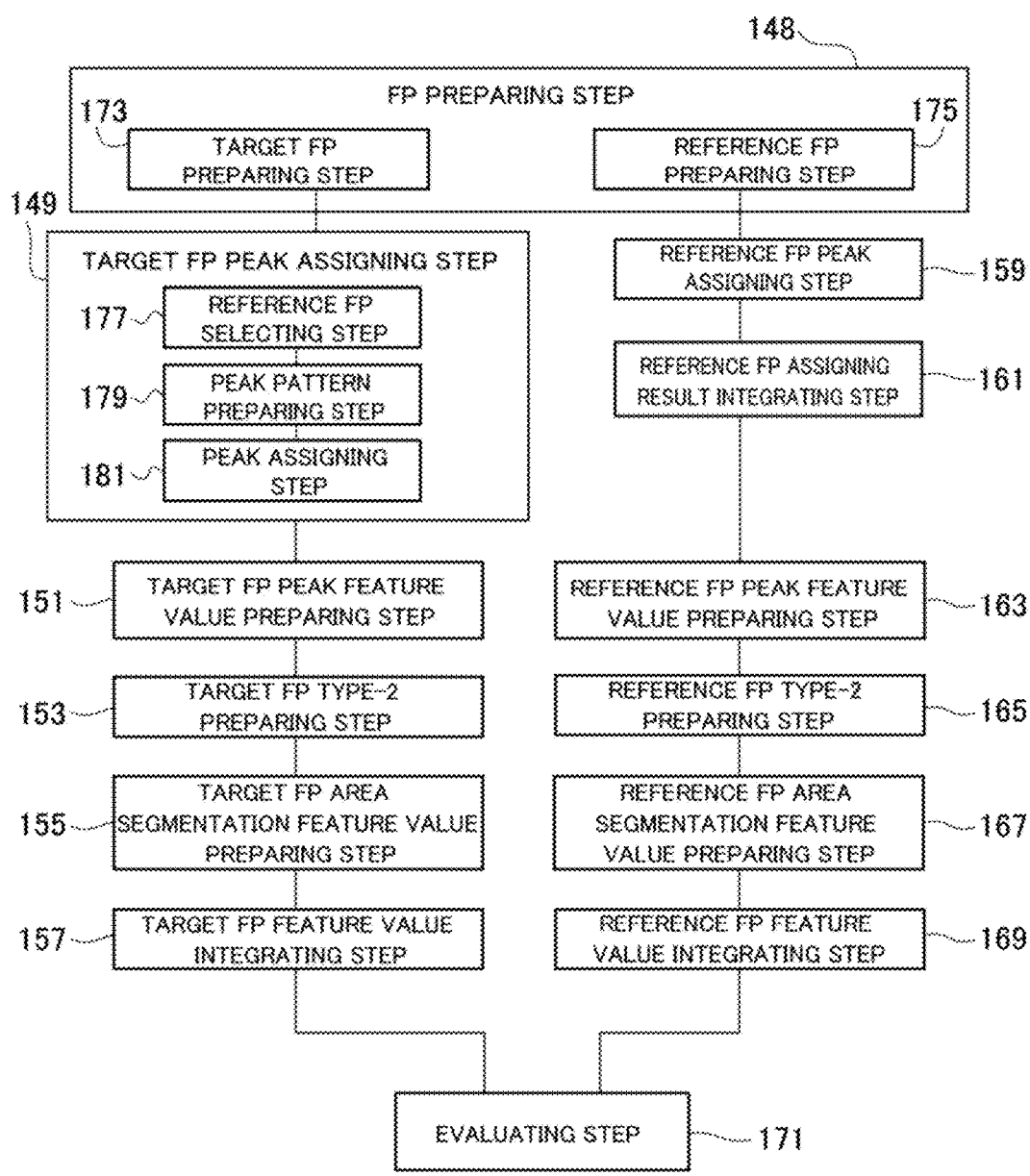
FIG. 92 is a process chart illustrating an evaluating method for a multicomponent drug according the first embodiment.

FIG. 92 is a process chart illustrating an evaluating method for a multicomponent drug as an evaluating method for a pattern according to the first embodiment of the present invention.

As illustrated in FIG. 92, the evaluating method for a multicomponent drug includes: a FP preparing step 148; a target FP peak assigning step 149; a target FP peak feature value preparing step 151; a target FP type-2 preparing step 153; a target FP area segmentation feature value preparing step 155; a target FP feature value integrating step 157; a reference FP peak assigning step 159; a reference FP assigning result integrating step 161; a reference FP peak feature value preparing step 163; a reference FP type-2 preparing step 165; a reference FP area segmentation feature value preparing step 167; a reference FP feature value integrating step 169; and an evaluating step 171.

The FP preparing step 148 includes a target FP preparing step 173 and a reference FP preparing step 175.

The target FP peak assigning step 149 includes a reference FP selecting step 177, a peak pattern preparing step 179, and a peak assigning step 181.

According to the present embodiment, the evaluating device 1 for a multicomponent drug carries out the FP preparing step 148, the target FP peak assigning step 149, the target FP peak feature value preparing step 151, the target FP type-2 preparing step 153, the target FP area segmentation feature value preparing step 155, the target FP feature value integrating step 157, the reference FP peak assigning step 159, the reference FP assigning result integrating step 161, the reference FP peak feature value preparing step 163, the reference FP type-2 preparing step 165, the reference FP area segmentation feature value preparing step 167, the reference FP feature value integrating step 169, and the evaluating step 171.

The FP preparing step 148 is performed by the function of the FP preparing part 3 illustrated in FIG. 1. Similarly, the target FP peak assigning step 149, the target FP peak feature value preparing step 151, the target FP type-2 preparing step 153, the target FP area segmentation feature value preparing step 155, the target FP feature value integrating step 157, the reference FP peak assigning step 159, the reference FP assigning result integrating step 161, the reference FP peak feature value preparing step 163, the reference FP type-2 preparing step 165, the reference FP area segmentation feature value preparing step 167, the reference FP feature value integrating step 169, and the evaluating step 171 are performed by using the respective functions of the target FP peak assigning part 5, the target FP peak feature value preparing part 7, the target FP type-2 preparing part 9, the target FP area segmentation feature value preparing part 11, the target FP feature value integrating part 13, the reference FP peak assigning part 15, the reference FP assigning result integrating part 17, the reference FP peak feature value preparing part 19, the reference FP type-2 preparing part 21, the reference FP area segmentation feature value preparing part 23, the reference FP feature value integrating part 25, and the evaluating part 27.

Here, the processes may be performed as respective functions of discrete computers. For example, it may be configured such that the target FP preparing step 173, the target FP peak assigning step 149, the target FP peak feature value preparing step 151, the target FP type-2 preparing step 153, the target FP area segmentation feature value preparing step 155, the target FP feature value integrating step 157, and the evaluating step 171 may be performed as functions of one computer, and the reference FP preparing step 175, the reference FP peak assigning step 159, the reference FP assigning result integrating step 161, the reference FP peak feature value preparing step 163, the reference FP type-2 preparing step 165, the reference FP area segmentation feature value preparing step 167, and the reference FP feature value integrating step 169 may be performed as functions of another computer.

In this case, reference FP integrated feature values are prepared by another computer and are supplied to the evaluating step 171.

In this way, the FP type-2 preparing step 153 gathers as the target FP type-2 peaks in which each one peak whose peaks has a height that is a maximum value or an area value in signal strength (the maximum value in this embodiment) and retention time points of the peaks detected from the 3D chromatogram.

The target FP area segmentation feature value preparing step 155 configures a FP area segmentation feature value preparing step segmenting the target FP type-2 into a plurality of areas so that the peaks of the target FP type-2 are subdivided into pieces and obtaining target FP area segmentation feature values based on an existence rate or existence amount of the subdivided peaks existing in each area.

Figure 121:
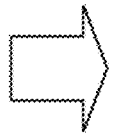

FIGS. 93 to 108 are flowcharts according to an evaluating program for a multicomponent drug, FIGS. 109 to 116 are flowcharts according to preparation of reference data, FIG. 117 is a table illustrating a data example of a 3D chromatogram, FIG. 118 is a table illustrating a data example of peak information, FIG. 119 is a table illustrating a data example of a FP, FIG. 120 is a table illustrating an assignment score calculation result example (determination result file) of the target FP to the reference FP, FIG. 121 is a table illustrating two intermediate file examples (an assignment candidate peak score table and an assignment candidate peak number table) prepared in a collating process of corresponding peaks between the target FP and the reference FP, FIG. 122 is a table illustrating a collation result file example that is a result of specifying corresponding peaks between the target FP and the reference FP, FIG. 123 is a table illustrating a data example of a reference group FP, FIG. 124 is a table illustrating a file example of peak feature value data of the target FP that are assigned to the reference group FP, FIG. 125 is a table illustrating a data example of the target and reference FP type-2, FIG. 126 is a table illustrating a target FP area segmentation feature value file example, FIG. 127 is a table illustrating a target FP feature value integrated file example, FIG. 128 is a table illustrating a reference type-2 group FP example, and FIG. 129 is a table illustrating a reference group integrated data example.

Figure 93:
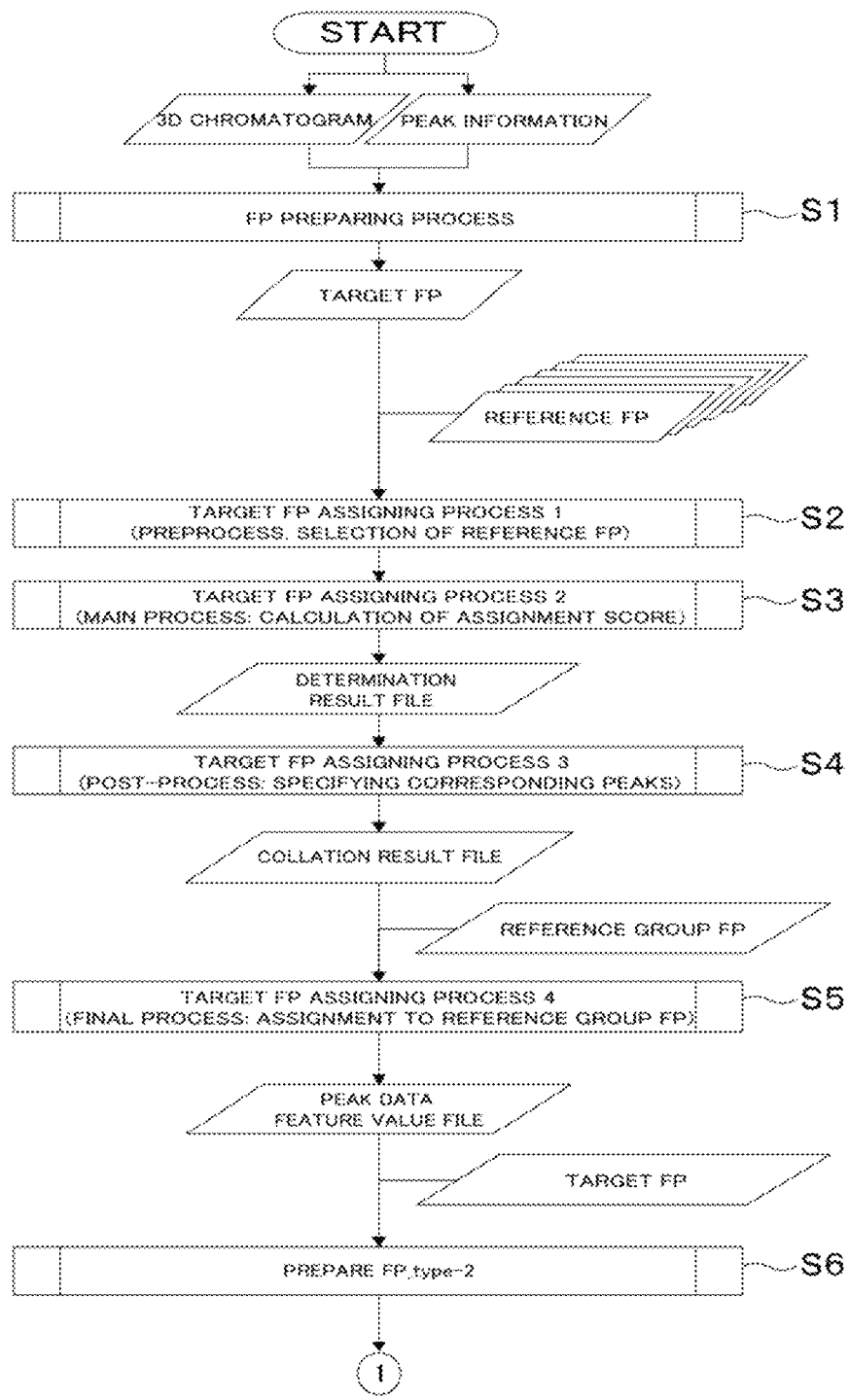
FIG. 93 is a quality evaluating flow chart for a multicomponent drug according the first embodiment.
Figure 94:
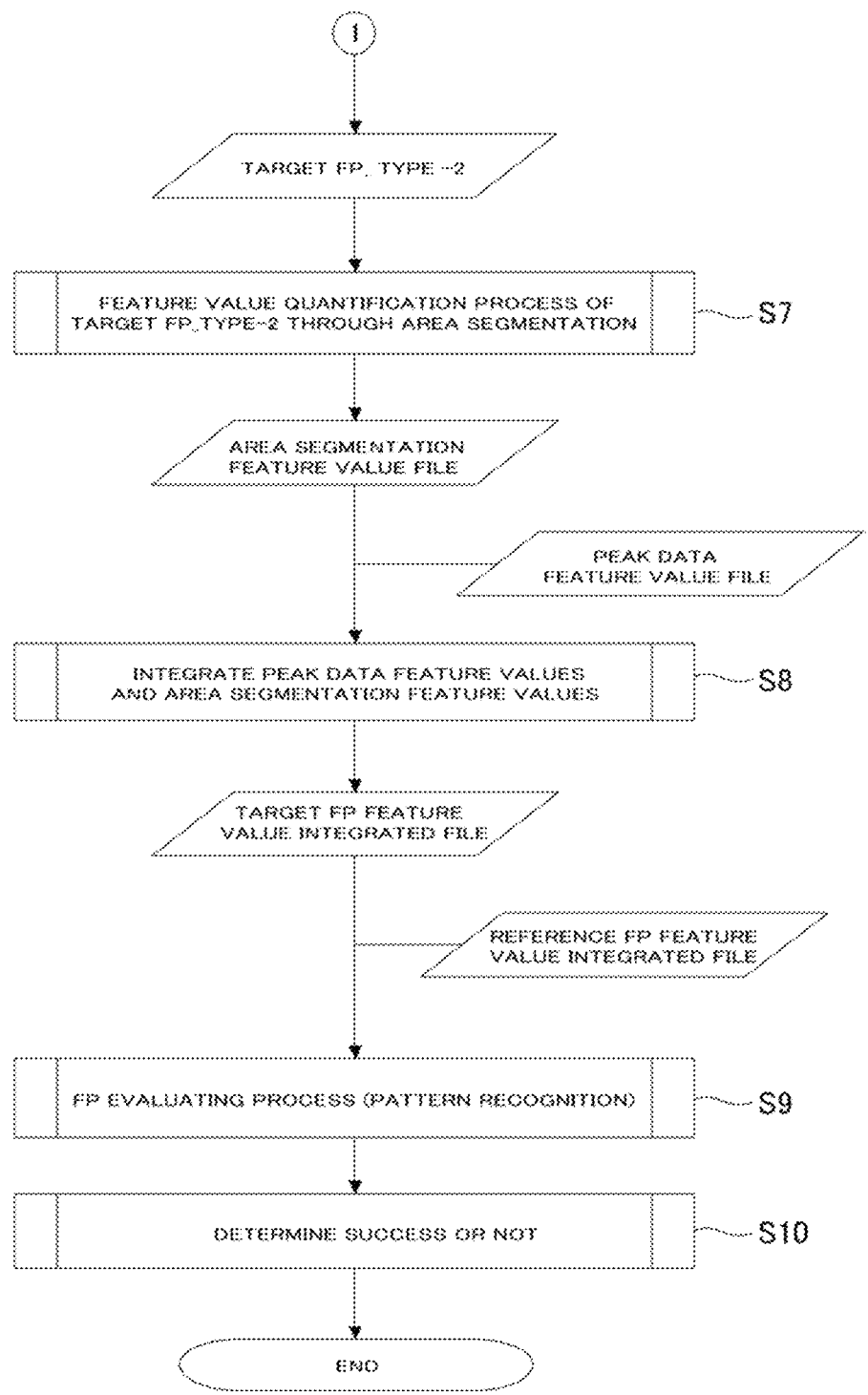
FIG. 94 is a quality evaluating flow chart for a multicomponent drug according the first embodiment.

FIGS. 93 and 94 are flowcharts illustrating steps of the whole processes performed for evaluating an evaluation target drug. It is started in accordance with system activation to cause a computer to execute the FP preparing function of the FP preparing part 3, the target FP peak assigning function of the target FP peak assigning part 5, the target FP peak feature value preparing function of the target FP peak feature value preparing part 7, the target FP type-2 preparing function of the target FP type-2 preparing part 9, the target FP area segmentation feature value preparing function of the target FP area segmentation feature value preparing part 11, the target FP feature value integrating function of the target FP feature value integrating part 13, the reference FP peak assigning function of the reference FP peak assigning part 15, the reference FP assigning result integrating function of the reference FP assigning result integrating part 17, the reference FP peak feature value preparing function of the reference FP peak feature value preparing part 19, the reference FP type-2 preparing function of the reference FP type-2 preparing part 21, the reference FP area segmentation feature value preparing function of the reference FP area segmentation feature value preparing part 23, the reference FP feature value integrating function of the reference FP feature value integrating part 25, and the evaluation function of the evaluating part 27.

The FP preparing function is realized in Step S1. The target FP peak assigning function is realized in Steps S2, S3, and S4. The target FP peak feature value preparing function is realized in Step S5. The target FP type-2 preparing function is realized in Step S6. The target FP area segmentation feature value preparing function is realized in Step S7. The target FP feature value integrating function is realized in Step S8. The evaluation function is realized in Steps S9 and S10.

In Step S1, the "FP preparing process" is performed with a 3D chromatogram and peak information at a specific detection wavelength as input data.

The 3D chromatogram is data that is acquired by analyzing an evaluation target drug through HPLC and it is configured as three-dimensional information including a retention time points, detection wavelengths, and peaks (signal strength) as represented as a data example 183 of the 3D chromatogram in FIG. 117. The peak information is data that is acquired by processing chromatogram data at a specific wavelength, which is acquired through the same HPLC analysis, with a HPLC data analyzing tool (for example, a "ChemStation" or the like). As represented as the peak information example 185 in FIG. 118, the peak information is data configured by the maximum values and area values of all the peaks detected as peaks and retention time points at those time point.

In Step S1, the target FP preparing part 29 (FIG. 2) of the computer functions to prepare the target FP 43 (FIG. 3A) base on the 3D chromatogram and the peak information and output the data as a file. The target FP 43, like a data example 187 of a FP in FIG. 119, is data configured by retention time points, peak heights, and UV spectra for respective peak heights.

In Step S2, the "target FP assigning process 1" is performed with input of the target FP and all the reference FPs output in Step S1.

In Step S2, the reference FP selecting part 33 of the computer functions to calculate the degree of matching in the retention time appearance pattern between the target FP 43 and all the reference FPs, to select a reference FP that is appropriate to the assignment of the target FP 43.

The reference FPs are FPs that are prepared by the same process as that of Step S1 based on the 3D chromatogram and peak information of drugs determined as normal products. In addition, the normal product is defined as a drug (reference kampo medicine) of which the safety and the effectiveness are checked, and a plurality of drugs with different product lots correspond thereto. The reference FP is data configured similarly to the FP data example 187 illustrated in FIG. 119.

In Step S3, the "target FP assigning process 2" is performed according to the target FP 43 and the reference FP selected in Step S2 as inputs.

In Step S3, the peak pattern preparing part 35 (FIG. 2) and the peak assigning part 37 (FIG. 2) of the computer function. Through the functions thereof, peak patterns are comprehensively prepared for all the peaks of the target FP 43 and the reference FP selected in Step S2 as illustrated in FIGS. 23 to 61, to calculate the degree of matching between the peak patterns (P_Sim illustrated in FIG. 63 or 64). Further, the degree of matching in the UV spectrum (UV_Sim illustrated in FIG. 66) between the target FP and the reference FP is calculated. Furthermore, the degree of matching of the assignment candidate peaks (SCORE illustrated in FIG. 67) is calculated based on these two kinds of the degrees of matching. The calculation result is output to a file similar to the determination result file example 189 in FIG. 120.

In Step S4, the "target FP assigning process 3" is performed according to the determination result file 189 output in Step S3 as an input.

In Step S4, the peak assigning part 37 of the computer functions to specify peaks of the reference FP that correspond to the respective peaks of the target FP between the target FP 43 and the reference FP based on the degree of matching of the assignment candidate peaks (SCORE). The result is output to a collation result file that is similar to a collation result file example 195 in FIG. 122.

In Step S5, the "target FP assigning process 4" is performed according to the collation result file output in Step S4 and the reference group FP 197 as inputs.

The reference group FP 197 is peak correspondence data over all the reference FPs prepared from the all reference FPs in the same process as that of Steps S2 to S4.

In Step S5, the target FP peak feature value preparing part 7 of the computer functions to assign each peak of the target FP 43 to peaks of the reference group FP 197 based on the collation result file of the target FP 43 as illustrated in FIGS. 68 and 69. The result is output to a file that is similar to a file example 199 of peak data feature values in FIG. 124.

In Step S6, a process of "preparing the FP_type-2" is performed with the peak data feature value file output in Step S5 and the target FP as inputs.

In Step S6, the target FP type-2 preparing part 9 of the computer functions to gather as a target FP type-2 (49) that is composed of remaining peaks with the exclusion of the peaks 47 that are specified by the target FP peak feature value preparing part 7 from the original target FP 43 and of retention time points thereof. The result is output to the FP type-2 file (a FP type-2 file example 201 in FIG. 125).

In Step S7, a "feature value quantification of the target FP-type 2 through area segmentation" is performed. In this process, the target FP area segmentation feature value preparing part 11 of the computer functions to prepare target FP area segmentation feature values through the area segmentation illustrated in FIG. 70. The result is output to the target FP area segmentation feature value file (a target FP area segmentation feature value file example 203 in FIG. 126).

In Step S8, a process of "integrating the peak data feature values and the area segmentation feature values" is performed.

In this process, the target FP feature value integrating part 13 of the computer functions to prepare target FP integrated feature values by integrating the target FP peak feature values 47 prepared by the target FP peak feature value preparing part 7 and the target FP area segmentation feature values 51 prepared by the target FP area segmentation feature value preparing part 11. The result is output to a target FP feature value integrated file (a target FP feature value integrated file example 205 in FIG. 127).

In Step S9, the evaluating part 27 of the computer functions to evaluate the equivalency between the target FP integrated feature values output in Step S8 and the reference FP integrated feature values using MT method and output the evaluation result as MD values as illustrated in FIGS. 87 to 91 (FIGS. 87 to 91).

In Step S10, a "determination of a success or not" is performed according to the MD value output in Step S9 as an input.

In Step S10, the evaluating part 27 of the computer functions to compare the MD value output in Step S9 and a threshold value (the upper limit of the MD value) set in advance so as to make a decision to pass or fail, i.e., whether the powder extract of the multicomponent drug meets the criteria for productization (the evaluation result 53 in FIG. 3A).

Figure 95:
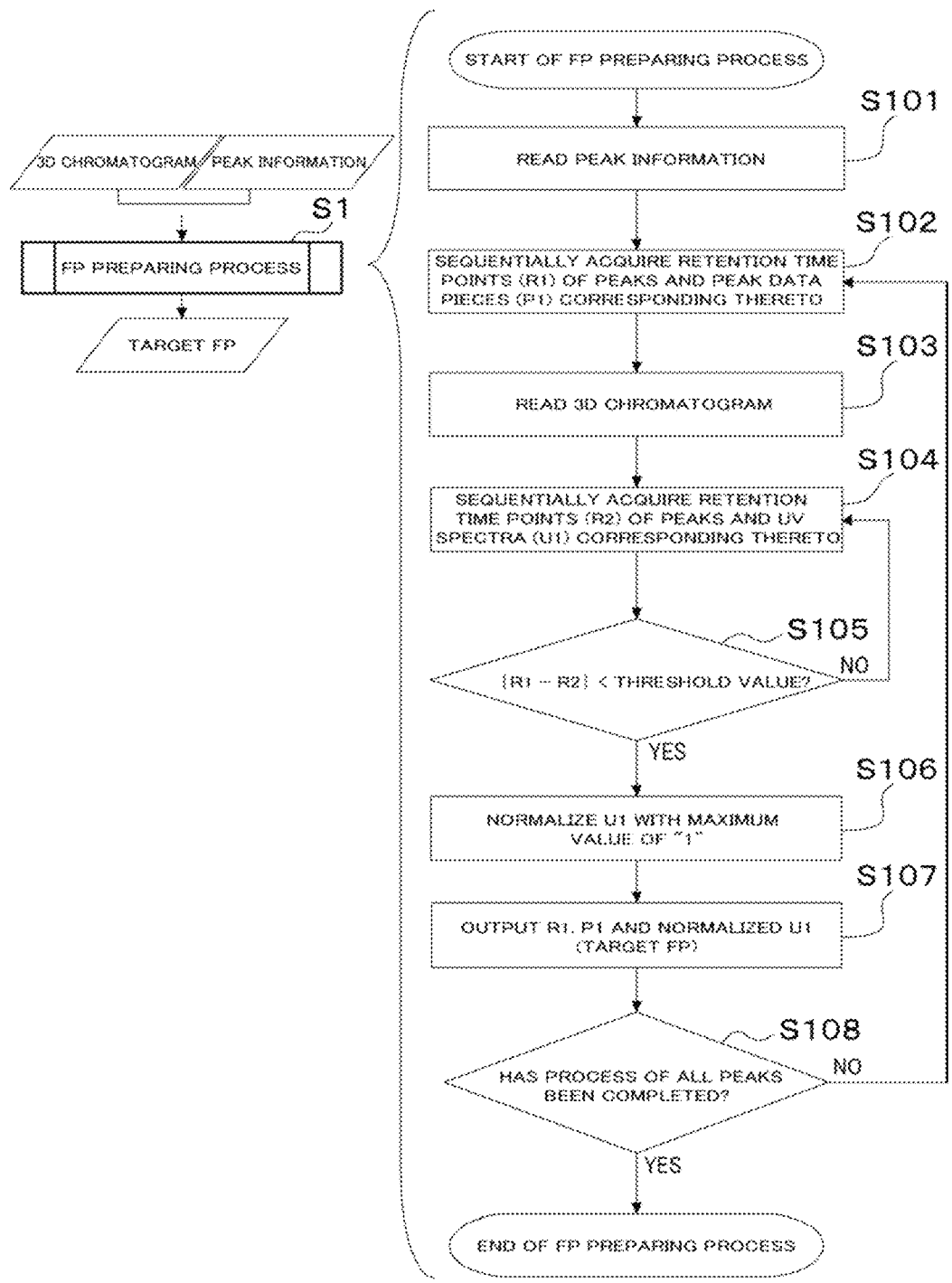
FIG. 95 is a data processing flowchart in a FP preparing function according to a single wavelength according the first embodiment.

FIG. 95 is a flowchart in a case where single-wavelength peak information of the "FP preparing process" in Step S1 illustrated in FIG. 93 is used.

FIG. 95 shows details of the step of preparing the evaluation target FP for a single wavelength, for example, 203 nm. In this process, based on the 3D chromatogram and the peak information at the detection wavelength being 203 nm, a FP is prepared to comprise retention time points, peaks and UV spectra detected at the detection wavelength of 203 nm.

In Step S101, a process of "reading peak information" is performed. In this process, peak information is read out as the first one of two kinds of data that are necessary for preparing a FP, and the procedure proceeds to Step S102.

In Step S102, a process of "sequentially acquiring a retention time point (R1) of a peak and peak data (P1) corresponding thereto" is performed. In this process, retention time points (R1) and peak data pieces (P1) of the peaks are sequentially acquired from the peak information one by one, and the procedure proceeds to Step S103.

In Step S103, a process of "reading a 3D chromatogram" is performed. In this process, a 3D chromatogram is read as the second one of the two kinds of data necessary for preparing the FP, and the procedure proceeds to Step S104.

In Step S104, a process of "sequentially acquiring a retention time point (R2) of a peak and a UV spectrum (U1) corresponding thereto" is performed. In this process, retention time points (R2) and UV spectra (U1) are acquired from the 3D chromatogram at each period that is a half of a sampling rate at the time of analyzing the HPLC, and the procedure proceeds to Step S105.

In Step S105, a process of determining "|R1−R2|≤Threshold Value?" is performed. In this process, it is determined whether or not the retention time points R1 and R2 read in Steps S102 and S104 correspond to each other within a threshold value range. If corresponding (YES), it is determined that two retention time points are the same and the UV spectrum of the peak at the retention time points R1 is U1. Then, the procedure proceeds to Step S106. If not corresponding (NO), it is determined that the two retention time points are not the same and the UV spectrum of the peak at a retention time point of R1 is not the UV spectrum U1. Then, the procedure proceeds to Step S104 so as to perform comparison with the next data of the 3D chromatogram. The threshold value used in this determination process is the "sampling rate/2" of the 3D chromatogram. In Step S105, it is determined that the UV spectrum extracted from the 3D chromatogram and having the smallest difference in retention time relative to a peak of the FP corresponds to that peak of the FP according to the setting of the threshold value and the like.

In Step S106, a process of "normalizing the UV spectrum U1 with the maximum value of '1'" is performed. In this process, the UV spectrum U1 determined as the UV spectrum of the retention time point R1 in Step S105 is normalized with the maximum value of "1," and the procedure proceeds to Step S107.

In Step S107, a process of "outputting R1, the peak P1 as well as the normalized U1 (target FP)" is performed. In this process, the R1 and P1 acquired from the peak information and the U1 normalized in S106 are output to the target FP, and the procedure proceeds to Step S108.

In Step S108, a determining process "Has the process for all the peaks been completed?" is performed. In this process, it is determined whether or not all the peaks included in the peak information have been processed. If the process has not been completed for all the peaks (NO), the procedure proceeds to Step S102 in order to process one or more peaks that have not been processed. The process of Steps S102 to S108 is repeated until the process for all the peaks is completed. If the process for all the peaks has been completed (YES), the FP preparing process is finished.

Figure 96:
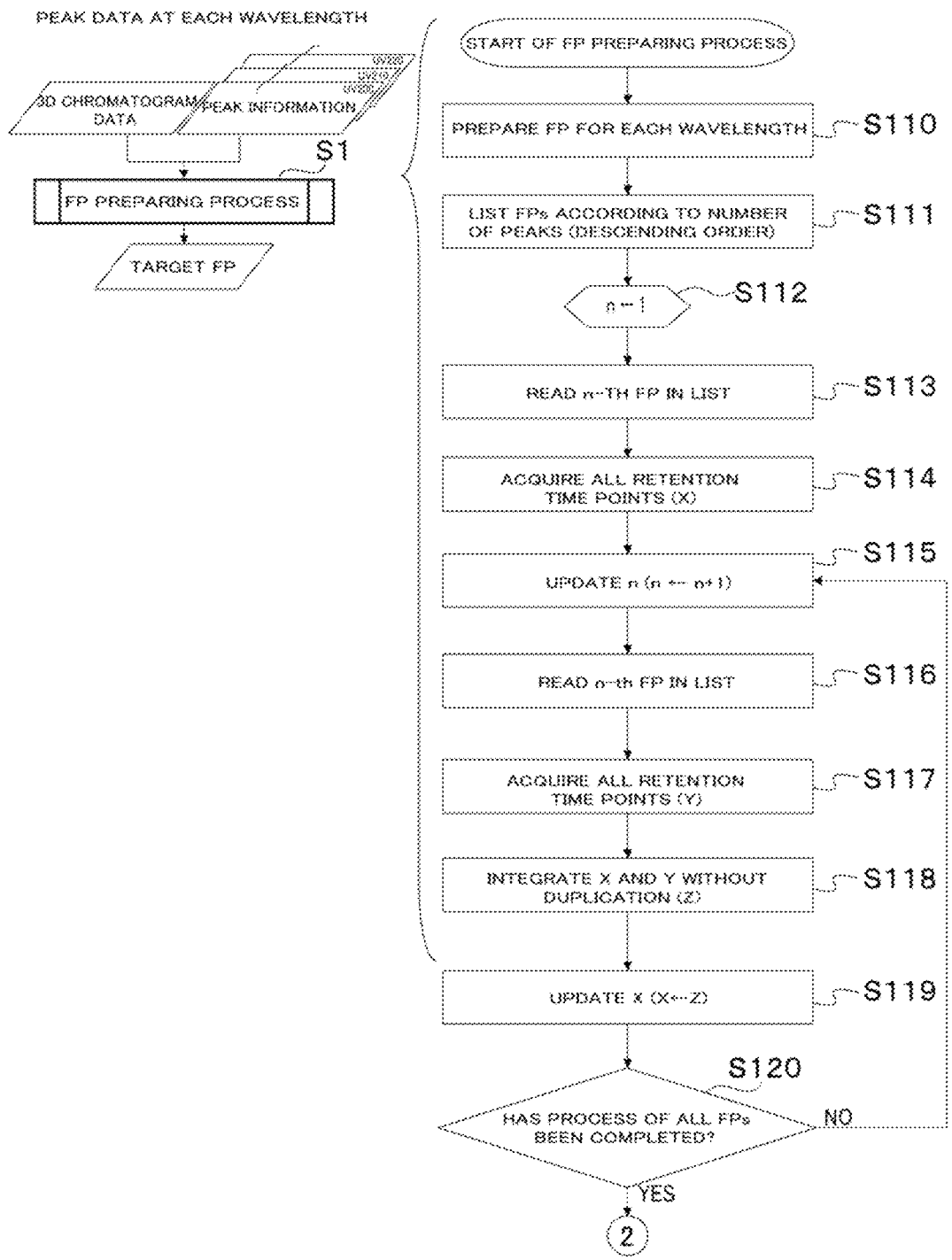
FIG. 96 is a data processing flowchart in a FP preparing function according to a plurality of wavelengths according the first embodiment.
Figure 97:
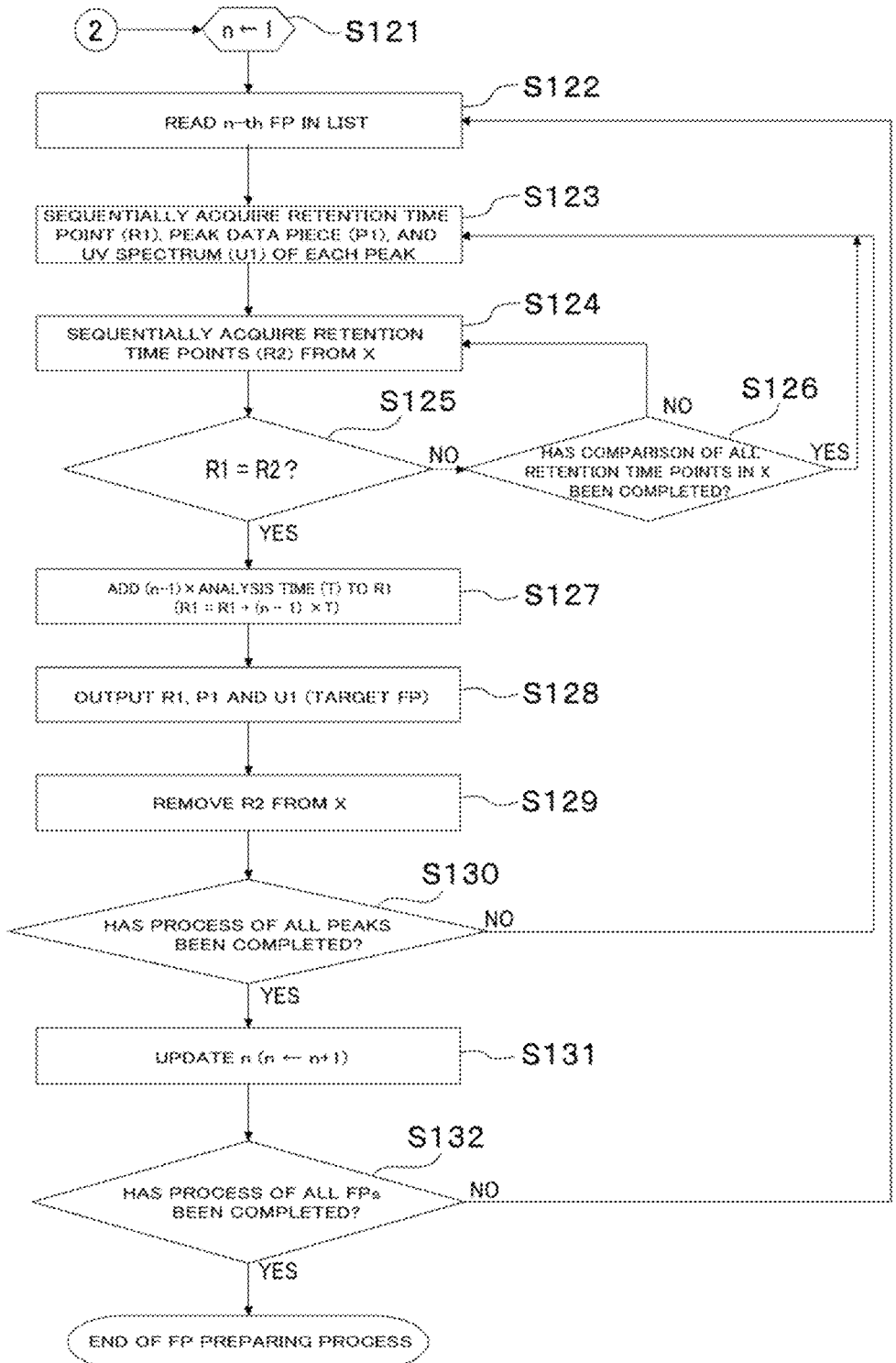
FIG. 97 is a data processing flowchart in the FP preparing function according to the plurality of wavelengths according the first embodiment.

FIGS. 96 and 97 are flowcharts of a case where peak information at a plurality of wavelengths are used instead of the peak information at the single wavelength in the "FP preparing process" of Step S1 illustrated in FIG. 93. For example, this is a case where a plurality of (n) wavelengths are selected in the direction of the detection wavelength axis including 203 nm to prepare a FP.

This FP preparing process is for preparing a FP that covers all the peaks of the 3D chromatogram with use of peak information of a plurality of wavelengths in a case where all the peaks detected in the 3D chromatogram cannot be covered for the single wavelength as illustrated in FIG. 95.

In addition, FIGS. 96 and 97 illustrate details of the step in which n FPs are prepared at respective wavelengths by performing the above-described FP preparing process by means of only a single wavelength, and, based on the FPs, a FP according to the plurality of wavelengths is prepared.

In Step S110, a process of "preparing a FP for each wavelength" is performed. In this process, the above-described FP preparing process using only the single wavelength is performed for each wavelength so as to prepare n FPs, and the procedure proceeds to Step S111.

In Step S111, a process of "listing the FPs according to the number of peaks (descending order)" is performed. In this process, the n FPs are listed in the descending order of the number of peaks, and the procedure proceeds to Step S112.

In Step S112, as initialization of a counter for sequentially processing n FPs, one is substituted into n (n←1), and the procedure proceeds to Step S113.

In Step S113, a process of "reading the n-th FP in the list" is performed. In this process, the n-th FP in the list is read, and the procedure proceeds to Step S114.

In Step S114, a process of "acquiring all the retention time points (X)" is performed. In this process, all the retention time point information of the FPs read in S113 is acquired, and the procedure proceeds to Step S115.

In Step S115, a process of "updating n (n n+1)" is performed. In this process, "n+1" is substituted into "n" as the update of "n" in order to advance the process to the next FP, and the procedure proceeds to Step S116.

In Step S116, a process of "reading the n-th FP in the list" is performed. In this process, the n-th FP in the list is read, and the procedure proceeds to Step S117.

In Step S117, a process of "acquiring all the retention time points (Y)" is performed. In this process, the retention time point information of all the FPs read in S116 is acquired, and the procedure proceeds to Step S118.

In Step S118, a process of "integrating X and Y without duplication (Z)" is performed. In this process, the retention time point information X acquired in S114 and retention time point information Y acquired in Step S117 are integrated without duplication, thereafter, the integrated information is stored in Z, and then, the procedure proceeds to Step S119.

In Step S119, a process of "updating X (X←Z)" is performed. In this process, as the update of X, Z stored in Step S118 is substituted for X, and the procedure proceeds to Step S120.

In Step S120, a determining process "Have all the FPs been processed?" is performed. In this process, it is determined whether or not all the n FPs prepared in Step S110 have been processed. If processed (YES), the procedure proceeds to Step S121. If there are one or more FPs that have not been processed (NO), the procedure proceeds to Step S115 in order to perform the process of Steps S115 to S120 for the FPs that have not been processed. Until the process for all the FPs is completed, the process of Steps S115 to S120 is repeated.

In Step S121, as the initialization of the counter for sequentially processing n FPs, "1" is substituted in n (n←1), and the procedure proceeds to Step S122.

In Step S122, a process of "reading the n-th FP in the list" is performed. In this process, the n-th FP in the list is read, and the procedure proceeds to Step S123.

In Step S123, a process of "sequentially acquiring a retention time point (R1), peak data (P1), and a UV spectrum (U1) of each peak" is performed. In this process, the retention time points (R1), the peak data pieces (P1), and the UV spectra (U1) of the peaks are sequentially acquired from the FP read in Step S122 peak by peak, and the procedure proceeds to Step S124.

In Step S124, a process of "sequentially acquiring the retention time points (R2) from X" is performed. In this process, retention time points (R2) are sequentially acquired from X in which the retention time points of all the FPs are stored without duplication one by one, and the procedure proceeds to Step S125.

In Step S125, a process of determining "R1=R2?" is performed. In this process, it is determined whether or not R1 acquired in Step S123 and R2 acquired in Step S124 are the same. If being the same (YES), the procedure proceeds to Step S127. If not being the same (NO), the procedure proceeds to Step S126.

In Step S126, a determining process "Has the comparison of all the retention time points of X been completed?" is performed. In this process, it is determined whether or not the comparison of R1 acquired in S123 with all the retention time points of X has been completed. If completed (YES), it is determined that the peak at the retention time point of R1 has been processed, and the procedure proceeds to Step S123 in order to move the process to the next peak. If not completed (NO), the procedure proceeds to Step S124 in order to advance the process to the next retention time point of X.

In Step S127, a process of "adding (n−1)×analysis time (T) to R1 (R1←R1+(n−1)×T)" is performed. In this process, for retention time points of peaks that are present in the first FP having the highest number of peaks in the list, the retention time points are unchanged, for the retention time points of peaks that are not present in the first FP in the list but are present in the second FP in the list, an analysis time (T) is added to R1, and, for the retention time points of peaks that are not present in the first to (n−1)-th FP in the list but are present in the n-th FP in the list, (n−1)×T is added to R1. Then, the procedure proceeds to Step S128.

In Step S128, a process of outputting "R1, P1, and U1 (target FP)" is performed. In this process, R1 processed in Step S127, P1 and U1 acquired in Step S123 are output to the target FP, and the procedure proceeds to Step S129.

In Step S129, a process of "removing R2 from X" is performed. In this process, since the processes at the retention time points R1 (=R2) have been completed in Steps S127 and S128, the retention time points (R2) that have been processed are removed from X, and the process proceeds to S130.

In Step S130, a determining process "Have all peak processes been completed?" is performed. In this process, it is determined whether or not the process has been completed for all the peaks of the n-th FP in the list. If completed (YES), the FP preparing process for the n-th FP in the list is finished to proceed to Step S131. If not completed (NO), the procedure proceeds to Step S123 in order to process any peak that has not been completed. Until the process for all the peaks is finished, the process of Steps S123 to S130 is repeated.

In Step S131, a process of "updating n (n←n+1)" is performed. In this process, in order to advance the process to the next FP, "n+1" is substituted into "n" as the update of "n", and the procedure proceeds to Step S132.

In Step S132, a determining process "Have all FP processes been completed?" is performed. In this process, it is determined whether or not all the n FPs prepared in Step S110 have been processed. If processed (YES), the FP preparing process is finished. If there are one or more FPs that have not been processed (NO), the procedure proceeds to Step S122 in order to perform the process of Steps S122 to S132 for the FPs that have not been processed. Until the process of all the FPs is completed, the process of Steps S122 to S132 is repeated.

Figure 98:
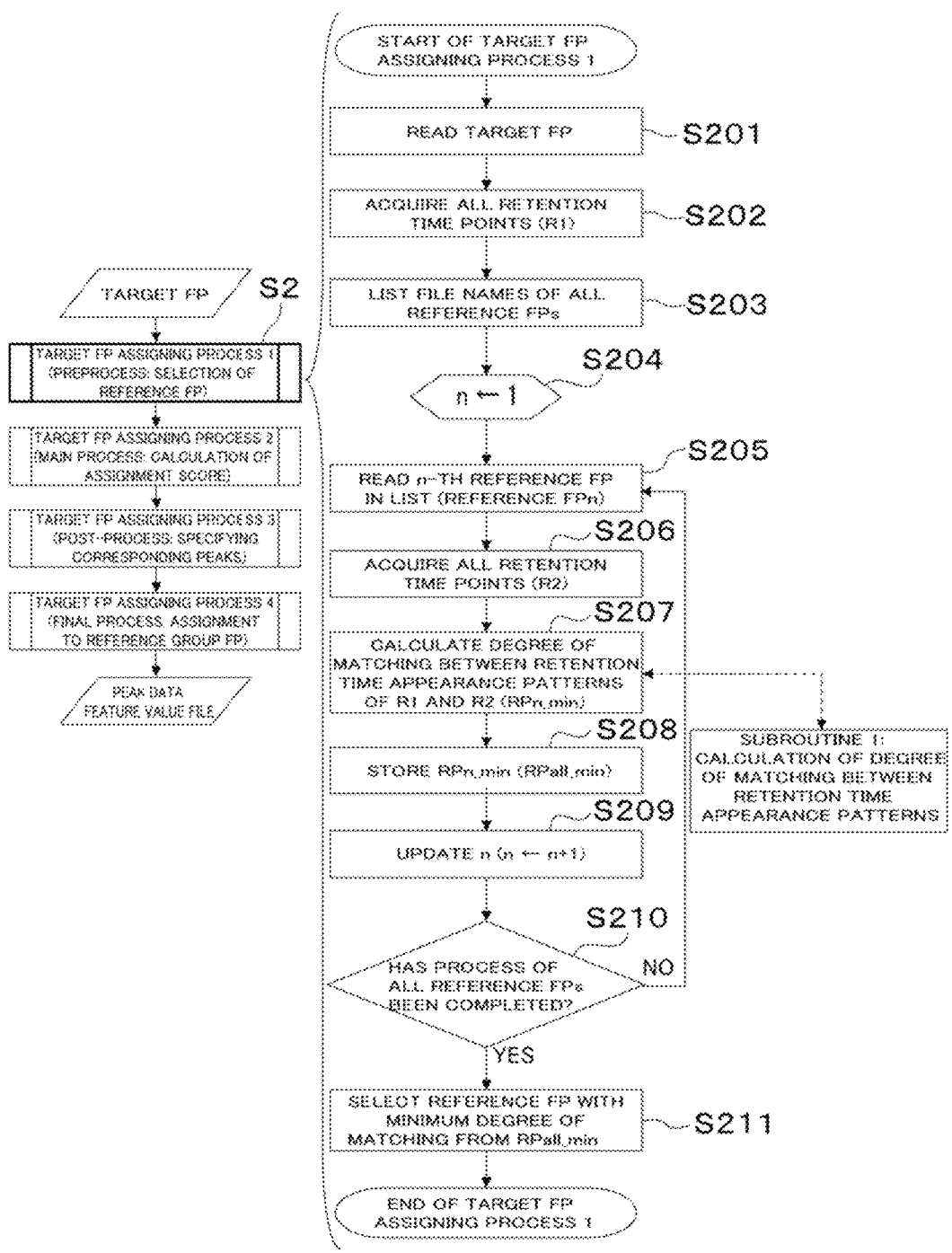
FIG. 98 is a data processing flowchart of a peak assigning process 1 (selection of a reference FP) according the first embodiment.

FIG. 98 is a flowchart illustrating details of the "target FP assigning process 1" of Step S2 illustrated in FIG. 93. This process is a preprocess of the assigning process and selects a reference FP that is appropriate to the assignment of the target FP 43 from among a plurality of reference FPs regarded as normal products.

In Step S201, a process of "reading a target FP" is performed. In this process, a FP that is an assignment target is read, and the procedure proceeds to Step S202.

In Step S202, a process of "acquiring all the retention time points (R1)" is performed. In this process, all the retention time point information of the target FP that is read in S201 is acquired, and the procedure proceeds to Step S203.

In Step S203, a process of "listing file names of all the reference FPs" is performed. In this process, the file names of all the reference FPs are listed in advance in order to sequentially process all the reference FPs later, and the procedure proceeds to Step S204.

In Step S204, "1" is substituted into "n" (n←1) as an initial value of a counter used for sequentially processing all the reference FPs, and the procedure proceeds to Step S205.

In Step S205, a process of "reading the n-th reference FP (reference $FP_n$) in the list" is performed. In this process, the n-th FP of the file name list of all the reference FPs listed in Step S203 is read, and the procedure proceeds to Step S206.

In Step S206, a process of "acquiring all the retention time points (R2)" is performed. In this process, all the retention time point information of the reference FP that are read in Step S205 is acquired, and the procedure proceeds to Step S207.

In Step S207, a process of "calculating the degree of matching between retention time appearance patterns of R1 and R2 ($RP_n\_min$)" is performed. In this process, $RP_n\_min$ is calculated based on the retention time point of the target FP that is acquired in Step S202 and the retention time point of the reference FP that is acquired in Step S206, and the procedure proceeds to Step S208. A detailed calculation flow of $RP_n\_min$ will be described with reference to "Subroutine 1" of FIG. 103 separately.

In Step S208, a process of "storing $RP_n\_min$ ($RP_{all}\_min$)" is performed. In this process, $RP_n\_min$ calculated in Step S207 is stored in $RP_{all}\_min$, and the procedure proceeds to Step S209.

In Step S209, a process of "updating n (n←n+1)" is performed. In this process, in order to advance the process to the next FP, "n+1" is substituted for "n" as the update of "n", and the procedure proceeds to Step S210.

In Step S210, a determining process "Have all reference FP processes been completed?" is performed. In this process, it is determined whether or not all the reference FPs have been processed. If processed (YES), the procedure proceeds to Step S211. If there are one or more reference FPs that have not been processed (NO), the procedure proceeds to Step S205 in order to perform the process of Steps S205 to S210 for the FPs that have not been processed. Until the process of all the reference FPs is completed, the process of Steps S205 to S210 is repeated.

In Step S211, a process of "selecting a reference FP demonstrating the minimum degree of matching from $RP_{all}\_min$" is performed. In this process, $RP_1\_min$ to $RP_n\_min$ calculated for all the reference FPs are compared with each other, to select a reference FP demonstrating the minimum degree of matching with respect to the retention time appearance pattern of the target FP, and the target FP assigning process 1 is finished.

Figure 99:
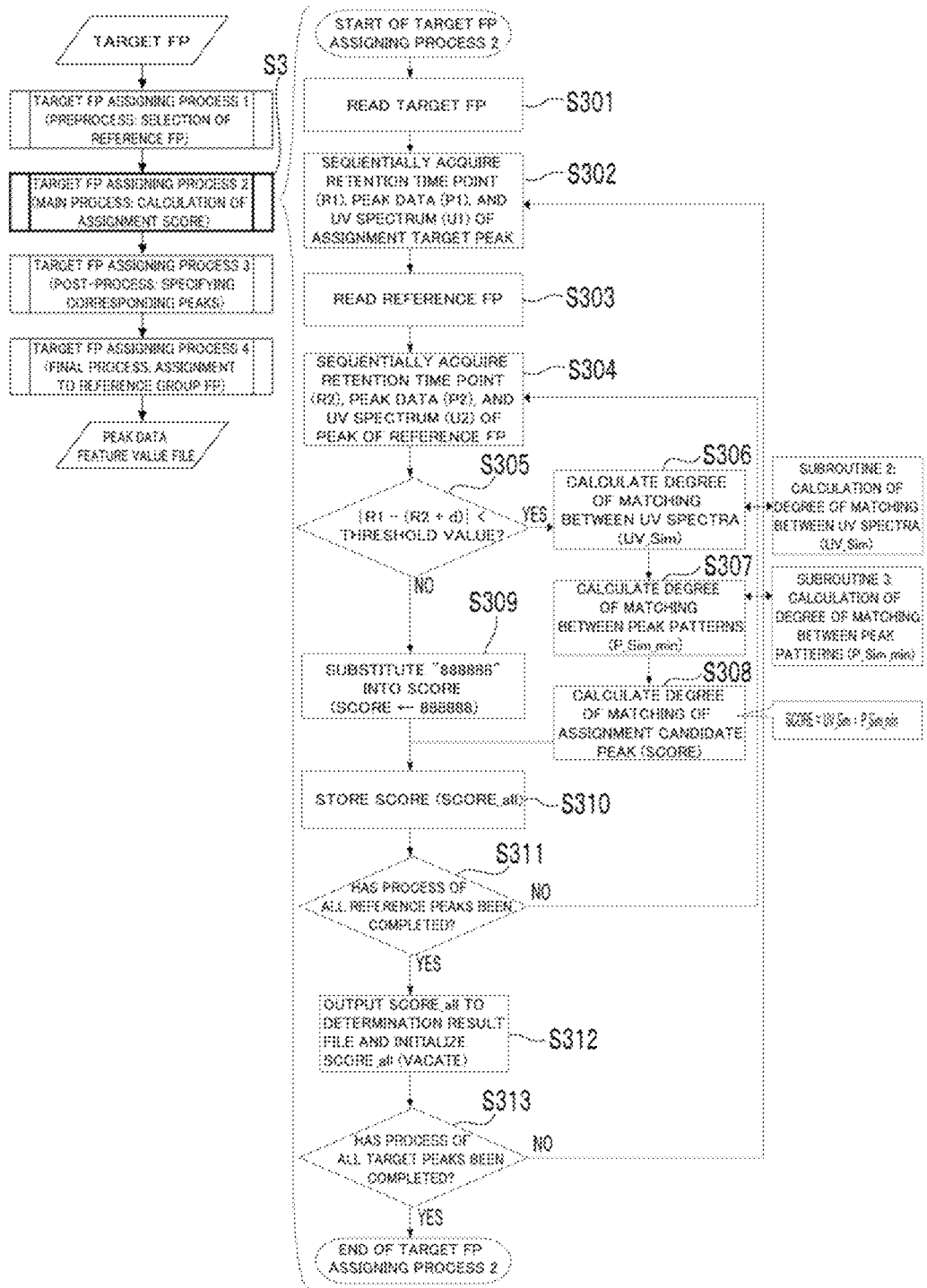
FIG. 99 is a data processing flowchart of a peak assigning process 2 (calculation of an assignment score) according the first embodiment.

FIG. 99 is a flowchart illustrating details of the "target FP assigning process 2" of Step S3 illustrated in FIG. 93. This process is a main process of the assigning process and calculates the degree (SCORE) of matching for each assignment candidate peak based on the degree of matching between peak patterns and the UV spectra of the target FP 43 and the reference FP selected in Step S2.

In Step S301, a process of "reading a target FP" is performed. In this process, a FP that is an assignment target is read, and the procedure proceeds to Step S302.

In Step S302, a process of "sequentially acquiring a retention time point (R1), peak data (P1), and a UV spectrum (U1) of an assignment target peak" is performed. In this process, the peaks of the target FP read in Step S301 are sequentially set as the assignment target peak to acquire R1, P1, and U1, and the procedure proceeds to Step S303.

In Step S303, a process of "reading the reference FP" is performed. In this process, the reference FP that is selected in the "Target FP Assigning Process 1" in FIG. 98 is read, and the procedure proceeds to Step S304.

In Step S304, a process of "sequentially acquiring a retention time point (R2), peak data (P2), and a UV spectrum (U2) of the peak of the reference FP" is performed. In this process, R2, P2, and U2 are acquired from the reference FP read in Step S303 for each peak, and the procedure proceeds to Step S305.

In Step S305, a determining process "|R1−(R2+d)|<Threshold Value?" is performed. In this process, it is determined whether or not R1 and R2 read in Steps S302 and S304 correspond to each other within the threshold value range. If corresponding (YES), it is determined that the peak of which the retention time point is R2 is an assignment candidate peak of the peak of which the retention time point is R1. Then, in order to calculate the degree of matching for the assignment candidate peak (SCORE), the procedure proceeds to Step S306. If not corresponding (NO), since the peak of which the retention time point is R2 and the peak of which the retention time point is R1 have a great difference in the retention time, it is determined that the peak cannot be set as the assignment candidate peak, and the procedure proceeds to Step S309. In addition, "d" used in this determination process is a value for correcting the retention time points of the peaks of the target FP and the reference FP, and the initial value is set to zero. A difference between the retention time points of peaks is acquired whenever being assigned during the progress of the process to update "d" with the value. In addition, the threshold value is an allowable range of the retention time points used for determining whether to be set as an assignment candidate peak.

In Step S306, a process of "calculating the degree of matching between UV spectra (UV_Sim)" is performed. In this process, UV_Sim is calculated based on U1 of the assignment target peak acquired in Step S302 and U2 of the assignment candidate peak acquired in S304, and the procedure proceeds to Step S307. In addition, a detailed calculation flow of UV_Sim will be described with reference to "Subroutine 2" in FIG. 86 separately.

In Step S307, a process of "calculating the degree of matching between peak patterns (P_Sim_min)" is performed. In this process, based on R1 and P1 of the assignment target peak acquired in Step S302 and R2 and P2 of the assignment candidate peak acquired in Step S304, peak patterns are comprehensively prepared for these peaks. In addition, P_Sim_min of these peak patterns is calculated, and the procedure proceeds to Step S308. A detailed calculation flow of P_Sim_min will be described with reference to "Subroutine 3" in FIG. 87 separately.

In Step S308, a process of "calculating the degree of matching for the assignment candidate peaks (SCORE)" is performed. In this process, from UV_Sim calculated in Step S306 and P_Sim_min calculated in Step S307, SCORE of the assignment target peak and the assignment candidate peak is calculated as:

$$SCORE = UV\_Sim \times P\_Sim\_min.$$

Then, the procedure proceeds to Step S310.

In Step S309, a process of "substituting 888888 into SCORE (SCORE←888888)" is performed. In this process, SCORE of a peak of an assignment target peak that does not correspond to an assignment candidate peak is set to "888888," and the procedure proceeds to Step S310.

In Step S310, a process of "storing SCORE (SCORE_all)" is performed. In this process, SCORE acquired in Step S308 or S309 is stored in SCORE_all, and the procedure proceeds to Step S311.

In Step S311, a determining process "Has the process of all reference peaks been completed?" is performed. In this process, it is determined whether or not all the peaks of the reference FP have been processed. If processed (YES), the procedure proceeds to Step S312. If there are one or more peaks that have not been processed (NO), the procedure proceeds to Step S304 in order to perform the process of S304 to S311 for the peaks that have not been processed. Until the process for all the peaks is completed, the process of Steps S304 to S311 is repeated.

In Step S312, a process of "outputting the SCORE_all to a determination result file to initialize (vacate) the SCORE_all" is performed. In this process, the SCORE_all is output to the determination result file, thereafter, the SCORE_all is initialized (vacated), and then, the procedure proceeds to Step S313.

In Step S313, a determining process "Has the process of all target peaks been completed?" is performed. In this process, it is determined whether all the peaks of the target FP have been processed. If processed (YES), the target FP assigning process 2 is finished. If there are one or more peaks that have not been processed (NO), the procedure proceeds to Step S302 in order to perform the process of Steps S302 to S313 for the unprocessed peaks. Until the process of all the peaks is completed, the process of S302 to S313 is repeated.

FIG. 120 illustrates an output determination result file example.

Figure 100:
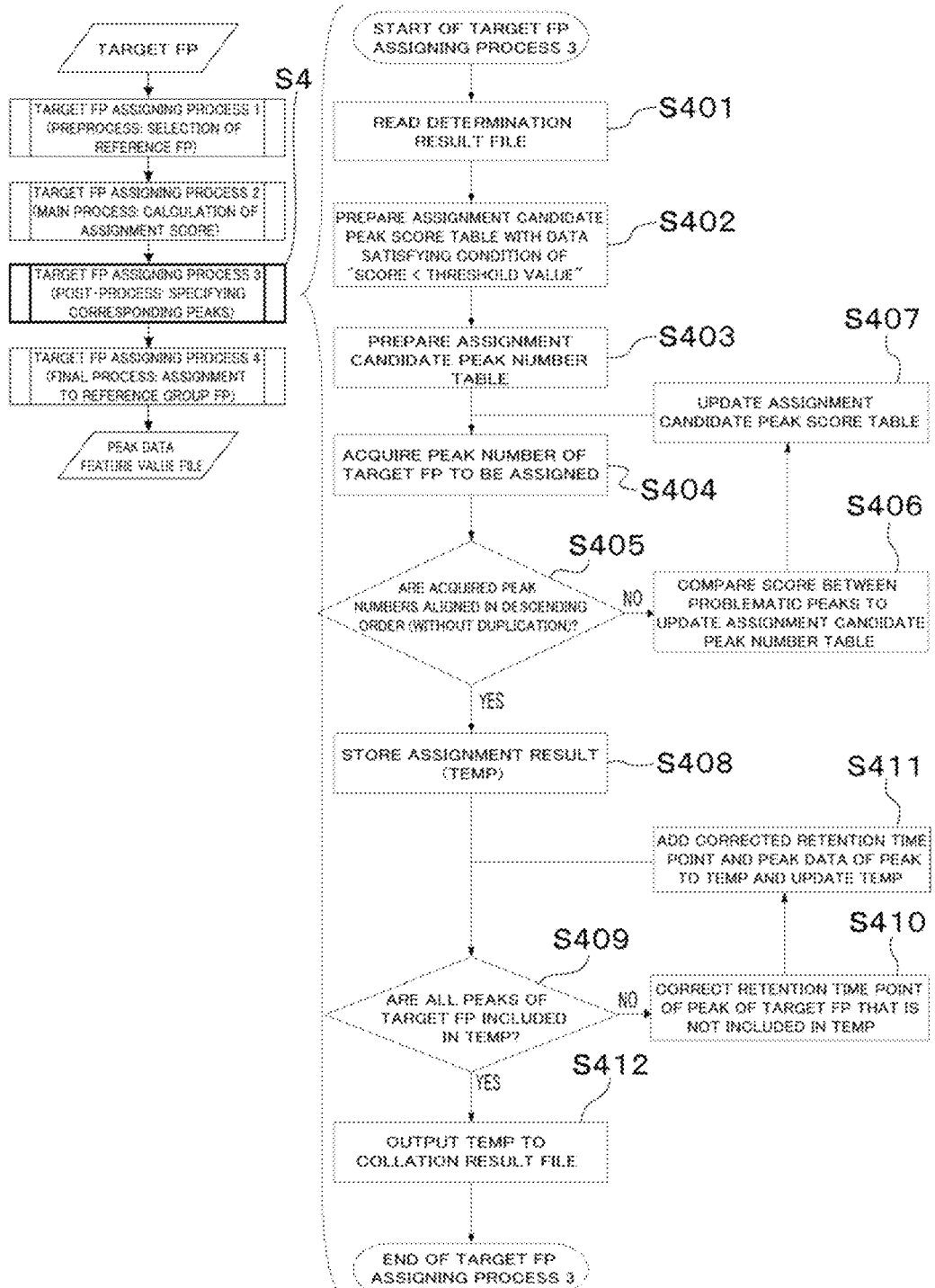
FIG. 100 is a data processing flowchart of a peak assigning process 3 (specifying a corresponding peak) according the first embodiment.

FIG. 100 is a flowchart illustrating the "target FP assigning process 3" of Step S4 in FIG. 93. This process is a post-process of the assignment and specifies the peak of the reference FP corresponding to each peak of the target FP based on the degree of matching between assignment candidate peaks (SCORE) calculated as described above.

In Step S401, a process of "reading a determination result file" is performed. In this process, the determination result file prepared by the "target FP assigning process 2" illustrated in FIG. 81 is read, and the procedure proceeds to Step S402.

In Step S402, a process of "preparing an assignment candidate peak score table with data satisfying the condition of "SCORE<Threshold value" is performed. In this process, an assignment candidate score table (the assignment candidate score table 191 of an upper diagram in FIG. 121) is prepared based on SCORE of the determination result file, and the procedure proceeds to Step S403. This assignment candidate peak score table is a table in which only SCOREs less than the threshold value in the SCORE calculated for the all peaks of the target FP are aligned in an ascending order for each peak of the reference FP. The smaller the value of SCORE is, the higher the possibility for peak to be assigned is. In addition, the threshold value is an upper limit value of the SCORE to determine whether to set as an assignment candidate.

In Step S403, a process of "preparing an assignment candidate peak number table" is performed. In this process, an assignment candidate peak number table (the assignment candidate peak number table 193 of a lower diagram in FIG. 121) is prepared based on the assignment candidate peak score table, and the procedure proceeds to Step S404. This assignment candidate peak number table is a table that is acquired by substituting each score included in the assignment candidate peak score table into a peak number of the target FP corresponding to the score. Accordingly, this table is a table that sequentially aligns the peak numbers of the target FP to be associated for each peak of the reference FP.

In Step S404, a process of "acquiring the peak numbers of the target FP to be assigned" is performed. In this process, a peak number of the target FP that is located at the highest position is acquired for each peak of the reference FP from the assignment candidate peak number table prepared in Step S403, and the procedure proceeds to Step S405.

In Step S405, a determining process "Are the acquired peak numbers aligned in a descending order (without duplication)?" is performed. In this process, it is determined whether or not the peak numbers of the target FP acquired in Step S404 are aligned in the descending order without duplication. If aligned (YES), it is determined that the peaks of the target FP corresponding to respective peaks of the reference FP can be settled, and the procedure proceeds to Step S408. If not aligned (NO), in order to reconsider one or more problematic peaks of the target FP to be assigned to peaks of the reference FP, the procedure proceeds to Step S406.

In Step S406, a process of "comparing SCOREs of problematic peaks to update the assignment candidate peak number table" is performed. In this process, SCOREs corresponding to the peak numbers of the target FP that have the problem are compared with use of the assignment candidate score table, and the assignment candidate peak number table is updated in which a peak number having a larger SCORE is substituted into a peak number located in the second, and the procedure proceeds to Step S407.

In Step S407, a process of "updating the assignment candidate peak store table" is performed. In this process, in accordance with the updated content of the assignment candidate peak number table in Step S406, the assignment candidate peak score table is updated, and the procedure proceeds to Step S404. Until there is no problem in the peak numbers of the target FP (there is no duplication, or the peak numbers are aligned in the descending order), the process of Steps S404 to S407 is repeated.

In Step S408, a process of "storing an assignment result (TEMP)" is performed. In this process, the peak numbers of all the peaks, the retention time points, and the peaks of the reference FP and peak data of the target FP that is specified as the peaks corresponding to these peak of the reference FP are stored in TEMP, and the procedure proceeds to Step S409.

In Step S409, a determining process "Are all the peaks of the target FP included in TEMP?" is performed. In this process, it is determined whether the peak data of all the peaks of the target FP is included in TEMP stored in Step S408. If all included (YES), it is determined that the process for all the peaks of the target FP has been completed, and the procedure proceeds to Step S412. If there is any excluded peak (NO), in order to add to peak data of the excluded peak to TEMP, the procedure proceeds to Step S410.

In Step S410, a process of "correcting the retention time point of the peak of the target FP that is not included in TEMP" is performed. In this process, the retention time point of the peak of the target FP (the peak of the target FP that is needed to be corrected) that is excluded from TEMP is corrected as a correction value=k1+(k2−k1)*(t0−t1)/(t2−t1): wherein:

k1: it is a retention time point of a peak having a shorter retention time point of two reference FP-side peaks that are assigned in the vicinity of a peak of a target FP for which correction is necessary;

k2: it is a retention time point of a peak having a larger retention time point of two reference FP-side peaks that are assigned in the vicinity of the peak of the target FP for which correction is necessary;

t0: it is a retention time point of the peak of the target FP for which correction is necessary;

t1: it is a retention time point of a peak having a shorter retention time point of two target FP-side peaks that are assigned in the vicinity of the peak of the target FP for which correction is necessary; and t2: it is a retention time point of a peak having a longer retention time point of two target FP-side peaks that are assigned in the vicinity of the peak of the target FP for which correction is necessary.

Then, the procedure proceeds to Step S411.

In Step S411, a process of "adding the corrected retention time point and the peak data thereof to TEMP, and updating TEMP" is performed. In this process, the retention time point of the peak of the target FP corrected in S410 and not included in TEMP is compared with the retention time points of the reference FP in TEMP, to add the corrected retention time point and peak data of the peak of the target FP that is not included in TEMP to a valid position in TEMP and update TEMP, and it proceeds to Step S409. Until all the peaks of the target FP are added, the process of Steps S409 to S411 is repeated.

In Step S412, a process of "outputting TEMP to a collation result file" is performed. In this process, TEMP that specifies the correspondence relation between all the peaks of the reference FP and the all the peaks of the target FP is output as a collation result file, and the target FP assigning process 3 is finished.

Figure 101:
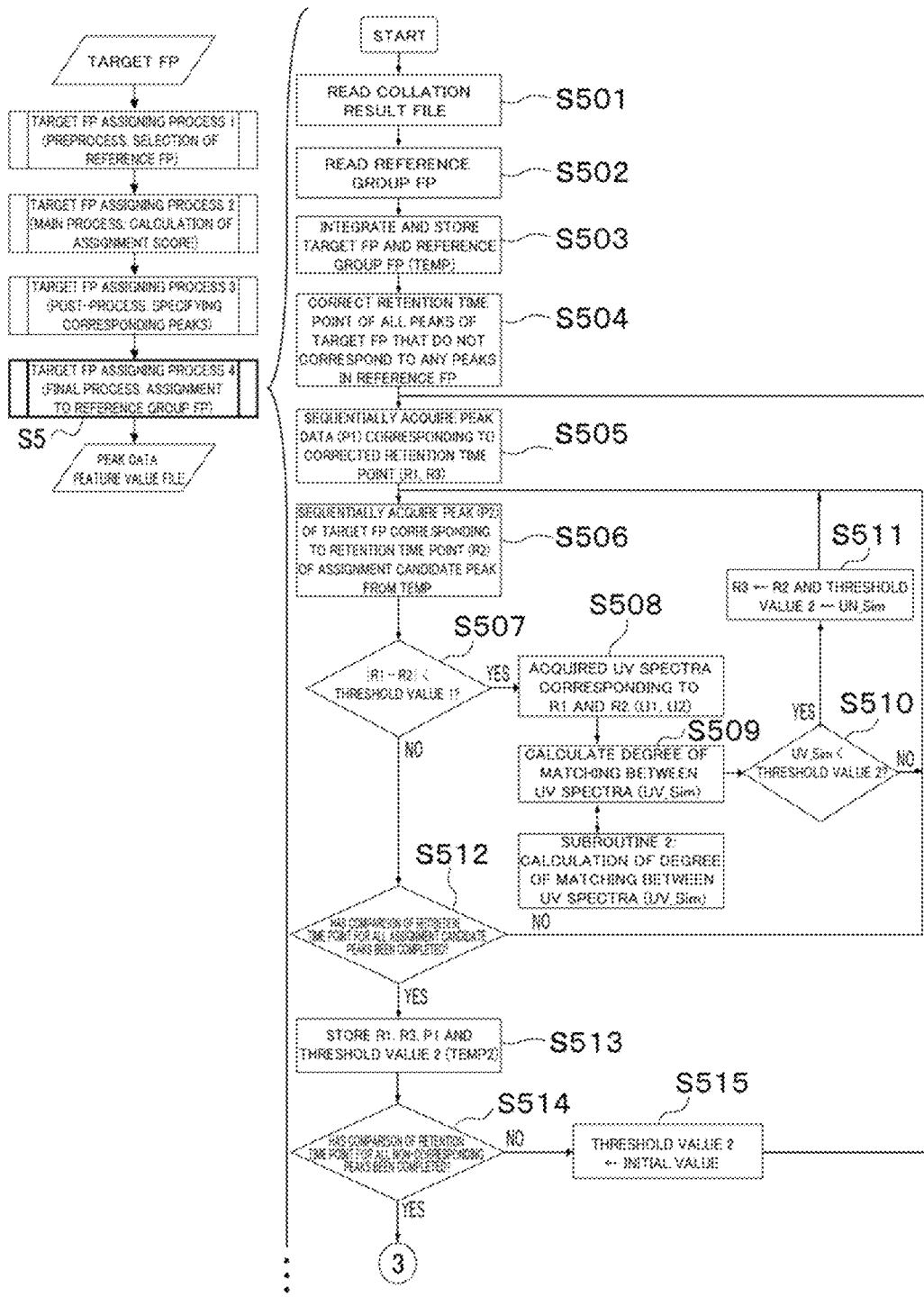
FIG. 101 is a data processing flowchart of a peak assigning process 4 (assignment to a reference group FP) according the first embodiment.
Figure 102:
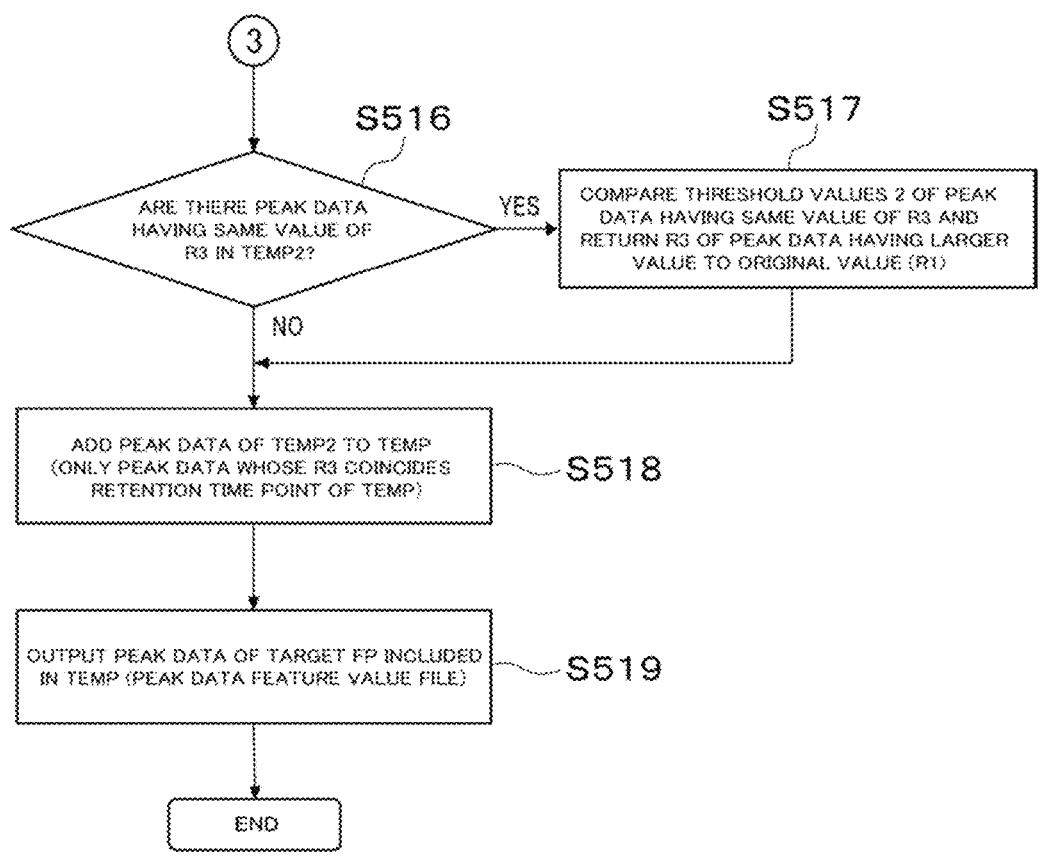
FIG. 102 is a data processing flowchart of the peak assigning process 4 (assignment to the reference group FP) according the first embodiment.

FIGS. 101 and 102 are flowcharts that illustrate details of the "target FP assigning process 4" of Step S5 illustrated in FIG. 93. This process is a final process of the assignment and assigns the peaks of the target FP to the respective peaks of the reference group FP (the reference group FP data example 197 in FIG. 123) based on the collation result file (the collation result file example 195 in FIG. 122) prepared in Step S4 of FIG. 93.

In addition, the reference group FP 197 is a FP that specifies the correspondence relation of peaks among all the reference FPs as described above. As the data example 197 of the reference group FP in FIG. 123, the reference group FP data 197 is data that is configured by reference group FP peak numbers, reference group retention time points, and peak heights. As illustrated in the reference group FP 45 in FIG. 3A, each peak can be denoted by an average value (black point)±standard deviation (vertical line).

In Step S501, a process of "reading a collation result file" is performed. In this process, the collation result file output in Step S412 illustrated in FIG. 100 is read, and the procedure proceeds to Step S502.

In Step S502, a process of "reading the reference group FP" is performed. In this process, the reference group FP 197 that is a final assignment opponent of each peak of the target FP is read, and the procedure proceeds to Step S503.

In Step S503, a process of "integrating and storing the target FP and the reference group FP (TEMP)" is performed. In this process, two files are integrated based on the peak data of the reference FP that is commonly present in the collation result file and the reference group FP 197 to store the result as TEMP, and the procedure proceeds to Step S504.

In Step S504, a process of "correcting the retention time points of all the peaks of the target FP that do not correspond to any peaks in the reference FP" is performed. In this process, the retention time points of all the peaks of the target FP that do not correspond to any peaks in the reference FP in the collation result file are corrected to the retention time points of TEMP stored in Step S503, and the procedure proceeds to Step S505. In addition, the correction for the retention time point is performed using the same method as that of Step S410 of the "Target FP Assigning Process 3" of Step S4 described above.

In Step S505, a process of "sequentially acquiring the peak data (P1) corresponding to the corrected retention time point (R1 and R3)" is performed. In this process, peak data pieces of peaks corresponding to retention time points corrected in Step S504 as R1 and R3 are sequentially acquired as P1, and the procedure proceeds to Step S506.

In Step S506, a process of "sequentially acquiring the peak data (P2) of the target FP corresponding to the retention time point (R2) of assignment candidate peak from TEMP" is performed. In this process, peak data pieces are sequentially acquired as P2 corresponding to the retention time points R2 at which no peak of the target FP are assigned from TEMP stored in Step S503, and the procedure proceeds to Step S507.

In Step S507, a determining process "|R1−R2|<threshold value 1?" is performed. In this process, it is determined whether or not a difference between the retention time points R1 and R2 acquired in Steps S505 and S506 is less than the threshold value 1. If a difference is less than the threshold value (YES), it is determined that there is a possibility that the retention time point of the target FP with the retention time point R corresponding to the retention time point of the reference FP with the peak of the retention time point R2, and the procedure proceeds to Step S508. If a difference between the retention time points R1 and R2 is the threshold value 1 or more (NO), it is determined that there is no possibility of the correspondence, and the procedure proceeds to Step S512.

In Step S508, a process of "acquiring UV spectra (U1, U2) corresponding to the retention time points R1 and R2" is performed. In this process, the UV spectra corresponding to the peaks of the retention time points of R1 and R2 that are determined to have the possibility of the correspondence in Step S507 are acquired from respective FPs, and the procedure proceeds to Step S509.

In Step S509, a process of "calculating the degree of matching between the UV spectra (UV_Sim)" is performed. In this process, the UV_Sim is calculated using the same method as that of Step S306 of the "Target FP Assigning Process 2" of Step S3 based on the UV spectra U1 and U2 acquired in Step S508, and the procedure proceeds to Step S510. In addition, a detailed calculation flow of the UV_Sim will be described with reference to "Subroutine 2" illustrated in FIG. 104 separately.

In Step S510, a determining process "UV_Sim<threshold value 2?" is performed. In this process, it is determined whether the UV_Sim calculated in Step S509 is less than the threshold value 2. If it is less than the threshold value 2 (YES), it is determined that the peak of the UV spectrum U1 corresponds to the peak of U2, and the procedure proceeds to Step S511. If the UV_Sim is the threshold value 2 or more (NO), it is determined that there is no correspondence, and the procedure proceeds to Step S507.

In Step S511, a process of "R3←R2, and threshold value 2←UV_Sim" is performed. In this process, the retention time point R3 (that is, R1) determined to have the correspondence in Step S510 is updated with R2 that is the retention time point of the corresponding opponent, thereafter, the threshold value 2 is updated with the value of UV_Sim, and the procedure proceeds to Step S507.

In Step S512, a determining process "Have the retention time points of all the assignment candidate peaks been compared?" is performed. In this process, it is determined whether comparisons of R1 with the retention time points of all the assignment candidate peaks have been compared. If completed (YES), the procedure proceeds to Step S513. If not completed (NO), the procedure proceeds to Step S507.

In Step S513, a process of "storing R1, R3 and P1 as well as the threshold value 2 (TEMP2)" is performed. In this process, the retention time point (R1) determined to have correspondence in Step S510 and a peak (P1) corresponding to R3 updated to the retention time point (R2) of the corresponding opponent are stored as well as the threshold value 2 (TEMP2) at this time, and the procedure proceeds to Step S507.

In Step S514, a determining process "Have the retention time points of all non-corresponding peaks been compared?" is performed. In this process, it is determined whether or not comparisons with the retention time points of the assignment candidate peaks have been completed in the retention time points of all non-corresponding peaks. If completed (YES), it is determined that the assignment process of all the non-corresponding peaks has been completed, and the procedure proceeds to Step S516. If not completed (NO), it is determined that one or more non-corresponding peaks that have not been processed remain, and the procedure proceeds to Step S515.

In Step S515, a process of "threshold value 2←initial value" is performed. In this process, the threshold value 2 that is updated to UV_Sim in Step S511 is returned to the initial value, and the procedure proceeds to Step S505.

In Step S516, a determining process "Are there peaks having the same value of R3 present in TEMP2?" is performed. In this process, it is determined whether or not a plurality of non-corresponding peaks are assigned to the same peak in TEMP. If there are non-corresponding peaks assigned to the same peak (YES), the procedure proceeds to Step S517. If such non-corresponding peak is not present (NO), the procedure proceeds to Step S518.

In Step S517, a process of "comparing the threshold values 2 of the peaks having the same values of R3 and returning R3 of the peak having a larger threshold value to its original value (R1)" is performed. In this process, the threshold values 2 of the peaks having the same value of R3 in TEMP2 are compared with each other, to return the value of R3 of the peak having a larger threshold value to its original value (in other words, R1), and the procedure proceeds to Step S518.

In Step S518, a process of "adding a peak of TEMP2 to TEMP (only a peak of whose R3 coincides with the retention time point of TEMP)" is performed. In this process, every peak of which R3 coincides with the retention time point of TEMP is added to TEMP, and the procedure proceeds to Step S519. Every peak of which R3 does not coincide with the retention time point of TEMP is not added, because there is no peak to be an assignment opponent in the reference group FP.

In Step S519, a process of "outputting the peaks of the target FP included in TEMP (peak feature value file)" is performed. In this process, the peak data of the target FP assigned to the reference group FP 197 is output as a peak data feature value file, to finish the target FP assigning process 4.

FIG. 124 illustrates an example of the peak data feature value file 199 output as described above.

Figure 103:
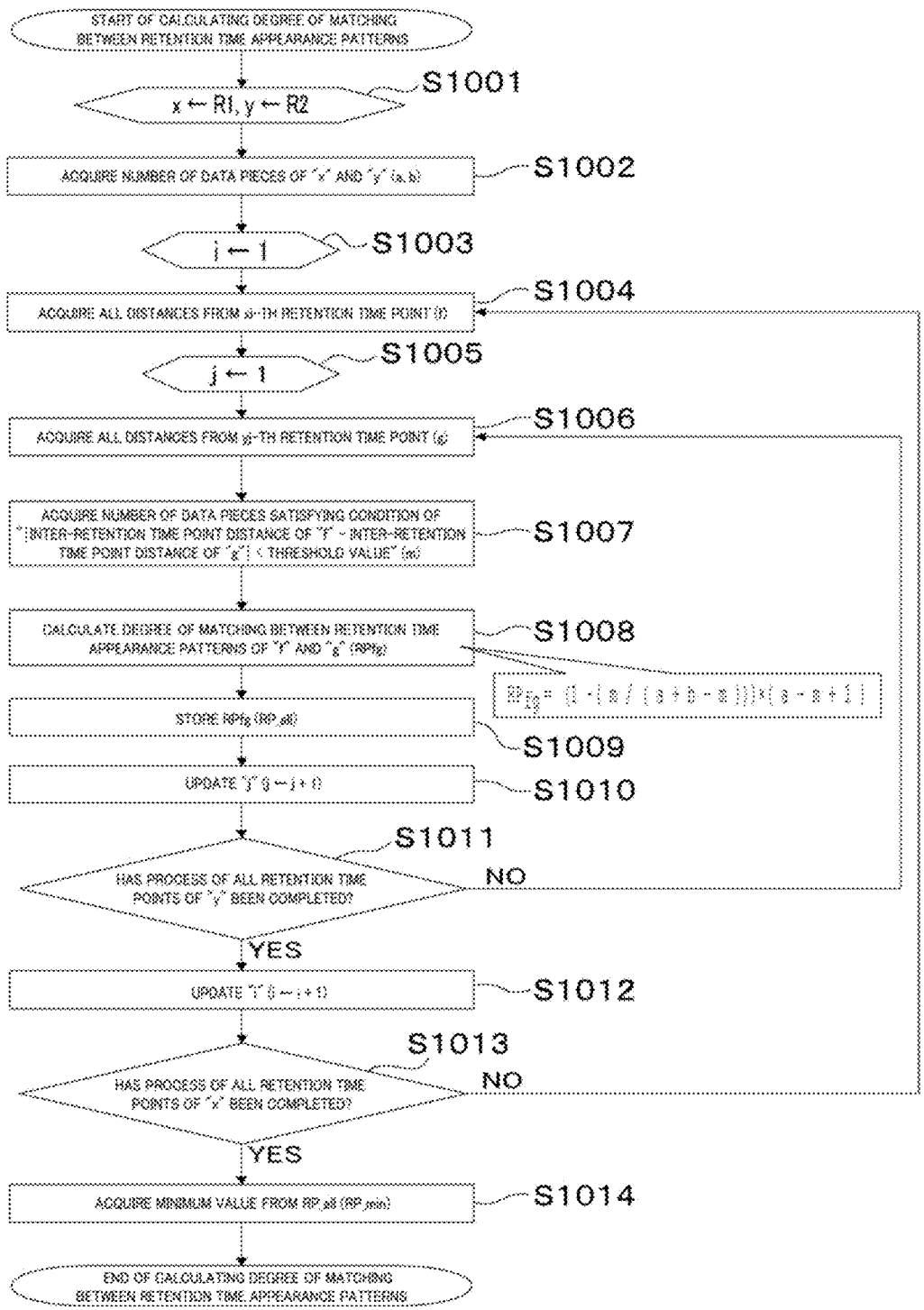
FIG. 103 is a flowchart of a process of calculating the degree of matching between retention time appearance patterns in the peak assigning process 1 (selection of the reference FP) according the first embodiment.

FIG. 103 is a flowchart illustrating details of the "Subroutine 1" of the "reference FP selecting process" illustrated in FIG. 98. This process calculates the degree of matching between retention time appearance patterns of FPs (for example, a target FP and a reference FP).

In Step S1001, a process of "x←R1 and y←R2" is performed. In this process, R1 and R2 acquired in Steps S202 and S206 illustrated in FIG. 98 are respectively substituted into "x" and "y", and the procedure proceeds to Step S1002.

In Step S1002, a process of "acquiring the numbers of data sets "x" and "y" (a, b)" is performed. In this process, the numbers of data pieces "x" and "y" are acquired as "a" and "b," respectively, and the procedure proceeds to Steps S1003.

In Step S1003, as an initial value of a counter used for sequentially invoking the retention time points of "x", "1" is substituted into "i" (i←1), and the procedure proceeds to Step S1004.

In Step S1004, a process of "acquiring entire distance from the xi-th retention time point (f)" is performed. In this process, all distances, from the xi-th retention time point, of retention time points after the xi-th retention time point are acquired as "f", and the procedure proceeds to Step S1005.

In Step S1005, as an initial value of a counter for sequentially invoking the retention time points of "y," "1" is substituted into "j" (j←1), and the procedure proceeds to Step S1006.

In Step S1006, a process of "acquiring all distances from the yj-th retention time point (g)" is performed. In this process, all distances, from the yj-th retention time point, of retention time points after the yj-th retention time point are acquired as "g," and the procedure proceeds to Step S1007.

In Step S1007, a process of "acquiring the number of data sets satisfying a condition of "|inter-retention time point distance of "f"–inter-retention time point distance of "g"|<threshold value" (m)" is performed. In this process, inter-retention time point distances "f" and "g" acquired in Steps S1004 and S1006 are compared with each other in a round-robin, the number of data pieces satisfying the condition of "|inter-retention time point distance of "f"–inter retention time point distance of "g"|<threshold value" is acquired as "m", and the procedure proceeds to Step S1008.

In Step S1008, a process of "calculating the degree of matching between the retention time appearance patterns of "f" and "g" ($RP_{fg}$)" is performed. In this process, $RP_{fg}$ is calculated based on "a" and "b" acquired in Step S1002 and "m" acquired in Step S1007 as:

$$RP_{fg} = (1-(m/(a+b-m))) \times (a-m+1).$$

Then, the procedure proceeds to Step S1009.

In Step S1009, a process of "storing $RP_{fg}$ (RP_all)" is performed. In this process, the degree of matching calculated in Step S1008 is stored in RP_all, and the procedure proceeds to Step S1010.

In Step S1010, a process of "updating "j" (j←j+1)" is performed. In this process, in order to perform the process of "y" at the next retention time point, "j+1" is substituted into "j" as the update of "j", and the procedure proceeds to Step S1011.

In Step S1011, a determining process "Has the process been completed at all the retention time points of "y"?" is performed. In this process, it is determined whether or not the process for all the retention time points of "y" has been completed. If completed (YES), it is determined that the process for all the retention time points of "y" has been completed, and the procedure proceeds to Step S1012. If not completed (NO), it is determined that one or more retention time points that have not been processed remain in "y," to proceed to Step S1006. In other words, the process of Steps S1006 to S1011 is repeated until all the retention time point of "y" is processed.

In Step S1012, a process of "updating "i" (i←i+1)" is performed. In this process, as the update of "i" for advancing the process of "x" to the next retention time point, "i+1" is substituted into "i," and the procedure proceeds to Step S1013.

In Step S1013, a determining process "Has the process been completed at all the retention time points of "x"?" is performed. In this process, it is determined whether or not the process for all the retention time point of "x" has been completed. If completed (YES), it is determined that the process for all the retention time points of "x" has been completed, to proceed to Step S1014. If not completed (NO), it is determined that one or more retention time points that have not been processed remain in "x", to proceed to Step S1004. In other words, the process of Steps S1004 to S1013 is repeated until all the retention time points of "x" are processed.

In Step S1014, a process of "acquiring a minimum value from RP_all (RP_min)" is performed. In this process, the minimum value in RP_all in which RPs for all the combinations of the retention time appearance patterns of the target FP and the reference FP are stored is acquired as RP_min, and RP_min is input to Step S207 of FIG. 98 to finish the process of calculating the degree of matching between the retention time appearance patterns.

FIG. 104 is a flowchart illustrating details of the "Subroutine 2" of the "target FP assigning process 2" of FIG. 99. In this process, the degree of matching between UV spectra is calculated.

In Step S2001, a process of "x←U1, y←U2, z←0" is performed. In this process, the UV spectra U1 and U2 acquired in Steps S302 and S304 of FIG. 99 are respectively substituted into "x" and "y", and furthermore, "0" is substituted as an initial value of sum (z) of squares of a distance of the UV spectra, and the procedure proceeds to Step S2002.

In Step S2002, a process of "acquiring the number of data pieces of "x" (a)" is performed. In this process, the number of data pieces of "x" is acquired as "a" and the procedure proceeds to Step S2003.

In Step S2003, as an initial value used for sequentially invoking absorbance at each detection wavelength configuring the UV spectrum U1 from "x," "1" is substituted into "i," and the procedure proceeds to Step S2004.

In Step S2004, a process of "acquiring xi-th data (b)" is performed. In this process, the i-th absorbance data of "x" into which the UV spectrum "U1" is substituted is acquired as "b," and the procedure proceeds to Step S2005.

In Step S2005, a process of "acquiring yi-th data (c)" is performed. In this process, the i-th absorbance data of "y" into which the UV spectrum "U2" is substituted is acquired as "c," and the procedure proceeds to Step S2006.

In Step S2006, a process of "calculating an inter-UV spectrum distance (d) and a sum (z) of squares of the inter-UV spectrum distances" is performed. In this process, the inter-UV spectrum distance "d" and the sum "z" of squares of the inter-UV spectrum distances are calculated as:

$$d = b-c; \text{ and}$$

$$z = z + d^2.$$

Then, the procedure proceeds to Step S2007.

In Step S2007, a process of "updating "i" (i i+1)" is performed. In this process, as the update of "i", "i+1" is substituted into "I," and the procedure proceeds to Step S2008.

In Step S2008, a determining process "Have the process of all data of "x" been completed ?" is performed. In this process, it is determined whether the process for all data of "x" and "y" have been completed. If completed (YES), it is determined that the process for all data of "x" and "y" has been completed, and the procedure proceeds to Step S2009. If not completed (NO), it is determined that there are one or more data pieces of "x" and "y" that have not been processed, and the procedure proceeds to Step S2004. In other words, the process of Steps S2004 to S2008 is repeated until all the absorbance data of "x" and "y" is processed.

In Step S2009, a process of "calculating the degree of matching between the UV spectra of "x" and "y" (UV_Sim)" is performed. In this process, the UV_Sim is calculated based on the sum "z" of squares of the inter-UV spectrum distances and the number "a" of data sets of "x" as follows:

$$UV\_Sim = \sqrt{(z/a)}.$$

UV_Sim is input to Step S306 in FIG. 99, to finish the process of calculating the degree of matching between UV spectra.

Figure 105:
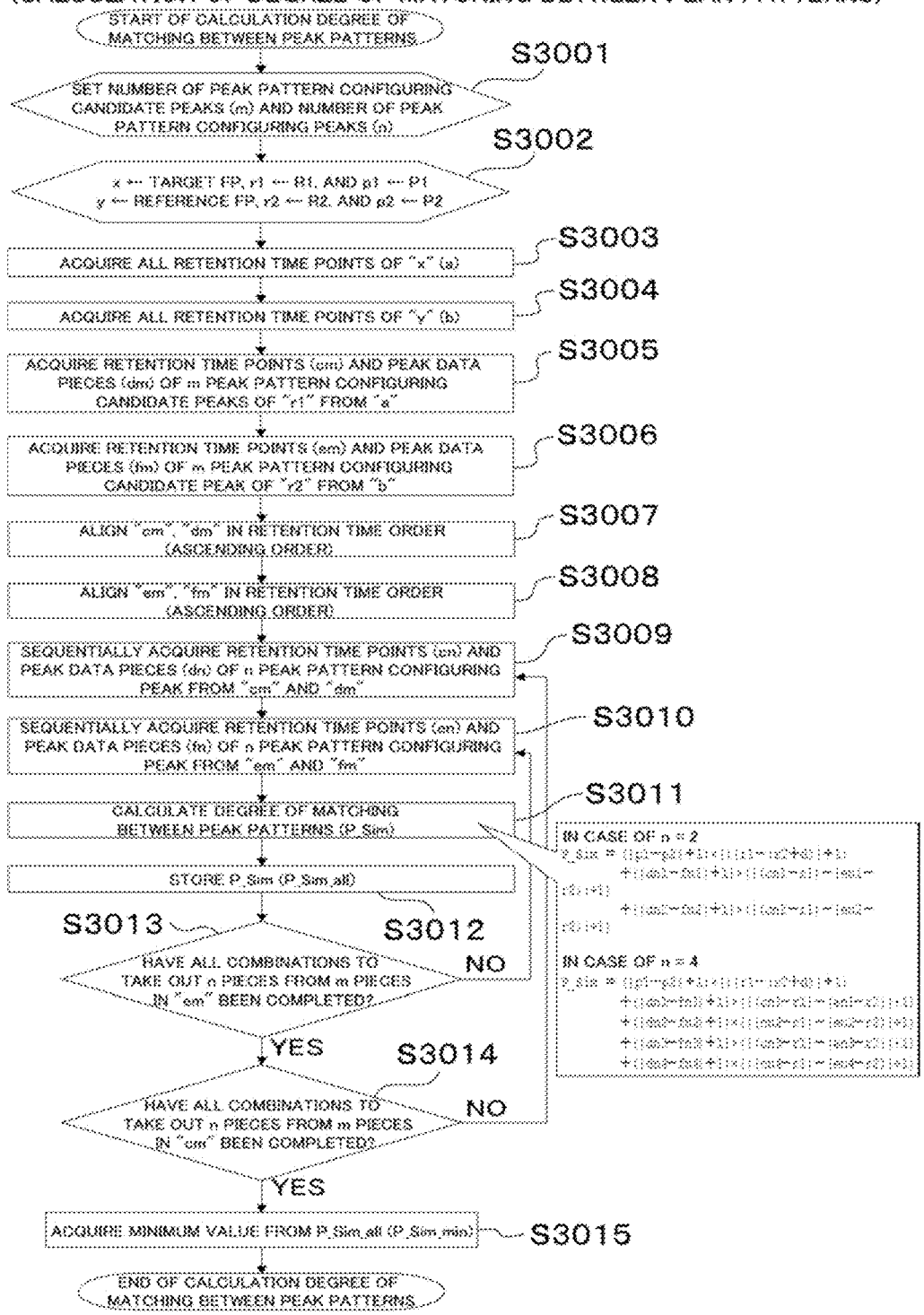
FIG. 105 is a flowchart of a process of calculating the degree of matching between peak patterns in the peak assigning process 2 (calculation of an assignment score) according the first embodiment.

FIG. 105 is a flowchart illustrating details of the "Subroutine 3" of the "target FP assigning process 2" of FIG. 99. In this process, the degrees of matching between peak patterns are calculated.

In Step S3001, a process of "setting the number (m) of peak pattern configuring candidates and the number (n) of peak pattern configuring peaks" is performed. In this process, as setting for comprehensively preparing peak patterns, the number (m) of peak pattern configuring candidates and the number (n) of peak pattern configuring peaks are set, and the procedure proceeds to Step S3002.

In Step S3002, a process of "x←target FP name, r1←R1, p1←P1, y←reference FP name, r2←R2, and p2←P2" is performed. In this process, the file names of the target FP and the reference FP that are necessary for the process, and the retention time points and the peak data acquired in Steps S302 and S304 of FIG. 99 are substituted into "x," "r1," and "p1," and "y," "r2," and "p2," and the procedure proceeds to Step S3003.

In Step S3003, a process of "acquiring all retention time points of "x" (a)" is performed. In this process, a file (target FP) having a name substituted into "x" in Step S3002 is read, all the retention time points of the file are acquired as "a," and the procedure proceeds to Step S3004.

In Step S3004, a process of "acquiring all retention time points of "y" (b)" is performed. In this process, a file (reference FP) having a name substituted into "y" in Step S3002 is read, all the retention time points of the file are acquired as "b," and the procedure proceeds to Step S3005.

In Step S3005, a process of "acquiring the retention time points (cm) and peak data (dm) of m peak pattern configuring candidate peaks of "r1" from "a"" is performed. In this process, retention time points of m peak pattern configuring candidate peaks of "r1" that are retention time points of the assignment target peaks are acquired as "cm" and "dm" from "a," and the procedure proceeds to Step S3006. Here, m peak pattern configuring candidate peaks are m peaks with retention time points close to "r1."

In Step S3006, a process of "acquiring the retention time points (em) and peak data (fm) of m peak pattern configuring candidate peaks of "r2" from "b"" is performed. In this process, retention time points of m peak pattern configuring candidate peaks of "r2" that are the retention time points of the assignment target peaks are acquired as "em" and the peak data thereof as "fm" from "b," and the procedure proceeds to Step S3007. Here, m peak pattern configuring candidate peaks are m peaks with retention time points close to "r2."

In Step S3007, a process of "aligning "cm" and "dm" in the retention time order (ascending order)" is performed. In this process, "cm" and "dm" acquired in Step S3005 are rearranged so as to be in the ascending order of the retention time, and the procedure proceeds to Step S3008.

In Step S3008, a process of "aligning "em" and "fm" in the retention time order (ascending order)" is performed. In this process, "em" and "fm" acquired in Step S3006 are rearranged so as to be in the ascending order of the retention time, and the procedure proceeds to Step S3009.

In Step S3009, a process of "sequentially acquiring retention time points (cn) and peak data (dn) of n peak pattern configuring peaks from "cm" and "dm"" is performed. In this process, the retention time points of n peak pattern configuring peaks are sequentially acquired as "cn" and the peak data thereof as "dn" from "cm" and "dm" of m peak pattern configuring candidate peaks, and the procedure proceeds to Step S3010.

In Step S3010, a process of "sequentially acquiring retention time points (en) and peak data (fn) of n peak pattern configuring peaks from "em" and "fm"" is performed. In this process, retention time points of n peak pattern configuring peaks are sequentially acquired as "en" and the peak data thereof as "fn" from "em" and "fm" of m peak pattern configuring candidate peaks, and the procedure proceeds to Step S3011.

In Step S3011, a process of "calculating the degree of matching between peak patterns (P_Sim)" is performed. In this process, the degree (P_Sim) of matching between peak patterns is calculated based on "r1" and "p1" of the assignment target peaks, "cn" and "dn" of n peak pattern configuring peaks, "r2" and "p2" of the assignment candidate peaks, and "en" and "fn" of n peak pattern configuring peaks, which have been acquired until now, in the case of n=4 as an example as represented in FIG. 64 as follows:

$$P\_Sim(73-95) = (|p1-p2|+1) \times (|(r1-(r2+d)|+1) +$$
$$(|dn1-fn1|+1) \times (|(cn1-r1)-(en1-r2)|+1) +$$
$$(|dn2-fn2|+1) \times (|(cn2-r1)-(en2-r2)|+1) +$$
$$(|dn3-fn3|+1) \times (|(cn3-r1)-(en3-r2)|+1) +$$
$$(|dn4-fn4|+1) \times (|(cn4-r1)-(en4-r2)|+1).$$

Then, the procedure proceeds to Step S3012.

In Step S3012, a process of "storing P_Sim (P_Sim_all)" is performed. In this process, P_Sim calculated in Step S3011 is sequentially stored in P_Sim_all, and the procedure proceeds to Step S3013.

In Step S3013, a determining process "Have all the combinations to take out n pieces from m pieces included in "em" been completed?" is performed. In this process, it is determined whether or not the process has been completed for all the combinations to take out n peaks pattern configuration peaks out from m peak pattern configuring candidate peaks. If completed (YES), it is determined that the preparation of comprehensive peak patterns and the calculation of the degrees of matching for the patterns have been completed for the assignment candidate peaks, to proceed to Step S3014. If not completed (NO), it is determined that one or more combinations to take out n pieces out from m pieces have not been completed, to proceed to Step S3010. In other words, the process of Steps S3010 to S3013 is repeated until the process is completed for all the combinations acquired by taking n pieces out from m pieces.

In Step S3014, a determining process "Have all the combinations to take out m pieces from n pieces included in "cm" been completed?" is performed. In this process, it is determined whether or not the process has been completed for all the combinations to take out n peak pattern configuring peaks from m peak pattern configuring candidate peaks of the assignment target peaks. If completed (YES), it is determined that the preparation of comprehensive peak patterns and the calculation of the degrees of matching for the patterns have been completed for the assignment candidate peak, to proceed to Step S3015. If not completed (NO), it is determined that one or more combinations to take out n pieces from m pieces have not been completed, to proceed to Step S3009. In other words, the process of Steps S3009 to S3014 is repeated until the process is completed for all the combinations to take n pieces out from m pieces.

In Step S3015, a process of "acquiring a minimum value from P_Sim_all (P_Sim_min)" is performed. In this process, the minimum value of the P_Sim-all stored in S3012 is acquired as P_Sim_min, and the P_Sim_min is input to Step S307 of FIG. 99 to finish the process of calculating the degree of matching between peak patterns.

Figure 106:
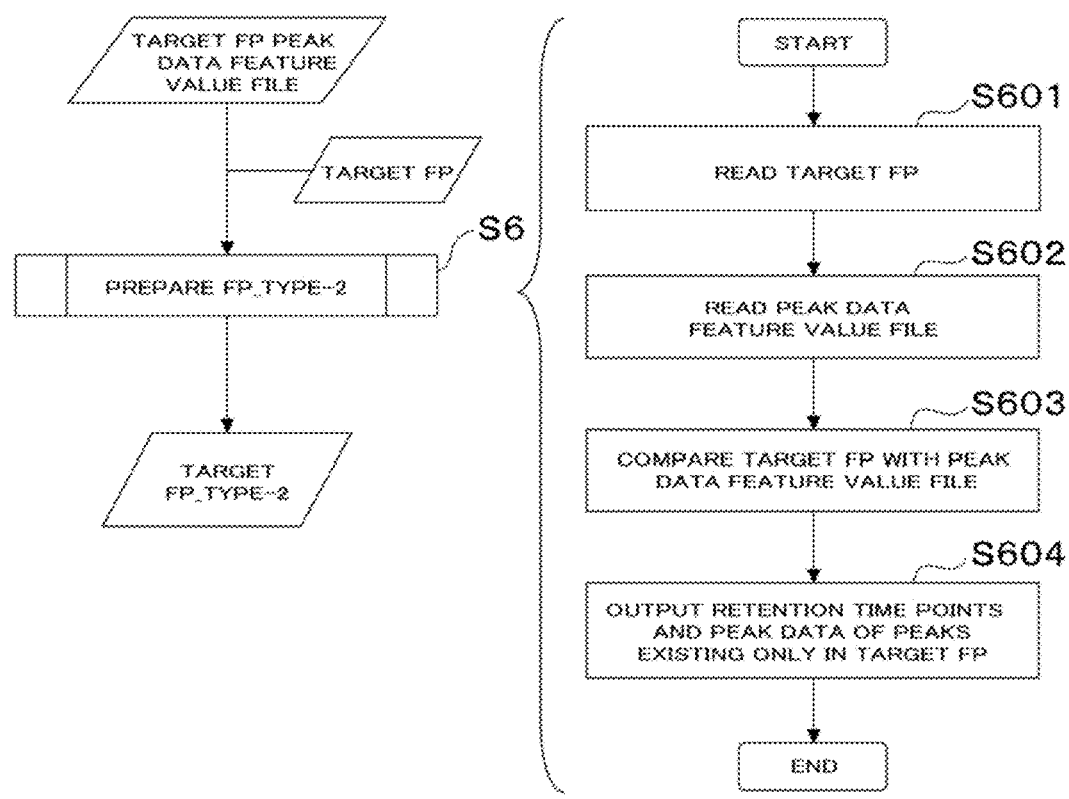
FIG. 106 is a flowchart illustrating details of the "preparation of FP type-2" according the first embodiment.

FIG. 106 is a flowchart illustrating details of the "preparation of FP type-2" of Step S6 in FIG. 93.

In Step S601, a process of "reading a target FP" is performed. In this process, a file of the target FP 43 (a data example 187 of the FP in FIG. 119) is read, and the procedure proceeds to Step S602.

In Step S602, a process of "reading a peak data feature value file" is performed. In this process, relating to the target FP 43, the peak data feature value file (a file example 199 of the peak data feature values in FIG. 124) is read, and the procedure proceeds to Step S603. The peak data feature value file example includes the peak information of the target FP 43 assigned to the peaks of the reference group FP 45 by the target FP peak feature value preparing part 7.

In Step S603, a process of "comparing the target FP with the peak data feature value file with each other" is performed. In this process, the file of the target FP 43 is compared with the peak data feature value file. Through this comparison, remaining peaks of the target FP 43 that have not assigned to the peaks of the reference group FP 45 are specified to proceed to Step S604.

In Step S604, a process of "outputting retention time points and peak data of peaks that are present only in the target FP" is performed. In this process, the retention time points and the peak data of the remaining peaks of the target FP 43 are output to a data file (a data example 201 of the reference and target FP type-2 in FIG. 125) of the target FP type-2.

Figure 107:
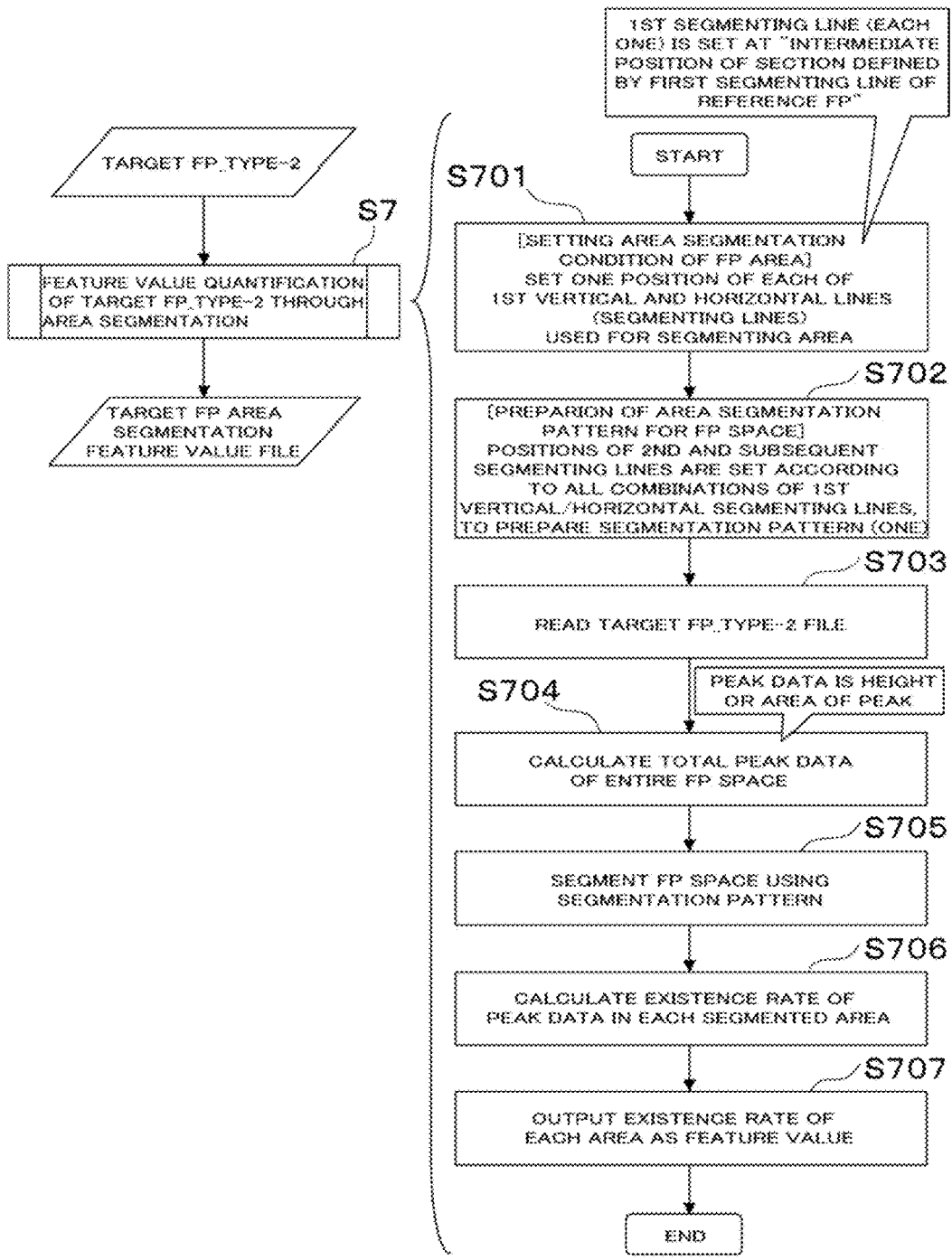
FIG. 107 is a flowchart illustrating details of a "feature value quantification process of the target FP_type-2 as feature values through area segmentation" according the first embodiment.

FIG. 107 is a flowchart illustrating details of the "process of quantifying the target FP type-2 as feature values through area segmentation" of Step S7 in FIG. 94.

In Step S701, a process of "setting area segmentation conditions of a FP space" is performed. In this process, in order to segment the area of the target FP type-2, one position for each of the 1st vertical and horizontal lines (segmenting lines) is set. Due to this setting, for example as illustrated in FIGS. 76 and 77, the vertical and horizontal segmenting lines (1st) are set as segmenting lines to a FP space. However, in the case of the target FP type-2, amplitude is not related because there is no change in a position of an area. After the vertical and horizontal lines (1st) are set in Step S701, the procedure proceeds to Step S702.

In Step S702, a process of "preparing an area segmentation pattern in the FP space" is performed. In this process, positions of 2nd and subsequent segmenting lines are set according to all the combinations of the 1st vertical and horizontal segmenting lines, thereby preparing a segmentation pattern (one). Due to this process, for example as illustrated in FIG. 78, the area segmentation for the FP space is performed by the vertical and horizontal segmenting lines. After the area segmentation is performed, the procedure proceeds to Step S703.

In Step S703, a process of "reading a file of the target FP type-2" is performed. Through this process, the file of the target FP type-2 is read, and the procedure proceeds to Step S704.

In Step S704, a process of "calculating total peak data of the entire FP space" is performed. This process, for example, a sum of heights of all the peaks that are present in respective lattices 145 segmented as illustrated in FIG. 79 is calculated (FIG. 81), and the procedure proceeds to Step S705.

In Step S705, a process of "segmenting the FP space by the segmentation pattern" is performed. In this process, the area of the target FP type-2 read in Step S703 is segmented according to the area segmentation pattern set in Step S702 as illustrated in FIG. 79, and the procedure proceeds to Step S706.

In Step S706, a process of "calculating an existence rate of peak data within a segmented area" is performed. In this process, an existence rate of peaks within each lattice 145 is calculated as the feature value=sum of peak heights within area/sum of heights of all the peaks. The calculation result is as illustrated in FIG. 86. After the calculation is completed, the procedure proceeds to Step S707.

In Step S707, a process of "outputting the existence rate of each area as a feature value" is performed. This process outputs a FP area segmentation feature value file (a target FP area segmentation feature value file example 203 in one way illustrated in FIG. 126) in one way.

Figure 108:
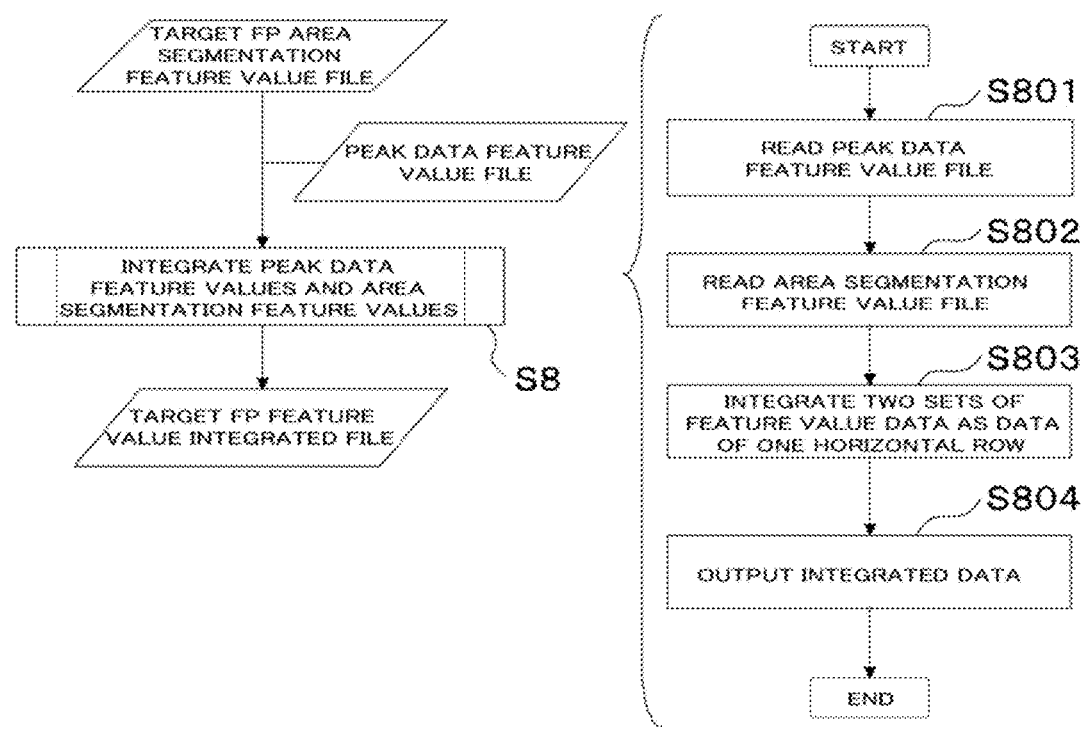
FIG. 108 is a flowchart illustrating details of "integration of peak feature values of a target FP and area segmentation feature values" according the first embodiment.

FIG. 108 is a flowchart illustrating detail of the "integration of peak data feature values and area segmentation feature values" of Step S8 illustrated in FIG. 94.

In Step S801, a process of "reading the peak data feature value file" is performed. Through this process, a file similar to the file example 199 of the peak data feature values that is illustrated in FIG. 124 is read, and the procedure proceeds to Step S802.

In Step S802, a process of "reading the area segmentation feature value file" is performed. Through this process, the target FP area segmentation feature value file 203 illustrated in FIG. 126 is read, and the procedure proceeds to Step S803.

In Step S803, a process of "integrating two sets of feature value data as data of a horizontal one row" is performed. Through this process, the file of the peak data feature values (the file example 199 of the peak data feature values illustrated in FIG. 124) and the target FP area segmentation feature value file (the target FP area segmentation feature value file example 203 illustrated in FIG. 126) are integrated as the target FP feature value integrated file (a target FP feature value integrated file example 205 in FIG. 127) of one row, and the procedure proceeds to Step S804.

In Step S804, a process of "outputting the integrated data" is performed. This process outputs the target FP feature value integrated file 205 illustrated in FIG. 127.

A reference FP feature value integrated file for comparing the target FP feature value integrated data with the reference FP feature value integrated data is prepared as illustrated in FIGS. 109 to 116.

Figure 109:
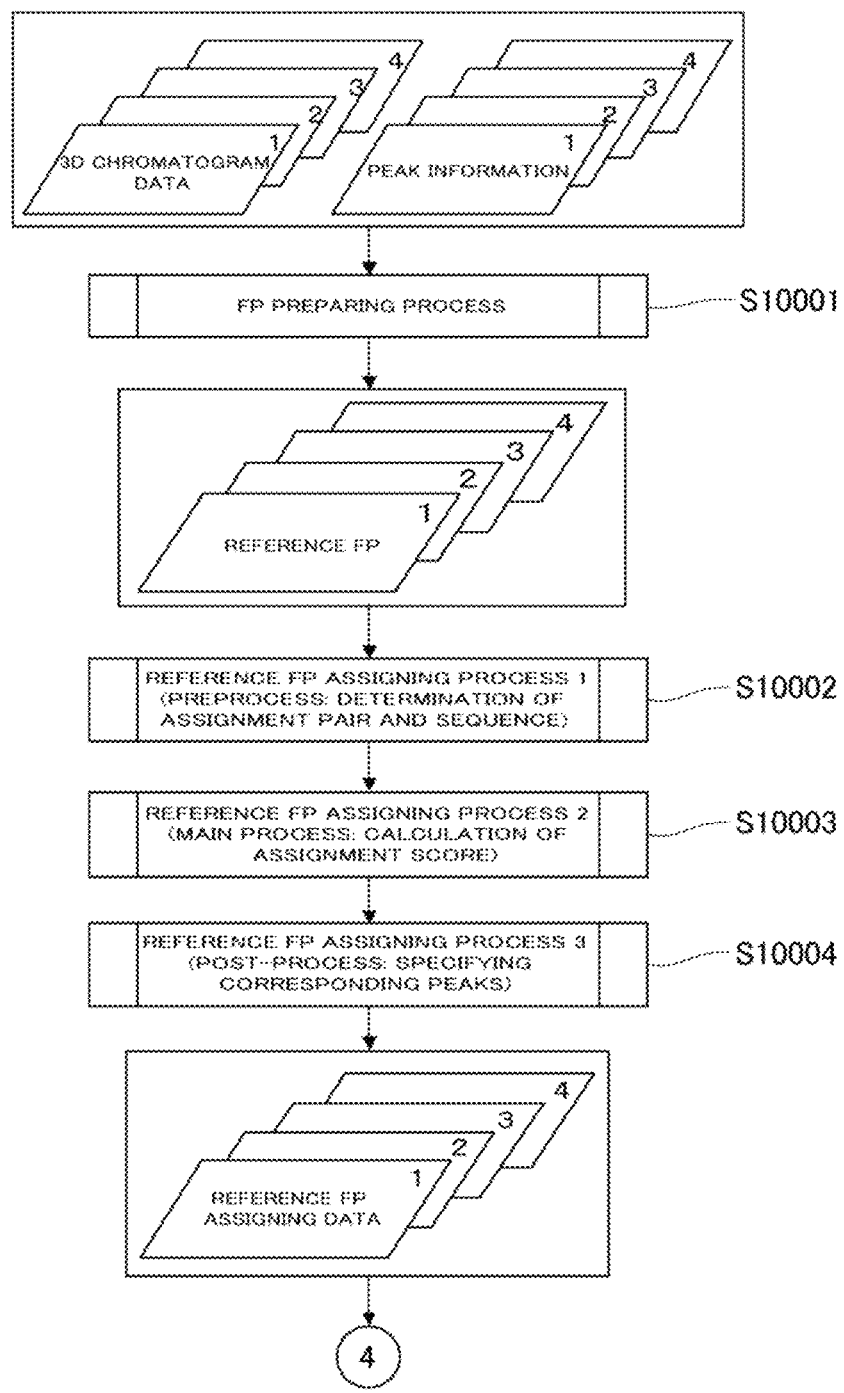
FIG. 109 is a flowchart for preparing a reference FP feature value integrated file according the first embodiment.
Figure 110:
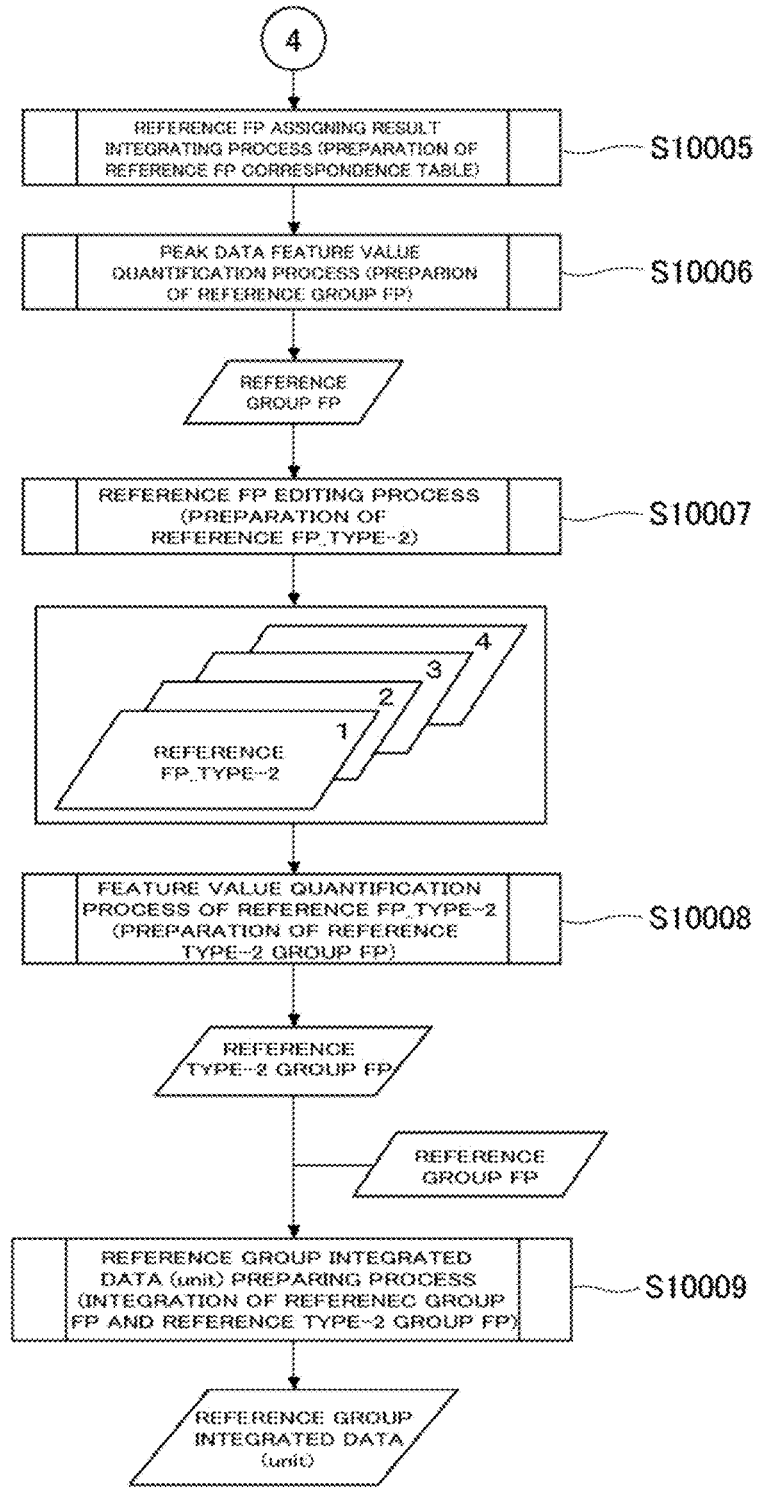
FIG. 110 is a flowchart for preparing the reference FP feature value integrated file according the first embodiment.

FIGS. 109 and 110 are flowcharts for preparing the reference FP feature value integrated file, to cause the computer to execute the FP preparing function of the reference FP preparing part 31, the reference FP peak assigning function of the reference FP peak assigning part 15, the reference FP assigning result integrating function of the reference FP assigning result integrating part 17, the reference FP peak feature value preparing function of the reference FP peak feature value preparing part 19, the reference FP type-2 preparing function of the reference FP type-2 preparing part 21, the reference FP area segmentation feature value preparing function of the reference FP area segmentation feature value preparing part 23, and the reference FP feature value integrating function of the reference FP feature value integrating part 25.

The reference FP preparing function is realized in Step S10001. The reference FP peak assigning function is realized in Steps S10002, S10003, and S10004. The reference FP assigning result integrating function is realized in Step S10005. The reference FP peak feature value preparing function is realized in Step S10006. The reference FP type-2 preparing function is realized in Step S10007. The reference FP area segmentation feature value preparing function is realized in Step S10008. The reference FP feature value integrating function is realized in Step S10009.

Steps S10001 to S10004 correspond to Steps S1 to S4 relating to the preparation of the target FP feature value integrated file of FIGS. 93 and 94, and Steps S1007 to S10009 correspond to Steps S6 to S8 of the same.

In Step S10001, the "FP preparing process" is performed using a 3D chromatogram and peak information at a specific detection wavelength as inputs.

Both the 3D chromatogram and the peak data are included for each one of a plurality of evaluation reference drugs (reference kampo medicines) that are evaluation criteria.

In Step S10001, the reference FP preparing part 31 (FIG. 2) of the FP preparing part 3 of the computer functions to prepare a reference FP in the same way as the target FP 43 (FIG. 3A) based on the 3D chromatogram and the peak information, and data of the reference FP is output as a file.

In Step S10002, the "reference FP assigning process 1" is performed using all reference FPs output in Step S10001 as inputs.

In Step S10002, the reference FP peak assigning part 15 of the computer functions, for all the reference FPs, selects combinations from among all the reference FPs in order to calculate assignment scores for the selected combinations in the selected order, and the procedure proceeds to Step S10003.

In Step S10003, the "reference FP assigning process 2" is performed according to the selected combinations of the reference FPs as an input.

In Step S10003, for all the peaks of the combinations of the reference FPs that are selected in Step S2, peak patterns are comprehensively prepared as illustrated in FIGS. 23 to 61. Then, the degree of matching between the peak patterns (P_Sim illustrated in FIG. 63 or 64) is calculated. In addition, the degrees of matching between UV spectra (UV_Sim illustrated in FIG. 66) of the peaks of the selected combinations of the reference FPs are calculated. Furthermore, the degrees of matching of the assignment candidate peaks (SCORE illustrated in FIG. 67) are calculated based on these two degrees of matching. The calculation result is output as a determination result file (the determination result file example 189 in FIG. 120).

In Step S10004, the "reference FP assigning process 3" is performed according to the determination result file output in Step S10003 as an input.

In Step S10004, between the reference FPs in the selected combinations, peaks of the reference FPs in the selected combinations, which correspond to each other, are specified based on the degree of matching between the assignment candidate peaks (SCORE). The result is output as the reference FP assigning data for each reference FP.

In Step S10005, the "reference FP assigning result integrating process" is performed according to all the reference FP assigning data output in Step S10004 as an input.

In Step S10005, the reference FP assigning result integrating part 17 of the computer functions to prepare a reference FP correspondence table by integrating all the FP assigning data with reference to the peak correspondence relation of the individual reference FP specified by the reference FP peak assigning part 15, and proceeds to Step S10006.

In Step S10006, the reference FP peak feature value preparing part 19 of the computer functions to prepare a peak feature value (reference group FP) according to all the reference FPs based on the reference FP correspondence table that is prepared by the reference FP assigning result integrating part 17. In the process at the reference FP peak feature value preparing part 19, statistic values (a maximum value, a minimum value, a medium value, an average value, and the like) are calculated for each peak (column) in the reference FP correspondence table, to select the peak (column) based on the calculated information. The selected peak (column) is output as the reference group FP (the reference group FP example 197 illustrated in FIG. 123).

In Step S10007, a process of "preparation of the FP type-2" is performed according to the reference group FP output in Step S10006 and all the reference FPs as inputs.

In Step S10007, the reference FP type-2 preparing part 21 of the computer functions similar to the target FP type-2 preparing part 9 and, in the same way as Step S6 illustrated in FIG. 93, prepares each FP as a reference FP type-2 (the FP type-2 file example 201 in FIG. 125) composed of remaining peaks with the exclusion of the peaks quantified as the feature values from each of a plurality of reference FPs and of the retention time points thereof.

In Step S10008, a process of "feature value quantification of the reference FP_type-2" is performed. In this process, the reference FP area segmentation feature value preparing part 23 of the computer functions to prepare the reference FP area segmentation feature values through the area segmentation illustrated in FIGS. 73 to 85. The result is output as a reference type-2 group FP (a reference type-2 group FP example 207 in FIG. 128).

In Step S10009, a process of "reference data preparing process" is performed. In this process, the reference FP feature value integrating part 25 of the computer functions to prepare the feature value data of all the reference FPs by integrating the reference group FP prepared by the reference FP peak feature value preparing part 19 and the reference type-2 group FP prepared by the reference FP area segmentation feature value preparing part 23. The result is output as reference group integrated data (a reference group integrated data example 209 in FIG. 129).

Figure 111:
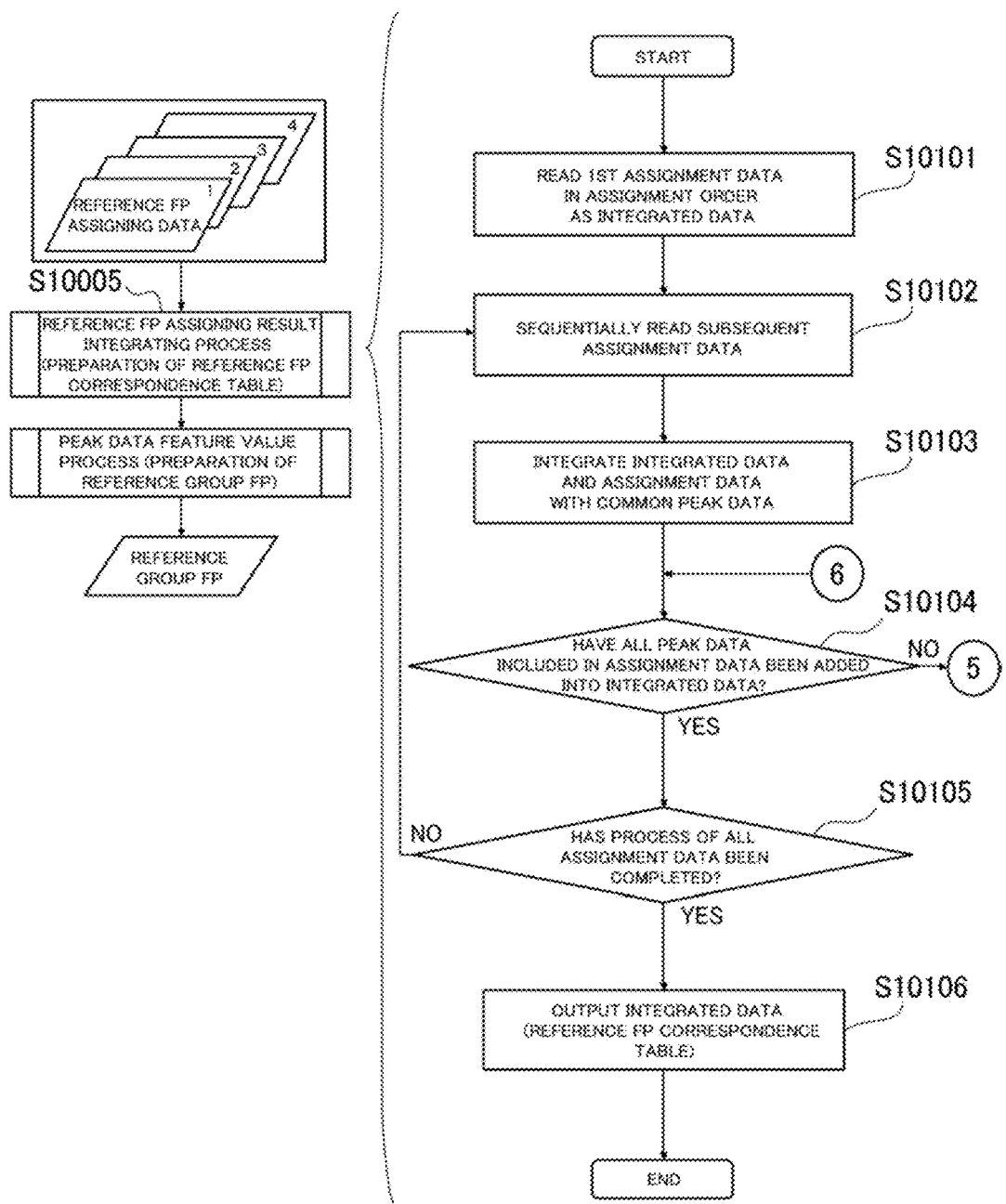
FIG. 111 is a flowchart illustrating details of a "reference FP assigning result integrating process (preparation of a FP correspondence table)" according the first embodiment.
Figure 112:
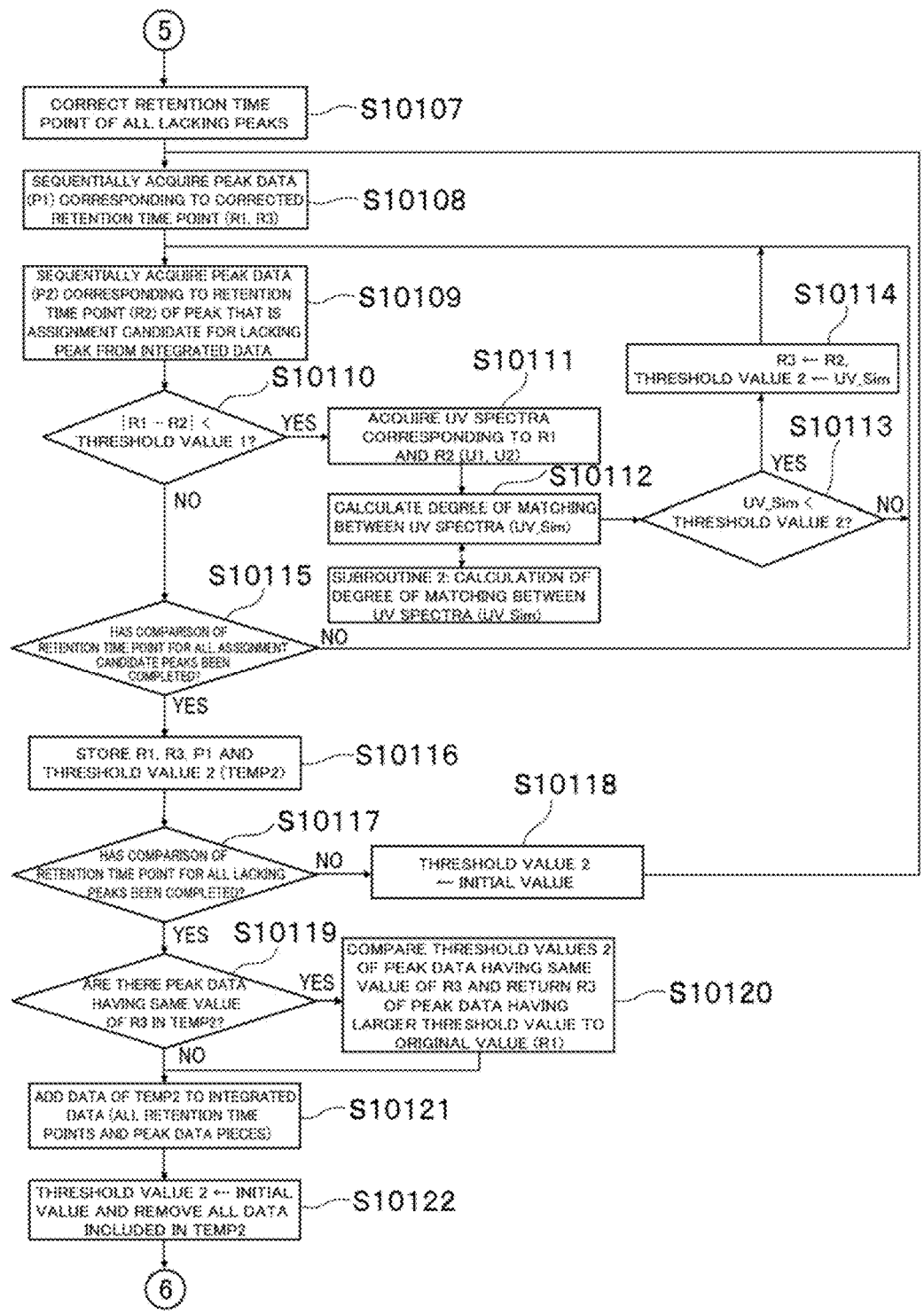
FIG. 112 is a flowchart illustrating details of the "reference FP assigning result integrating process (preparation of a reference FP correspondence table)" according the first embodiment.

FIGS. 111 and 112 are flowcharts that illustrate details of the "reference FP assigning result integrating process (preparation of the reference FP correspondence table)" of Step S10005 in FIG. 110.

In Step S10101, a process of "reading the 1st assignment data in the assignment order as integrated data" is performed. In this process, the reference FP assigning data, in which the assignment process is performed first to specify the correspondence relation of the peaks in Step S10004, is read as the integrated data. Then, the procedure proceeds to Step S10102.

In Step S10102, a process of "sequentially reading 2nd and subsequent data" is performed. In this process, at first the reference FP assigning data, in which the assignment process is secondarily performed to specify the correspondence relation of the peaks in Step S10004, is read as integrated data. Then, the procedure proceeds to Step S10103.

In Step S10103, a process of "integrating the integrated data and the assignment data as common peak data" is performed. In this process, the two files are integrated based on the peak data of the reference FP commonly-existing in the integrated data and the assignment data, the integrated data is updated as a result thereof, and the procedure proceeds to Step S10104.

In Step S10104, a determining process "Have all the peaks included in the assignment data been added to the integrated data?" is performed. In this process, it is determined whether or not all the peaks in the assignment data have been added to the integrated data. If added (YES), the procedure proceeds to Step S10105. If there are one or more peaks (lacking peaks) that have not been added (NO), in order to add the lacking peaks to the integrated data, the procedure proceeds to Step S10107. In addition, in the process (S10107 to S10120) of adding the lacking peaks to the integrated data, the same process as that of Steps S504 to S517 in S5 (target FP assigning process 4) is performed.

In Step S10121, a process of "adding data of TEMP2 to the integrated data (all the retention time points and peaks)" is performed. In this process, all the retention time points (R3) and the peaks (P1) in TEMP2 are added to corresponding positions in the integrated data, and the procedure proceeds to Step S10122.

In Step S10122, a process of "setting threshold value 2←initial value, and deleting all the data in TEMP2" is performed. In this process, the threshold value 2 updated to UV_Sim is returned to the original value, all the data is removed from TEMP2 storing data such as retention time points and peaks of all the lacking peaks and the like, and the process is returned to Step S10104.

In Step S10105 to which it proceeds from Step S10104, a determining process "Has the process of all the assignment data been completed?" is performed. In this process, it is determined whether or not the process for all reference data has been completed. If completed (YES), in order to output the reference FP correspondence table that is the integration result of all the assignment data, the procedure proceeds to Step S10106. If not completed (NO), the procedure is returned to Step S10102 to sequentially process the remaining assignment data.

In Step S10106, a process of "outputting the integrated data (reference FP correspondence table)" is performed. In this process, the result integrating all the assignment data is output as the reference FP correspondence table, to finish the process of preparing the reference FP correspondence table.

Figure 113:
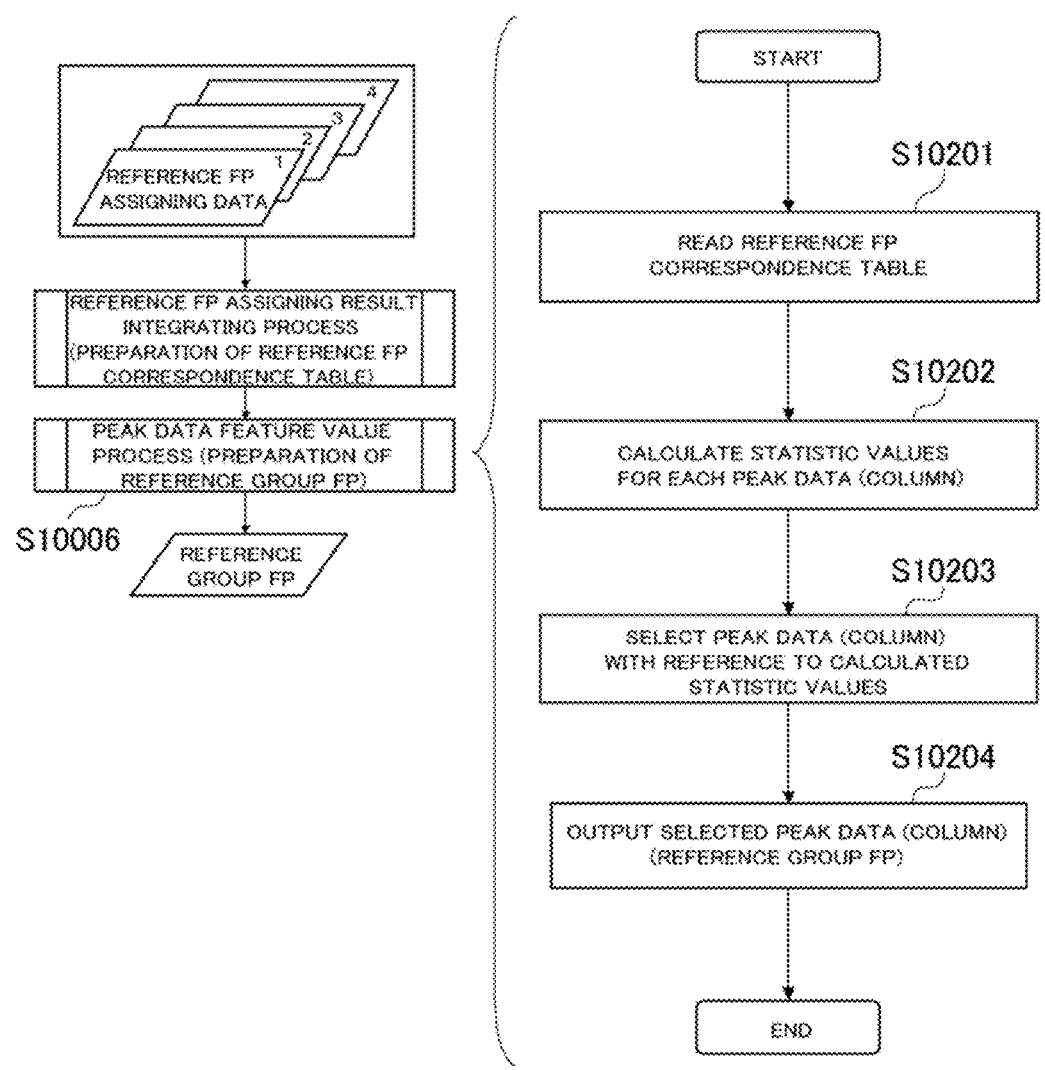
FIG. 113 is a flowchart illustrating details of a "peak-feature value quantification process (preparation of a reference group FP)" according the first embodiment.

FIG. 113 is a flowchart illustrating details of the "peak feature value quantification process of peak feature values (preparation of a reference group FP)" of Step S10006 illustrated in FIG. 109.

In Step S10201, a process of "reading the reference FP correspondence table" is performed. In this process, the reference FP correspondence table prepared in Step S10005 is read to proceed to Step S10202.

In Step S10202, a process of "calculating statistic values for each peak (column)" is performed. In this process, the statistic values (a maximum value, a minimum value, a medium value, an average value, a variance, a standard deviation, an existence number, and an existence ratio) are calculated for each peak (column) of the reference FP correspondence table. Then, the procedure proceeds to Step S10203.

In Step S10203, a process of "selecting a peak (column) with reference to the calculated statistic values" is performed. In this process, a peak is selected with reference to the statistic values calculated in Step S10102, to proceed to Step S10204.

In Step S10204, a process of "outputting the selected peak (column) (reference group FP)" is performed. In this process, the selecting result of the peak (column) according to the statistic values is output as the reference group FP, to finish the process of preparing a reference group FP.

FIG. 123 illustrates a reference FP correspondence table example 197 output as described above.

Figure 114:
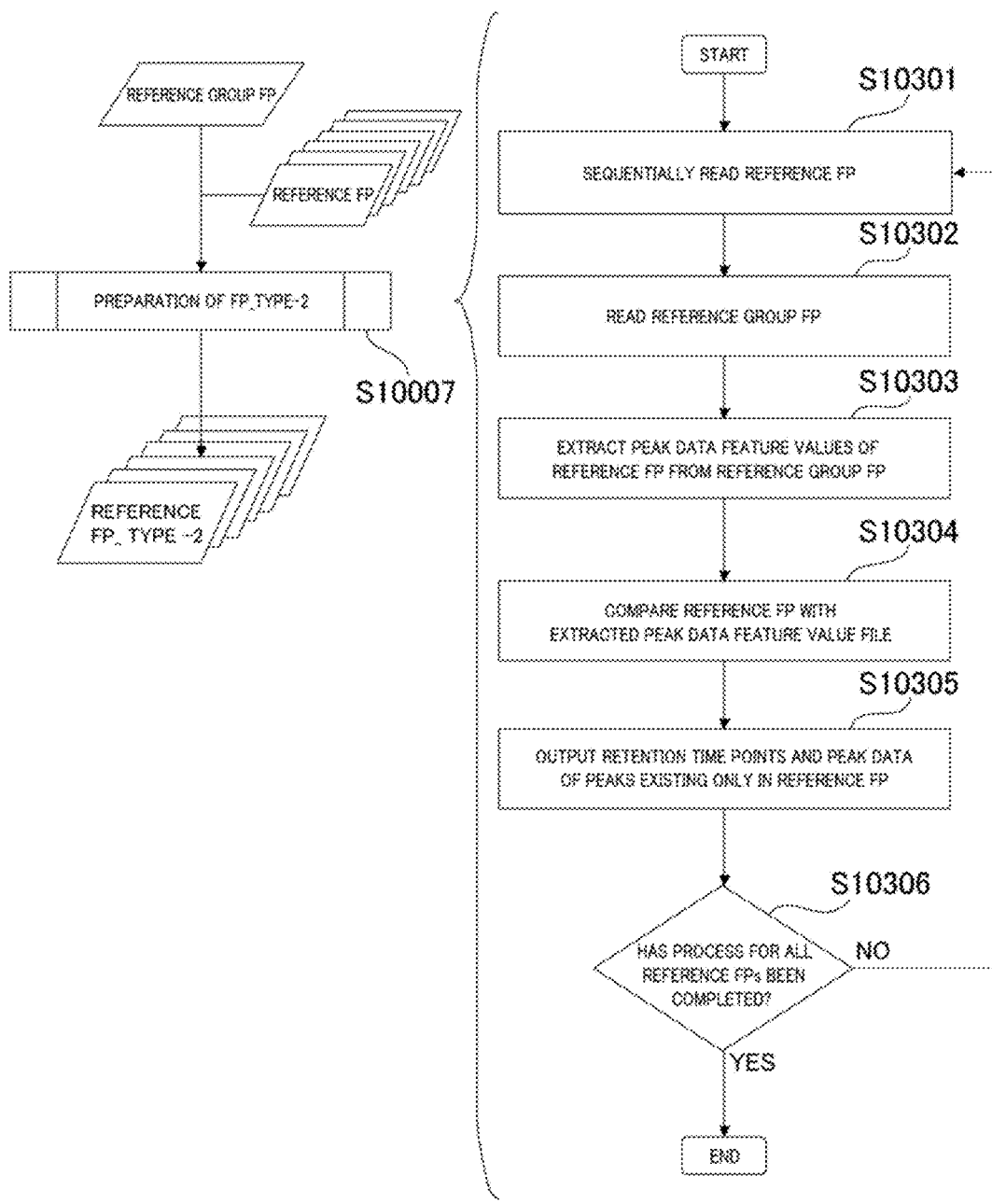
FIG. 114 is a flowchart illustrating details of a "process of preparing reference FP_type-2" according the first embodiment.

FIG. 114 is a flowchart illustrating details of the "reference FP editing process (preparation of a reference FP type-2)" of Step S10007 in FIG. 110.

In Step S10301, a process of "sequentially reading the reference FPs" is performed. In this process, a file (a data example 187 of a FP in FIG. 119) of a plurality of reference FPs is read, and the procedure proceeds to Step S10302.

In Step S10302, a process of "reading the reference group FP" is performed. In this process, a data file (the reference group FP example 197 in FIG. 123) of the reference group FP is read, and the procedure proceeds to Step S10303.

In Step S10303, a process of "extracting peak data feature values of the reference FP from the reference group FP" is performed. In this process, peak data feature values that are processed to be assigned to the reference FP are extracted from the file of the reference group FP 45, and the procedure proceeds to Step S10304.

In Step S10304, a process of "comparing the reference FP with the extracted peak data feature value file" is performed, the reference FP is compared with the peak data feature value file, and the procedure proceeds to Step S10305.

In Step S10305, a process of "outputting the retention time points and the peak data of peaks that are present only in the reference FP" is performed, the peaks of the peak data feature value file are excluded from the reference FP, and the procedure proceeds to Step S10306.

In Step S10306, a determining process "Has process completed for all the reference FPs?" is performed. In this process, if the process has been completed for all the reference FPs (YES), Step S10007 is terminated. If the process has not been completed for all the reference FPs (NO), Steps of S10301 to S10305 are repeated. Accordingly, the plurality of reference FPs are sequentially processed, and the file (the data example 201 of the target and the reference FP type-2 illustrated in FIG. 125) of the reference FP type-2 is prepared from each reference FP with the exclusion of the peaks of the peak data feature value file.

Figure 115:
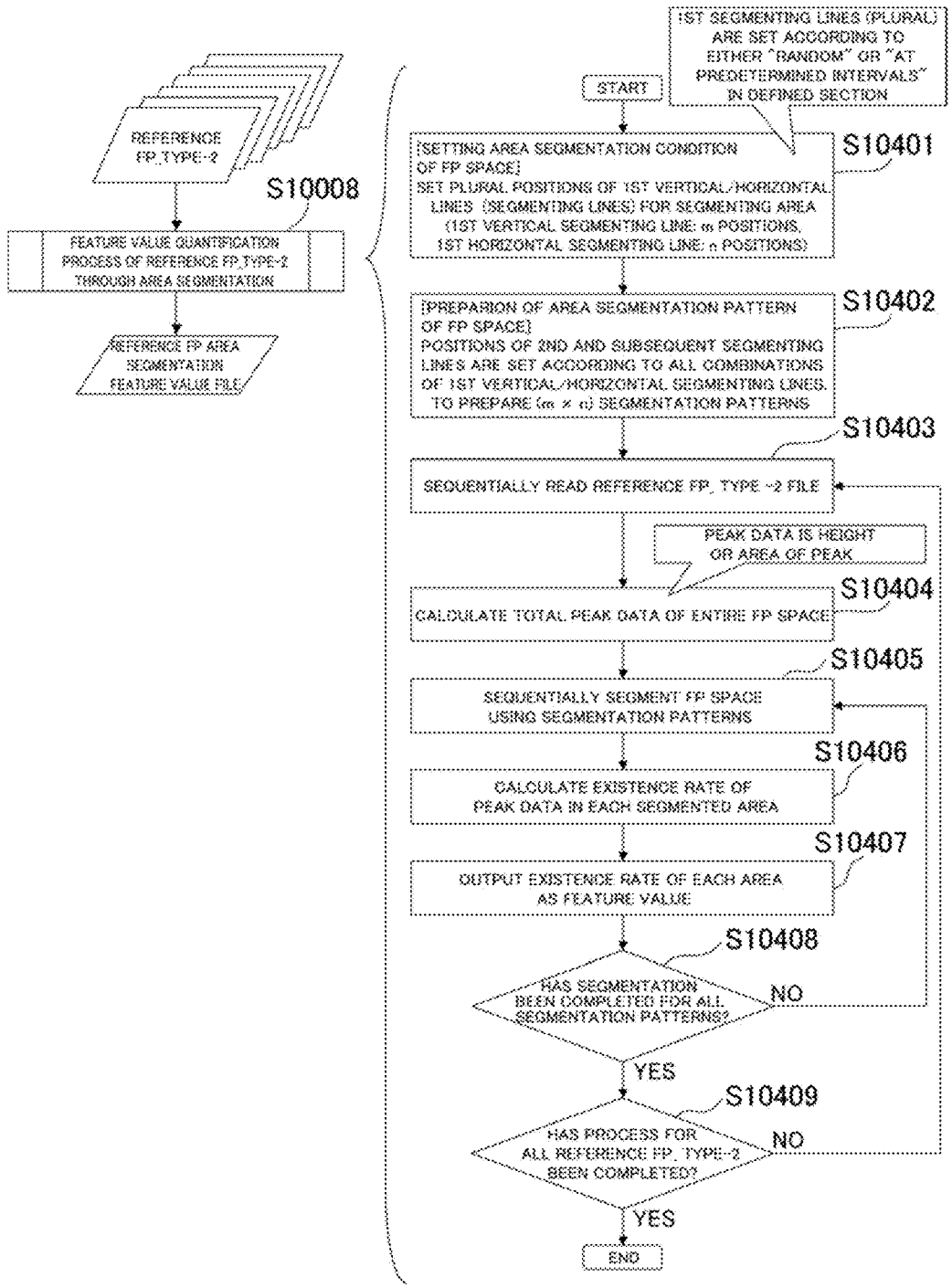
FIG. 115 is a flowchart illustrating a "feature value quantification process of a reference FP as feature values through area segmentation" in detail according the first embodiment.

FIG. 115 is a flowchart illustrating details of the "feature value quantification process of the reference FP_type-2 through area segmentation" of Step S10008 in FIG. 110.

In Step S10401, a process of "setting area segmentation conditions of the FP space" is performed. In this process, in order to segment the area of the reference FP type-2, a plurality of the positions of the 1st vertical and horizontal lines (segmenting lines) are set. Due to this setting, for example as illustrated in FIGS. 76 and 77, a plurality of vertical and horizontal segmenting lines (1st) 141 and 143 are set as segmenting lines in the FP space. After setting the plurality of the vertical and horizontal segmenting lines (1st) 141 and 143, the procedure proceeds to Step S10402.

In Step S10402, a process of "setting an area segmentation pattern in the FP space" is performed. In this process, positions of 2nd and subsequent segmenting lines are set according to all the combinations of all the combinations of the 1st vertical and horizontal segmenting lines, thereby preparing (m×n) segmentation patterns. Through this setting, for example as illustrated in FIG. 78, a plurality of patterns of the area segmentation according to the vertical and horizontal segmenting lines 141 and 143 are set to the FP space. After the area segmentation, the procedure proceeds to Step S10403.

In Step S10403, a process of "sequentially reading the file of the reference FP type-2" is performed. Through this process, the file of the reference FP type-2 is read to proceed to Step S10404.

In Step S10404, a process of "calculating total peak data of the entire FP space" is performed. In this process, for example, a sum of heights of peaks that are present in all the respective lattices 145 segmented as illustrated in FIG. 79 is calculated (FIG. 81), and the procedure proceeds to Step S10405.

In Step S10405, a process of "sequentially segmenting the FP space by the segmentation patterns" is performed. In this process, the area of the FP space is sequentially segmented according to a plurality of area segmentation patterns set in Step S10402, and the procedure proceeds to Step S10406.

In Step S10406, a process of "calculating an existence rate of peak data within the segmented area" is performed. In this process, for example, a sum of heights of peaks that are present in all the lattices 145 that are segmented as illustrated in FIG. 79 is calculated (FIG. 81), and the peak existence rate within each lattice 145 illustrated in FIG. 79 is calculated as the feature value=sum of peak heights within area/sum of heights of all the peaks. The calculation result, for example, is as illustrated in FIGS. 83 to 85. After the calculation is completed, the procedure proceeds to Step S10408.

In Step S10408, a process of "completing the segmentation to all the segmentation patterns" is performed. In this process, it is determined whether or not the feature value process is completed for all the plural area segmentation patterns set in Step S10402. If the feature value process is completed (YES), the procedure proceeds to Step S10409. If the feature value process has not been completed (NO), the procedure proceeds to Step S10405. Steps of S10405 to S10408 are repeated until the feature value process for all the area segmentation pattern is completed.

In Step S10409, a determining process "Has the process been completed for all the reference FP_type-2?" is performed. In this process, it is determined whether or not the feature value process has been completed for a plurality of all the reference FP type-2 prepared for each of the plurality of reference FPs. If all the reference FP type-2's are completed (YES), Step S10008 is terminated. If all the reference FP type-2's have not been completed (NO), the procedure proceeds to Step S10403. Steps S10403 to S10409 are repeated until the feature value process for the reference FP type-2 is completed.

FIG. 128 shows a reference type-2 group FP example 207.

Figure 116:
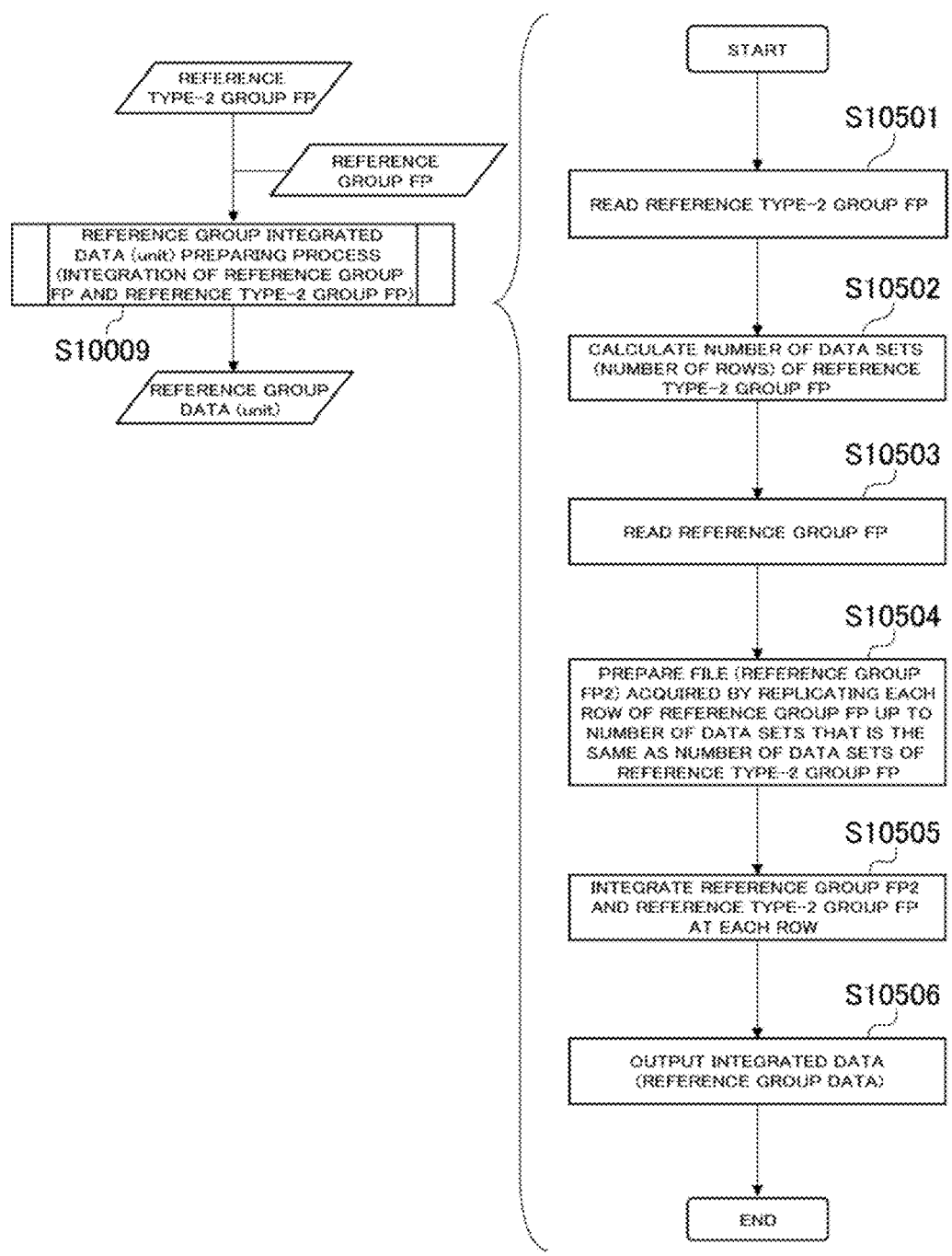
FIG. 116 is a flowchart according to the feature value integrating process of a reference FP according the first embodiment.

FIG. 116 is a flowchart illustrating details of the "reference data preparing process" of Strep S10009 in FIG. 110.

In Step S10501, a process of "reading an area segmentation feature value file" is performed. Through this process, a reference FP area segmentation feature value file (a reference type-2 group FP example 207 in FIG. 128) is read, and the procedure proceeds to Step S10502.

In Step S10502, a process of "calculating the number of segmentation patterns at the time of segmenting the area" is performed. Through this process, the number of the segmentation patterns for the area segmentation is calculated. The number of the segmentation patterns is calculated, as described with reference to FIGS. 70 to 80, for example, in 100 ways. After the calculation, the procedure proceeds to Step S10503.

In Step S10503, a process of "reading the reference group FP" is performed, the reference group FP is read, and the procedure proceeds to Step S10504.

In Step S10504, a process of "preparing files (reference group FP 2) acquired by replicating each row of the reference group FP as many as the number of segmentation patterns" is performed. In this process, in order to integrate the reference group FP and the area segmentation feature value file, the row of the reference group FP is replicated in correspondence with the number of the segmentation patterns, thereby preparing the reference group FP-2. For example, the reference group FP file example 197 in FIG. 123 is replicated so as to be in correspondence with the peak data feature value (reference group FP 2) of the reference group integrated data example 209 in FIG. 129. After the replication, the procedure proceeds to Step S10505.

In Step S10505, a process of "integrating the reference group FP-2 and the area segmentation feature value file at each row" is performed. In this process, the data of the reference group FP-2 replicated in Step S10504 and the data of the area segmentation feature value file are integrated at each row, and the procedure proceeds to Step S10506.

In Step S10506, a process of "outputting integrated data" is performed. In this process, the reference FP feature value integrated file (the reference group integrated data example 209 in FIG. 129) according to the integration result is output.

As explained above, the evaluating method for a multicomponent material according to the first embodiment of the present invention prepares the target FP peak feature values that are quantified as feature values based on the target FP 43 and a plurality of reference FPs, prepares the target FP type-2 of the remaining peaks of the target FP 43 that are excluded from the feature value quantification, segments the target FP type-2 into a plurality of areas, prepares the target FP area segmentation feature values based on an existence rate of peaks that are present in each area, prepares the target FP integrated feature values by integrating the target FP peak feature values and the target FP area segmentation feature values, and compares and evaluates the target FP integrated feature values and the reference FP integrated feature values that correspond to the target FP integrated feature values and are based on the plurality of reference FPs of multicomponent materials being evaluation criteria.

Through the comparison and evaluation, the method determines whether the target FP integrated feature values including the target FP peak feature values and the target FP area segmentation feature values are within the permissible range. In a case where the target FP integrated feature values are within the permissible range, the powder extract of the multicomponent drug is determined as an accepted one meeting the criteria for productization.

Accordingly, the peaks of the target peak that are not included in the target FP peak feature values can be additionally evaluated, thereby certainly improving the accuracy of the evaluation of the quality of whether the powder extract of the multicomponent drug as the evaluation target drug meets the criteria for productization.

As a result, the formulating method of this embodiment surely subjects a powder extract of a multicomponent drug determined as an accepted one meeting the criteria for productization with high accuracy to the dosage form processing to make the powder extract into a product. This reduces variation in multicomponent drugs to be subjected to the dosage form processing and realizes high quality of products.

In particular, this embodiment compares and evaluates the target FP integrated feature values and reference FP integrated feature values to find a MD value using MT method. IF the MD value is equal to or less than the threshold value, the target FP integrated feature values including the target FP area segmentation feature values are determined as values within the permissible range. Accordingly, the powder extract is determined as the accepted one meeting the criteria for productization.

With this, the formulating method conducts the evaluation of whether the powder extract meets the criteria for productization with higher accuracy.

Further, the formulating method of this embodiment mixes the powder extract of the multicomponent drug determined as a rejected one that does not meet the criteria for productization with one or more other powder extracts that do not meet the criteria for productization to form a mixed extract without subjecting the evaluated powder extract to the dosage form processing, evaluates whether the mixed extract meets the criteria for productization, and subjects the mixed extract determined as an accepted one meeting the criteria for productization to the dosage form processing.

Thus, even the powder extract that does not meet the criteria for productization is made into a product by mixing with the other powder extracts.

Furthermore, MD values are used to determine a mixing rate of powder extracts to be mixed and the powder extracts are mixed with the determined mixing rate to form the mixed extract having a MD value that is equal to or less than the threshold value.

Accordingly, the formulating method surely produces the mixed extract having the MD value being equal to or less than the threshold value, i.e., meeting the criteria for productization and therefore improves the accuracy and the efficiency of the productization of the mixed extract of the multicomponent drug.

The target FP 43 prepared by the target FP preparing step 173 is configured as three-dimensional information (peaks, retention time points, and UV spectra) similar to the 3D chromatogram 41. Accordingly, the target FP 43 is data that directly succeed to the information that is peculiar to the drug. In spite of that, the volume of data is compressed at the ratio of about 1/70, compared to the 3D chromatogram 41, the amount of information to be processed can be greatly reduced to increase the processing speed.

The target FP preparing step 173 prepares a FP by composing a plurality of FPs at different detection wavelengths. Accordingly, for even a multicomponent drug acquired by combining components all of which cannot be detected using one wavelength, a quality evaluation covering all the components can be performed by composing FPs at a plurality of detection wavelengths.

The target FP preparing step 173 prepares a FP that includes all the peaks detected in the 3D chromatogram. Accordingly, the target FP preparing step is suite for an evaluation of the quality of a kampo medicine that is a multicomponent drug.

The reference FP selecting step 177 compares retention time appearance patterns of FPs with each other, to select a reference FP having a high degree of matching between patterns as a reference FP that is appropriate to the assignment of the target FP. Accordingly, in the peak assigning step 181, the assignment process can be performed between FPs having similar patterns, whereby assignment with high accuracy can be performed.

The peak pattern preparing step 179 comprehensively prepares peak patterns with use of a plurality of peripheral peaks for each of the assignment target peak and the assignment candidate peak. Accordingly, even if there is a difference between the whole patterns of the target FP and the reference FP more or less, assignment can be performed through the peak assigning step 181 with high accuracy.

In the peak assigning step 181, in addition to the degree of matching between peak patterns prepared by the peak pattern preparing step 179, the degree of matching between UV spectra of the assignment target peak and the assignment candidate peak is used for specifying the peak to be assigned. Accordingly, the assignment can be performed with high accuracy.

The peak assigning step 181 assigns all the peaks of the target FP to the peaks of the reference FP all together. Accordingly, the assignment process can be performed with high efficiency.

The evaluating step 171 collects a FP that is composed by multiple components as multi-dimensional data as a MD value in one dimension by MT method, to easily compare and evaluate a plurality of evaluation target lots. Accordingly, it is suited for evaluating a multicomponent based drug that is composed of multiple components.

The target FP area segmentation feature value preparing step 155 performs the segmentation of the areas with a plurality of vertical segmenting lines 141 that are parallel to the signal strength axis and a plurality of horizontal segmenting lines 143 that are parallel to the time axis.

Accordingly, the area segmentation is simplified, thereby increasing the processing speed.

The plurality of horizontal segmenting lines 143 are set at geometric sequence ratio intervals in a direction in which the signal strength increases.

Accordingly, the area can be finely segmented in a portion having a high peak density, thereby efficiently performing the calculation of the peak existence rate through the area segmentation.

The evaluating method for a multicomponent drug further includes the reference FP preparing step 175, the reference FP peak assigning step 159, the reference FP assigning result integrating step 161, the reference FP peak feature value preparing step 163, the reference FP type-2 preparing step 165, the reference FP area segmentation feature value preparing step 167, and the reference FP feature value integrating step 169.

Accordingly, the reference FP integrated feature values are prepared by integrating the reference FP peak feature values and the reference FP area segmentation feature values and can be compared with the target FP integrated feature values in the evaluating step 171, thereby improving the accuracy and the efficiency of the quality evaluation of an evaluation target drug.

The reference FP area segmentation feature value preparing step 167 changes the position of each area and prepares the reference FP area segmentation feature values before and after the change.

Accordingly, even in a case where retention time points or peak heights change due to a slight variation of the analysis condition or the like and value of each lattice 145 markedly changes in a single pattern, the existence amount of peaks within each lattice 145 can be acquired regardless of such variation, thereby improving the accuracy and the efficiency of the quality evaluation of an evaluation target drug.

The reference FP area segmentation feature value preparing step 167 performs the segmentation of the areas with the plurality of vertical segmenting lines 141 that are parallel to the signal strength axis and the plurality of horizontal segmenting lines 143 that are parallel to the time axis.

Accordingly, the area segmentation is simplified, thereby increasing the processing speed.

The plurality of horizontal segmenting lines 143 are set at geometric sequence ratio intervals in a direction in which the signal strength increases.

Accordingly, the area can be finely segmented in a portion having a high peak density, thereby efficiently performing the calculation of the peak existence rate through the area segmentation.

The reference FP area segmentation feature value preparing step 167 changes and sets each of the vertical and horizontal segmenting lines 141 and 143 so as to be moved parallel within a set range, thereby changing the position of each area 145.

Accordingly, the change in the position of each area 145 can be efficiently performed through a simple process.

The formulating apparatus 301 for a multicomponent drug according to the embodiment of the present invention operates the parts 3, 5, 7, 9, 11, 13, 15, 17, 19, 21, 23, 25, and 27 of the evaluating device 1 to improve the accuracy and efficiency of the evaluation of whether a powder extract of a multicomponent drug meets the criteria for productization.

As a result, the formulating apparatus 301 subjects a powder extract of a multicomponent drug determined as an accepted one meeting the criteria for productization with high accuracy to the dosage form processing to make the powder extract into a product.

According to the embodiment, the formulating apparatus 301 includes the extract producing device 307 extracting an essence from a raw material crude drug to produce a powder extract of a multicomponent drug, the first pipeline 323 led from the extract producing device 307 to the dosage form processing device 311, the first stocker 309 arranged on the first pipeline 323 to accommodate the produced powder extract, the sampler 341 obtaining a sample from the powder extract accommodated in the first stocker 309 and feeding the obtained sample to the chromatographic device 343, and the control unit 308 controlling the sampler 341 to feed the sample to the chromatographic device 343 and then controlling the first pipeline 323 to convey the powder extract from the first stocker 309 to the dosage form processing device 311 in response to a determination made at the evaluating device 1 that the powder extract meets the criteria for productization.

The formulating apparatus 301 of this embodiment automatically conducts the formulating process in which the powder extract is produced from the raw material crude drug and the powder extract meeting the criteria for productization is subjected to the dosage form processing. Further, the pipeline 323 is extended from the dosage form processing device 311 to the packing device 313 and automatically conducts also the packing of the formulated drug subsequent to the dosage form processing.

The formulating apparatus 301 includes the second pipeline 327 led from and back to the first stocker 309, and the second stockers 329 arranged on the second pipeline 327 for accommodating powder extracts that do not meet the criteria for productization. The control unit 308 controls the second pipeline 327 to convey that powder extract from the first stocker 309 to an empty one of the second stokers 329 in response to a determination made at the evaluating device 1 that the powder extract does not meet the criteria for productization.

Accordingly, the formulating apparatus 301 automatically stores the produced powder extract without the dosage form processing if that powder extract does not meet the criteria for productization.

The formulating apparatus 301 includes the mixing device 330 arranged on the second pipeline 327. The control unit 308 controls the second pipeline 327 to convey two or more powder extracts accommodated in the second stockers 329 to the mixing device 330 at which the conveyed extracts are mixed to form the mixed extract and to convey the mixed extract from the mixing device 330 to the first stocker 309 at which the mixed extract is accommodated and then controls the sampler 341 to feed the sample of the mixed extract to the chromatographic device 343.

Accordingly, the formulating apparatus 301 automatically conducts the evaluation of whether the produced mixed extract meets the criteria for productization and automatically subjects the mixed extract to the dosage form processing or store the mixed extract according to the evaluation.

In addition, the formulating apparatus 301 realizes the formulating method to obtain the same effects as the formulating method.

In the case of FIGS. 63, 64, and 105, the calculation of the degree of matching between peak patterns (P_Sim) is performed based on a difference between peak heights of comparison targets in the above-described embodiment in which the FPs are prepared with use of peak heights.

In formulating method and apparatus 301, there may be a case where a peak represents a maximum value of a signal strength (height) as described above or a case where a peak represents an area value (peak area) of a signal strength in a form of a height.

Even in the case where the FP is prepared with use of peak areas, the area values are represented in a form of height to prepare the FP. Accordingly, the FP has the same representation as that of the case where the FP is prepared with use of the peak heights as in the above-described embodiment. Therefore, similar to the case where the FP is prepared with the peak heights, the FP can be evaluated by the process of the above-described embodiment.

However, in the case where the FP is prepared with the peak areas, differences between the peak values of comparison targets are larger. Accordingly, it is appropriate that the calculation is made based on a ratio so as to make the handling thereof easy.

Hereinafter, the degree of matching between peak patterns (P_Sim) that is calculated based on the ratios will be represented for exemplary cases where n=2 and n=4.

In a case where n=2, the calculation is represented as follows:

$$P\_Sim = (p1/p2^{\#1}) \times$$
$$(|(r1-(r2+d)|+1) + (dn1/fn1^{\#1}) \times (|(cn1-r1)-(en1-r2)|$$
$$+ (dn2/fn2^{\#1}) \times (|(cn2-r1)-(en2-r2)|+1).$$

In a case where n=4, the calculation is represented as follows:

$$P\_Sim = (p1/p2^{\#1}) \times$$
$$(|(r1-(r2+d)|+1) + (dn1/fn1^{\#1}) \times (|(cn1-r1)-(en1-r2)|$$
$$+ (dn2/fn2^{\#1}) \times (|(cn2-r1)-(en2-r2)|+1) +$$
$$(dn3/fn3^{\#1}) \times (|(cn3-r1)-(en3-r2)|+1) +$$
$$(dn4/fn4^{\#1}) \times (|(cn4-r1)-(en4-r2)|+1).$$

Here, $^{\#1}$ represents a ratio (larger value/smaller value) of two comparison target values.

In addition, also in the case where the FP is prepared by means of the peak heights, the degree of matching between peak patterns (P_Sim) can be calculated based on a ratio, and, also in the case where the FP is prepared by means of the peak areas, similarly to the case of a difference between the peak heights, the degree of matching between peak patterns (P_Sim) can be acquired based on a difference between peak area values.

FIG. 130 is a modified example of "Subroutine 2" that is applied instead of that illustrated in FIG. 104 and is a flowchart illustrating details of the modified example of "Subroutine 2" in the "target FP assigning process 2" illustrated in FIG. 99. The degree of matching between UV spectra is calculated by the process according to this modified example.

In the modified example of this Subroutine 2, a process of adding inclination information of the moving average of a UV pattern (DNS) to the RMSD of Subroutine 2 in FIG. 104 can be performed. The DNS is represented in an equation to be described later and is defined as the number of mismatches of inclination codes (+/−) when the moving inclination of the moving average values in the UV pattern are compared between two patterns. In other words, the DNS is a value that represents an evaluation of the matching state of the positions of the maximum and minimum values of the UV patterns.

By adding the DNS information to the RMSD, the degree of matching between waveforms of UV spectra can be calculated more accurately.

In Subroutine 2 according to the modified example of FIG. 130, Steps S2001 to S2008 are almost the same as those of Subroutine 2 in FIG. 104. However, in Step S2001, initial setting of "Interval 1←w1 and Interval 2←w2" is additionally performed, to be used for calculating the moving average and the moving inclination to be described later.

In Subroutine 2 of this modified example, Steps S2010 to S2013 are added so as to add the DNS, so that it enables Step S2009A to calculate the degree of matching to which the DNS is added.

In Step S2010, a determining process "Is the DNS added?" is performed If the DNS is determined to be added (YES), the procedure proceeds to Step S2011. If the DNS is determined not to be added (NO), the procedure proceeds to Step S2009A. For example, whether the DNS is added or not is based on the initial setting. The determination whether the DNS is added or not is based on, for example, an initial setting. For example, if the FP is prepared by means of peak areas, the DNS is set to be added; and if the FP is prepared by means of peak heights, the DNS is set to be not added.

However, also in the case of the above-described embodiment in which the FP is prepared by means of peak heights, the degree of matching between UV patterns can be calculated through a process to which the DNS is added; and also in the case where the FP is prepared by means of peak areas, the degree of matching between UV patterns can be calculated through the process of the above-described embodiment to which the DNS is not added.

In Step S2011, a process of "calculating the moving averages of "x" and "y" in interval 1 (w1)" is performed, to find the moving averages for interval 1 (w1). Interval 1 (w1) is an interval relating to the wavelength of the UV data. In a case where w1=3 in the initial setting of Step S2001, interval 1 (3) is set and the average of the UV intensities of three wavelengths is acquired. More specifically, description will be made later with reference to a table represented in FIG. 131.

In Step S2012, the process of "calculating the moving inclinations of "x" and "y" in interval 2 (w2)" is performed to find the moving inclinations in interval 2 (w2). Interval 2 (w2) is an interval relating to the moving average acquired in Step S2011. If w2=3 in the initial setting performed in Step S2001, interval 2 (3) is set to acquire inclinations of (±) over the three moving averages based on the moving average calculated in Step S2011. More specifically, description will be made later with reference to a table illustrated in FIG. 101.

In Step S2013, a process of "calculating the number of mismatches between the codes of the moving inclinations of "x" and "y" (DNS)" is performed, to calculate the number of matches in the inclinations of (±) based on the moving inclinations calculated in Step S2012. The moving inclination of (+) represents rising to the right in FIG. 66, and the moving inclination of (−) represents falling to the right.

When proceeding from Step S2013 to Step S2009A, the degree of matching to which the DNS is added is calculated in the process of Step S2009A.

In Step S2009A, a process of "calculating the degree of matching between UV spectra of "x" and "y" (UV_Sim)" is performed. In the calculation process of the degree of matching to which the DNS is added, the UV_Sim is calculated based on the sum "z" of squares of inter-UV spectrum distance, the number "a" of data of "x" and the DNS as:

$$UV\_Sim=\sqrt{(z/a)} \times 1.1^{DNS}.$$

This UV_Sim is input to Step S306 in FIG. 81, to finish the process of calculating the degree of matching between UV spectra.

In addition, the process performed in a case where the process proceeds from Step S2010 to Step S2009A is the same as that of Step S2009 in FIG. 86.

FIG. 131 is a table illustrating a calculating example of moving averages and moving inclinations.

In FIG. 131, the upper row represents an example of UV data, the intermediate row represents an example of calculation of moving averages, and the lower row represents an example of calculation of moving inclinations. As examples of the UV data, the UV intensity is represented as a1 to a7 instead of specific numeric values. For example, the UV intensity of 220 nm is a1, the UV intensity of 221 nm is a2, and the like. Also in the example of calculation of the moving averages and moving inclinations, UV intensities a1 to a7 are used instead of specific numeric values.

For the example of interval 1 (w1=3), the moving averages are calculated as m1, m2 . . . as respective values calculated for an interval (a1, a2, a3), an interval (a2, a3, a4) . . . in Step S2012 (see FIG. 130). In addition, for the example of the interval 2 (3), the moving inclinations are calculated as s 1 . . . as respective values calculated for an interval (m1, m2, m3), an interval (m2, m3, m4) . . . in Step S2013 (see FIG. 130). For example, a difference m3−m1 between the moving averages is the moving inclination, and (±) thereof are extracted.

In this way, when preparing the FP by means of peak areas, in the assignment process for the reference group FP and the reference FP assigning result integrating step, the degree of matching between UV patterns can be calculated through the process to which the DNS is added. With this calculation, even if a distance (dis) between two corresponding points illustrated in FIG. 66 is larger relative to the FP prepared by means of peak heights, the handling thereof can be easily performed, thereby calculating the degree of matching between UV patterns with high accuracy.

FIG. 132 is a schematic block diagram illustrating a formulating apparatus according to the second embodiment of the present invention. The second embodiment has the same basic structure as the first embodiment and therefore corresponding parts are represented with the same reference numerals to omit the repetition in the explanation.

The formulating apparatus 301 according to the second embodiment further includes a third stocker 345 and a blower 347 in comparison with the first embodiment of FIG. 1A. The third stocker 45 is arranged or laid downstream of the dosage form processing device 311 on the first pipeline 323. The blower 347 on the first pipeline 323 is arranged downstream of the third stocker 345.

According to the embodiment, the formulating apparatus 301 accommodates in the third stocker 345 granules produced through the dosage form processing at the dosage form processing device 311, evaluates whether the granules meet the criteria for productization at the evaluating device 1, and conveys the granules determined as accepted ones meeting the criteria for productization to the packing device 313 using the blower 347.

The third stocker 345 is a general tank or the like similar to the first stocker 309. The third stocker 345 includes a sensor 345*a*. The sensor 345*a* is a load cell or the like similar to the sensor 309*a* of the first stocker 309.

According to the embodiment, the control unit 308 determines a conveying state of the granules to the third stocker 345 according to the detecting signal from the sensor 345*a* of the third stocker 345. Then, the control unit 308 controls the sampler 341 according to the conveying state to obtain the sample of the granules stored in the third stocker 345 and feed the obtained sample to the chromatographic device 343.

In response to the feeding, the chromatographic device 343 obtains a 3D chromatogram and outputs the same to the evaluating device 1, and the evaluating device 1 evaluates whether the granules meet the criteria for productization based on the chromatogram and outputs the evaluating result to the control unit 308.

The control unit 308 controls the blower 345 to convey the granules from the third stocker 345 to the packing device 313 in the case where the granules meet the criteria for productization according to the evaluating result.

The second embodiment, therefore, conclusively confirms that the granules meet the criteria after producing the granules and before packing the same. This allows only the granules meeting the criteria to be surely packed.

This embodiment is particularly advantageous for production of the granules from the mixed extract. Namely, the mixed extract of the embodiment is produced to meet the criteria for productization and therefore it is not required to evaluate whether the mixed extract accommodated in the first stocker 309 meets the criteria.

Accordingly, the second embodiment conclusively confirms that the granules stored in the third stocker 345 meet the criteria without confirmation for the mixed extract stored in the first stocker 309, to omit repeated evaluation and improve the efficiency for productization.

In addition, the second embodiment obtains the same effects as the first embodiment.

FIG. 133 is a schematic block diagram illustrating a formulating apparatus according to the third embodiment of the present invention. The third embodiment has the same basic structure as the first embodiment and therefore corresponding parts are represented with the same reference numerals to omit the repetition in the explanation.

The formulating apparatus 301 according to the embodiment conducts evaluation of granules without conducting evaluation of a powder extract.

For this, the dosage form processing device 311 is arranged or laid downstream of the extraction producing device 307 and a powder extraction produced at the extract producing device 307 is conveyed to the dosage form processing device 311 through the first pipeline 323 to produce granules.

On the downstream side of the dosage form processing device 311, the first stocker 309 is arranged to accommodate the granules. To the granules accommodated in the first stocker 309, the evaluating line 306 evaluates whether to meet the criteria for productization.

The evaluating result or determination is input to the control unit 308 and the control unit 308 controls the blower 325 to convey the granules from the first stocker 309 to the packing device 313 in the case where the granules meet the criteria for productization. The packing device 313 subdivides and packs the conveyed granules.

The third embodiment, therefore, packs granules meeting the criteria for productization and does not pack granules not meeting that criteria based on the high-accuracy evaluation at the evaluating device 1, thereby to surely pack the granules for the multicomponent drug meeting that criteria to make the same into a product.

In the feature value preparing method, the feature value preparing program, and the feature value preparing device for a pattern or FP according to embodiments of the present invention, if the FP is prepared with use of peak areas, it may be applied such that the signal strength axis is set as an area value axis, and the signal strength is set as an area value.

Although the embodiments of the present invention are applied to an evaluation of a kampo medicine as a multicomponent drug, it is applicable to an evaluation of other multicomponent materials.

In this embodiment, although the area segmentation feature values are prepared for the target FP type 2 or the reference FP type 2, area segmentation feature values may be prepared for the target FP or the reference FP.

Namely, the present invention may segment a target FP itself into a plurality of areas with absence of peak assignment in principle.

For example, the present invention may segment the target FP prepared at the target FP preparing part 29 of the evaluating device 1 into a plurality of areas at the target FP area segmentation feature value preparing part 11, to prepare target FP area segmentation feature values. In this case, the evaluating part 27 should find a MD value by comparing and evaluating the target FP area segmentation feature values and the reference FP area segmentation feature values and determine whether the target FP area segmentation feature values are within the permissible range according to the MD value.

This allows the high quality evaluation to be performed by comparing and evaluating all peaks including fine peaks of the target FP and reference FP even if peak assignment cannot be performed with high accuracy. This reduces variation in multicomponent drugs to be subjected to the dosage form processing and realizes high quality of products.

In addition, the present invention is widely applicable to what includes a target pattern area segmentation feature value preparing step of segmenting a pattern whose peak change in a time series into a plurality of areas to prepare pattern area segmentation feature values based on the existence rate or the existence amount of peaks existing in each area.

In the FP of the above-described embodiment, although all the peaks on the 3D chromatogram are set as targets, the FP may be prepared with the exclusion of fine data such as peaks each having a peak area corresponding to 5% or less on the 3D chromatogram.

In the above-described embodiment, the FP is prepared based on the peak heights, and evaluations represented in FIGS. 87 to 91 are acquired. However, even in a case where the FP is prepared based on peak areas, it finds MD values with use of MT method through the same sequence as that of the above-described embodiment that prepares based on the peak height, the evaluations can be acquired as those of FIGS. 87 to 91.

The chromatogram is not limited to the 3D chromatogram, and a FP that is composed of peaks and retention time points, in which the UV spectrum is not included, may be used. In such a case, the process can be performed similarly to the above-described embodiment with the exception of the degree of matching between UV spectra. retention time pointsretention time pointsretention time pointsretention time points.

What is claimed is:

1. A method of formulating a multicomponent drug, comprising:
   obtaining, with chromatography equipment and a first processor, a chromatogram from a base of the multicomponent drug;
   evaluating, with a second processor, whether the base meets criteria for productization by evaluating a fingerprint based on the obtained chromatogram; and
   if the base meets the criteria for productization, subjecting, under control of a third processor, the base to productization using a dosage form processing at a dosage form processing device, to produce a formulated drug having a given dosage-form, wherein
   the evaluating, with the second processor, whether the base meets the criteria for productization by evaluating the fingerprints comprises:
   gathering, as the fingerprint, peaks where a peak is defined by a local maximum or an area value in signal strength and a retention time point from the chromatogram;
   converting the fingerprint into a histogram with a vertical axis representing, as height, the local maximum or the area value in signal strength and an abscissa axis representing the retention time point and wherein the peaks are bars extending parallel to the vertical axis;
   segmenting the histogram of the fingerprint, with a plurality of vertical segmenting lines parallel to the vertical axis of the histogram and a plurality of horizontal segmenting lines parallel to the abscissa axis of the histogram, into a plurality of grid areas wherein each of the grid areas is bounded by a pair of mutually adjacent ones of the vertical segmenting lines and a pair of mutually adjacent ones of the horizontal segmenting lines so as to cover all bars of the histogram with the grid areas;
   obtaining, as a fingerprint area segmentation feature value of said each grid area, an existence rate or existence amount of the bar segments for said each grid area, the existence rate obtained by dividing a sum of heights of the bar segments within said each grid area by a sum of heights of all the bar segments and the existence amount being the sum of the heights of the bar segments within said each grid area;
   comparing and evaluating the fingerprint area segmentation feature values of the grid areas and predetermined reference values using a Mahalanobis-Taguchi method to find a Mahalanobis distance between the fingerprint area segmentation feature values and the predetermined reference values; and
   determining the base of the multicomponent drug as an accepted one that meets the criteria for productization if the Mahalanobis distance is equal to or less than a predetermined threshold value and the base of the multicomponent drug as a rejected one that does not meet the criteria for productization if the Mahalanobis distance exceeds the predetermined threshold value; and wherein:
   the base which meets the criteria for productization and is subjected, under the control of the third processor, to the productization using the dosage form processing at the dosage form processing device, to produce the formulated drug having the given dosage-form, is the base which is the accepted one according to the determining of the accepted one.

2. The method according to claim 1, further comprising:
   if the base is a rejected one that does not meet the criteria for productization, mixing, under the control of the third processor, the base with one or more other bases that are rejected ones that do not meet the criteria for productization using a mixing mechanism to form a mixed base without subjecting the evaluated base to the dosage form processing;
   obtaining a chromatogram from the mixed base with the chromatography equipment and the first processor;
   determining, with the second processor, whether the mixed base is an accepted one that meets the criteria for productization based on the obtained chromatogram of the mixed base; and
   if the mixed base is the accepted one subjecting, under the control the third processor, the mixed base to the productization using the dosage form processing at the dosage form processing device.

3. The method according to claim 2, wherein
   mixing the base with one or more other bases that are the rejected ones includes determining, with the third processor, a mixing rate that is a ratio of quantities of the bases to be mixed based on the Mahalanobis distances of the bases to be mixed and mixing, under the control of the third processor, the bases to be mixed at the determined mixing rate with the mixing mechanism to form the mixed base having a Mahalanobis distance that is equal to or less than the predetermined threshold value.

4. The method according to claim 1, wherein
   the horizontal segmenting lines are set, with the second processor, at geometric sequence ratio intervals in a direction in which the signal strength or the area value increases.

5. The method according to claim 1, wherein
   obtaining the fingerprint area segmentation feature value includes changing, with the second processor, a position of each grid area of the histogram to prepare the fingerprint area segmentation feature values before and after the change.

6. The method according to claim 5, wherein
   obtaining the fingerprint area segmentation feature value includes Changing and setting, with the second processor, each of the vertical and horizontal segmenting lines so as to be moved parallel within a set range, thereby changing the position of each grid area.

7. An apparatus for formulating a multicomponent drug, comprising:
   chromatography equipment and a first processor, obtaining a chromatogram from a base of the multicomponent drug;
   a second processor connected to the first processor via a data line and obtaining the chromatogram from the first processor;
   a dosage form processing device subjecting the base to productization using a dosage form processing, to produce a formulated drug having a given dosage-form; and
   a third processor connected to the second processor via a data line, wherein
   the second processor is programmed to:
   gather from the chromatogram, as the fingerprint, peaks where a peak is defined by a local maximum or an area value in signal strength and a retention time point from the chromatogram;
   convert the fingerprint into a histogram with a vertical axis representing, as height, the local maximum or the area value in signal strength and an abscissa axis representing the retention time point and wherein the peaks are bars extending parallel to the vertical axis;

segment the histogram of the fingerprint, with a plurality of vertical segmenting lines parallel to the vertical axis of the histogram and a plurality of horizontal segmenting lines, into a plurality of grid areas wherein each of the grid areas is bounded by a pair of mutually adjacent ones of the vertical segmenting lines so as to cover all bars of the histogram with the grid areas;

obtain, as a fingerprint area segmentation feature value of said each grid area, an existence rate or existence amount of the bar segments for said each grid area, the existence rate obtained by dividing a sum of heights of the bar segments within said each area by a sum of heights of all the bar segments and the existence amount being the sum of the heights of the bar segments within said each grid area;

compare and evaluate the fingerprint area segmentation feature values of the grid areas and predetermined reference values using a Mahalanobis-Taguchi method to find a Mahalanobis distance between the fingerprint area segmentation feature values and the predetermined reference values; and determine the base of the multicomponent drug as an accepted one that meets the criteria for productization if the Mahalanobis distance is equal to or less than a predetermined threshold value and the base of the multicomponent drug as a rejected one that does not meet the criteria for productization if the Mahalanobis distance exceeds the predetermined threshold value; and the third processor is programmed to conduct the dosage form processing of the base at the dosage form processing device if the base is the accepted one.

8. The apparatus according to claim 7, further comprising:
a mixing mechanism; and wherein:
the third processor is programmed to, if the base is a rejected one that does not meet the criteria for productization, cause the mixing mechanism to mix the base with one or more other bases that are rejected ones that do not meet the criteria for productization to form a mixed base the first processor is programmed to obtain a chromatogram from the mixed base using the chromatography equipment, the second processor is programmed to determine whether the mixed base is an accepted one that meets the criteria for productization based on the obtained chromatogram of the mixed base, and the third processor is programmed to control that, if the mixed base is the accepted one that meets the criteria for productization, the mixed base is subjected to productization using the dosage form processing at the dosage form processing device.

9. The apparatus according to claim 8, wherein
the third processor is programmed to:
determine a mixing rate that is a ratio of quantities of the bases to be mixed based on the Mahalanobis distances of the bases to be mixed; and
cause the mixing mechanism to mix the bases to be mixed at the determined mixing rate to form the mixed base having a Mahalanobis distance that is equal to or less than the predetermined threshold value.

10. The apparatus according to claim 7, wherein
the horizontal segmenting lines are set, with the second processor, at geometric sequence ratio intervals in a direction in which the signal strength or the area value increases.

11. The apparatus according to claim 7, wherein
the second processor is programmed to change a position of said each grid area to prepare the fingerprint area segmentation feature values before and after the change.

12. The apparatus according to claim 11, wherein
the second processor is programmed to change and set each of the vertical and horizontal segmenting lines so as to be moved parallel within a set range, thereby changing the position of said each grid area.

* * * * *